(12) United States Patent
Charifson et al.

(10) Patent No.: US 9,051,319 B2
(45) Date of Patent: Jun. 9, 2015

(54) INHIBITORS OF INFLUENZA VIRUSES REPLICATION

(71) Applicant: Vertex Pharmaceuticals Incorporated, Cambridge, MA (US)

(72) Inventors: Paul S. Charifson, Framingham, MA (US); Michael P. Clark, Concord, MA (US); Upul K. Bandarage, Lexington, MA (US); Randy S. Bethiel, Lexington, MA (US); Michael J. Boyd, Winchester, MA (US); Ioana Davies, Watertown, MA (US); Hongbo Deng, Southborough, MA (US); John P. Duffy, Northborough, MA (US); Luc J. Farmer, Montreal (CA); Huai Gao, Arlington, MA (US); Wenxin Gu, Concord, MA (US); Joseph M. Kennedy, Charlestown, MA (US); Brian Ledford, Norton, MA (US); Mark W. Ledeboer, Acton, MA (US); Francois Maltais, Tewksbury, MA (US); Emanuele Perola, Brookline, MA (US); Tiansheng Wang, Concord, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/099,054

(22) Filed: Dec. 6, 2013

(65) Prior Publication Data
US 2014/0094473 A1    Apr. 3, 2014

Related U.S. Application Data

(63) Continuation of application No. PCT/US2012/049097, filed on Aug. 1, 2012.

(60) Provisional application No. 61/513,793, filed on Aug. 1, 2011.

(51) Int. Cl.
*A61K 31/454* (2006.01)
*C07D 471/04* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS

| | | |
|---|---|---|
| 5,051,412 A | 9/1991 | Macor |
| 5,304,121 A | 4/1994 | Sahatjian |
| 5,338,849 A | 8/1994 | Festal et al. |
| 5,395,840 A | 3/1995 | Miiller et al. |
| 5,886,026 A | 3/1999 | Hunter et al. |
| 6,099,562 A | 8/2000 | Ding et al. |
| 6,169,181 B1 * | 1/2001 | Romines et al. ............ 544/298 |
| 6,265,403 B1 | 7/2001 | Fraley et al. |
| 6,313,126 B1 | 11/2001 | Mewshaw et al. |
| 6,699,883 B1 | 3/2004 | Doemling et al. |
| 6,825,190 B2 | 11/2004 | Moon et al. |
| 6,900,201 B2 | 5/2005 | Noe et al. |
| 7,041,687 B2 | 5/2006 | Binch et al. |
| 7,135,550 B2 | 11/2006 | Come et al. |
| 7,432,375 B2 | 10/2008 | Graczyk et al. |
| 7,491,730 B2 | 2/2009 | Forster et al. |
| 7,507,826 B2 | 3/2009 | Salituro et al. |
| 7,514,448 B2 | 4/2009 | Green et al. |
| 7,645,769 B2 | 1/2010 | Khan et al. |
| 7,659,283 B2 | 2/2010 | Collier et al. |
| 7,700,609 B2 | 4/2010 | Jimenez et al. |
| 7,767,816 B2 | 8/2010 | Farmer et al. |
| 7,795,259 B2 | 9/2010 | Binch et al. |
| 7,872,129 B2 | 1/2011 | Forster et al. |
| 8,017,619 B2 | 9/2011 | Jimenez et al. |
| 8,017,781 B2 | 9/2011 | Brenchley et al. |
| 8,101,770 B2 | 1/2012 | Charrier et al. |

(Continued)

FOREIGN PATENT DOCUMENTS

| | | |
|---|---|---|
| EP | 0557171 | 8/1993 |
| EP | 1748829 | 7/2007 |

(Continued)

OTHER PUBLICATIONS

Schmidtke, M. et al., "A rapid assay for evaluation of antiviral activity against coxsackie virus B3, influenza virus A, and herpes simplex virus type 1", Elsevier, Journal of Virological Methods, vol. 95, 2001, pp. 133-143.
Tobita, K. et al., "Plaque Assay and Primary Isolation of Influenza A Viruses in an Established Line of Canine Kidney Cells (MDCK) in the Presence of Trypsin", Med. Microbiol. Immunol., vol. 162, 1975, pp. 9-14.
Alvarez, Mercedes et al., "Synthesis of 3-Aryl- and 3-Heteroaryl-7-azaindoles", Synthesis, Thieme Stuttgart, New York, No. 4, 1999, pp. 615-620.
Amano, Mutsuki et al., "Formation of Actin Stress Fibers and Focal Adhesions Enhanced by Rho-Kinase", Science, vol. 275, Feb. 28, 1997, pp. 1308-1311.

(Continued)

*Primary Examiner* — Soren Harward
*Assistant Examiner* — Jeanmarie Calvillo
(74) *Attorney, Agent, or Firm* — Honigman Miller Schwartz and Cohn LLP; Andrew N. Weber; Jonathan P. O'Brien

(57) ABSTRACT

Methods of inhibiting the replication of influenza viruses in a biological sample or patient, of reducing the amount of influenza viruses in a biological sample or patient, and of treating influenza in a patient, comprises administering to said biological sample or patient an effective amount of a compound represented by Structural Formula (I), or a pharmaceutically acceptable salt thereof, wherein the values of Structural Formula (I) are as described herein. A compound is represented by Structural Formula (I) or a pharmaceutically acceptable salt thereof, wherein the values of Structural Formula (I) are as described herein. A pharmaceutical composition comprises an effective amount of such a compound or pharmaceutically acceptable salt thereof, and a pharmaceutically acceptable carrier, adjuvant or vehicle.

2 Claims, 11 Drawing Sheets

(56) References Cited

U.S. PATENT DOCUMENTS

| | | |
|---|---|---|
| 8,163,917 B2 | 4/2012 | Farmer et al. |
| 8,173,635 B2 | 5/2012 | Jimenez et al. |
| 8,188,281 B2 | 5/2012 | Salituro et al. |
| 8,242,272 B2 | 8/2012 | Jimenez et al. |
| 8,247,421 B2 | 8/2012 | Mortimore et al. |
| 8,288,400 B2 | 10/2012 | Jimenez et al. |
| 8,338,597 B2 | 12/2012 | Charrier et al. |
| 8,367,697 B2 | 2/2013 | Jimenez et al. |
| 8,445,681 B2 | 5/2013 | Brenchley et al. |
| 8,450,489 B2 | 5/2013 | Farmer et al. |
| 8,501,446 B2 | 8/2013 | Salituro et al. |
| 8,513,414 B2 | 8/2013 | Tanoury et al. |
| 8,518,953 B2 | 8/2013 | Pierce et al. |
| 8,530,489 B2 | 9/2013 | Mortimore et al. |
| 8,580,802 B2 | 11/2013 | Salituro et al. |
| 8,598,361 B2 | 12/2013 | Jimenez et al. |
| 8,722,889 B2 | 5/2014 | Salituro et al. |
| 8,796,453 B2 | 8/2014 | Tanoury et al. |
| 8,822,681 B2 | 9/2014 | Farmer et al. |
| 8,829,007 B2 | 9/2014 | Charifson et al. |
| 2002/0052386 A1 | 5/2002 | Armistead et al. |
| 2002/0065270 A1 | 5/2002 | Moriarty et al. |
| 2002/0147189 A1 | 10/2002 | Cai et al. |
| 2002/0183329 A1 | 12/2002 | Gross et al. |
| 2002/0183352 A1 | 12/2002 | Stack et al. |
| 2002/0183353 A1 | 12/2002 | Stack et al. |
| 2002/0183354 A1 | 12/2002 | Tran et al. |
| 2002/0193400 A1 | 12/2002 | Husbands et al. |
| 2003/0078268 A1 | 4/2003 | Zhao et al. |
| 2003/0100579 A1 | 5/2003 | Gross et al. |
| 2003/0153560 A1 | 8/2003 | Salituro et al. |
| 2003/0166668 A1 | 9/2003 | Van Zandt et al. |
| 2004/0009968 A1 | 1/2004 | Binch et al. |
| 2004/0009996 A1 | 1/2004 | Moon et al. |
| 2004/0043388 A1 | 3/2004 | Come et al. |
| 2004/0044203 A1 | 3/2004 | Wittman et al. |
| 2004/0236110 A1 | 11/2004 | Ladouceur et al. |
| 2005/0137201 A1 | 6/2005 | Aronov et al. |
| 2005/0148603 A1 | 7/2005 | Jimenez et al. |
| 2005/0208582 A1 | 9/2005 | Ohi et al. |
| 2005/0228005 A1 | 10/2005 | Moon et al. |
| 2005/0288290 A1 | 12/2005 | Borzilleri et al. |
| 2006/0003968 A1 | 1/2006 | Green et al. |
| 2006/0004014 A1 | 1/2006 | Hoffman et al. |
| 2006/0122185 A1 | 6/2006 | Green et al. |
| 2006/0122213 A1 | 6/2006 | Pierard et al. |
| 2006/0183761 A1 | 8/2006 | Ledeboer et al. |
| 2006/0183911 A1 | 8/2006 | Charrier et al. |
| 2006/0258662 A1 | 11/2006 | Binch et al. |
| 2007/0043063 A1 | 2/2007 | Salituro et al. |
| 2007/0049615 A1 | 3/2007 | Ibrahim et al. |
| 2007/0066641 A1 | 3/2007 | Ibrahim et al. |
| 2007/0072896 A1 | 3/2007 | Khan et al. |
| 2007/0135466 A1 | 6/2007 | Ledeboer et al. |
| 2007/0203142 A1 | 8/2007 | Farmer et al. |
| 2007/0207995 A1 | 9/2007 | Salituro et al. |
| 2007/0213327 A1 | 9/2007 | Collier et al. |
| 2009/0048250 A1 | 2/2009 | Aronov et al. |
| 2009/0088445 A1 | 4/2009 | Ledeboer et al. |
| 2009/0118278 A1 | 5/2009 | Forester et al. |
| 2009/0176763 A1 | 7/2009 | Salituro et al. |
| 2009/0291937 A1 | 11/2009 | Jimenez et al. |
| 2010/0099686 A1 | 4/2010 | Charrier et al. |
| 2010/0120792 A1 | 5/2010 | Ivashchenko et al. |
| 2010/0189773 A1 | 7/2010 | Mortimore et al. |
| 2010/0280026 A1 | 11/2010 | Jimenez et al. |
| 2010/0311743 A1 | 12/2010 | Farmer et al. |
| 2011/0081364 A1 | 4/2011 | Binch et al. |
| 2011/0224197 A1 | 9/2011 | Henkle et al. |
| 2011/0263575 A1 | 10/2011 | Pierard et al. |
| 2012/0010197 A1 | 1/2012 | Charrier et al. |
| 2012/0028966 A1 | 2/2012 | Charrier et al. |
| 2012/0122879 A1 | 5/2012 | Charrier et al. |
| 2012/0149680 A1 | 6/2012 | Jimenez et al. |
| 2012/0165307 A1 | 6/2012 | Farmer et al. |
| 2012/0171245 A1 | 7/2012 | Charifson et al. |
| 2012/0183577 A1 | 7/2012 | Jimenez et al. |
| 2012/0190699 A1 | 7/2012 | Charrier et al. |
| 2012/0258958 A1 | 10/2012 | Salituro et al. |
| 2012/0309963 A1 | 12/2012 | Mortimore et al. |
| 2013/0102782 A1 | 4/2013 | Tanoury et al. |
| 2013/0184259 A1 | 7/2013 | Charrier et al. |
| 2013/0237516 A1 | 9/2013 | Farmer et al. |
| 2013/0303764 A1 | 11/2013 | Tanoury et al. |
| 2013/0310418 A1 | 11/2013 | Brenchley et al. |
| 2013/0345197 A1 | 12/2013 | Salituro et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0018352 A1 | 1/2014 | Pierard et al. |
| 2014/0045812 A1 | 2/2014 | Mortimore et al. |
| 2014/0142119 A1 | 5/2014 | Charifson et al. |
| 2014/0249138 A1 | 9/2014 | Salituro et al. |

FOREIGN PATENT DOCUMENTS

| | | |
|---|---|---|
| JP | 2003-519143 | 6/2003 |
| JP | 2003-532635 | 11/2003 |
| JP | 2008-156370 | 7/2008 |
| WO | 88/01997 | 3/1988 |
| WO | 95/33748 | 12/1995 |
| WO | 99/21859 | 5/1999 |
| WO | 00/40554 | 7/2000 |
| WO | 00/40581 | 7/2000 |
| WO | 00/43393 | 7/2000 |
| WO | 00/64898 | 11/2000 |
| WO | 01/01986 | 1/2001 |
| WO | 01/14374 | 3/2001 |
| WO | 01/87887 | 11/2001 |
| WO | 02/14317 | 2/2002 |
| WO | 02/20013 | 3/2002 |
| WO | 02/051837 | 7/2002 |
| WO | 02/072587 | 9/2002 |
| WO | 02/085896 | 10/2002 |
| WO | 02/085911 | 10/2002 |
| WO | 02/088129 | 11/2002 |
| WO | 02/088131 | 11/2002 |
| WO | 02/088135 | 11/2002 |
| WO | 02/088136 | 11/2002 |
| WO | 02/088140 | 11/2002 |
| WO | 02/088144 | 11/2002 |
| WO | 02/088146 | 11/2002 |
| WO | 02/089811 | 11/2002 |
| WO | 02/092602 | 11/2002 |
| WO | 03/000688 | 1/2003 |
| WO | 03/091246 | 11/2003 |
| WO | 03/101968 | 12/2003 |
| WO | 03/101990 | 12/2003 |
| WO | 2004/013140 | 2/2004 |
| WO | 2004/014912 | 2/2004 |
| WO | 2004/016609 | 2/2004 |
| WO | 2004/016610 | 2/2004 |
| WO | 2004/043388 | 5/2004 |
| WO | 2004/076454 | 9/2004 |
| WO | 2004/078756 | 9/2004 |
| WO | 2004/082638 | 9/2004 |
| WO | 2004/089913 | 10/2004 |
| WO | 2004/106298 | 12/2004 |
| WO | 2005/000813 | 1/2005 |
| WO | 2005/028475 | 3/2005 |
| WO | 2005/044181 | 5/2005 |
| WO | 2005/062795 | 7/2005 |
| WO | 2005/085244 | 9/2005 |
| WO | 2005/095400 | 10/2005 |
| WO | 2005/105213 | 11/2005 |
| WO | 2005/123736 | 12/2005 |
| WO | 2006/009755 | 1/2006 |
| WO | 2006/015123 | 2/2006 |
| WO | 2006/030031 | 3/2006 |
| WO | 2006/038001 | 4/2006 |
| WO | 2006/041773 | 4/2006 |
| WO | 2006/050076 | 5/2006 |
| WO | 2006/052913 | 5/2006 |
| WO | 2006/063167 | 6/2006 |

(56) References Cited

FOREIGN PATENT DOCUMENTS

| WO | 2006/069258 | 6/2006 |
|---|---|---|
| WO | 2006/124863 | 11/2006 |
| WO | 2006/127587 | 11/2006 |
| WO | 2007/002325 | 1/2007 |
| WO | 2007/002433 | 1/2007 |
| WO | 2007/084557 | 7/2007 |
| WO | 2007/095188 | 8/2007 |
| WO | 2007/107221 | 9/2007 |
| WO | 2007/117494 | 10/2007 |
| WO | 2007/129195 | 11/2007 |
| WO | 2007/146057 | 12/2007 |
| WO | 2008/003958 | 1/2008 |
| WO | 2008/005457 | 1/2008 |
| WO | 2008/076392 | 6/2008 |
| WO | 2008/079346 | 7/2008 |
| WO | 2008/112642 | 9/2008 |
| WO | 2008/112646 | 9/2008 |
| WO | 2008/112651 | 9/2008 |
| WO | 2008/113711 | 9/2008 |
| WO | 2008/123800 | 10/2008 |
| WO | 2009/023269 | 2/2009 |
| WO | 2009/040556 | 4/2009 |
| WO | 2009/046983 | 4/2009 |
| WO | 2009/145814 | 12/2009 |
| WO | 2010/008454 | 1/2010 |
| WO | 2010/008459 | 1/2010 |
| WO | 2010/011756 | 1/2010 |
| WO | 2010/148197 | 12/2010 |
| WO | 2011/000566 | 1/2011 |
| WO | 2011/008915 | 1/2011 |
| WO | 2011/137022 | 3/2011 |
| WO | 2011/130146 | 10/2011 |
| WO | 2012/083121 | 6/2012 |
| WO | 2012/083122 | 6/2012 |
| WO | 2013/006634 | 1/2013 |
| WO | 2013/070606 | 5/2013 |
| WO | 2013/184985 | 12/2013 |

OTHER PUBLICATIONS

Amano, Mutsuki et al., "Identification of a Putative Target for Rho as the Serine-Threonine Kinase Protein Kinase N", Science vol. 271, 199602-02, pp. 648-650.

Berge, Stephen M. et al., "Pharmaceutical Salts" Journal of Pharmaceutical Sciences, vol. 66, No. 1, Jan. 1977, pp. 1-19.

Bettayeb, Karima et al., "Meriolins, a New Class of Cell Death-Inducing Kinase Inhibitors with Enhanced Selectivity for Cyclin-Dependent Kinases", Cancer Research, vol. 67, No. 17, Sep. 1, 2007, pp. 8325-8334.

Burns, Timothy F. et al., "Silencing of the Novel p53 Target Gene Snk/Plk2 Leads to Mitotic Catastrophe in Paclitaxel (Taxol)-Exposed Cells", Molecular and cellular Biology, vol. 23, No. 16, Aug. 2003, pp. 5556-5571.

Catlett-Falcone, Robyn et al, "Constitutive Activation of Stat3 Signaling Confers Resistance to Apoptosis in Human U266 Myeloma Cells", Immunity, vol. 10, Jan. 1999, pp. 105-115.

Chelucci, Giorgio et al., "An easy route to optically active 1-substituted-1-pyridyl-methylamines by diastereoselective reduction of enantiopure N-tert-butanesulfinyl ketimines", Tetrahedron: Asymmetry, Elsevier, 2006, vol. 17, No. 22, pp. 3163-3169.

Chiba, Yoshihiko et al., "Augmented acetylcholine-induced translocation of RhoA in bronchial smooth muscle from antigen-induced airway hyperresponsive rats", British Journal of Pharmacology, vol. 133, 2001, pp. 886-890.

Chiba, Yoshihiko et al., "Augmented acetylcholine-induced, Rho-mediated Ca2+ sensitization of bronchial smooth muscle contraction in antigen-induced airway hyperresponsive rats", British Journal of Pharmacology, vol. 127, 1999, pp. 597-600.

Chiba, Yoshihiko et al., "Characteristics of muscarinic cholilnoceptors in airways of antigen-induced airway hyperresponsive rats", Comp. Biochem. Physiol. C Pharmacol. Toxicol. Endocrinol., vol. 111C, No. 3, 1995, pp. 351-35.

Chitaley, Kanchan et al., "Antagonism of Rho-kinase stimulates rat penile erection via a nitric oxide-independent pathway", Nature Medicine, Nature Publishing Group, vol. 7, No. 1, Jan. 2001, pp. 119-122.

Eto, Masato et al., "Thrombin Suppresses Endothelial Nitric Oxide Synthase and Upregulates Endothelin-Converting Enzyme-1 Expression by Distinct Pathways", Circulation Research, vol. 89, 2001, pp. 583-585.

Eto, Yasuhiro et al., "Gene transfer of dominant negative Rho kinase suppresses neointimal formation after balloon injury in pigs", Am. J. Physiol. Heart Circ. Physiol., American Physiological Society, vol. 278, 2000, pp. H1744-H1750.

Fan, Yu et al., "Apoptosis induction with polo-like kinase-1 antisense phosph-orothioate oligodeoxynucleotide of colon cancer cell line SW480", World J. Gastroenterol, vol. 11, No. 29, 2005, pp. 4596-4599.

Fernandez, David et al., "Synthesis of Polyheterocyclic Nitrogen-Containing Marine Natural Products#", Monatshefte Fur Chemie, Chemical Monthly, AU, vol. 135, 2004, pp. 615-627.

Fournier, Alyson E. et al., "Rho Kinase Inhibition Enhances Axonal Regeneration in the Injured CNS", The Journal of Neuroscience, vol. 23, No. 4, Feb. 15, 2003, pp. 1416-1423.

Frank, David A, "STAT Signaling in the Pathogenesis and Treatment of Cancer", Molecular Medicine, vol. 5, Jul. 1999, pp. 432-456.

Fresneda, Pilar M. et al., "Synthesis of the indole alkaloids meridianins from the tunicate *Aplidium meridianum*", Tetrahedron, Pergamon, vol. 57, No. 12, 2001, pp. 2355-2363.

Fu, Xiahong et al., "The effects of the Rho-kinase inhibitor Y-27632 on arachidonic acid-, GTPgammaS-, and phorbol ester-induced induced Ca2+-sensitization of smooth muscle", FEBS Letters, vol. 440, 1998, pp. 183-187.

Fukata, Yuko et al., "Rho-Rho-kinase pathway in smooth muscle contraction and cytoskeletal reorganization of non-muscle cells", Trends Pharmacological Sciences, vol. 22, No. 1, Jan. 2001, pp. 32-39.

Galli, Stephan J., MD, "New Concepts About the Mast Cell", New England Journal of Medicine, vol. 328, No. 4, 1993, pp. 257-265.

Garcia-Bustos, Jose F. et al., "PIK1, an essential phosphatidylinositol 4-kinase associated with the yeast nucleus", The EMBO Journal, vol. 13, No. 10, 1994, pp. 2352-2361.

Genda, Takuya et al., "Cell Motility Mediated by Rho and Rho-Associated Protein Kinase Plays a Critical Role in Intrahepatic Metastasis of Human Hepatocellular Carcinoma", Hepatology, vol. 30, No. 4, Oct. 1999, pp. 1027-1036.

Gordon, John R. et al, "Mast cells as a source of both preformed and immunologically inducible TNF-alpha/cachectin", Nature, vol. 346, Jul. 19, 1990, pp. 274-276.

Guan, Ran et al., "Small Interfering RNA-Mediated Polo-Like Kinase 1 Depletion Preferentially Reduces the Survival of p53-Defective, Oncogenic Transformed Cells and Inhibits Tumor Growth in Animals", Cancer Res., vol. 65, No. 7, Apr. 1, 2005, pp. 2698-2704.

Ha, Hyung-Ho et al., "Novel heterocycle-substituted pyrimidines as inhibitors of NF-κB transcription regulation related to TNF-alpha cytokine release", Bioorganic & Medicinal Chemistry Letters, Elsevier, vol. 18, 2008, pp. 653-656.

Hamanaka, Ryoji et al., "Polo-like Kinase Is a Cell Cycle-regulated Kinase Activated during Mitosis", Journal of Biological Chemistry, vol. 270, No. 36, Sep. 8, 1995, pp. 21086-21091.

Hanks, Steven K. et al., "Protein kinases 6. The eukaryotic protein kinase superfamily: kinase (catalytic) domain structure and classification", FASEB J., vol. 9, No. 8, 1995, pp. 576-596.

Harrington, Elizabeth A. et al., "VX-680, a potent and selective small-molecule inhibitor of the Aurora kinases, suppresses tumor growth in vivo", Nature Medicine, vol. 10, No. 3, Feb. 22, 2004, pp. 262-267.

Hatanaka, Masashi. et al., "Preparation and antioxidant activity of alpha-pyridoin and its derivatives", Bioorganic & Medicinal Chemistry, Elsevier, 2005, vol. 13, pp. 6763-6770.

Herbert, R. et al., "1H-Pyrrolo[2,3-b]pyridines. Part II. Fragmentation of Some 1H-Pyrrolo[2,3-b]pyridines induced by Electron Impact", J. Chem. Soc., Phys. Org., 1970, pp. 459-463.

Hernandez-Perera, Octavio et al., "Involvement of Rho GTPases in the Transcriptional Inhibition of Preproendothelin-1 Gene Expres-

(56) References Cited

OTHER PUBLICATIONS sion by Simvastatin in Vascular Endothelial Cells", Circulation Research, vol. 87, 2000, pp. 616-622.
Hiles, Ian D. et al., "Phosphatidylinositol 3-Kinase: Structure and Expression of the 110 kd Catalytic Subunit", Cell, vol. 70, No. 3, Aug. 7, 1992, pp. 419-429.
Hirose, Masaya et al., "Molecular Dissection of the Rho-associated Protein Kinase (p160ROCK)-regulated Neurite Remodeling in Neuroblastoma N1E-115 Cells", Journal of Cell Biology, vol. 141, No. 7, Jun. 29, 1998, pp. 1625-1636.
Honjo, Meguni et al., "Effects of Protein Kinase Inhibitor, HA1077 on Intraocular Pressure and Outflow Facility in Rabbit Eyes", Arch. Ophthalmol, vol. 119, Aug. 2001, pp. 1171-1178.
Hoshijima, Masahiko et al., "The Low Molecular Weight GTPase Rho Regulates Myofibril Formation and Organization in Neonatal Rat Ventricular Myocytes", The Journal of Biological Chemistry, USA, vol. 273, No. 13, Mar. 27, 1998, pp. 7725-7730.
Huang, Shenlin, et al., "Synthesis of 2-amino-4-(7-azaindol-3-yl)pyrimidines as cyclin dependent kinase 1 (CDK1) inhibitors", Bioorganic & Medicinal Chemistry Letters, Elsevier, vol. 16, 2006, pp. 4818-4821.
Hudson, J.W. et al., "Late mitotic failure in mice lacking Sak, a polo-like kinase", Current Biology, vol. 11, No. 6, Mar. 20, 2001, pp. 441-446.
Iizuka, Kunihiko et al., "Evaluation of Y-27632, a Rho-kinase inhibitor, as a bronchodilator in guinea pigs", European Journal of Pharmacology, vol. 406, No. 2, 2000, pp. 273-279.
Ikeda, Fusao et al., "Reduction of Hepatic Ischemia/Reperfusion-Induced Injury by a Specific ROCK/Rho Kinase Inhibitor Y-27632", Journal of Surgical Research, Elsevier Science (USA), vol. 109, 2003, pp. 155-160.
International Search Report issued for PCT Application No. PCT/US2005/010846 Dated Aug. 19, 2005.
International Search Report issued for PCT Application No. PCT/US2007/001225 Dated Jul. 20, 2007.
International Search Report issued for PCT Application No. PCT/US2007/026190 Dated May 20, 2008.
International Search Report issued for PCT Application No. PCT/US2008/009786 Dated Jan. 19, 2009.
International Search Report issued for PCT Application No. PCT/US2009/001534 Dated Apr. 2, 2010.
International Search Report issued for PCT Application No. PCT/US2010/038988 dated Aug. 20, 2010.
International Search Report issued for PCT Application No. PCT/US2012/045431 dated Feb. 5, 2013.
International Search Report issued for PCT Application No. PCT/US2012/049097 Dated Sep. 25, 2012.
International Search Report issued for PCT Application No. PCT/US2012/063712 dated Jan. 8, 2013.
IPRP issued for PCT/US2005/010846 Dated Oct. 4, 2006.
IPRP issued for PCT/US2007/001225 Dated Jul. 22, 2008.
IPRP issued for PCT/US2010/038988 dated Dec. 20, 2011.
Ishibashi, Toshiyuki et al., "Inhibition of Rho/Rho-kinase signaling downregulates plasminogen activator inhibitor-1 synthesis in cultured human monocytes", Biochimica Et Biophysica Acta, Elsevier, vol. 1590, 2002, pp. 123-130.
Ishizaki, Toshimasa et al., "p160ROCK, a Rho-associated coiled-coil forming protein kinase, works downstream of Rho and induces focal adhesions", FEBS Letters, vol. 404, No. 2, 1997, pp. 118-124.
Ishizaki, Toshimasa et al., "The small GTP-binding protein Rho binds to and activates a 160 kDa Ser/Thr protein kinase homologous to myotonic dystrophy kinase", The EMBO Journal, vol. 15, No. 8, 1996, pp. 1885-1893.
Itoh, Kazuyuki et al., "An essential part for Rho-associated kinase in the transcellular invasion of tumor cells", Nature Medicine, vol. 5, No. 2, Feb. 1999, pp. 221-225.
Kandabashi, Tadashi, MD et al., "Inhibition of Myosin Phosphatase by Upregulated Rho-Kinase Plays a Key Role for Coronary Artery Spasm in a Porcine Model with Interleukin-1beta", Circulation, vol. 101, No. 11, Mar. 21, 2000, pp. 1319-1323.

Karpov, Alexei S. et al., "Concise Synthesis of Meridianins by Carbonylative Alkynylation and a Four-Component Pyrimidine Synthesis", Angewandte Chemie., International Edition, Wiley VCH Verlag, Weinheim, DE, vol. 44, 2005, pp. 6951-6956.
Katsumata, Naoki et al., "Enhanced Myosin Light Chain Phosphorylations as a Central Mechanism for Coronary Artery Spasm in a Swine Model With Interleukin-1beta", Circulation, vol. 96, No. 12, 1997, pp. 4357-4363.
Kelly, Terence A. et al., "Novel Non-Nucleoside Inhibitors of Human Immunodeficiency Virus Type 1 Reverse Transcriptase. 6. 2-Indol-3-yl and 2-Azaindol-3-yl-dipyridodiazepinones1", Journal of Medicinal Chemistry, vol. 40, No. 15, 1997, pp. 2430-2433.
Kimura, Kazushi et al., "Regulation of Myosin Phosphatase by Rho and Rho-Associated Kinase (Rho-Kinase)", Science, vol. 273, Jul. 12, 1996, pp. 245-248.
Kirken, R. A., "Targeting Jak3 for Immune Suppression and Allograft Acceptance", Transplantation Proceedings, Elsevier, vol. 33, No. 7-8, 2001, pp. 3268-3270.
Klages, Birgit et al., "Activation of G12/G13 Results in Shape Change and Rho/Rho-Kinase-mediated Myosin Light Chain Phosphorylation in Mouse Platelets", Journal of Cell Biology, vol. 144, No. 4, Feb. 9, 1999, pp. 745-754.
Knighton, Daniel R. et al., "Crystal Structure of the Catalytic Subunit of Cyclic Adenosine Monophosphate-Dependent Protein Kinase", Science, vol. 253, Jul. 26, 1991, pp. 407-414.
Kunz, Jeannette et al., "Target of Rapamycin in Yeast, TOR2, Is an Essential Phosphatidylinositol Kinase Homolog Required for G1 Progression", Cell, vol. 73, No. 3, May 7, 1993, pp. 585-596.
Kupittayanant, S. et al., "The effects of inhibiting Rho-associated kinase with Y-27632 on force and intracellular calcium in human myometrium", Pflugers Arch—Eur J Physiol, vol. 443, 2001, pp. 112-114.
Kuwahara, Koichiro et al., "The effects of the selective ROCK inhibitor, Y27632, on ET-1-induced hypertrophic response in nenatal rat cardiac myocytes—possible involvement of Rho/ROCK pathway in cardiac muscle cell hypertrophy" Federation of European Biochemial Societies Letters, vol. 452, 1999, pp. 314-318.
Lane, Heidi A. et al., "Antibody Microinjection Reveals an Essential Role for Human Polo-like Kinase 1 (Plk1) in the Functional Maturation of Mitotic Centrosomes", Journal of Cell Biology, vol. 135, No. 6-2, Dec. 1996, pp. 1701-1713.
Laufs, Ulrich et al., "Post-transcriptional Regulation of Endothelial Nitric Oxide Synthase mRNA Stability by Rho GTPase", The Journal of Biological Chemistry, USA, vol. 273, No. 37, Sep. 11, 1998, pp. 24266-24271.
Leung, Thomas et al., "A Novel Serine/Threonine Kinase Binding the Ras-related RhoA GTPase Which Translocates the Kinase to Peripheral Membranes", Journal of Biological Chemistry, vol. 270, No. 49, Dec. 8, 1995, pp. 29051-29054.
Leung, Thomas et al., "The p160 RhoA-Binding Kinase ROKalpha is a Member of a Kinase Family and is Involved in the Reorganization of the Cytoskeleton", Molecular and Cellular Biology, vol. 16, No. 10, Oct. 1996, pp. 5313-5327.
Li, Jun et. al "SAK, a New Polo-Like Kinase, Is Transcriptionally Repressed by p53 and Induces Apoptosis upon RNAi Silencing", Neoplasia, vol. 7, No. 4, Apr. 2005, pp. 312-323.
Li, Zhongkui et al., "Function of Polo-like Kinase 3 in NF-κB-mediated Proapoptotic Response", Journal of Biological Chemistry, vol. 280, No. 17, Apr. 29, 2005, pp. 16843-16850.
Liu, Xiaoqi et al., "Polo-like kinase (Plk)1 depletion induces apoptosis in cancer cells", Proc. Nat'l. Acad. Sci., USA, vol. 100, No. 10, May 13, 2003, pp. 5789-5794.
Lowery, Drew M. et al., "Structure and function of Polo-like Kinases", Oncogene, Nature Publishing Group, vol. 24, 2005, pp. 248-25.
M.A. MalllKOBCKNN, "JleKapcTBeHHble cpeAcTBa", 2001, vol. 1, p. 14.
Ma, Sheng et al., "Role of Plk2 (Snk) in Mouse Development and Cell Proliferation", Molecular and Cellular Biology, vol. 23, No. 19, Oct. 2003, pp. 6936-6943.
Macmillan, Jennifer C. et al., "Comparative Expression of the Mitotic Regulators SAK and PLK in Colorectal Cancer", Annals of Surgical Oncology, vol. 8, No. 9, 2001, pp. 729-740.

(56) References Cited

OTHER PUBLICATIONS

Madaule, Pascal et al., "A novel partner for the GTP-bound forms of rho and rac", FEBS Letters, vol. 377, No. 2, 1995, pp. 243-248.

Madaule, Pascal et al., "Role of citron kinase as a target of the small GTPase Rho in cytokinesis", Nature, vol. 394, Jul. 30, 1998, pp. 491-494.

Malaviya, Ravi et al., "Genetic and Biochemical Evidence for a Critical Role of Janus Kinase (JAK)-3 in Mast Cell-Mediated Type I Hypersensitivity Reactions", Biochemical and Biophysical Research Communications, vol. 257, No. 3, 1999, pp. 807-813.

Malaviya, Ravi et al., "Targeting Janus Kinase 3 in Mast Cells Prevents Immediate Hypersensitivity Reactions and Anaphylaxis", Journal of Biological Chemistry, vol. 274, No. 38, Sep. 17, 1999, pp. 27028-27038.

Martinez, Ana et al. "Glycogen Synthase Kinase 3 Inhibitors in the Next Horizon for Alzheimer's Disease Treatment", International Journal of Alzheimer's Disease, vol. 2011, 2011 pp. 1-7.

Masumoto, Akihiro et al., "Possible Involvement of Rho-kinase in the Pathogenesis of Hypertension in Humans", Hypertension, vol. 38, No. 6, Dec. 2001, pp. 1307-1310.

Masumoto, Akihiro et al., "Suppression of Coronary Artery Spasm by the Rho-Kinase Inhibitor Fasudil in Patients With Vasospastic Angina", Circulation, vol. 105, 2002, pp. 1545-1547.

Matsui, Takeshi et al., "Rho-associated kinase, a novel serine/threonine kinase, as a putative target for small GTP binding protein Rho", The EMBO Journal, vol. 15, No. 9, 1996, pp. 2208-2216.

Mills, Thomas M. et al., "Effect of Rho-kinase inhibition on vasoconstriction in the penil circulation", J. Appl. Physiol., vol. 91, 2001, pp. 1269-1273.

Miyagi, Yasushi, M.D., Ph.D. et al., "Upregulation of rho A and rho kinase messenger RNAs in the basilar artery of a rat model of subarachnoid hemorrhage", J. Neurosurg., vol. 93, No. 3, Sep. 2000, pp. 471-476.

Mizunuma, Kazuyuki et al., "Prevention of Ischemia-Reperfusion-Induced Hepatic Microcirculatory Disruption by Inhibiting Stellate Cell Contraction Using ROCK Inhibitor1", Transplantation, USA, vol. 75, No. 5, Mar. 15, 2003, pp. 579-586.

Morishige, Kunio et al., "Asenovirus-Mediated Transfer of Dominant-Negative Rho-Kinase Induces a Regression of Coronary Arteriosclerosis in Pigs In Vivo", Arterioscler. Thromb. Vasc. Biol., vol. 21, Apr. 2001, pp. 548-555.

Mukai, Yasushi et al., "Involvement of Rho-kinase in hypertensive vascular disease: a novel therapeutic target in hypertension", The FASEB Journal, vol. 15, No. 6, Apr. 2001, pp. 1062-1064.

Müller-Ladner, Ulf et al., "Activation of the IL-4 STAT Pathway in Rheumatoid Synovium", Journal of Immunology, vol. 164, No. 4, 2000, pp. 3894-3901.

Nakagawa, 0samu et al., "ROCK-I and ROCK-II, two isoforms of Rho-associated coiled-coil forming protein serine/threonine kinase in mice", FEBS Letters, vol. 392, No. 2, 1996, pp. 189-193.

Narayanan, A. et al., "Developments in antivirals against influenza, smallpox and hemorrhagic fever viruses", Expert Opinion on Investigational Drugs, Ashley Publications Ltd., London, GB, vol. 20, No. 2, Feb. 1, 2011, pp. 239-254.

Nielsen, Mette et al., "Constitutive activation of a slowly migrating isoform of Stat3 in mycosis fungoides: Tyrphostin AG490 inhibits Stat3 activation and growth of mycosis fungoides tumor cell lines", Proc. Nat. Acad. Sci., USA, vol. 94, No. 13, Jun. 1997, pp. 6764-6769.

Niggli, Verena, "Rho-kinase in human neutrophils: a role in signalling for myosin light chain phosphorylation and cell migration", FEBS Letters, vol. 445, No. 1, 1999, pp. 69-72.

Niiro, Naohisa et al., "Up-Regulation of rho A and rho-Kinase mRHAs in the Rat Myometrium during Pregnancy", Biochemiacl and Biophysical Research Communications, vol. 230, 1997, pp. 356-359.

Nilius, Bernd et al., "Role of Rho and Rho kinase in the activation of volume-regulated anion channels in bovine endothelial cells", Journal of Physiology, vol. 516, No. 1, 1999, pp. 67-74.

Nobes, Catherine D. et al., "Rho GTPases Control Polarity, Protrusion, and Adhesion during Cell Movement", Journal of Cell Biology, vol. 144, No. 6, Mar. 2, 1999, pp. 1235-1244.

Pungpo, Pornpan et al., "Three-dimensional quantitative structure-activity relationship study on HIV-1 reverse transcriptase inhibitors in the class of dipyridodiazepinone derivatives, using comparative molecular field analysis" Journal of Molecular Graphics and Modeling, Elsevier Science Inc., vol. 18, 2000, pp. 581-590.

Rao, P. Vasantha et al., "Modulation of Aqueous Humor Outflow Facility by the Rho Kinase-Specific Inhibitor Y-27632", Investigative Ophthalmology & Visual Science, vol. 42, No. 5, Apr. 2001, pp. 1029-1037.

Rees, Rowland W. et al., "Y-27632, a Rho-Kinase Inhibitor, Inhibits Proliferation and Adrenergic Contraction of Prostatic Smooth Muscle Cells", The Journal of Urology, USA, vol. 170, Dec. 2003, pp. 2517-2522.

Retzer, Michaela et al., "Mildly oxidised low density lipoprotein induces platelet shape change via Rho-kinase-dependent phosphorylation of myosin light chain and moesin", Federation of European Biochemial Societies Letters, vol. 466, 2000, pp. 70-74.

Rizki, Aylin et al., "Polo-like Kinase 1 Is Involved in Invasion through Extracellular Matrix", American Association of Cancer Research, vol. 67, No. 23, Dec. 1, 2007, pp. 11106-11110.

Sah, Valerie P. et al., "Rho Is Required for Galphaq and alphal-Adrenergic Receptor Signaling in Cardiomyocytes", The Journal of Biological Chemistry, USA, vol. 27, No. 49, Dec. 6, 1996, pp. 31185-31190.

Sahai, Erik et al., "Transformation mediated by RhoA requires activity of ROCK kinases", Current Biology, vol. 9, No. 3, 1999, pp. 136-145.

Sanborn, M.D., William J. et al., "Tofacitinib, an Oral Janus Kinase Inhibitor, in Active Ulcerative Colitis", The New England Journal of Medicine, vol. 367, No. 7, Aug. 16, 2012, pp. 616-624.

Sato, Motohiko et al., "Involvement of Rho-Kinase-Mediated Phosphorylation of Myosin Light Chain in Enhancement of Cerebral Vasospasm", Circulation Research, vol. 87, No. 2, Aug. 4, 2000, pp. 195-200.

Satoh, Shin-Ichi et al., "Antiischemic Properties of Fasudil in Experimental Models of Vasospastic Angina", Jpn. J. Pharmacol., vol. 87, 2001, pp. 34-40.

Satoh, Shinji et al., "Augmented Agonist-induced Ca2+-Sensitization of Coronary Artery Contraction in Genetically Hypertensive Rats: Evidence for Altered Signal Transduction in the Coronary Smooth Muscle Cells", J. Clin. Invest., vol. 94, No. 4, Oct. 1994, pp. 1397-1403.

Sawada, Naoki et al., "Inhibition of Rho-Associated Kinase Results in Suppression of Neointimal Formation of Balloon-Injured Arteries", Circulation, vol. 101, May 2, 2000, pp. 2030-2023.

Schwaller, Juerg et al., "Transformation of hematopoietic cell lines to growth-factor independence and induction of a fatal myelo- and lymphoproliferative disease in mice by retrovirally transduced TEL/JAK2 fusion genes", The EMBO Journal, vol. 17, No. 18, 1998, pp. 5321-5333.

Seasholtz, Tammy M. et al., "Rho and Rho Kinase Mediate Thrombin-Stimulated Vascular Smooth Muscle Cell DNA Synthesis and Migration", Circulation Research, vol. 84, No. 4, 1999, pp. 1186-119.

Segain, Jean-Pierre et al., "Rho Kinase Blockade Prevents Inflammation Via Nuclear Factor kB Inhibition: Evidence in Crohn's Disease and Experimental Colitis", Gastroenterology, vol. 124, No. 5, May 2003, pp. 1180-1187.

Seidel, H. Martin et al., "Pharmaceutical intervention in the JAK/STAT signaling pathway", Oncogene, vol. 19, No. 21, 2000, pp. 2645-2656.

Shibata, Rei et al., Role of Rho-Associated Kinase in Neointima Formation After Vascular Injury, Circulation, vol. 130, Jan. 16, 2001, pp. 284-289.

Shimokawa, Hiroaki et al., "Anti-anginal Effect of Fasudil, a Rho-Kinase Inhibitor, in Patients With Stable Effort Angina: A Multicenter Study", Journal of Cardiovascular Pharmacology, vol. 40, No. 5, 2002, pp. 751-761.

(56) References Cited

OTHER PUBLICATIONS

Shimokawa, Hiroaki et al., "Cellular and Molecular Mechanisms of Coronary Artery Spasm: Lessons From Animal Models", Jpn. Cir. J., vol. 64, No. 1, 2000, pp. 1-12.
Shimokawa, Hiroaki et al., "Long-term inhibition of Rho-kinase induces a regression of arteriosclerotic coronary lesions in a percine model in vivo", Cardiovascular Research, Elsevier, vol. 51, 2001, pp. 169-177.
Shimokawa, Hiroaki et al., "Rho-kinase as a Novel Therapeutic Target in Treatment Cardiovascilar Diseases", Journal of Cardiovascular Pharmacology, vol. 39, No. 3, 2002, pp. 319-327.
Smith, Mark R. et al., "Malignant Transformation of Mammalian Cells Initiated by Constitutive Expression of the Polo-like Kinase1", Biochemical and Biophysical Research Communications, vol. 234, No. 2, 1997, pp. 397-405.
Somlyo, Avril V. et al., Rho-Kinase Inhibitor Retards Migration and in Vivo Dissemination of Human Prostate Cancer Cells, Biochemical and Biophysical Research Communications, vol. 269, No. 3, 2000, pp. 652-659.
Strebhardt, Klaus et al., "Targeting polo-like kinase 1 for cancer therapy", Nature Reviews, Cancer, Nature Publishing Group, London, GB, vol. 6, No. 4, Apr. 1, 2006, pp. 321-330.
Stump, Kristine L. et al., "A highly selective, orally active inhibitor of Janus kinase 2, CEP-33779, ablates disease in two mouse models of rheumatoid arthritis", Arthritis Research & Therapy, BioMed Central, London, GB, vol. 13, No. 2, Apr. 21, 2011, p. 1, abstract.
Sudbeck, Elise A. et al., "Structure-based Design of Specific Inhibitors of Janus Kinase 3 as Apoptosis-inducing Antileukemic Agents", Clinical Cancer Research, vol. 5, No. 6, Jun. 1999, pp. 1569-1582.
Suzuki, Kotaro et al., "Role of common cytokine receptor gamma chain (gamma(c))- and Jak3-dependent signaling in the proliferation and survival of murine mast cells", Blood, 2000, 96(6), pp. 2172-2180.
Tachibana, E. et al., "Intra-arterial infusion of fasudil hydrochloride for treating vasospasm following subarachnoid haemorrhage", Acta Neurochir (Wien), 1999, 141(1), pp. 13-19.
Tahara, Masahiro et al., "RhoA/Rho-Kinase Cascade Is Involved in Oxytocin-Induced Rat Uterine Contraction", Endocrinology, vol. 143, No. 3, Mar. 2002, pp. 920-929.
Trieu, Vuong N. et al., "A Specific Inhibitor of Janus Kinase-3 Increases Survival in a Transgenic Mouse Model of Amyotrophic Lateral Sclerosis", Biochemical and Biophysical Research Communications, vol. 267, No. 1, 2000, pp. 22-25.
Uehata, Masayoshi et al., "Calcium sensitization of smooth muscle mediated by a Rho-associated protein kinase in hypertension", Nature, vol. 389, Oct. 30, 1997, pp. 990-994.
Utsunomiya, T. et al., "Antianginal effects of hydroxyfasudil, a Rho-kinase inhibitor, in a canine model of effort angina", British Journal of Pharmacology, vol. 134, No. 8, 2001, pp. 1724-1730.
Venkatesh, Srini et al., "Role of the Development Scientist in Compound Lead Selection and Optimization", Journal of Pharmaceutical Sciences, vol. 89, No. 2, Feb. 2000, pp. 145-154.
Wada, Makoto et al "siRNA targeting PLK-1 induces apoptosis of synoviocytes in rheumatoid arthritis", Biochemical and Biophysical Research Communications, vol. 357, No. 2, 2007, pp. 353-359.
Watanabe, Go et al., "Protein Kinase N (PKN) and PKN-Related Protein Rhophilin as Targets of Small GTPase Rho", Science, vol. 271, Feb. 2, 1996, pp. 645-648.
Weichert, Wilko et al., "Polo-like kinase isoform expression is a prognostic factor in ovarian carcinoma", British Journal of Cancer, vol. 90, No. 4, 2004, pp. 815-821.
Weichert, Wilko et al., "Polo-like kinase isoforms in breast cancer: expression patterns and prognostic implications", Virchows Archiv, vol. 446, No. 4, 2005, pp. 442-450.
Written Opinion of the International Searching Authority issued for PCT Application No. PCT/US2005/010846 Dated Aug. 19, 2005.
Written Opinion of the International Searching Authority issued for PCT Application No. PCT/US2007/001225 Dated Jul. 20, 2007.
Written Opinion of the International Searching Authority issued for PCT Application No. PCT/US2007/025688 Dated Apr. 6, 2008.
Written Opinion of the International Searching Authority issued for PCT Application No. PCT/US2007/026190 Dated May 20, 2008.
Written Opinion of the International Searching Authority issued for PCT Application No. PCT/US2008/009786 Dated Jan. 19, 2009.
Written Opinion of the International Searching Authority issued for PCT Application No. PCT/US2009/001534 Dated Apr. 2, 2010.
Written Opinion of the International Searching Authority issued for PCT Application No. PCT/US2009/003716 Dated Nov. 20, 2009.
Written Opinion of the International Searching Authority issued for PCT Application No. PCT/US2009/003723 Dated Nov. 20, 2009.
Yanazume, Tetsuhiko et al., "Rho/ROCK Pathway Contributes to the Activation of Extracellular Signal-regulated Kinase/GTA-4 during Myocardial Cell Hypertrophy", The Journal of Biological Chemistry, USA, vol. 277, No. 10, Mar. 8, 2002, pp. 8618-8625.
Yoshii, Akihiro et al. "Relaxation of Contracted Rabbit Tracheal and Human Bronchial Smooth Muscle by Y-27632 through Inhibition of Ca2+ Sensitization", American Journal of Respiratory Cell and Molecular Biology, vol. 20, No. 6, 1999, pp. 1190-1200.
Yu, Chao-Lan et al., "Constitutive Activation of the Janus Kinase-STAT Pathway in T Lymphoma Overexpressing the Lck protein tyrosine kinase1", Journal of Immunology, vol. 159, No. 11, 1997, pp. 5206-5210.
Zhou, Yan et al., "Nonsteroidal Anti-Inflammatory Drugs Can Lower Amyloidogenic Aβ42 by Inhibiting Rho", Science, vol. 302, No. 14, Nov. 2003, pp. 1215-1218.

* cited by examiner

INHIBITORS OF INFLUENZA VIRUSES REPLICATION

RELATED APPLICATIONS

This application is a continuation of PCT Application No. PCT/US2012/049097, filed Aug. 1, 2012, which claims priority to U.S. Provisional Application No. 61/513,793, filed Aug. 1, 2011. Each of these references is incorporated herein by reference in its entirety.

BACKGROUND OF THE INVENTION

Influenza spreads around the world in seasonal epidemics, resulting in the deaths of hundreds of thousands annually—millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogoto virus.

The Influenza virus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which has unusual zoonotic potential), H1N2 (endemic in humans and pigs), H9N2, H7N2, H7N3 and H10N7.

The Influenza virus B genus has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza A, B and C viruses are very similar in structure. The virus particle is 80-120 nanometers in diameter and usually roughly spherical, although filamentous forms can occur. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

HA and NA are large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins have been targets for antiviral drugs. Furthermore, they are antigens to which antibodies can be raised. Influenza A viruses are classified into subtypes based on antibody responses to HA and NA, forming the basis of the H and N distinctions (vide supra) in, for example, H5N1.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with neuraminidase inhibitors being particularly effective, but viruses can develop resistance to the standard antiviral drugs.

Thus, there is still a need for drugs for treating influenza infections, such as for drugs with expanded treatment window, and/or reduced sensitivity to viral titer.

SUMMARY OF THE INVENTION

The present invention generally relates to methods of treating influenza, to methods of inhibiting the replication of influenza viruses, to methods of reducing the amount of influenza viruses, and to compounds and compositions that can be employed for such methods.

In one embodiment, the present invention is directed to a compound represented by Structural Formula (I):

or a pharmaceutically acceptable salt thereof, wherein:

$X^1$ is —F, —Cl, —$CF_3$, —CN, or $CH_3$;

$X^2$ is —H, —F, or —Cl;

$Z^1$ is N or CH;

$Z^2$ is N or $CR^0$;

$Z^3$ is CH or N;

Y is —$C(R^4R^5)$—$[C(R^6R^7)]_n$-Q or —$C(R^4)$═$C(R^6)$-Q;

$R^0$ is —H, —F, or CN;

$R^1$, $R^2$, and $R^3$ are each and independently —$CH_3$, —$CH_2F$, —$CF_3$, —$C_2H_5$, —$CH_2CH_2F$, —$CH_2CF_3$; or optionally $R^2$ and $R^3$, or $R^1$, $R^2$ and $R^3$, together with the carbon atom to which they are attached, form a 3-10 membered carbocyclic ring;

$R^4$ and $R^5$ are each and independently —H;

$R^6$ and $R^7$ are each and independently —H, —OH, —$CH_3$, or —$CF_3$; or optionally, $R^5$ and $R^7$ together with the carbon atoms to which they are attached form a cyclopropane ring; and each Q is independently —C(O)OR, —OH, —$CH_2OH$, —S(O)R', —$P(O)(OH)_2$, —$S(O)_2R'$, —$S(O)_2$—NR"R"', or a 5-membered heterocycle selected from the group consisting of:

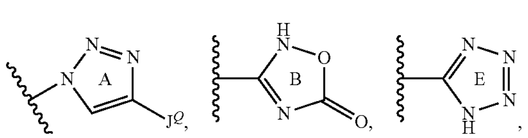

and

-continued 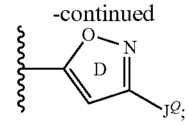 $J^Q$ is —H, —OH or —$CH_2OH$;

R is —H or $C_{1-4}$ alkyl;

R' is —OH, $C_{1-4}$ alkyl, or —$CH_2C(O)OH$;

R" is —H or —$CH_3$;

R"' is —H, a 3-6 membered carbocyclic ring, or $C_{1-4}$ alkyl optionally substituted with one or more substituents selected from the group consisting of halogen, —$OR^a$ and —C(O)$OR^a$;

$R^a$ is —H or $C_{1-4}$ alkyl; and n is 0 or 1.

In another embodiment, the present invention is directed to a pharmaceutical composition comprising a compound disclosed herein (e.g., a compound represented by any one of Structural Formulae (I)-(X), or a pharmaceutically acceptable salt thereof) and a pharmaceutically acceptable carrier, adjuvant or vehicle.

In yet another embodiment, the present invention is directed to a method of inhibiting the replication of influenza viruses in a biological sample or patient, comprising the step of administering to said biological sample or patient an effective amount of a compound disclosed herein (e.g., a compound represented by any one of Structural Formulae (I)-(X), or a pharmaceutically acceptable salt thereof).

In yet another embodiment, the present invention is directed to a method of reducing the amount of influenza viruses in a biological sample or in a patient, comprising administering to said biological sample or patient an effective amount of a compound disclosed herein (e.g., a compound represented by any one of Structural Formulae (I)-(X), or a pharmaceutically acceptable salt thereof).

In yet another embodiment, the present invention is directed to a method of method of treating influenza in a patient, comprising administering to said patient an effective amount of a compound disclosed herein (e.g., a compound represented by any one of Structural Formulae (I)-(X), or a pharmaceutically acceptable salt thereof).

The present invention also provides use of the compounds described herein for inhibiting the replication of influenza viruses in a biological sample or patient, for reducing the amount of influenza viruses in a biological sample or patient, or for treating influenza in a patient.

Also provided herein is use of the compounds described herein for the manufacture of a medicament for treating influenza in a patient, for reducing the amount of influenza viruses in a biological sample or in a patient, or for inhibiting the replication of influenza viruses in a biological sample or patient.

Also provided herein are the compounds represented by Structural Formula (XX):

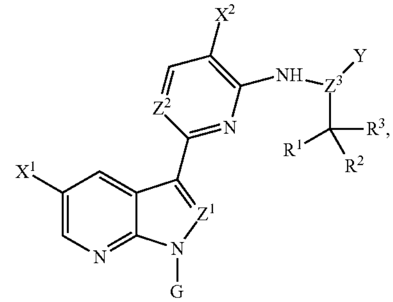

or a pharmaceutically acceptable salt thereof. Without being bound to a particular theory, the compounds of Structural Formula (XX) can be used for synthesizing the compounds of Formula (I). The variables of Structural Formula (XX) are each and independently as defined herein; and when $Z^1$ is N, G is trityl (i.e., C(Ph)$_3$ where Ph is phenyl), and when $Z^1$ is CH, G is tosyl (Ts: CH$_3$C$_6$H$_4$SO$_2$) or trityl.

The invention also provides methods of preparing a compound represented by Structural Formula (I) or a pharmaceutically acceptable salt thereof. In one embodiment, the methods employ the steps of:

i) reacting compound A:

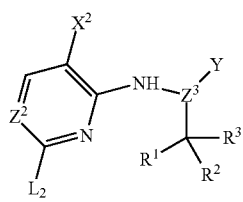
(A)

with compound B:

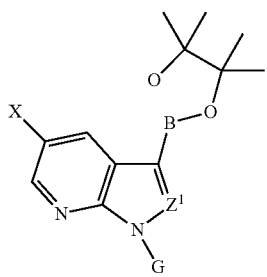
(B)

to form a compound represented by Structural Formula (XX):

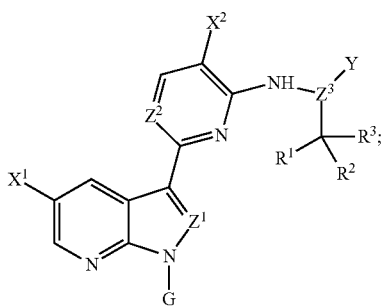
(XX)

and
ii) deprotecting the G group of the compound of Structural Formula (XX) under suitable conditions to form the compound of Structural Formula (I), wherein:
the variables of Structural Formulae (I) and (XX), and compounds (A) and (B) are independently as defined herein; and
$L^2$ is a halogen; and
when $Z^1$ is N, G is trityl; when $Z^1$ is CH, G is tosyl or trityl.
In yet another embodiment, the methods employ the steps of:

i) reacting compound K or L:

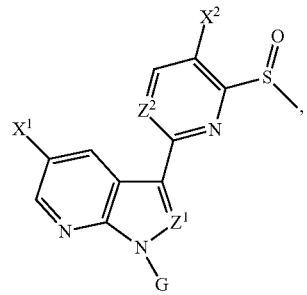
(K)

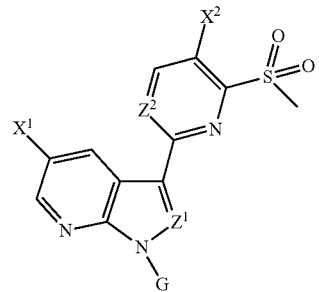
(L)

with compound D: NH$_2$—Z$^3$(C(R$^1$R$^2$R$^3$))—Y to form a compound represented by Structural Formula (XX):

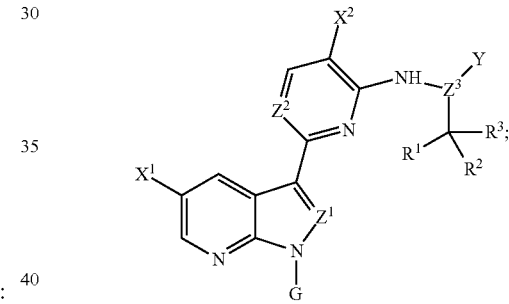
(XX)

and
ii) deprotecting the G group of the compound of Structural Formula (XX) under suitable conditions to form the compound of Structural Formula (I), wherein:
the variables of Structural Formulae (I) and (XX), and compounds (L), (K), and (D) are each and independently as defined herein; and
when $Z^1$ is N, G is trityl; when $Z^1$ is CH, G is tosyl or trityl.
In yet another embodiment, the methods employ the steps of:
i) reacting Compound (G) with Compound (D):

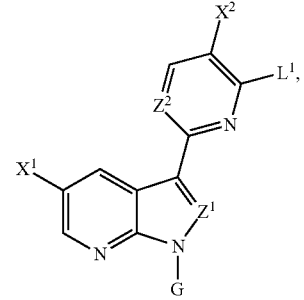
(G)

NH$_2$—Z$^3$(C(R$^1$R$^2$R$^3$))—Y (D), under suitable conditions to form a compound represented by Structural Formula (XX):

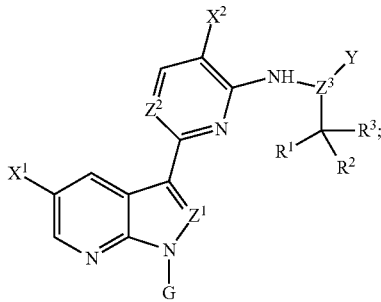

(XX)

and ii) deprotecting the G group of the compound of Structural Formula (XX) under suitable conditions to form the compound of Structural Formula (I), wherein:

the variables of Structural Formulae (I) and (XX), and Compounds (G) and (D) are each and independently as defined herein;

$L^1$ is a halogen; and when $Z^1$ is N, G is trityl; when $Z^1$ is CH, G is tosyl or trityl.

DETAILED DESCRIPTION OF THE INVENTION

Figure 1:
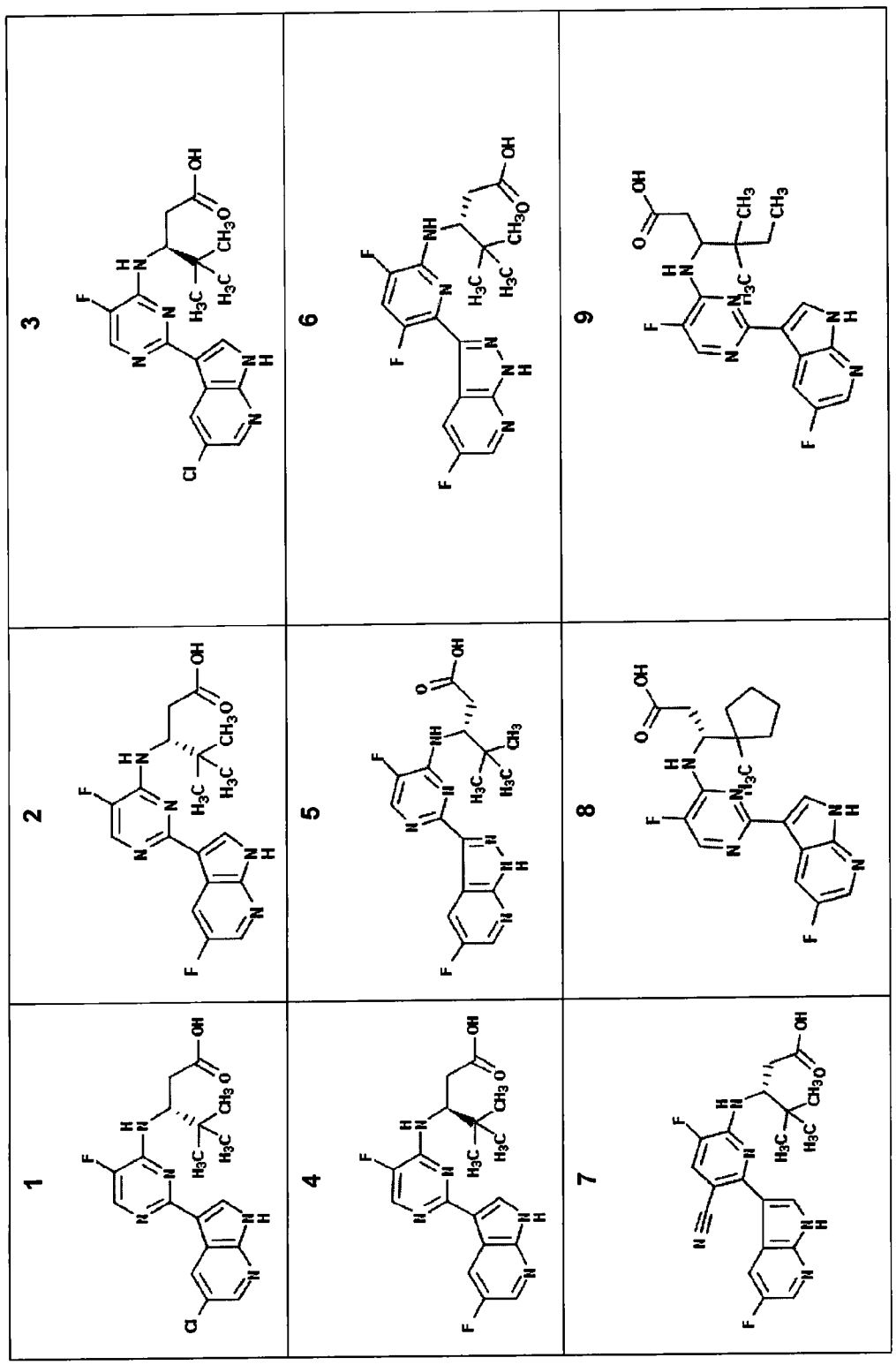
FIG. 1 shows certain compounds of the invention.
Figure 1:
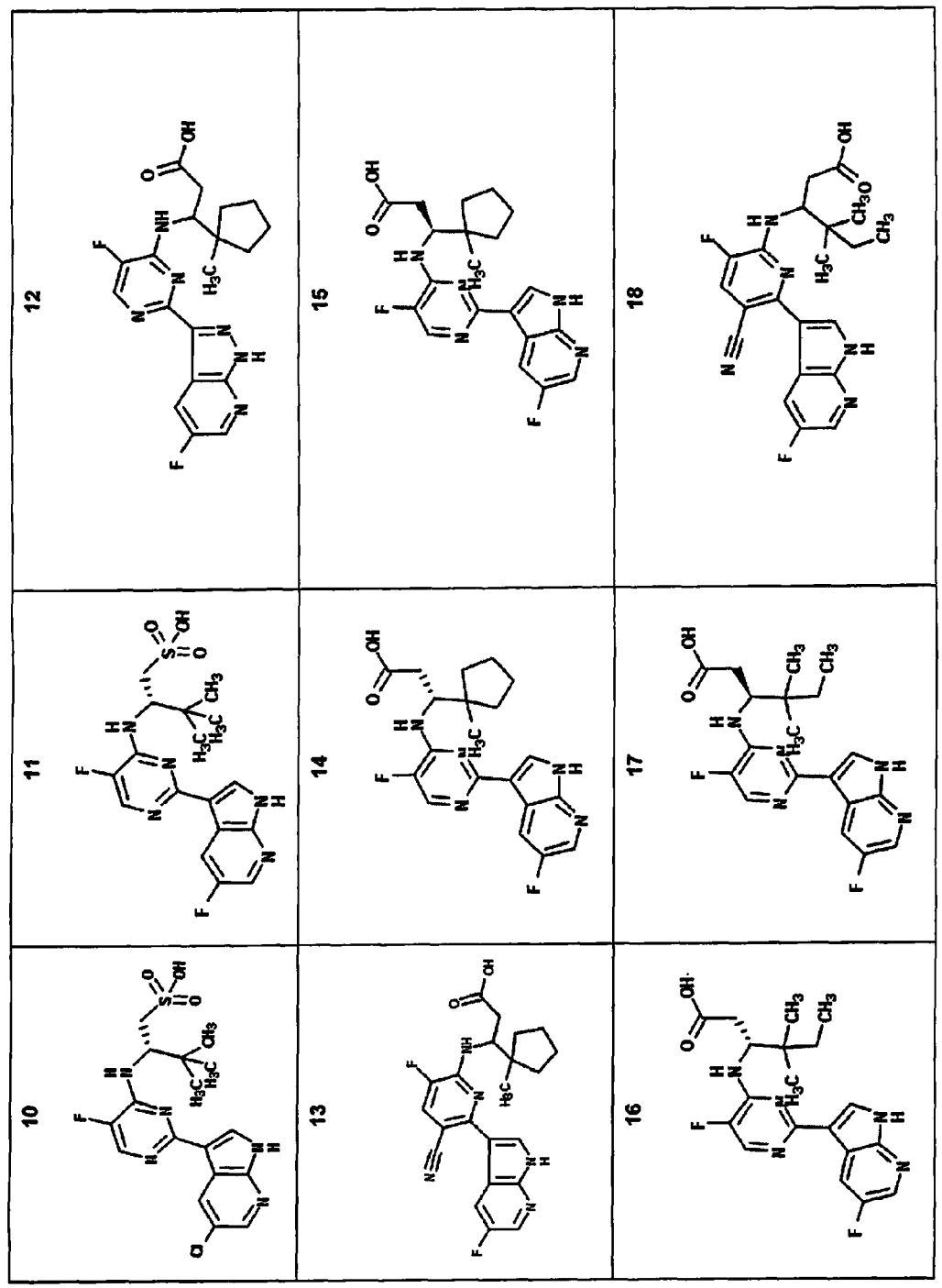
Figure 1:
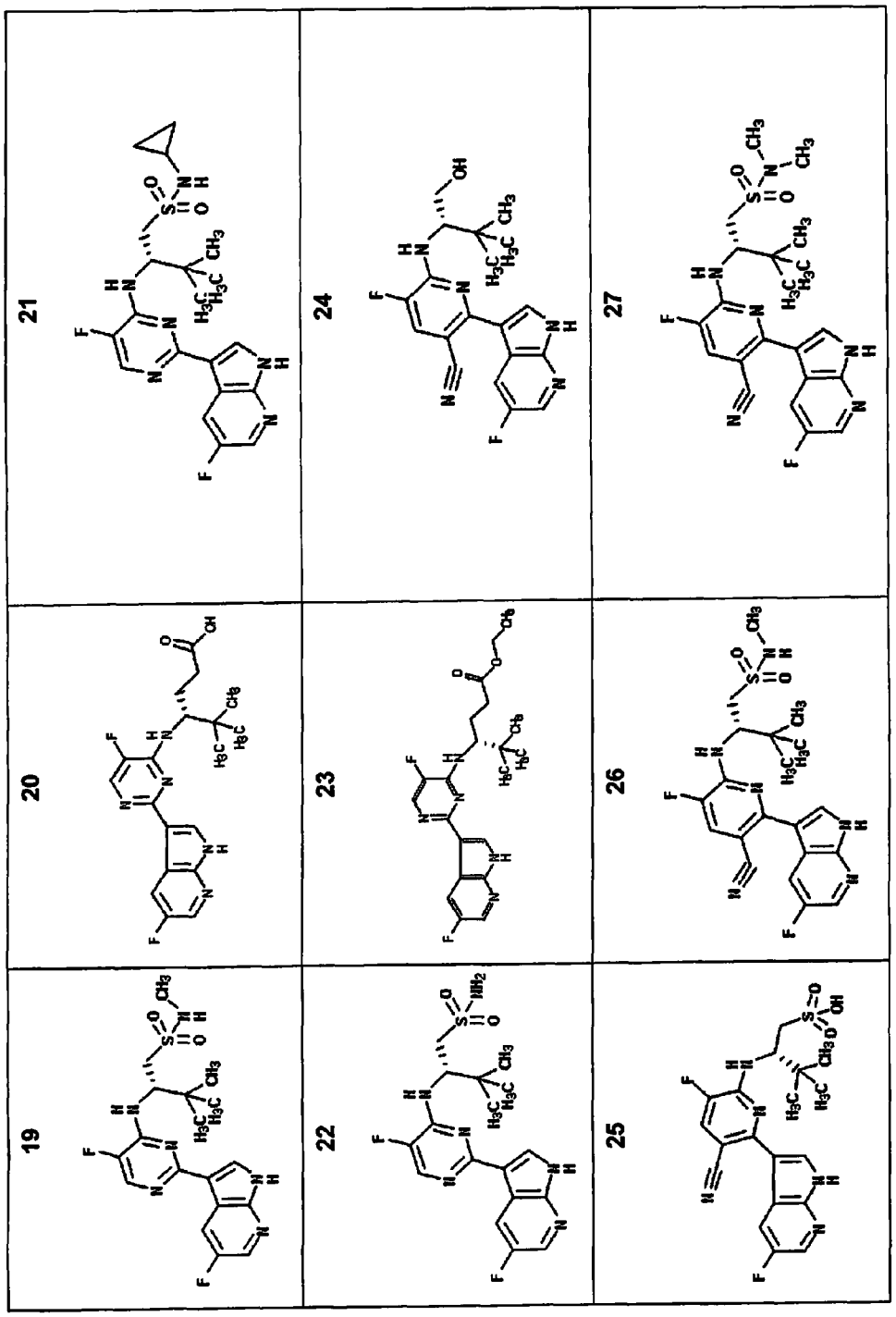
Figure 1:
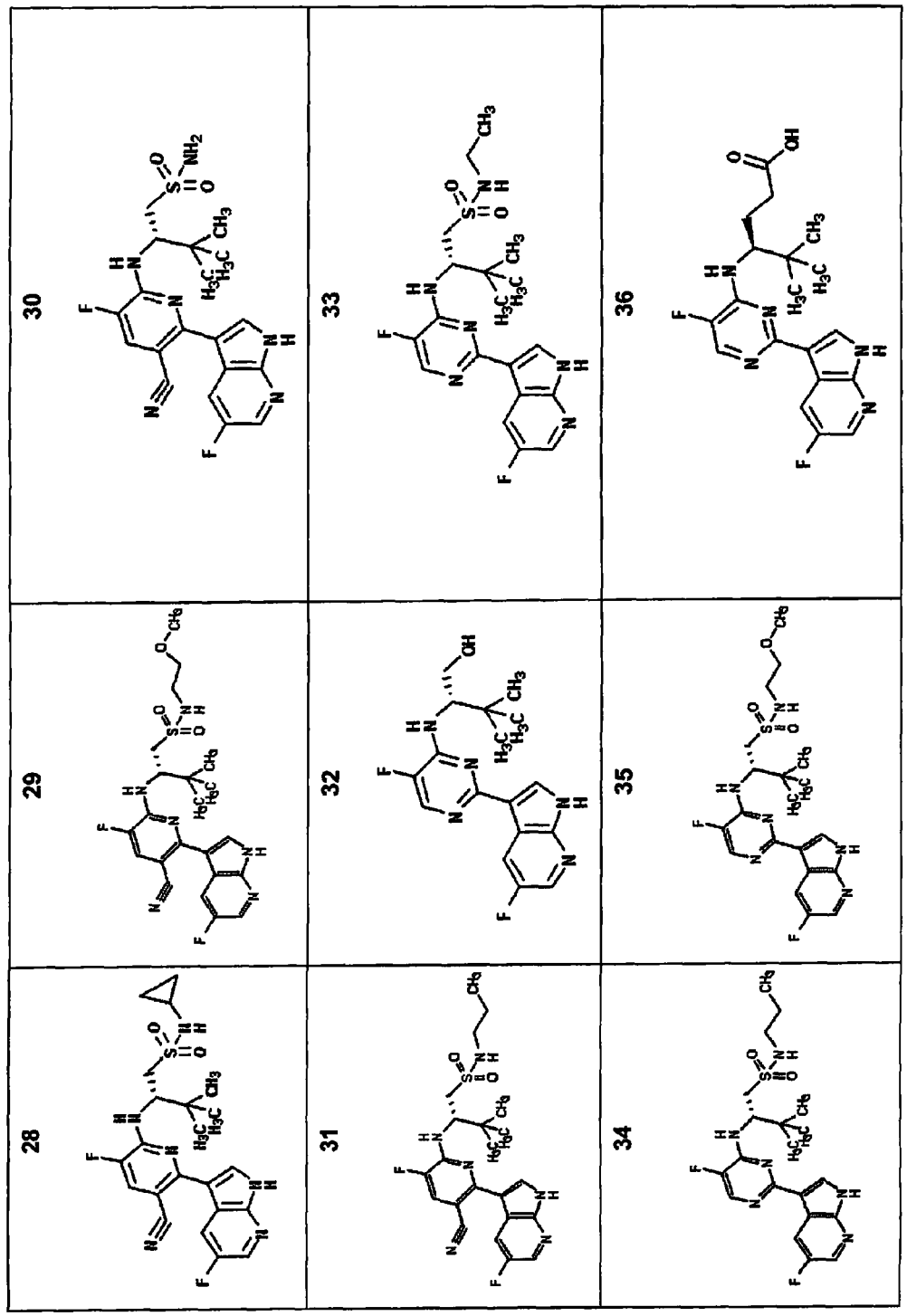
Figure 1:
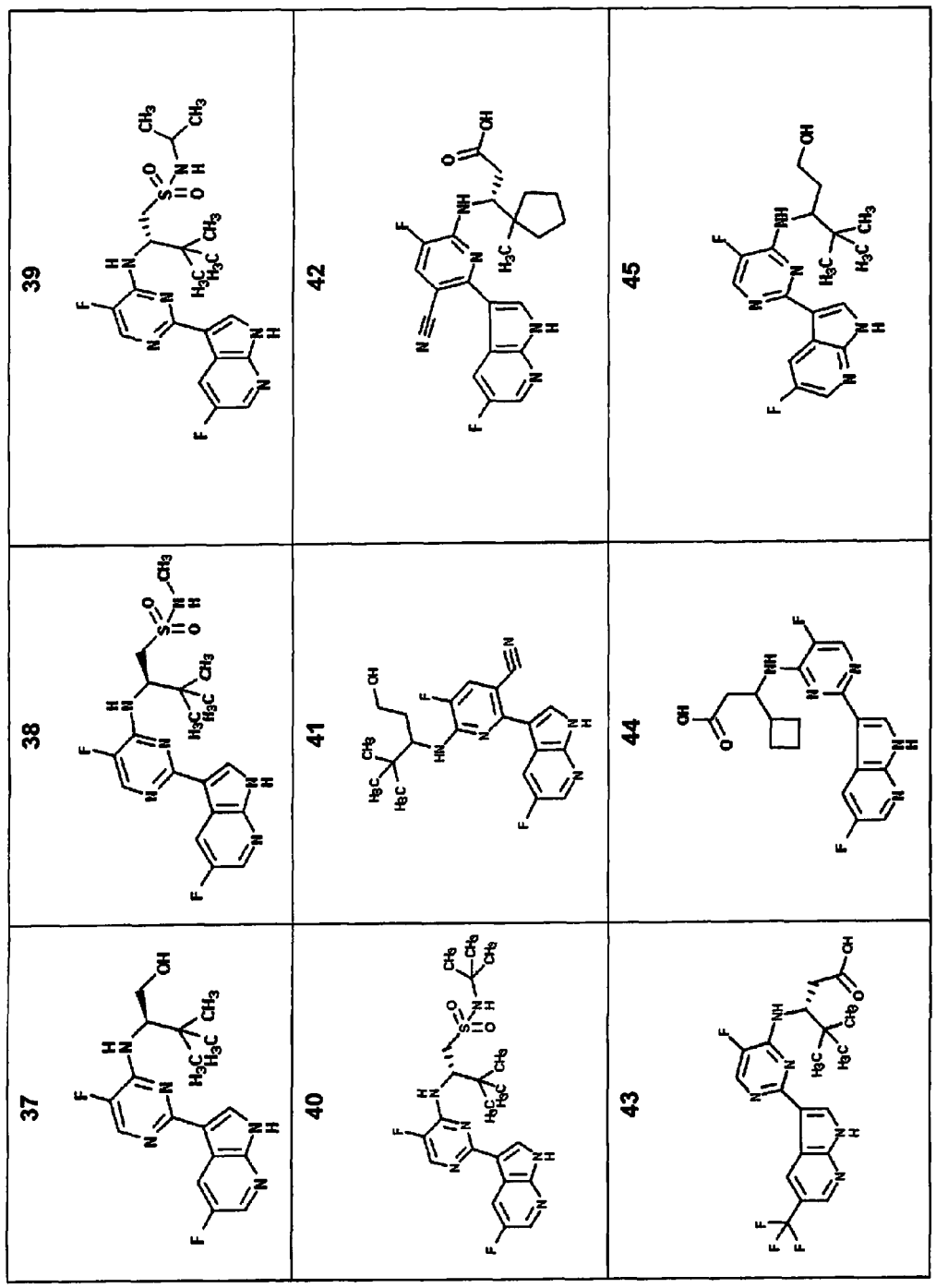
Figure 1:
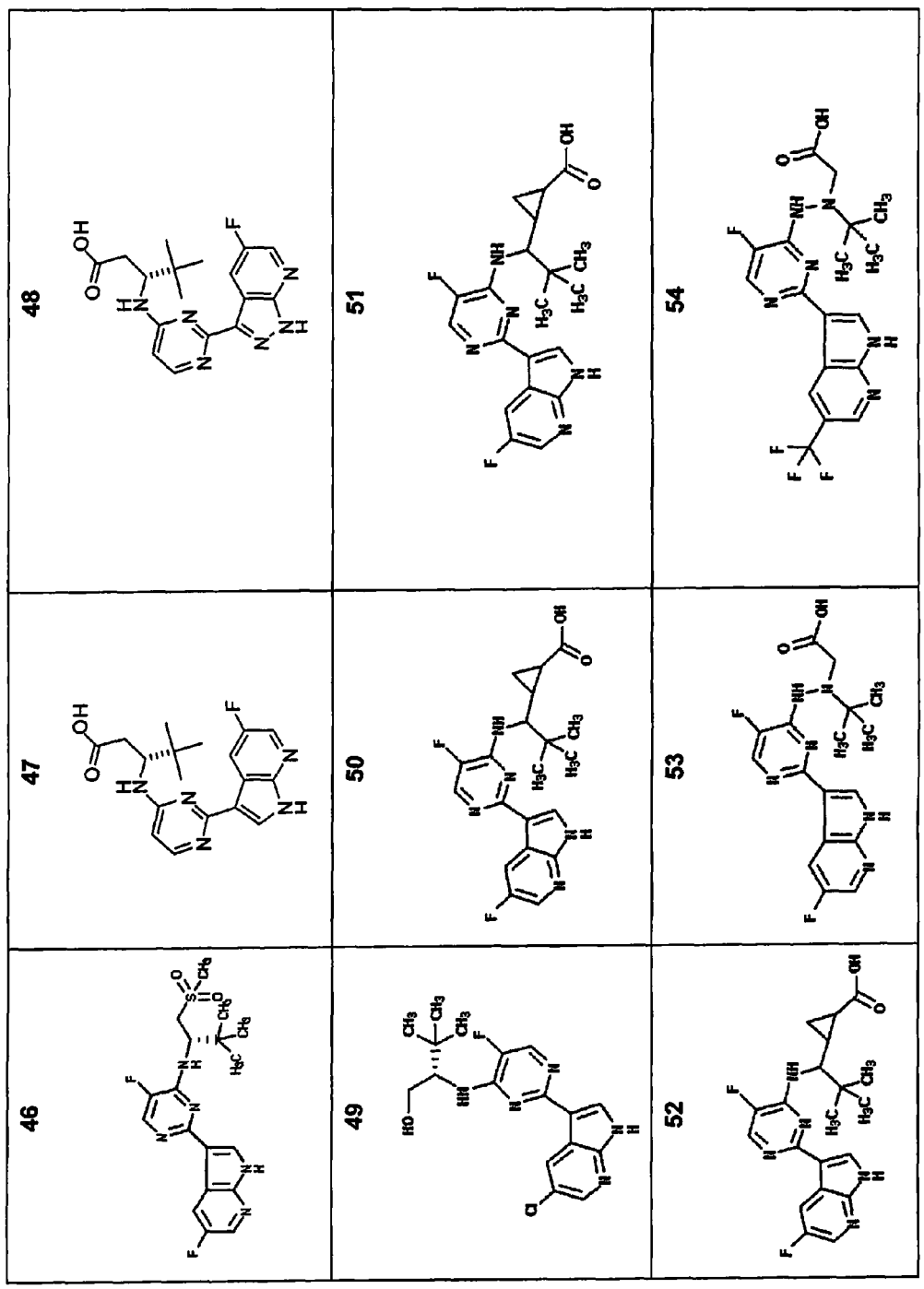
Figure 1:
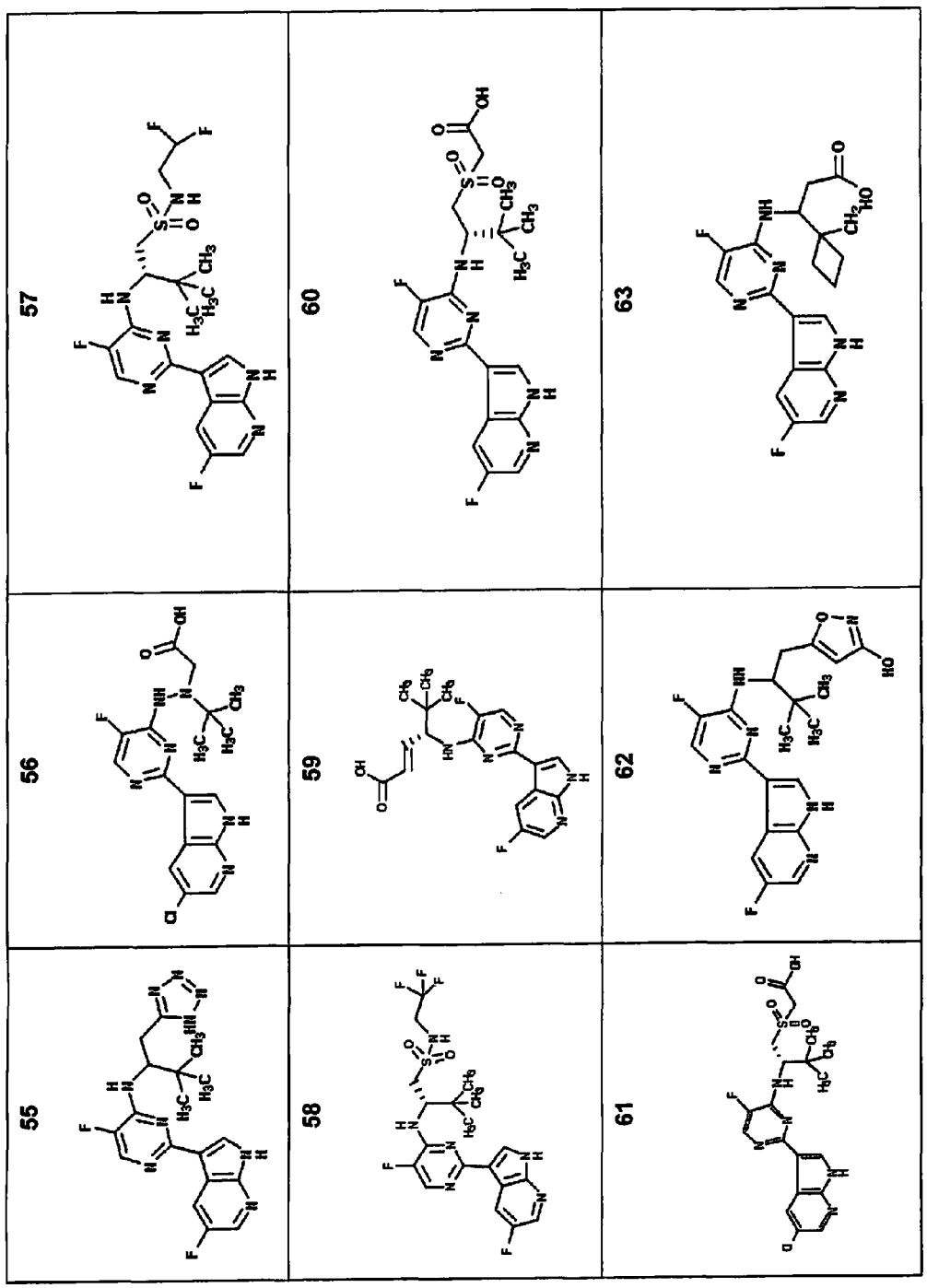
Figure 1:
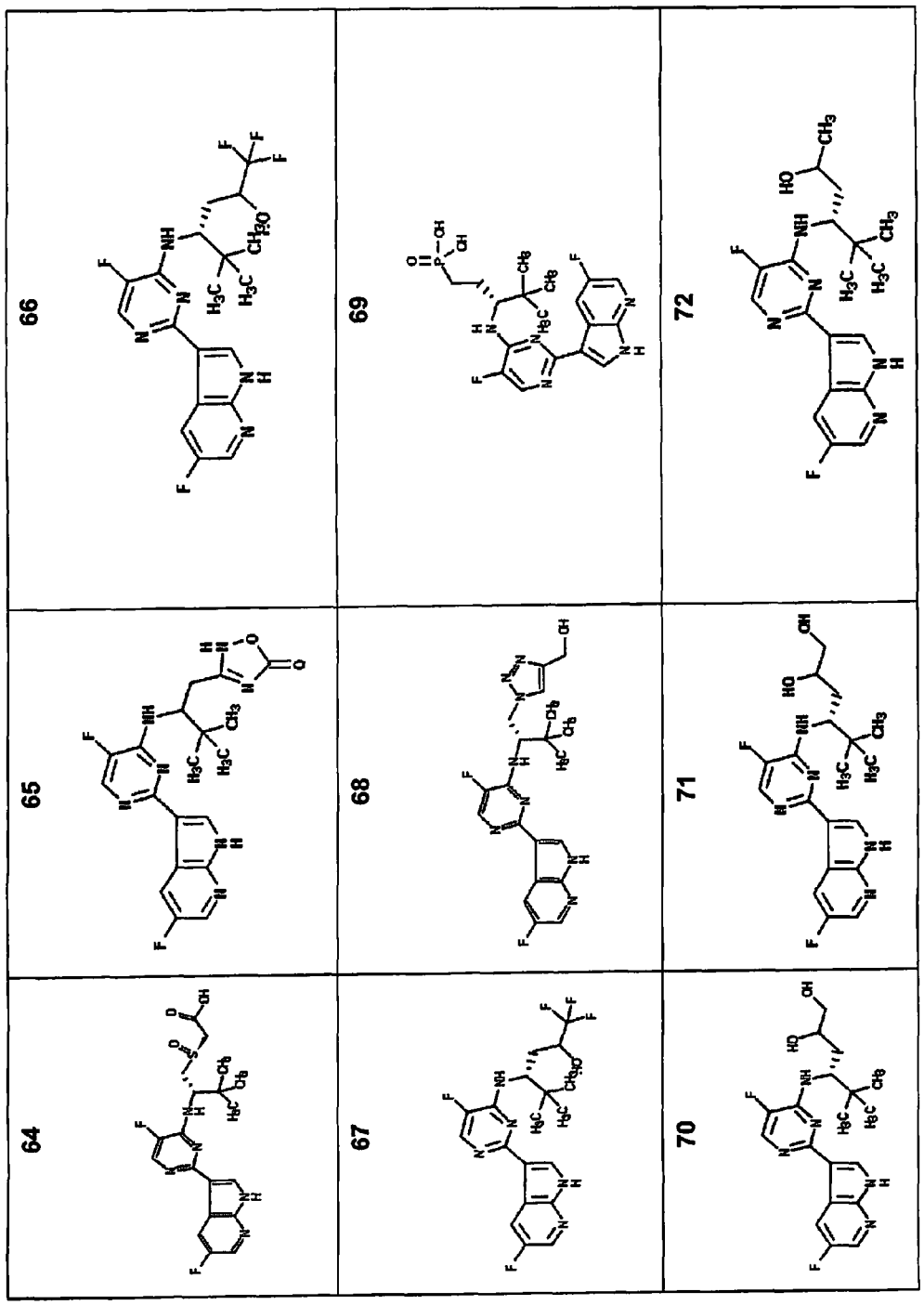
Figure 1:
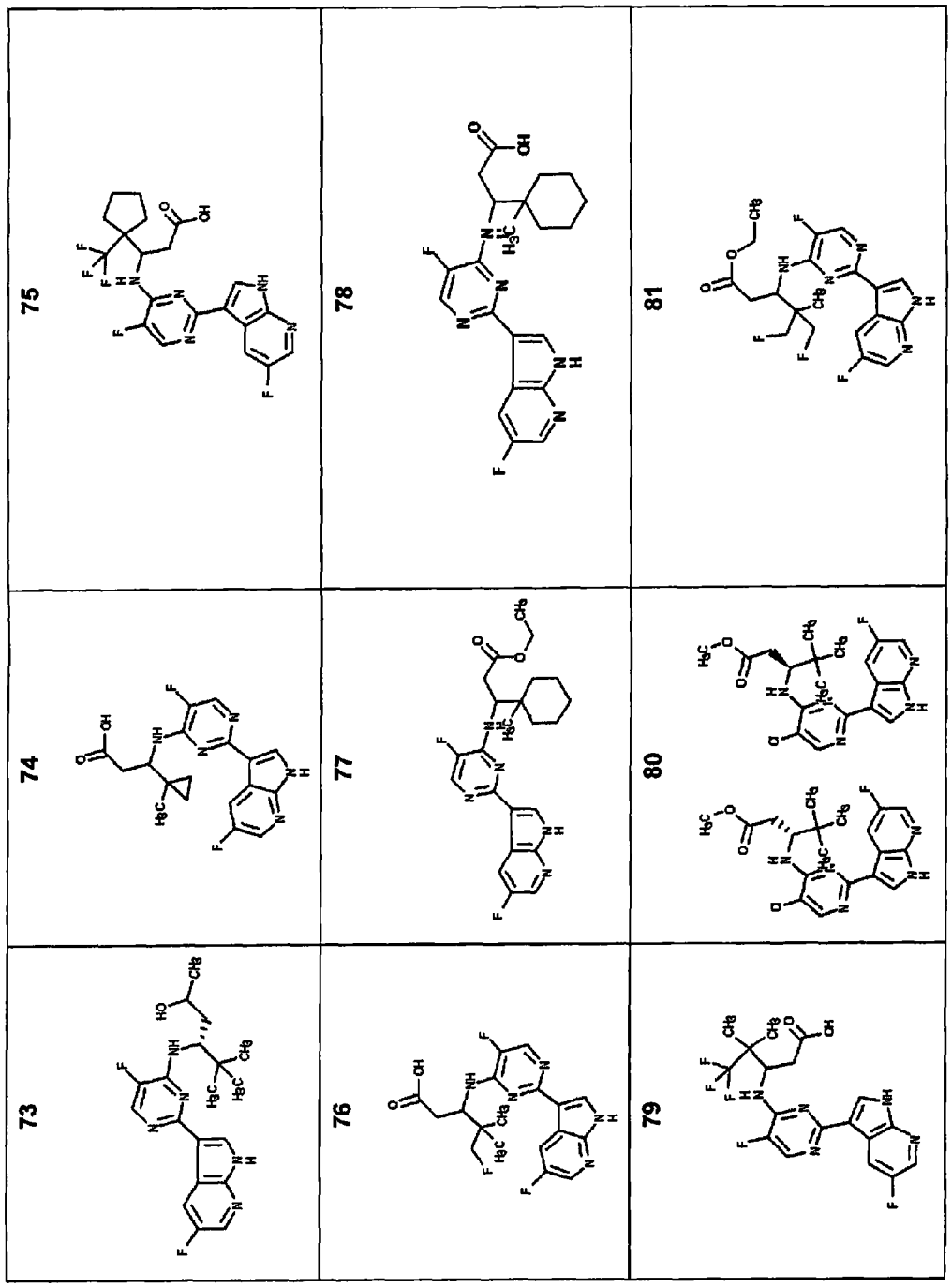
Figure 1:
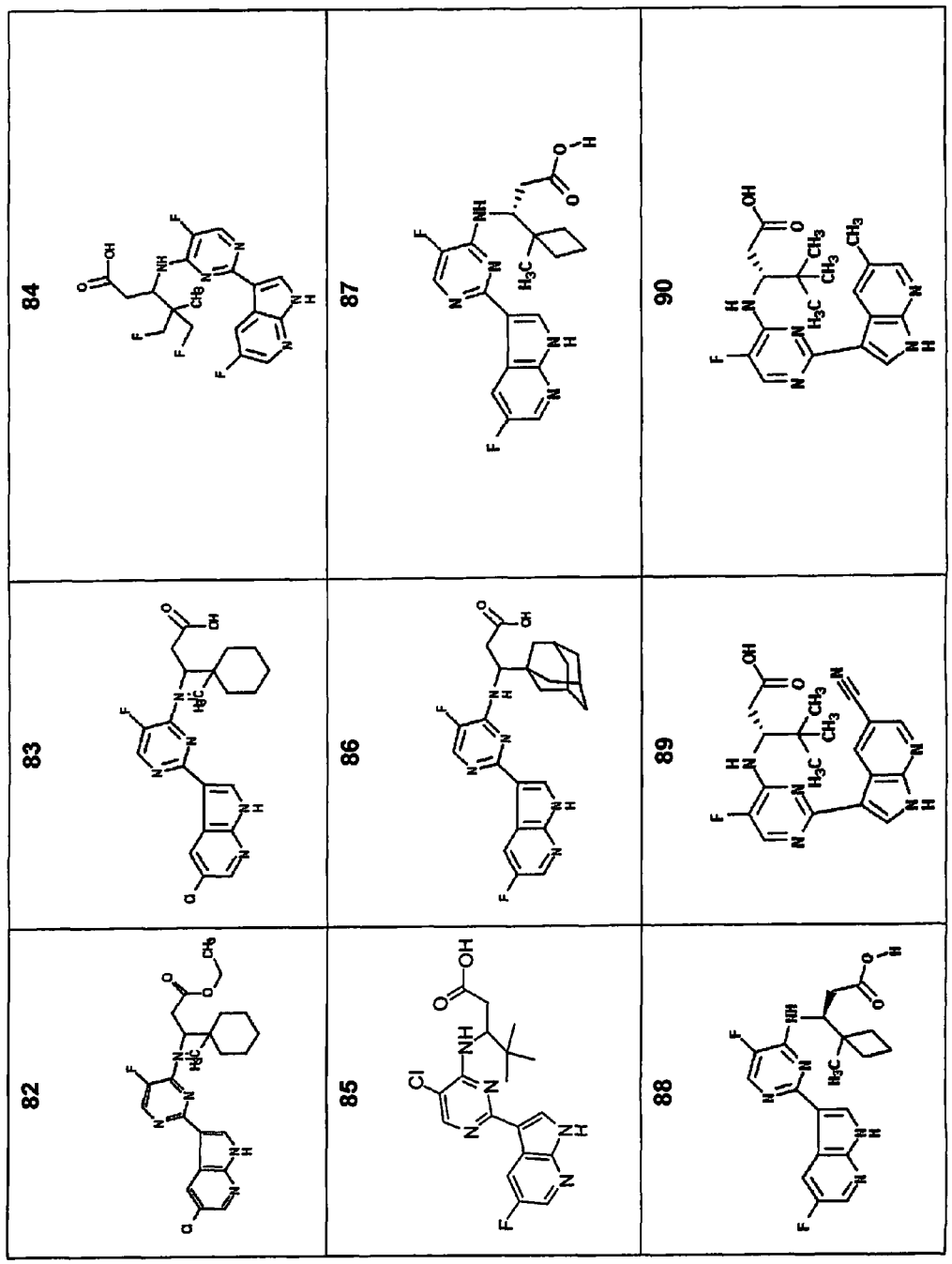
Figure 1:
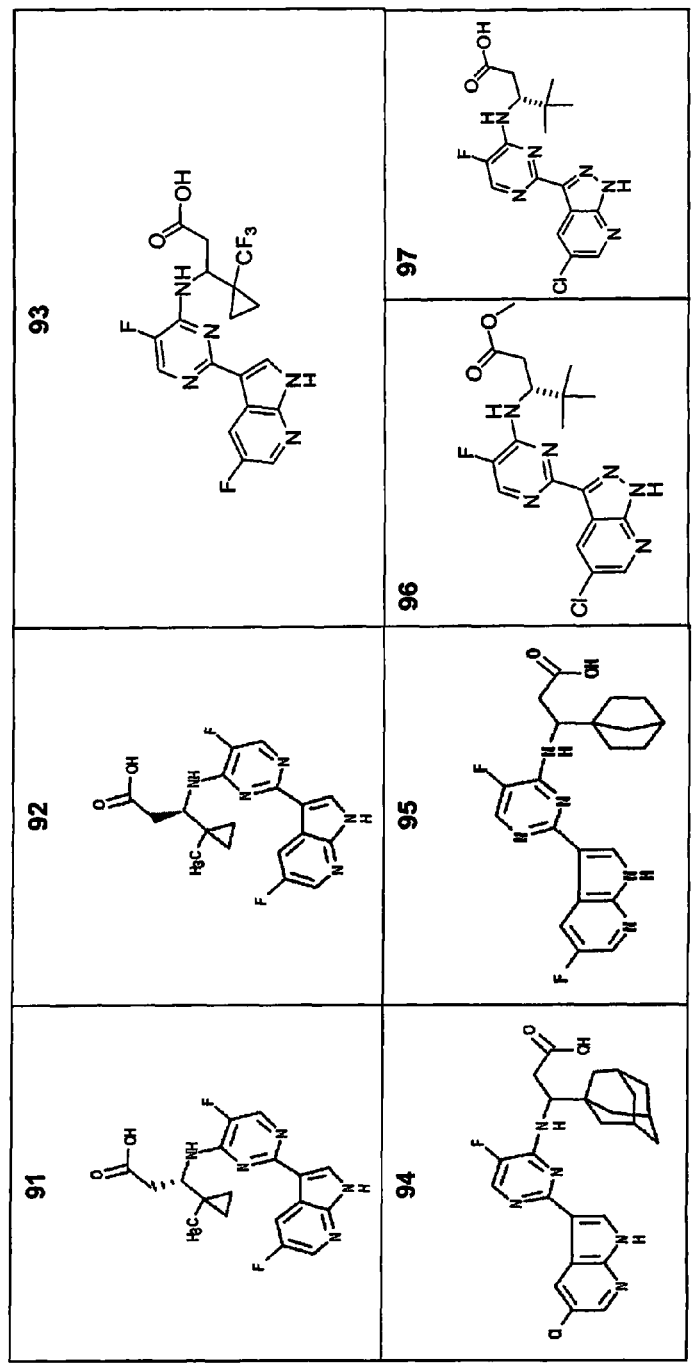

The compounds of the invention are as described in the claims. In some embodiments, the compounds of the invention are represented by any one of Structural Formulae (I)-(X), or pharmaceutically acceptable salts thereof, wherein the variables are each and independently as described in any one of the claims. In some embodiments, the compounds of the invention are represented by any chemical formulae depicted in Table 1 and FIG. 1, or pharmaceutically acceptable salts thereof. In some embodiments, the compounds of the invention are presented by Structural Formulae (I)-(X), or a pharmaceutically acceptable salt thereof, wherein the variables are each and independently as depicted in the chemical formulae in Table 1 and FIG. 1.

In one embodiment, the compounds of the invention are represented by Structural Formula (I) or pharmaceutically acceptable salts thereof:

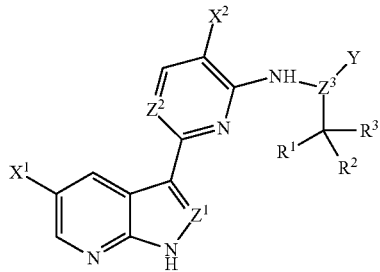

wherein the values of the variables of Structural Formula (I) are as described below.

The first set of values of the variables of Structural Formula (I) is as follows:

$X^1$ is —F, —Cl, —CF$_3$, —CN, or CH$_3$. In one aspect, $X^1$ is —F, —Cl, or —CF$_3$. In another aspect, $X^1$ is —F or —Cl.

$X^2$ is —H, —F, —Cl, or —CF$_3$. In one aspect, $X^2$ is —F, —Cl, or —CF$_3$. In another aspect, $X^2$ is —F or —Cl.

$Z^1$ is N or CH. In one aspect, $Z^1$ is CH. In another aspect, $Z^1$ is N.

$Z^2$ is N or CR$^0$. In one aspect, $Z^2$ is N, C—F, or C—CN. In another aspect, $Z^2$ is N.

$Z^3$ is CH or N. In one aspect, $Z^3$ is CH.

Y is —C(R$^4$R$^5$)—[C(R$^6$R$^7$)]$_n$-Q or —C(R$^4$)═C(R$^6$)-Q.

$R^0$ is —H, —F, or CN.

$R^1$, $R^2$, and $R^3$ are each and independently —CH$_3$, —CH$_2$F, —CF$_3$, —C$_2$H$_5$, —CH$_2$CH$_2$F, —CH$_2$CF$_3$; or optionally $R^2$ and $R^3$, or $R^1$, $R^2$ and $R^3$, together with the carbon atom to which they are attached, form a 3-10 membered carbocyclic ring (including bridged carbocyclic ring, such as adamantly ring). In one aspect, $R^1$, $R^2$, and $R^3$ are each and independently —CH$_3$, or —C$_2$H$_5$, or optionally $R^2$ and $R^3$, or $R^1$, $R^2$ and $R^3$, together with the carbon atom to which they are attached, form a 3-10 membered carbocyclic ring. In another aspect, each of $R^1$, $R^2$, and $R^3$ is independently —CH$_3$, —CH$_2$F, —CF$_3$, or —C$_2$H$_5$; or $R^1$ is —CH$_3$, and $R^2$ and $R^3$ together with the carbon atom to which they are attached form a 3-6 membered carbocyclic ring. In another aspect, $R^1$, $R^2$, and $R^3$ are each and independently —CH$_3$, —CH$_2$F, —CF$_3$, or —C$_2$H$_5$. In yet another aspect, $R^1$, $R^2$, and $R^3$ are each and independently —CH$_3$, or optionally $R^2$ and $R^3$, or $R^1$, $R^2$ and $R^3$, together with the carbon atom to which they are attached, form a 3-6 membered carbocyclic ring. Specific examples of carbocyclic ring include cyclopropyl, cyclobutyl, cyclopentyl, cylcohexyl, and bridged rings, such as adamantly group. In yet another aspect, $R^1$, $R^2$, and $R^3$ are each and independently —CH$_3$.

$R^4$ and $R^5$ are each and independently —H.

$R^6$ and $R^7$ are each and independently —H, —OH, —CH$_3$, or —CF$_3$; or optionally, $R^5$ and $R^7$ together with the carbon atoms to which they are attached form a cyclopropane ring. In one aspect, $R^6$ and $R^7$ are each and independently —H, —OH, —CH$_3$, or —CF$_3$. In another aspect, $R^6$ and $R^7$ are each and independently —H.

Each Q is independently —C(O)OR, —OH, —CH$_2$OH, —S(O)R', —P(O)(OH)$_2$, —S(O)$_2$R', —S(O)$_2$—NR"R''', or a 5-membered heterocycle selected from the group consisting of:

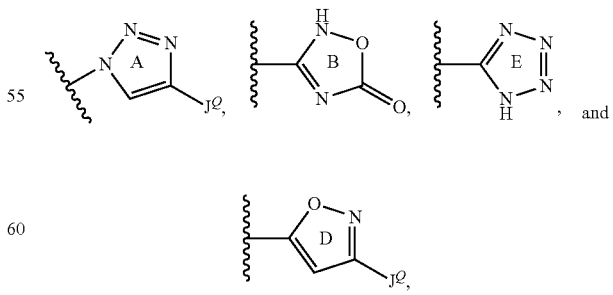

wherein $J^Q$ is —H, —OH or —CH$_2$OH. Specific examples of the 5-membered heterocycles include:

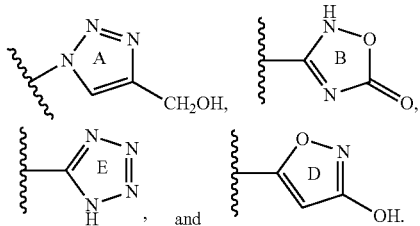

In one aspect, each Q is independently —C(O)OR, —OH, —CH$_2$OH, —S(O)$_2$R', —S(O)$_2$—NR"R''', or a 5-membered heterocycle selected from the group consisting of:

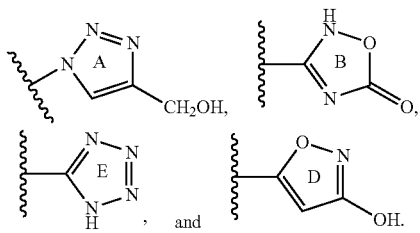

In another aspect, each Q is independently —C(O)OH, —OH, —CH$_2$OH, —S(O)$_2$R', —S(O)$_2$—NR"R''', or a 5-membered heterocycle selected from the group consisting of:

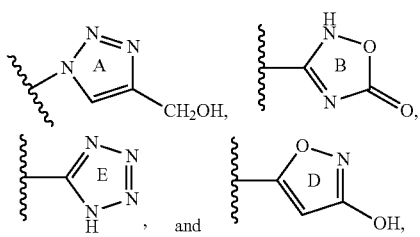

In another aspect, each Q is independently —C(O)OR, —OH, —S(O)$_2$R', or —S(O)$_2$—NR"R'''. In yet another aspect, each Q is independently —C(O)OH, —OH, —S(O)$_2$R', or —S(O)$_2$—NR"R'''.

R is —H or C$_{1-4}$ alkyl. In one aspect, R is —H.

R' is —OH, C$_{1-4}$ alkyl, or —CH$_2$C(O)OH. In one aspect, R' is —OH or —CH$_2$C(O)OH.

R" is —H or —CH$_3$. In one aspect, R" is —H.

R''' is —H, a 3-6 membered carbocyclic ring, or C$_{1-4}$ alkyl optionally substituted with one or more substituents selected from the group consisting of halogen, —OR$^a$ and —C(O)OR$^a$. In one aspect, R''' is —H, a 3-6 membered carbocyclic ring, or optionally substituted C$_{1-4}$ alkyl. In another aspect, R''' is —H or optionally substituted C$_{1-4}$ alkyl.

R$^a$ is —H or C$_{1-4}$ alkyl. In one aspect, R$^a$ is —H.

n is 0 or 1.

The second set of values of the variables of Structural Formula (I) is as follows:
$X^1$ is —F or —Cl.
$X^2$ is —F or —Cl.
Values of the other variables are each and independently as described above in the first set of values of the variables of Structural Formula (I).

The third set of values of the variables of Structural Formula (I) is as follows:
$X^1$ is —F or —Cl.
$Z^1$ is CH.
Values of the other variables are each and independently as described above in the first set of values of the variables of Structural Formula (I).

The fourth set of values of the variables of Structural Formula (I) is as follows:
$X^2$ is —F or —Cl.
$Z^1$ is CH.
Values of the other variables are each and independently as described above in the first set of values of the variables of Structural Formula (I).

The fifth set of values of the variables of Structural Formula (I) is as follows:
$X^1$ is —F or —Cl.
$Z^1$ is N
Values of the other variables are each and independently as described above in the first set of values of the variables of Structural Formula (I).

The sixth set of values of the variables of Structural Formula (I) is as follows:
$X^2$ is —F or —Cl.
$Z^1$ is N
Values of the other variables are each and independently as described above in the first set of values of the variables of Structural Formula (I).

The seventh set of values of the variables of Structural Formula (I) is as follows:
$X^1$ is —F or —Cl.
$X^2$ is —F or —Cl.
$Z^1$ is CH.
Values of the other variables are each and independently as described above in the first set of values of the variables of Structural Formula (I).

The eighth set of values of the variables of Structural Formula (I) is as follows:
$X^1$ is —F or —Cl.
$X^2$ is —F or —Cl.
$Z^1$ is N.
Values of the other variables are each and independently as described above in the first set of values of the variables of Structural Formula (I).

The ninth set of values of the variables of Structural Formula (I) is as follows:
$X^1$ is —F or —Cl.
$Z^2$ is N, C—F, or C—CN.
Values of the other variables are each and independently as described above in the first set of values of the variables of Structural Formula (I).

The tenth set of values of the variables of Structural Formula (I) is as follows:
$X^2$ is —F or —Cl
$Z^2$ is N, C—F, or C—CN.
Values of the other variables are each and independently as described above in the first set of values of the variables of Structural Formula (I).

The eleventh set of values of the variables of Structural Formula (I) is as follows:
$Z^1$ is CH.
$Z^2$ is N, C—F, or C—CN.
Values of the other variables are each and independently as described above in the first set of values of the variables of Structural Formula (I).

The eleventh set of values of the variables of Structural Formula (I) is as follows:
$Z^1$ is N.
$Z^2$ is N, C—F, or C—CN.

Values of the other variables are each and independently as described above in the first set of values of the variables of Structural Formula (I).

The twelfth set of values of the variables of Structural Formula (I) is as follows:

$X^1$ is —F or —Cl.
$X^2$ is —F or —Cl.
$Z^1$ is N.
$Z^2$ is N, C—F, or C—CN.

Values of the other variables are each and independently as described above in the first set of values of the variables of Structural Formula (I).

The thirteenth set of values of the variables of Structural Formula (I) is as follows:

$X^1$, $X^2$, $Z^1$, and $Z^2$ are each and independently as described above in any one of the first through twelfth sets of values of the variables of Structural Formula (I).

Each of $R^1$, $R^2$, and $R^3$ is independently —CH$_3$, —CH$_2$F, —CF$_3$, or —C$_2$H$_5$; or $R^1$ is —CH$_3$, and $R^2$ and $R^3$ together with the carbon atom to which they are attached form a 3-6 membered carbocyclic ring.

Values of the other variables are each and independently as described above in the first set of values of the variables of Structural Formula (I).

The fourteenth set of values of the variables of Structural Formula (I) is as follows:

$X^1$, $X^2$, $Z^1$, $Z^2$, $R^1$, $R^2$, and $R^3$ are each and independently as described above in any one of the first through thirteenth sets of values of the variables of Structural Formula (I).

$R^6$ and $R^7$ are each and independently —H, —OH, —CH$_3$, or —CF$_3$.

Values of the other variables are each and independently as described above in the first set of values of the variables of Structural Formula (I).

The fifteenth set of values of the variables of Structural Formula (I) is as follows:

$X^1$, $X^2$, $Z^1$, $Z^2$, $R^1$, $R^2$, $R^3$, $R^6$, and $R^7$ are each and independently as described above in any one of the first through fourteenth sets of values of the variables of Structural Formula (I).

Each Q is independently —C(O)OR, —OH, —CH$_2$OH, —S(O)$_2$R', —S(O)$_2$—NR"R'", or a 5-membered heterocycle selected from the group consisting of:

Values of the other variables are each and independently as described above in the first set of values of the variables of Structural Formula (I).

The sixteenth set of values of the variables of Structural Formula (I) is as follows:

$X^1$, $X^2$, $Z^1$, $Z^2$, $R^1$, $R^2$, $R^3$, $R^6$, and $R^7$ are each and independently as described above in any one of the first through fourteenth sets of values of the variables of Structural Formula (I).

Each Q independently is —C(O)OR, —OH, —S(O)$_2$R', or —S(O)$_2$—NR"R'".

Values of the other variables are each and independently as described above in the first set of values of the variables of Structural Formula (I).

The seventeenth set of values of the variables of Structural Formula (I) is as follows:

$X^1$, $X^2$, $Z^1$, $Z^2$, $R^1$, $R^2$, $R^3$, $R^6$, and $R^7$ are each and independently as described above in any one of the first through fourteenth sets of values of the variables of Structural Formula (I).

Each Q independently is —C(O)OH, —OH, —S(O)$_2$R', or —S(O)$_2$—NR"R'".

Values of the other variables are each and independently as described above in the first set of values of the variables of Structural Formula (I).

The eighteenth set of values of the variables of Structural Formula (I) is as follows:

$X^1$, $X^2$, $Z^1$, $Z^2$, $R^1$, $R^2$, $R^3$, $R^6$, and $R^7$ are each and independently as described above in any one of the first through fourteenth sets of values of the variables of Structural Formula (I).

Each Q independently is —C(O)OH, —S(O)$_2$R', or —S(O)$_2$—NR"R'".

Values of the other variables are each and independently as described above in the first set of values of the variables of Structural Formula (I).

The nineteenth set of values of the variables of Structural Formula (I) is as follows:

$X^1$, $X^2$, $Z^1$, $Z^2$, $R^1$, $R^2$, $R^3$, $R^6$, $R^7$, and Q are each and independently as described above in any one of the first through sixteenth sets of values of the variables of Structural Formula (I).

R' is —OH or —CH$_2$C(O)OH.
R" is —H.
R'" is —H, a 3-6 membered carbocyclic ring, or optionally substituted C$_{1-4}$ alkyl.

Values of the other variables are each and independently as described above in the first set of values of the variables of Structural Formula (I).

The twentieth set of values of the variables of Structural Formula (I) is as follows:

$X^1$, $X^2$, $Z^1$, $Z^2$, $R^1$, $R^2$, $R^3$, $R^6$, and $R^7$ are each and independently as described above in any one of the first through sixteenth sets of values of the variables of Structural Formula (I).

Each Q independently is —C(O)OH, —S(O)$_2$OH, —S(O)$_2$CH$_2$C(O)OH, —S(O)$_2$—NH(C$_{1-4}$ alkyl).

Values of the other variables are each and independently as described above in the first set of values of the variables of Structural Formula (I).

In another embodiment, the compounds of the invention are represented by any one of Structural Formulae (II)-(V), or pharmaceutically acceptable salts thereof:

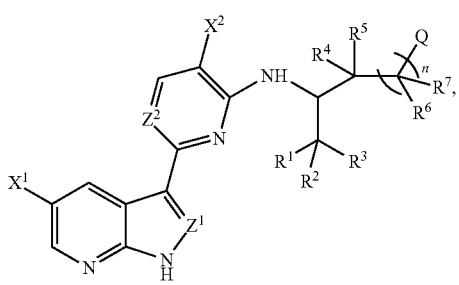

(III)

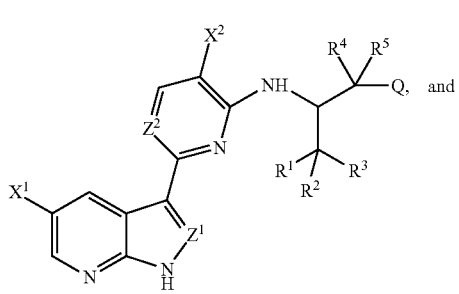

(IV)

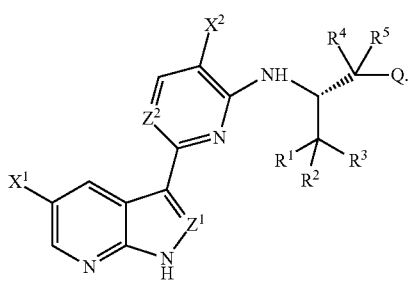

(V)

wherein values of the variables of Structural Formulae (II)-(V) are each and independently as described above in any one of the first through twentieth sets of values of the variables of Structural Formula (I).

In another embodiment, the compounds of the invention are represented by any one of the Structural Formulae (VI)-(X), or pharmaceutically acceptable salts thereof:

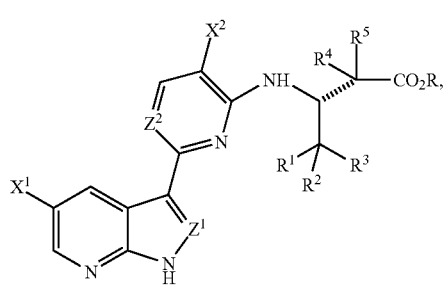

(VI)

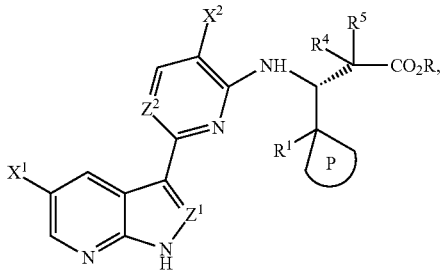

(VII)

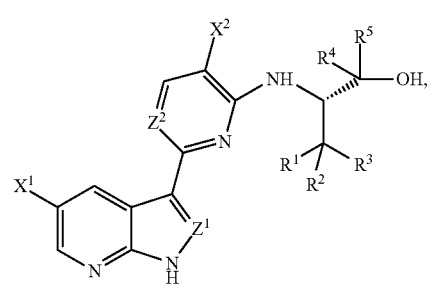

(VIII)

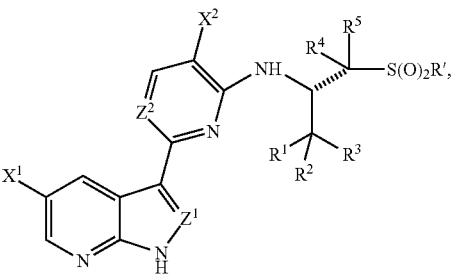

(IX)

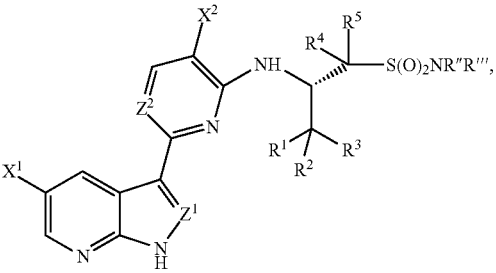

(X)

or a pharmaceutically acceptable salt thereof, wherein: $R^1$, $R^2$, and $R^3$ are each and independently —$CH_3$, —$CH_2F$, —$CF_3$, —$C_2H_5$, —$CH_2CH_2F$, —$CH_2CF_3$; and ring P is 3-6 membered carbocyclic ring; and wherein values of the other variables of Structural Formulae (VI) and (X) are each and independently as described above in any one of the first through twentieth sets of values of the variables of Structural Formula (I).

The twenty first set of values of the variables of Structural Formulae (II)-(X) is as follows:

R is H;
R' is —OH or —$CH_2C(O)OH$.
R" is —H.
R'" is —H, a 3-6 membered carbocyclic ring, or optionally substituted $C_{1-4}$ alkyl.

Values of the other variables are each and independently as described above.

It is noted that, for example, Structural Formulae (VI), (VIII), and (IX) can also be shown as follows, respectively:

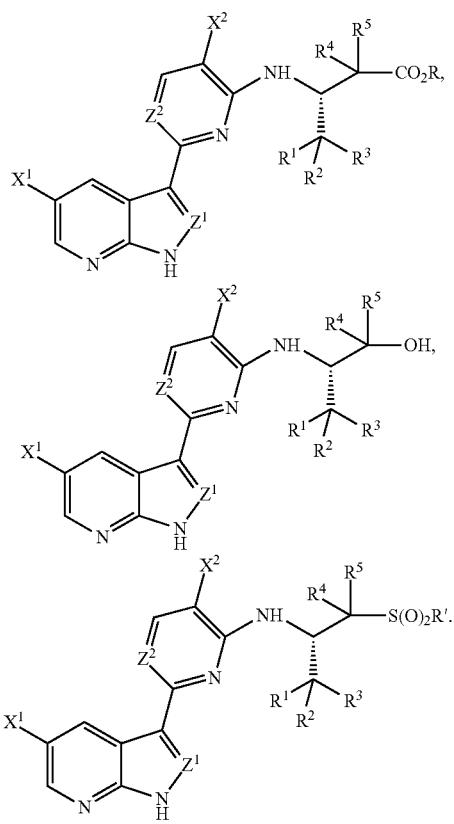

In yet another embodiment, the compounds of the invention are represented by any one of Structural Formulae (I)-(X) or a pharmaceutically acceptable salt thereof, wherein values of the variables are each and independently as shown in the compounds of Table 1 or FIG. 1.

In yet another embodiment, the compounds of the invention are represented by any one of the structural formulae depicted in Table 1 and FIG. 1, or a pharmaceutically acceptable salt thereof.

As used herein, a reference to compound(s) of the invention (for example, the compound(s) of Structural Formula (I), or compound(s) of claim 1) will include pharmaceutically acceptable salts thereof.

The compounds of the invention described herein can be prepared by any suitable method known in the art. For example, they can be prepared in accordance with procedures described in WO 2005/095400, WO 2007/084557, WO 2010/011768, WO 2010/011756, WO 2010/011772, WO 2009/073300, and PCT/US2010/038988 filed on Jun. 17, 2010. For example, the compounds shown in Table 1 and FIG. 1 and the specific compounds depicted above can be prepared by any suitable method known in the art, for example, WO 2005/095400, WO 2007/084557, WO 2010/011768, WO 2010/011756, WP 2010/011772, WO 2009/073300, and PCT/US2010/038988, and by the exemplary syntheses described below under Exemplification.

The present invention provides methods of preparing a compound represented by any one of Structural Formulae (I)-(X). In one embodiment, the compounds of the invention can be prepared as depicted in General Schemes 1-4. Any suitable condition(s) known in the art can be employed in the invention for each step depicted in the schemes.

In a specific embodiment, as shown in General Scheme 1, the methods comprise the step of reacting Compound (A) with Compound (B) under suitable conditions to form a compound of Structural Formula (XX), wherein each of $L^1$ and $L^2$ independently is a halogen (F, Cl, Br, or I), G is trityl and the remaining variables of Compounds (A), (B) and Structural Formula (XX) are each and independently as described above for Structural Formulae (I)-(X). Typical examples for $L^1$ and $L^2$ are each and independently Cl or Br. The methods further comprise the step of deprotecting the G group under suitable conditions to form the compounds of Structural Formula (I). Any suitable condition(s) known in the art can be employed in the invention for each step depicted in the schemes. For example, any suitable condition described in WO 2005/095400 and WO 2007/084557 for the coupling of a dioxaboraolan with a chloro-pyrimidine can be employed for the reaction between Compounds (A) and (B). Specifically, the reaction between compounds (A) and (B) can be performed in the presence of $Pd(PPh_3)_4$ or $Pd_2(dba)_3$ (dba is dibenzylidene acetone). For example, the de-tritylation step can be performed under an acidic condition (e.g., trifluoroacetic acid (TFA)) in the presence of, for example, $Et_3SiH$ (Et is ethyl). Specific exemplary conditions are described in the Exemplification below Optionally, the method further comprises the step of preparing Compound (A) by reacting Compound (E) with Compound (D). Any suitable conditions know in the art can be employed in this step, and Compounds (E) and (D) can be prepared by any suitable method known in the art. Specific exemplary conditions are described in the Exemplification below.

General Scheme 1

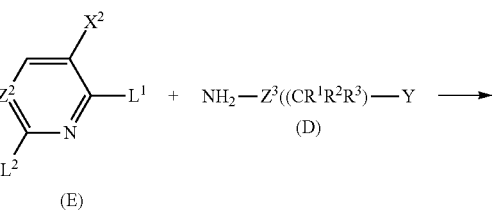

(E)      (D)

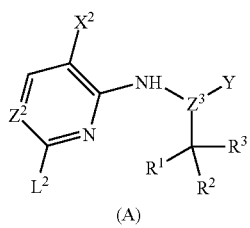

(A)

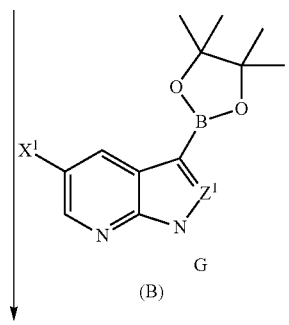

(B)

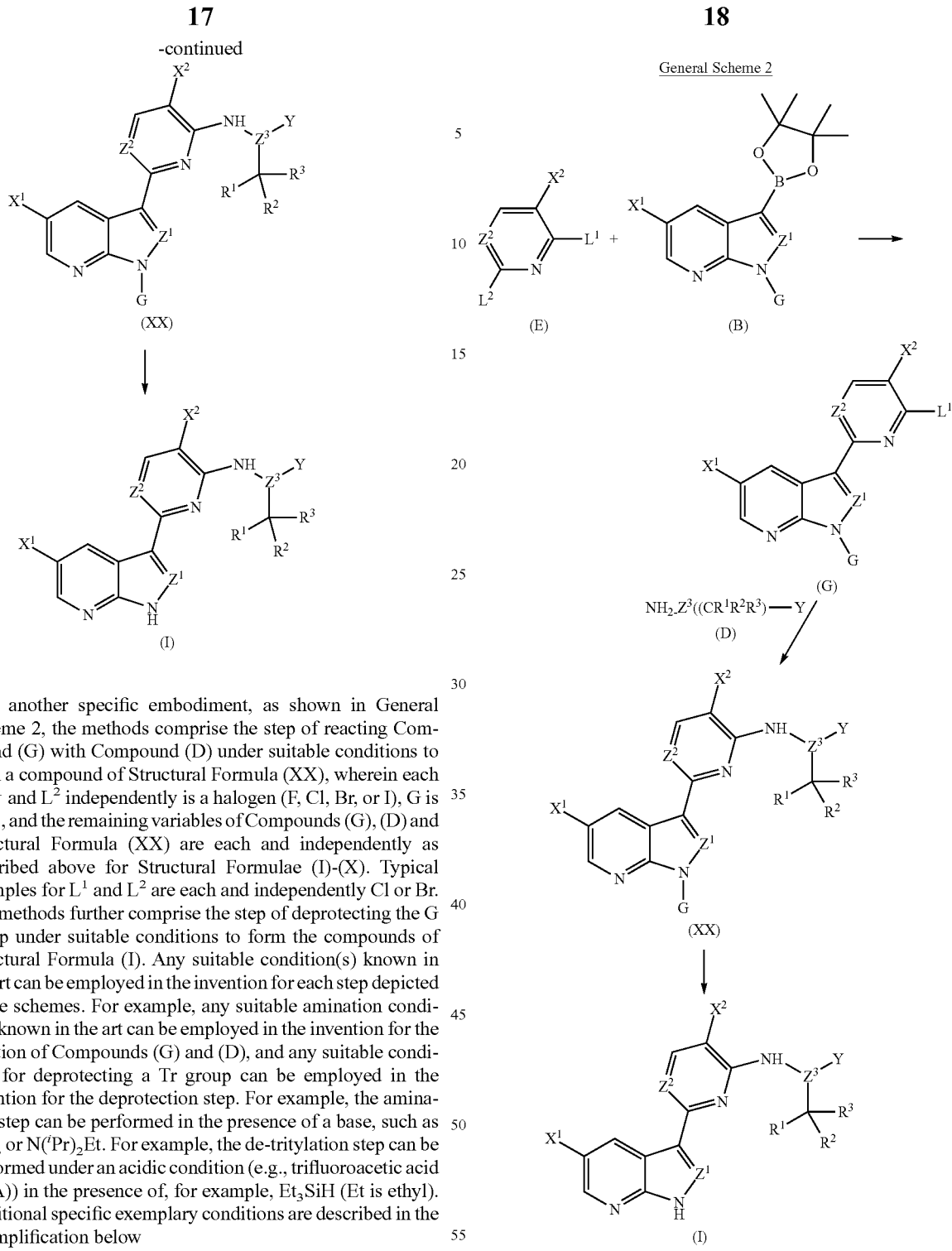

In another specific embodiment, as shown in General Scheme 2, the methods comprise the step of reacting Compound (G) with Compound (D) under suitable conditions to form a compound of Structural Formula (XX), wherein each of $L^1$ and $L^2$ independently is a halogen (F, Cl, Br, or I), G is trityl, and the remaining variables of Compounds (G), (D) and Structural Formula (XX) are each and independently as described above for Structural Formulae (I)-(X). Typical examples for $L^1$ and $L^2$ are each and independently Cl or Br. The methods further comprise the step of deprotecting the G group under suitable conditions to form the compounds of Structural Formula (I). Any suitable condition(s) known in the art can be employed in the invention for each step depicted in the schemes. For example, any suitable amination condition known in the art can be employed in the invention for the reaction of Compounds (G) and (D), and any suitable condition for deprotecting a Tr group can be employed in the invention for the deprotection step. For example, the amination step can be performed in the presence of a base, such as $NEt_3$ or $N(^iPr)_2Et$. For example, the de-tritylation step can be performed under an acidic condition (e.g., trifluoroacetic acid (TFA)) in the presence of, for example, $Et_3SiH$ (Et is ethyl). Additional specific exemplary conditions are described in the Exemplification below Optionally, the method further comprises the step of preparing Compound (G) by reacting Compound (E) with Compound (B). Any suitable conditions know in the art can be employed in this step. For example, any suitable condition described in WO 2005/095400 and WO 2007/084557 for the coupling of a dioxaboralan with a chloro-pyrimidine can be employed for the reaction between Compounds (E) and (B). Specifically, the reaction between compounds (E) and (B) can be performed in the presence of $Pd(PPh_3)_4$ or $Pd_2(dba)_3$ (dba is dibenzylidene acetone). Specific exemplary conditions are described in the Exemplification below.

In yet another specific embodiment, as shown in General Scheme 3, the methods comprise the step of reacting Compound (K) with Compound (D) under suitable conditions to form a compound of Structural Formula (XX), wherein G is trityl and the remaining variables of Compounds (K), (D) and Structural Formula (XX) are each and independently as described above for Structural Formulae (I)-(X). The methods further comprise the step of deprotecting the G group under suitable conditions to form the compounds of Structural Formula (I). Any suitable condition(s) known in the art can be employed in the invention for each step depicted in the schemes. For example, any suitable reaction condition known in the art, for example, in WO 2005/095400 and WO 2007/084557 for the coupling of an amine with a sulfinyl group can be employed for the reaction of Compounds (K) with Compound (D). For example, Compounds (D) and (K) can be coupling of a dioxaborolan with a chloro-pyrimidine can be employed for the reaction between Compounds (H) and (B). Specifically, the reaction between compounds (H) and (B) can be performed in the presence of Pd(PPh$_3$)$_4$ or Pd$_2$(dba)$_3$ (dba is dibenzylidene acetone). Specific exemplary conditions are described in the Exemplification below.

General Scheme 3

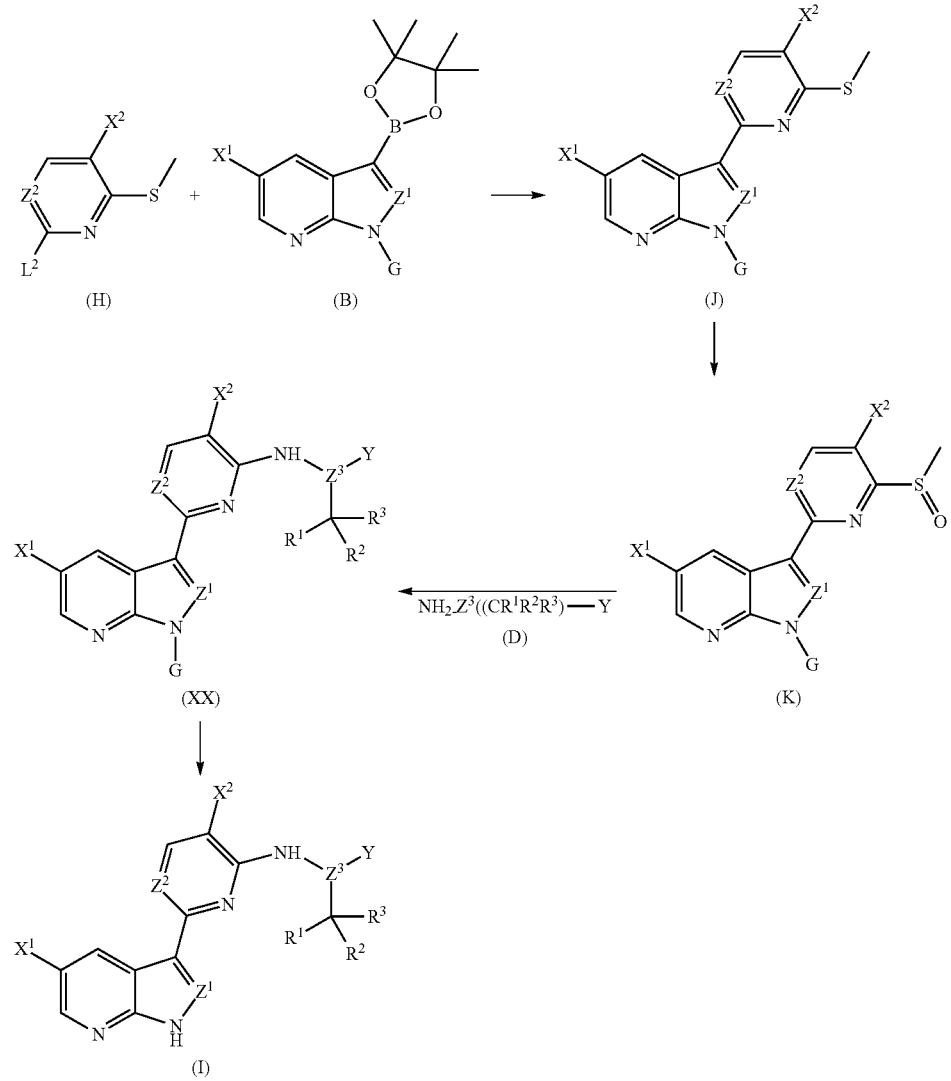

reacted in the presence of a base, such as NEt$_3$ or N($^i$Pr)$_2$(Et). For example, the de-tritylation step can be performed under an acidic condition (e.g., trifluoroacetic acid (TFA)) in the presence of, for example, Et$_3$SiH (Et is ethyl). Additional specific exemplary conditions are described in the Exemplification below Optionally, the method further comprises the step of preparing Compound (K) by oxidizing Compound (J), for example, by treatment with meta-chloroperbenzoic acid.

Optionally, the method further comprises the step of preparing Compound (J) by reacting Compound (H) with Compound (B). Any suitable conditions know in the art can be employed in this step. For example, any suitable condition described in WO 2005/095400 and WO 2007/084557 for the In yet another specific embodiment, as shown in General Scheme 4, the methods comprise the step of reacting Compound (L) with Compound (D) under suitable conditions to form a compound of Structural Formula (XX), wherein G is trityl and the remaining variables of Compounds (L), (D) and Structural Formula (XX) are each and independently as described above for Structural Formulae (I)-(X). The methods further comprise the step of deprotecting the G group under suitable conditions to form the compounds of Structural Formula (I). Any suitable condition(s) known in the art can be employed in the invention for each step depicted in the schemes. For example, any suitable reaction condition known in the art, for example, in WO 2005/095400 and WO 2007/084557 for the coupling of an amine with a sulfonyl group can be employed for the reaction of Compounds (L) with Compound (D). For example, Compounds (D) and (L) can be reacted in the presence of a base, such as $NEt_3$ or $N(^iPr)_2(Et)$. For example, the de-tritylation step can be performed under an acidic condition (e.g., trifluoroacetic acid (TFA)) in the presence of, for example, $Et_3SiH$ (Et is ethyl). Additional specific exemplary conditions are described in the Exemplification below Optionally, the method further comprises the step of preparing Compound (L) by oxidizing Compound (J), for example, by treatment with meta-chloroperbenzoic acid.

Optionally, the method further comprises the step of preparing Compound (J) by reacting Compound (H) with Compound (B). Reaction conditions are as described above for General Scheme 3.

In some embodiments, the present invention is directed to a compound represented by Structural Formula (XX), wherein the variables of Structural Formula (XX) are each and independently as defined in any one of the claims and G is trityl. Specific examples of the compounds represented by Structural formula (XX) are shown below in the Exemplification. Some specific examples include: Compounds 3a, 8a, 28a, 34a, 39a, 42a, 51a, 57a, 80a, 84a, 90a, 101a, 119a, 144a, 148a, 154a, 159a, 170a, 176a, 182a, 184a, 191a, 197a, 207a, and 218a, which are shown in the Exemplification below.

DEFINITIONS AND GENERAL TERMINOLOGY

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B.

General Scheme 4

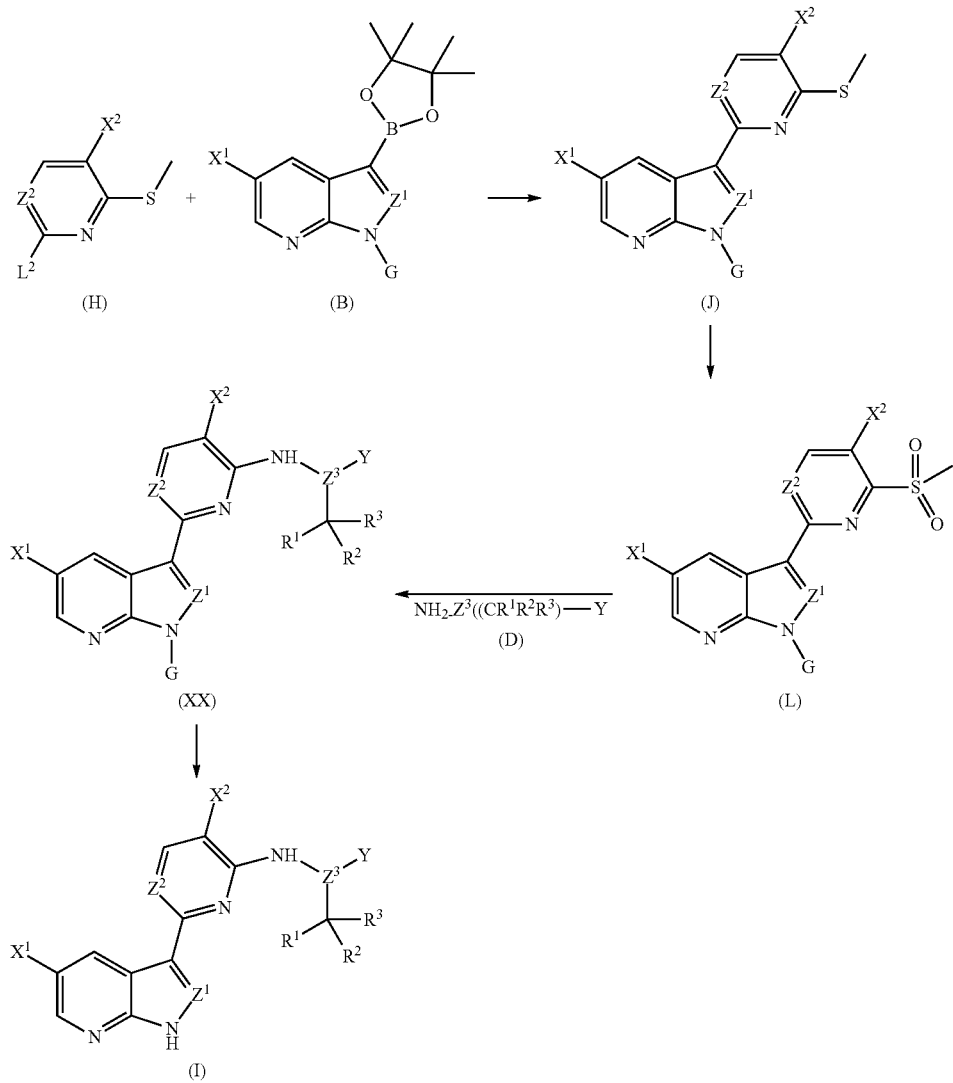

Compounds (A)-(K) can be prepared by any suitable method known in the art. Specific exemplary synthetic methods of these compounds are described below in the Exemplification. In one embodiment, Compounds (A), (G), (J), (K) and (L) can be prepared as described in General Schemes 1-4.

and March, J., John Wiley & Sons, New York: 2001, the entire contents of which are hereby incorporated by reference.

As described herein, compounds of the invention may optionally be substituted with one or more substituents, such as illustrated generally below, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. For example, if X is optionally substituted $C_1$-$C_3$alkyl or phenyl; X may be either optionally substituted $C_1$-$C_3$ alkyl or optionally substituted phenyl. Likewise, if the term "optionally substituted" follows a list, said term also refers to all of the substitutable groups in the prior list unless otherwise indicated. For example: if X is $C_1$-$C_3$alkyl or phenyl wherein X is optionally and independently substituted by $J^X$, then both $C_1$-$C_3$alkyl and phenyl may be optionally substituted by $J^X$.

The phrase "up to", as used herein, refers to zero or any integer number that is equal or less than the number following the phrase. For example, "up to 3" means any one of 0, 1, 2, and 3. As described herein, a specified number range of atoms includes any integer therein. For example, a group having from 1-4 atoms could have 1, 2, 3, or 4 atoms.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl and acetylene.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_1$-$C_6$ alkyl or $C_1$-$C_4$ alkyl. In some embodiments, the "alkenyl" is $C_2$-$C_6$ alkenyl or $C_2$-$C_4$ alkenyl. In some embodiments, the "alkynyl" is $C_2$-$C_6$ alkynyl or $C_2$-$C_4$ alkynyl.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", or "aryloxyalkyl" refers to carbocyclic aromatic ring systems. The term "aryl" may be used interchangeably with the terms "aryl ring" or "aryl group".

"Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo", "cyclic", "cyclic group" or "cyclic moiety", include mono-, bi-, and tri-cyclic ring systems including cycloaliphatic, heterocycloaliphatic, carbocyclic aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic carbocyclic aryls, and bicyclic heteroaryls.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, carbocyclic aryl, heteroaryl, alkoxy, cycloalkyloxy, heterocycloalkyloxy, (carbocyclic aryl)oxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, (carbocyclic aryl)carbonylamino, aralkylcarbonylamino, (heterocycloalkyl)carbonylamino, (heterocycloalkylalkyl) carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "bridge" refers to a bond or an atom or an unbranched chain of atoms connecting two different parts of a molecule. The two atoms that are connected through the bridge (usually but not always, two tertiary carbon atoms) are denoted as "bridgeheads".

As used herein, the term "spiro" refers to ring systems having one atom (usually a quaternary carbon) as the only common atom between two rings.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein an optionally substituted aralkyl can be substituted on both the alkyl and the aryl portion. Unless otherwise indicated as used herein optionally substituted aralkyl is optionally substituted on the aryl portion.

In some embodiments, an aliphatic or heteroaliphatic group, or a non-aromatic heterocyclic ring may contain one or more substituents. Suitable substituents on the saturated carbon of an aliphatic or heteroaliphatic group, or of a heterocyclic ring are selected from those listed above. Other suitable substitutents include those listed as suitable for the unsaturated carbon of a carbocyclic aryl or heteroaryl group and additionally include the following: =O, =S, =NNHR*, =NN(R*)$_2$, =NNHC(O)R*, =NNHCO$_2$(C$_{1-4}$ alkyl), =NNHSO$_2$(C$_{1-4}$ alkyl), or =NR*, wherein each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

In some embodiments, optional substituents on the nitrogen of a heterocyclic ring include those used above. Other suitable substituents include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R$^+$ is unsubstituted.

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of a carbocyclic aryl or heteroaryl group are selected from those listed above. Other suitable substituents include: halogen; —R$^o$; —OR$^o$; —SR$^o$ ; 1,2-methylenedioxy; 1,2-ethylenedioxy; phenyl (Ph) optionally substituted with R$^o$; —O(Ph) optionally substituted with R$^o$; —(CH$_2$)$_{1-2}$(Ph), optionally substituted with R$^o$; —CH=CH(Ph), optionally substituted with R$^o$; —NO$_2$; —CN; —N(R$^o$)$_2$; —NR$^o$C(O)R$^o$; —NR$^o$C(S)R$^o$; —NR$^o$C(O)N(R$^o$)$_2$; —NR$^o$C(S)N(R$^o$)$_2$; —NR$^o$CO$_2$R$^o$; —NR$^o$NR$^o$C(O)R$^o$; —NR$^o$NR$^o$; C(O)N(R$^o$)$_2$; —NR$^o$NR$^o$CO$_2$R$^o$; —C(O)C(O)R$^o$; —C(O)CH$_2$C(O)R$^o$; —CO$_2$R$^o$; —C(O)R$^o$; —C(S)R$^o$; —C(O)N(R$^o$)$_2$; —C(S)N(R$^o$)$_2$; —OC(O)N(R$^o$)$_2$; —OC(O)R$^o$; —C(O)N(OR$^o$)R$^o$; —C(NOR$^o$) R$^o$; —S(O)$_2$R$^o$; —S(O)$_3$R$^o$; —SO$_2$N(R$^o$)$_2$; —S(O)R$^o$; —NR$^o$SO$_2$N(R$^o$)$_2$; —NR$^o$SO$_2$R$^o$; —N(OR$^o$)R$^o$; —C(=NH)—N(R$^o$)$_2$; or —(CH$_2$)$_{0-2}$NHC(O)R$^o$; wherein each independent occurrence of R$^o$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, two independent occurrences of R$^o$, on the same substituent or different substituents, taken together with the atom(s) to which each R$^o$ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R$^o$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, CHO, N(CO)(C$_{1-4}$ aliphatic), C(O)N(C$_{1-4}$ aliphatic), wherein each of the foregoing C$_{1-4}$aliphatic groups of R$^o$ is unsubstituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

The term "unsaturated", as used herein, means that a moiety has one or more units of unsaturation.

As detailed above, in some embodiments, two independent occurrences of R$^o$ (or R$^+$, or any other variable similarly defined herein), may be taken together with the atom(s) to which each variable is bound to form a 5-8-membered heterocyclyl, carbocyclic aryl, or heteroaryl ring or a 3-8-membered cycloalkyl ring. Exemplary rings that are formed when two independent occurrences of R$^o$ (or R$^+$, or any other variable similarly defined herein) are taken together with the atom(s) to which each variable is bound include, but are not limited to the following: a) two independent occurrences of R$^o$ (or R$^+$, or any other variable similarly defined herein) that are bound to the same atom and are taken together with that atom to form a ring, for example, N(R$^o$)$_2$, where both occurrences of R$^o$ are taken together with the nitrogen atom to form a piperidin-1-yl, piperazin-1-yl, or morpholin-4-yl group; and b) two independent occurrences of R$^o$ (or R$^+$, or any other variable similarly defined herein) that are bound to different atoms and are taken together with both of those atoms to form a ring, for example where a phenyl group is substituted with two occurrences of OR$^o$

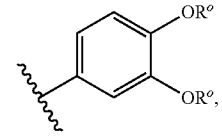

these two occurrences of R$^o$ are taken together with the oxygen atoms to which they are bound to form a fused 6-membered oxygen containing ring:

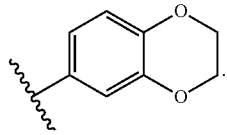

It will be appreciated that a variety of other rings can be formed when two independent occurrences of R$^o$ (or R$^+$, or any other variable similarly defined herein) are taken together with the atom(s) to which each variable is bound and that the examples detailed above are not intended to be limiting.

The term "hydroxyl" or "hydroxy" or "alcohol moiety" refers to —OH.

As used herein, an "alkoxycarbonyl," which is encompassed by the term carboxy, used alone or in connection with another group refers to a group such as (alkyl-O)—C(O)—.

As used herein, a "carbonyl" refers to —C(O)—.

As used herein, an "oxo" refers to =O.

As used herein, the term "alkoxy", or "alkylthio", as used herein, refers to an alkyl group, as previously defined, attached to the molecule through an oxygen ("alkoxy" e.g., —O-alkyl) or sulfur ("alkylthio" e.g., —S-alkyl) atom.

As used herein, the terms "halogen", "halo", and "hal" mean F, Cl, Br, or I.

As used herein, the term "cyano" or "nitrile" refer to —CN or —C≡N.

The terms "alkoxyalkyl", "alkoxyalkenyl", "alkoxyaliphatic", and "alkoxyalkoxy" mean alkyl, alkenyl, aliphatic or alkoxy, as the case may be, substituted with one or more alkoxy groups.

The terms "haloalkyl", "haloalkenyl", "haloaliphatic", and "haloalkoxy" mean alkyl, alkenyl, aliphatic or alkoxy, as the case may be, substituted with one or more halogen atoms. This term includes perfluorinated alkyl groups, such as —CF$_3$ and —CF$_2$CF$_3$.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. In some embodiments, the cyanoalkyl is (NC)-alkyl-.

The terms "aminoalkyl", "aminoalkenyl", "aminoaliphatic", and "aminoalkoxy" mean alkyl, alkenyl, aliphatic or alkoxy, as the case may be, substituted with one or more amino groups, wherein the amino group is as defined above. In some embodiments, the aminoaliphatic is a C1-C6 aliphatic group substituted with one or more —NH$_2$ groups. In some embodiments, the aminoalkyl refers to the structure $(R^X R^Y)$N-alkyl-, wherein each of $R^X$ and $R^Y$ independently is as defined above. In some specific embodiments, the aminoalkyl is C1-C6 alkyl substituted with one or more —NH$_2$ groups. In some specific embodiments, the aminoalkenyl is C1-C6 alkenyl substituted with one or more —NH$_2$ groups. In some embodiments, the aminoalkoxy is —O(C1-C6 alkyl) wherein the alkyl group is substituted with one or more —NH$_2$ groups.

The terms "hydroxyalkyl", "hydroxyaliphatic", and "hydroxyalkoxy" mean alkyl, aliphatic or alkoxy, as the case may be, substituted with one or more —OH groups.

The terms "alkoxyalkyl", "alkoxyaliphatic", and "alkoxyalkoxy" mean alkyl, aliphatic or alkoxy, as the case may be, substituted with one or more alkoxy groups. For example, an "alkoxyalkyl" refers to an alkyl group such as (alkyl-O)-alkyl-, wherein alkyl is as defined above.

The term "carboxyalkyl" means alkyl substituted with one or more carboxy groups, wherein alkyl and carboxy are as defined above.

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. For example, a substituent drawn as

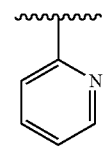

also represents

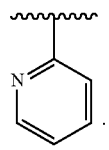.

Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogs, can also be therapeutically useful.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters. Pharmaceutically acceptable prodrugs of the compounds described herein include, without limitation, esters, amino acid esters, phosphate esters, metal salts and sulfonate esters.

Uses of Disclosed Compounds

One aspect of the present invention is generally related to the use of the compounds described herein or pharmaceutically acceptable salts, or pharmaceutically acceptable compositions comprising such a compound or a pharmaceutically acceptable salt thereof, for inhibiting the replication of influenza viruses in a biological sample or in a patient, for reducing the amount of influenza viruses (reducing viral titer) in a biological sample or in a patient, and for treating influenza in a patient.

In one embodiment, the present invention is generally related to the use of compounds represented by any one of Structural Formulae (I)-(X), or pharmaceutically acceptable salts thereof for any of the uses specified above:

In yet another embodiment, the present invention is directed to the use of any compound selected from the compounds depicted in Table 1 or a pharmaceutically acceptable salt thereof, for any of the uses described above.

In some embodiments, the compounds are represented by any one of Structural Formulae (I)-(X), and the variables are each independently as depicted in the compounds of Table 1.

In yet another embodiment, the compounds described herein or pharmaceutically acceptable salts thereof can be used to reduce viral titre in a biological sample (e.g. an infected cell culture) or in humans (e.g. lung viral titre in a patient).

The terms "influenza virus mediated condition", "influenza infection", or "Influenza", as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenzavirus A, Influenzavirus B, Influenzavirus C, Isavirus and Thogotovirus. Influenzavirus A genus has one species, influenza A virus which can be subdivided into different serotypes based on the antibody response to these viruses: H1N1, H2N2, H3N2, H5N1, H7N7, H1N2, H9N2, H7N2, H7N3 and H10N7. Influenzavirus B genus has one species, influenza B virus. Influenza B almost exclusively infects humans and is less common than influenza A. Influenzavirus C genus has one species, Influenzavirus C virus, which infects humans and pigs and can cause severe illness and local epidemics. However, Influenzavirus C is less common than the other types and usually seems to cause mild disease in children.

In some embodiments of the invention, influenza or influenza viruses are associated with Influenzavirus A or B. In some embodiments of the invention, influenza or influenza viruses are associated with Influenzavirus A. In some specific embodiments of the invention, Influenzavirus A is H1N1, H2N2, H3N2 or H5N1.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the invention depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically $\frac{1}{10}$ to $\frac{1}{1000}$), the virus is allowed to go through several rounds of replication over 48-72 hours, then the amount of cell death is measured using a decrease in cellular ATP content compared to uninfected controls. A second type of cell assay that can be employed in the invention depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer (or titre)" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}$, $10^{-2}$, $10^{-3}$, . . . , $10^{-8}$. The lowest concentration of virus that still infects cells is the viral titer.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc). It also includes the use among populations who require protection from the influenza but who either do not get protection after vaccination (e.g. due to weak immunse system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc).

According to the US CDC, an influenza "outbreak" is defined as a sudden increase of acute febrile respiratory illness (AFRI) occurring within a 48 to 72 hour period, in a group of people who are in close proximity to each other (e.g. in the same area of an assisted living facility, in the same household, etc) over the normal background rate or when any subject in the population being analyzed tests positive for influenza. One case of confirmed influenza by any testing method is considered an outbreak.

A "cluster" is defined as a group of three or more cases of AFRI occurring within a 48 to 72 hour period, in a group of people who are in close proximity to each other (e.g. in the same area of an assisted living facility, in the same household, etc).

As used herein, the "index case", "primary case" or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, etc.

In one embodiment, the methods of the invention are a preventative or "pre-emptive" measure to a patient, specifically a human, having a predisposition to complications resulting from infection by an influenza virus. The term "pre-emptive" as used herein as for example in pre-emptive use, "pre-emptively", etc, is the prophylactic use in situations in which an "index case" or an "outbreak" has been confirmed, in order to prevent the spread of infection in the rest of the community or population group.

In another embodiment, the methods of the invention are applied as a "pre-emptive" measure to members of a community or population group, specifically humans, in order to prevent the spread of infection.

As used herein, an "effective amount" refers to an amount sufficient to elicit the desired biological response. In the present invention the desired biological response is to inhibit the replication of influenza virus, to reduce the amount of influenza viruses or to reduce or ameliorate the severity, duration, progression, or onset of a influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), tree times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Various types of administration methods can be employed in the invention, and are described in detail below under the section entitled "Administration Methods."

Combination Therapy

An effective amount can be achieved in the method or pharmaceutical composition of the invention employing a compound of the invention (including a pharmaceutically acceptable salt or solvate (e.g., hydrate)) alone or in combination with an additional suitable therapeutic agent, for example, an antiviral agent or a vaccine. When "combination therapy" is employed, an effective amount can be achieved using a first amount of a compound of the invention and a second amount of an additional suitable therapeutic agent (e.g. an antiviral agent or vaccine).

In another embodiment of this invention, a compound of the invention and the additional therapeutic agent, are each administered in an effective amount (i.e., each in an amount which would be therapeutically effective if administered alone). In another embodiment, a compound of the invention and the additional therapeutic agent, are each administered in an amount which alone does not provide a therapeutic effect (a sub-therapeutic dose). In yet another embodiment, a compound of the invention can be administered in an effective amount, while the additional therapeutic agent is administered in a sub-therapeutic dose. In still another embodiment, a compound of the invention can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

In one embodiment, the present invention is directed to methods of combination therapy for inhibiting Flu viruses replication in biological samples or patients, or for treating or preventing Influenza virus infections in patients using the compounds or pharmaceutical compositions of the invention. Accordingly, pharmaceutical compositions of the invention also include those comprising an inhibitor of Flu virus replication of this invention in combination with an anti-viral compound exhibiting anti-Influenza virus activity.

Methods of use of the compounds and compositions of the invention also include combination of chemotherapy with a compound or composition of the invention, or with a combination of a compound or composition of this invention with another anti-viral agent and vaccination with a Flu vaccine.

When co-administration involves the separate administration of the first amount of a compound of the invention and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of the invention and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of co-administration of a first amount of a compound of the invention and a second amount of an additional therapeutic agent can result in an enhanced or synergistic therapeutic effect, wherein the combined effect is greater than the additive effect that would result from separate administration of the first amount of a compound of the invention and the second amount of an additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using the compounds of the present invention is in combination with a Flu vaccine, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan. (See also Ruruta et al., Antiviral Reasearch, 82: 95-102 (2009), "T-705 (flavipiravir) and related compounds: Novel broad-spectrum inhibitors of RNA viral infections.") In some embodiments, the compounds described herein can be co-administered with a traditional influenza vaccine. In some embodiments, the compounds described herein can be co-administered with Zanamivir. In some embodiments, the compounds described herein can be co-administered with oseltamivir. In some embodiments, the compounds described herein can be co-administered with T-705.

Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient infected with influenza. The term "prophylactically effective amount" refers to an amount effective in preventing and/or substantially lessening the chances or the size of influenza virus infection outbreak. Specific examples of effective amounts are described above in the section entitled Uses of Disclosed Compounds.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

EXEMPLIFICATION

Example 1

Synthesis of Compounds of the Invention

The compounds disclosed herein can be prepared by any suitable method known in the art, for example, WO 2005/095400, WO 2007/084557, WO 2010/011768, WO 2010/011756, WP 2010/011772, WO 2009/073300, and PCT/US2010/038988 filed on Jun. 17, 2010. For example, the compounds shown in Table 1 and FIG. 1 can be prepared by any suitable method known in the art, for example, WO 2005/095400, WO 2007/084557, WO 2010/011768, WO 2010/011756, WP 2010/011772, WO 2009/073300, and PCT/US2010/038988, and by the exemplary syntheses described below. Generally, the compounds of the invention can be prepared as shown in those syntheses optionally with any desired appropriate modification.

Methodology for Synthesis and Characterization of Compounds

Syntheses of certain exemplary compounds of the invention are described below. NMR and Mass Spectroscopy data of certain specific compounds are summarized in Table 1. As used herein the term RT (min) refers to the LCMS retention time, in minutes, associated with the compound.

Preparation of Compound 1

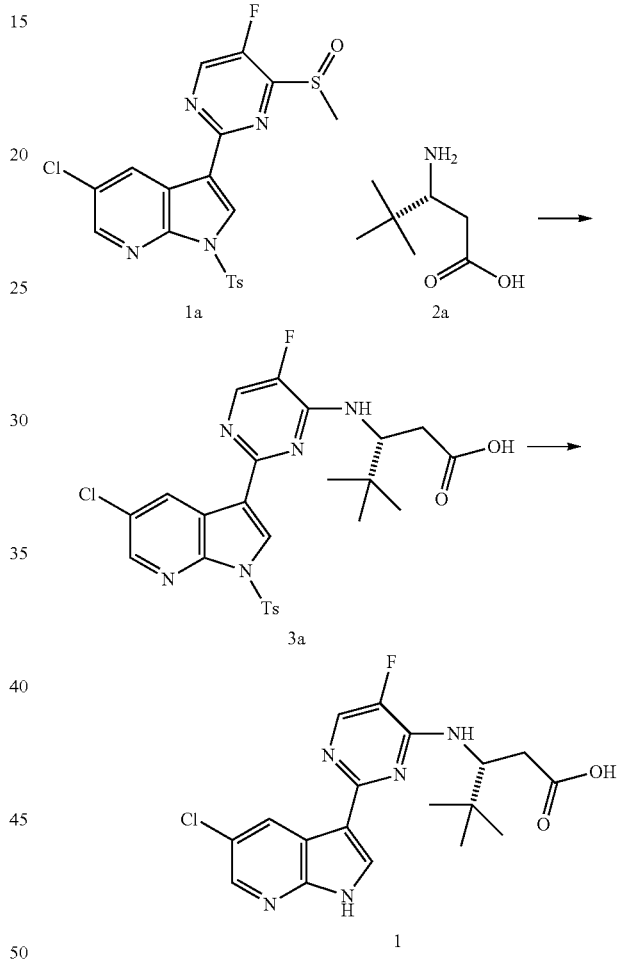

Synthetic Scheme 1

(a) Na$_2$CO$_3$, THF, CH$_3$CN, microwave, 135° C.; (b) NaOMe, MeOH, 0° C.;

Formation of (R)-3-(2-(5-chloro-1-tosyl-1H-pyrrolo[2,3-b]pyridin-3-yl)-5-fluoro-pyrimidin-4-ylamino)-4,4-dimethylpentanoic acid (3a)

To a solution of 5-chloro-3-(5-fluoro-4-methylsulfinyl-pyrimidin-2-yl)-1-(p-tolylsulfonyl)pyrrolo[2,3-b]pyridine, 1a, (0.100 g, 0.215 mmol: prepared in a similar manner as described below for Compound 25a in scheme 4) and (R)-3-amino-4,4-dimethylpentanoic acid, 2a, (0.031 g, 0.215 mmol) in tetrahydrofuran (1.66 mL) was added freshly ground Na$_2$CO$_3$ (0.068 g, 0.645 mmol) followed by acetonitrile (0.331 mL). The reaction mixture was heated to 135° C. for 30 minutes in a microwave reactor. The reaction mixture was slowly poured into 75 mL of 1N HCl. The pH of final solution was adjusted to 1. The aqueous was extracted with EtOAc (3×5 mL), washed with brine, dried over $Na_2SO_4$ and filtered to obtain a crude solid residue. The crude residue was purified via silica gel chromatography (0-10% MeOH—$CH_2Cl_2$ gradient) afforded 78 mg of the desired product 3a: LCMS Gradient 10-90%, 0.1% formic acid, 5 minutes, C18/ACN, RT=3.9 minutes (M+H) 546.22.

(R)-3-(2-(5-Chloro-1H-pyrrolo[2,3-b]pyridin-3-yl)-5-fluoropyrimidin-4-ylamino)-4,4-dimethylpentanoic acid (1)

To a cold (0° C.) solution of (R)-3-(2-(5-chloro-1-tosyl-1H-pyrrolo[2,3-b]pyridin-3-yl)-5-fluoro-pyrimidin-4-ylamino)-4,4-dimethylpentanoic acid, 3a, (0.08 g, 0.14 mmol) in MeOH (2.6 mL) was added sodium methanolate (2.91 mL of 25% w/v, 13.46 mmol). The reaction was stirred at room temperature for 30 min and then quenched by dilution into aqueous saturated ammonium chloride solution. The MeOH was evaporated in vacuo and the resulting aqueous phase diluted with EtOAc, then extracted with EtOAc (3×). The organics were dried ($Na_2SO_4$), filtered and concentrated in vacuo. Recrystallization from MeOH provided 52 mg of the desired product 1 as a white powder: $^1$H NMR (d6-DMSO) δ 12.25 (s, 1H): 12.0 (bs, 1H): 8.8 (s, 1H): 8.3 (s, 1H): 8.25 (s, 1H); 8.1 (s, 1H): 7.45 (d, 1H); 4.75 (t, 1H); 2.5 (m, 2H), 1.0 (s, 9H); LCMS Gradient 10-90%, 0.1% formic acid, 5 minutes, C18/ACN, RT=2.06 minutes (M+H) 392.21.

Preparation of Compounds 2, 43, 89 and 90

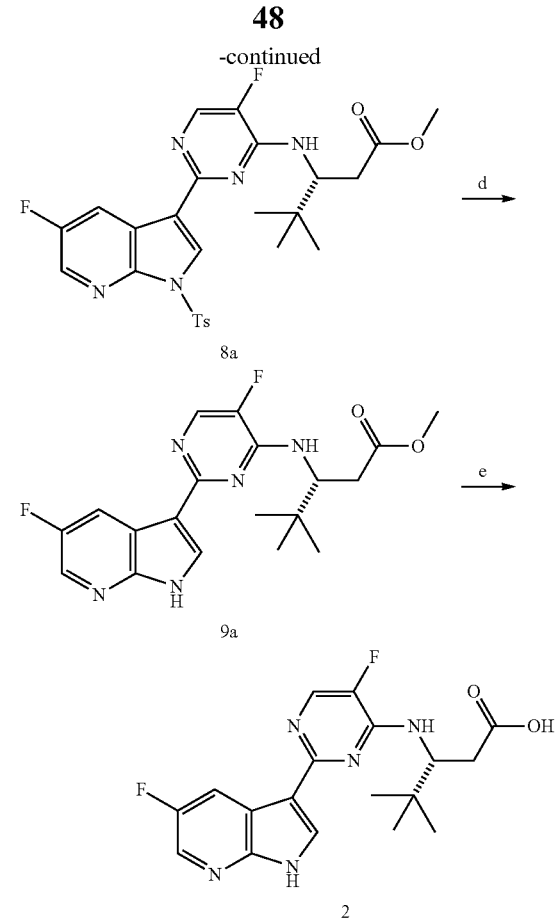

(a) AcCl, MeOH, reflux; (b) 2,4-dichloro-5-fluoropyrimidine, Et$_3$N, EtOH, THF, 55° C.; (c) 5-fluoro-1-(p-tolylsulfonyl)-3-(4,4,5,5,-tetramethyl-1,3,2-dioxaborolan-2-yl)pyrrolo[2,3-b]pyridine, 7a, Pd$_2$(dba)$_3$, XPhos, K$_3$PO$_4$, 2-MeTHF, H$_2$O, 115° C.; (d) HCl, dioxane, acetonitrile, 65° C.; (e) LiOH, THF, H$_2$O, 50° C.

Formation of (R)-1-methoxy-4,4-dimethyl-1-oxo-pentan-3-aminium chloride (5a)

(R)-3-amino-4,4-dimethylpentanoic acid, 2a, was dissolved in methanol (1.4 L). The solution was cooled in an ice bath and acetyl chloride (67.0 mL, 947.0 mmol) was added dropwise (maintaining the temperature below 10° C.). The reaction mixture was heated to 65° C. and stirred at that temperature for 3 h. The reaction mixture was cooled to room temperature and then flushed with toluene to remove volatiles. The crude material was used without further purification: $^1$H NMR (400 MHz, MeOH-d$_4$) δ 3.75 (s, 3H), 3.41 (t, 1H), 2.88 (dd, 1H), 2.64-2.46 (m, 1H), 1.04 (s, 9H).

Formation of (R)-methyl 3-((2-chloro-5-fluoropyrimidin-4-yl)amino)-4,4-dimethylpentanoate (6a)

(R)-1-methoxy-4,4-dimethyl-1-oxopentan-3-aminium chloride, 5a, (37 g, 189 mmol) was dissolved in a mixture of tetrahydrofuran (667 mL) and EtOH (74 mL). The solution was cooled in an ice bath. 2,4-dichloro-5-fluoro-pyrimidine (35 g, 208 mmol) was added, followed by the dropwise addition of triethylamine (85 mL, 606 mmol). The reaction mixture was heated at 55° C. for 17 h. The reaction mixture was then cooled to room temperature after which water (625 mL) and dichloromethane (625 mL) were added. The phases were Synthetic Scheme 2

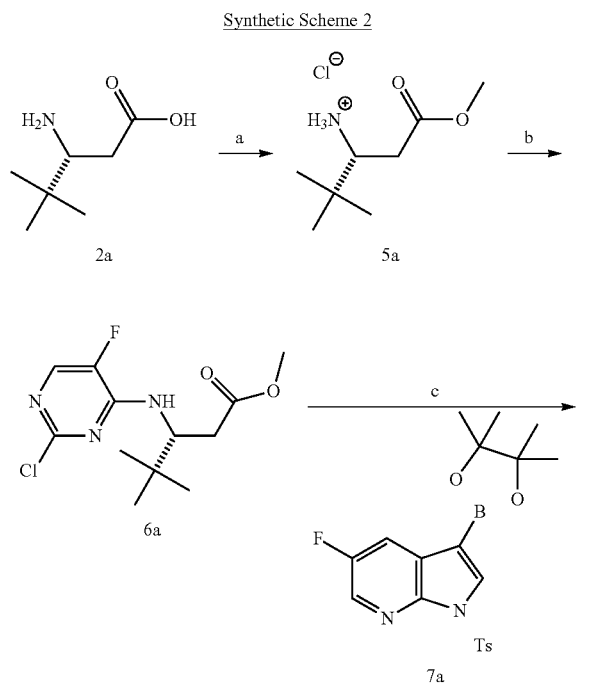

separated and the aqueous layer was washed with dichloromethane (625 mL). The organic layers were combined and washed with brine. The solvents were removed and the residue was purified on silica gel (EtOAc/Hexanes): LCMS Gradient 10-90%, 0.1% formic acid, 5 min, C18/ACN, RT=3.10 minutes (M+H) 291.02.

Formation of (R)-methyl 3-((5-fluoro-2-(5-fluoro-1-tosyl-1H-pyrrolo[2,3-b]pyridin-3-yl)pyrimidin-4-yl)amino)-4,4-dimethylpentanoate (8a)

A 2-MeTHF (253 mL)/water (56 mL) solution of 5-fluoro-1-(p-tolylsulfonyl)-3-(4,4,5,5-tetramethyl-1,3,2-dioxaborolan-2-yl)pyrrolo[2,3-b]pyridine, 7a, (24.3 g, 58.3 mmol), methyl (R)-methyl 3-((2-chloro-5-fluoropyrimidin-4-yl)amino)-4,4-dimethylpentanoate, 6a, (14.1 g, 48.6 mmol) and $K_3PO_4$ (30.9 g, 146 mmol) was purged with nitrogen for 0.75 h. XPhos (2.8 g, 5.8 mmol) and $Pd_2(dba)_3$ (1.1 g, 1.2 mmol) were added and the reaction mixture was stirred at 115° C. in a sealed tube for 2 h. The reaction mixture was cooled and the aqueous phase was removed. The organic phase was filtered through a pad of Celite and the mixture was concentrated to dryness. The residue was purified on silica gel (EA/Hex) to provide the desired product, 8a, (23.2 g): LCMS Gradient 10-90%, 0.1% formic acid, 5 min, C18/ACN, RT=2.18 minutes (M+H) 245.28.

Formation of (R)-methyl 3-((5-fluoro-2-(5-fluoro-1H-pyrrolo[2,3-b]pyridin-3-yl)pyrimidin-4-yl)amino)-4,4-dimethylpentanoate (9a)

To a solution of (R)-methyl 3-((5-fluoro-2-(5-fluoro-1-tosyl-1H-pyrrolo[2,3-b]pyridin-3-yl)pyrimidin-4-yl)amino)-4,4-dimethylpentanoate, 8a, (21 g, 39 mmol) in acetonitrile (157 mL) was added 4M HCl in dioxane (174 mL). The reaction mixture was heated to 65° C. for 4 h. The solution was cooled to room temperature and the solvents were removed under reduced pressure. The mixture was flushed with acetonitrile after which dichloromethane (100 mL), sat. aqueous $NaHCO_3$ (355 mL) and ethyl acetate (400 mL) were added. The phases were separated and the aqueous layer washed with ethyl acetate (500 mL). The organic layers were combined, dried ($Na_2SO_4$), filtered and concentrated in vacuo. The resulting residue was purified on silica gel (EtOAc/Hexanes) to provide the desired product, 9a, (12.1 g): LCMS Gradient 10-90%, 0.1% formic acid, 5 min, C18/ACN, RT=2.26 minutes (M+H) 391.05.

Formation (R)-3-((5-fluoro-2-(5-fluoro-1H-pyrrolo[2,3-b]pyridin-3-yl)pyrimidin-4-yl)amino)-4,4-dimethylpentanoic acid (2)

(R)-Methyl 3-((5-fluoro-2-(5-fluoro-1H-pyrrolo[2,3-b]pyridin-3-yl)pyrimidin-4-yl)amino)-4,4-dimethylpentanoate, 9a, (18.4 g, 47.1 mmol) was dissolved in tetrahydrofuran (275 mL) and aqueous 1M LiOH (141 mL) was added. The mixture was heated to 50° C. for 3.5 h. The reaction mixture was cooled to room temperature and 180 mL of water was added. The tetrahydrofuran was removed under reduced pressure and the residue was then flushed twice with hexanes. Diethylether (60 mL) was added and the layers separated. The pH of the aqueous layer was adjusted to 6 with 1N HCl. Ethyl acetate (540 mL) was added, the layers were separated and the aqueous layer was extracted with ethyl acetate (720 mL), then again with ethyl acetate (300 mL). The organic layers were combined, washed with brine (100 mL) and dried ($Na_2SO_4$). The solvents were removed while flushing with heptanes to provide the desired product, 2, (17.5 g): $^1$H NMR (400 MHz, DMSO-$d_6$) δ 12.23 (s, 1H), 12.03 (s, 1H), 8.68-8.52 (m, 1H), 8.27 (s, 1H), 8.19 (d, J=2.5 Hz, 1H), 8.13 (d, J=4.0 Hz, 1H), 7.39 (d, J=9.2 Hz, 1H), 4.83 (t, J=9.3 Hz, 1H), 2.71-2.51 (m, 2H), 0.97 (s, 9H); LCMS Gradient 10-90%, 0.1% formic acid, 5 min, C18/ACN, RT=1.96 minutes (M+H) 377.02.

The following analog was prepared in a similar fashion as the procedure described above for Compound 2:

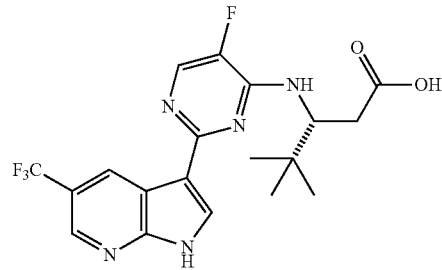

(R)-3-((5-fluoro-2-(5-(trifluoromethyl)-1H-pyrrolo[2,3-b]pyridin-3-yl)pyrimidin-4-yl)amino)-4,4-dimethylpentanoic acid (43)

$^1$H NMR (300 MHz, CDCl$_3$) δ 11.16 (s, 1H), 8.70 (s, 1H), 8.04 (d, J=3.2 Hz, 1H), 7.96 (s, 1H), 7.87 (s, 1H), 5.02 (d, J=8.1 Hz, 1H), 4.80 (t, J=9.6 Hz, 1H), 2.81 (d, J=9.9 Hz, 1H), 2.34 (t, J=11.3 Hz, 1H), 1.14 (s, 9H); LCMS Gradient 10-90%, 0.1% formic acid, 5 minutes, C18/ACN, Retention Time=2.49 minutes (M+H) 426.47.

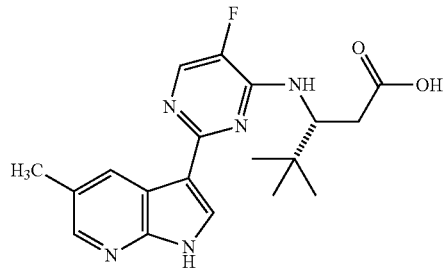 [SMILES: Cc1cnc2[nH]cc(-c3ncc(F)c(N[C@H](CC(=O)O)C(C)(C)C)n3)c2c1]

(R)-3-((5-fluoro-2-(5-methyl-1H-pyrrolo[2,3-b]pyridin-3-yl)pyrimidin-4-yl)amino)-4,4-dimethylpentanoic acid (90)

$^1$H NMR (300 MHz, CDCl$_3$) δ 8.68 (s, 1H), 8.43 (d, J=14.1 Hz, 2H), 8.23 (s, 1H), 4.96 (s, 2H), 2.88-2.55 (m, 4H), 2.45 (s, 3H), 1.00 (s, 9H); LCMS Gradient 10-90%, 0.1% formic acid, 5 minutes, C18/ACN, Retention Time=1.8 minutes (M+H) 372.5.

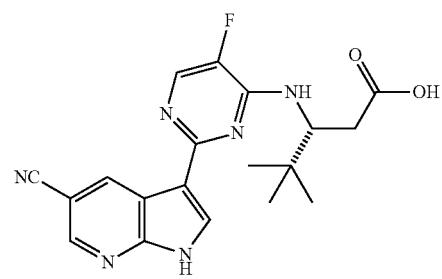 [SMILES: CC(C)(C)[C@@H](CC(=O)O)Nc1nc(-c2c[nH]c3ncc(C#N)cc23)ncc1F]

(R)-3-((2-(5-cyano-1H-pyrrolo[2,3-b]pyridin-3-yl)-5-fluoropyrimidin-4-yl)amino)-4,4-dimethylpentanoic acid (89)

LCMS Gradient 10-90%, 0.1% formic acid, 5 minutes, C18/ACN, Retention Time=2.1 minutes (M+H) 383.38.

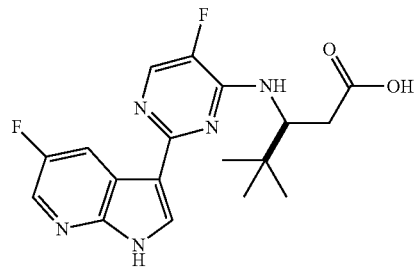 [SMILES: CC(C)(C)[C@H](CC(=O)O)Nc1nc(-c2c[nH]c3ncc(F)cc23)ncc1F]

(S)-3-((5-fluoro-2-(5-fluoro-1H-pyrrolo[2,3-b]pyridin-3-yl)pyrimidin-4-yl)amino)-4,4-dimethylpentanoic acid (4)

LCMS Gradient 10-90%, 0.1% formic acid, 5 minutes, C18/ACN, Retention Time=1.93 minutes (M+H) 376.21.

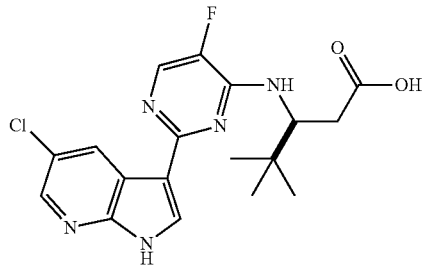 [SMILES: CC(C)(C)[C@H](CC(=O)O)Nc1nc(-c2c[nH]c3ncc(Cl)cc23)ncc1F]

(S)-3-((2-(5-chloro-1H-pyrrolo[2,3-b]pyridin-3-yl)-5-fluoropyrimidin-4-yl)amino)-4,4-dimethylpentanoic acid (3)

LCMS Gradient 10-90%, 0.1% formic acid, 5 minutes, C18/ACN, Retention Time=2.06 minutes (M+H) 392.21.

Preparation of Compound 69

Synthetic Scheme 3

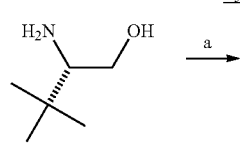

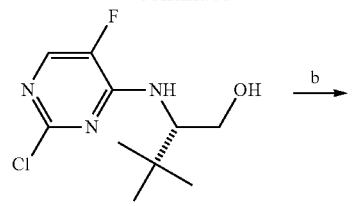

14a

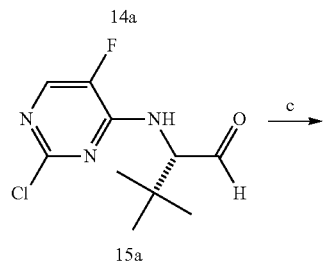

15a

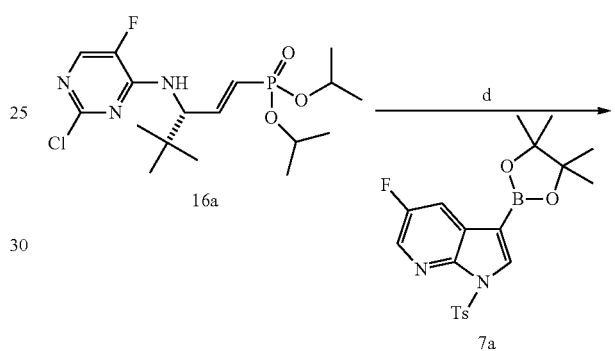

16a

7a

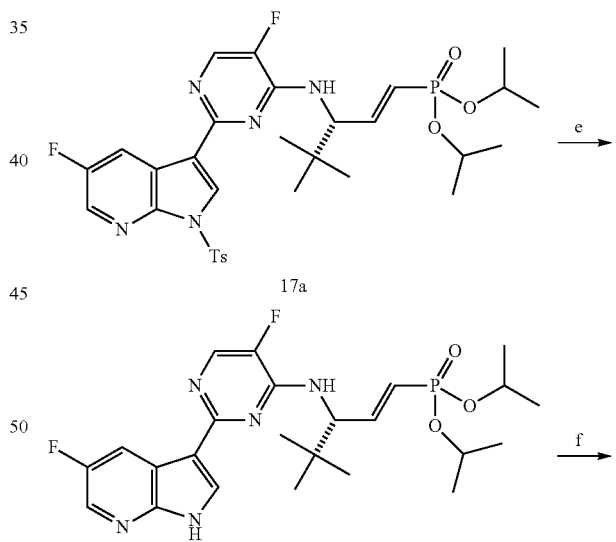

17a

18a

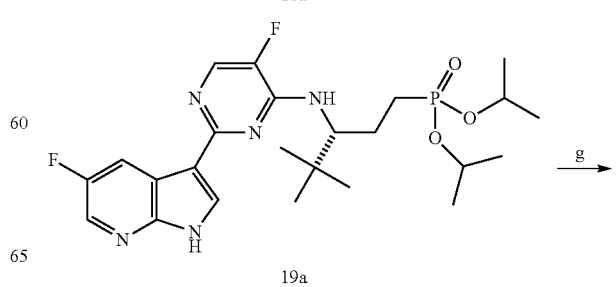

19a

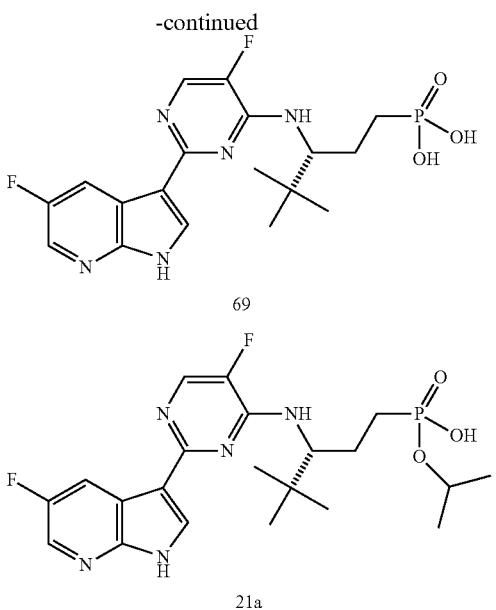

(a) 2,4-dichloro-5-fluoropyrimidine, Et₃N, DMF; (b) oxalyl chloride, DMF, DMSO, Et₃N, CH₂Cl₂; (c) [(ⁱPrO)₂PO]₂CH₂, NaH, THF; (d) 5-fluoro-1-(p-tolylsulfonyl)-3-(4,4,5,5-tetramethyl-1,3,2-dioxaborolan-2-yl)pyrrolo[2,3-b]pyridine, 7a, Pd₂(dba)₃, XPhos, K₃PO₄, 2-MeTHF, H₂O, 100° C.; (e) NaOMe, MeOH; (f) H₂, Pd/C, MeOH, 40 psi; (g) trimethylsilyliodide, CH₂Cl₂.

Formation of (S)-2-((2-chloro-5-fluoropyrimidin-4-yl)amino)-3,3-dimethylbutan-1-ol (14a)

To a mixture of (2S)-2-amino-3,3-dimethyl-butan-1-ol (5.0 g, 42.7 mmol) and 2,4-dichloro-5-fluoro-pyrimidine (5.7 g, 42.7 mmol) in DMF (50 mL) was added triethylamine (7.1 mL, 51.2 mmol). After 90 minutes, the reaction was diluted into aqueous saturated NH₄Cl solution and extracted twice with EtOAc. The combined organic phases were washed twice with brine, dried (MgSO₄), filtered and concentrated in vacuo. The crude residue was purified via silica gel chromatography (0-10% MeOH/CH₂Cl₂ gradient) to afford 6.7 g of the desired product, 1, as a sticky solid: LCMS Gradient 10-90%, 0.1% formic acid, 5 minutes, C18/ACN, RT=2.48 minutes (M+H) 248.32.

Formation of (S)-2-((2-chloro-5-fluoropyrimidin-4-yl)amino)-3,3-dimethylbutanal (15a)

To a cold (−78° C.) solution of oxalyl chloride (1.06 mL, 12.11 mmol) in dichloromethane (10 mL) was added dimethyl sulfoxide (1.43 mL, 20.18 mmol) dropwise. After stirring the mixture for 10 minutes at −78° C., a suspension of (2S)-2-[(2-chloro-5-fluoro-pyrimidin-4-yl)amino]-3,3-dimethyl-butan-1-ol, 14a, (1.0 g, 4.04 mmol) in dichloromethane (10 mL) was added. The reaction mixture was stirred for 30 minutes at −78° C. and triethylamine (3.38 mL, 24.22 mmol) was added. The mixture was slowly warmed to 0° C. over 2 hours. The mixture was diluted into aqueous saturated NaHCO₃ solution and extracted twice with EtOAc. The combined organic phases were dried (MgSO₄), filtered and concentrated in vacuo. The crude residue was purified via silica gel chromatography (0-15% EtOAc/CH₂Cl₂ gradient) to afford 680 mg of the desired product as a white solid.

Formation of (R,E)-diisopropyl (3-((2-chloro-5-fluoropyrimidin-4-yl)amino)-4,4-dimethylpent-1-en-1-yl)phosphonate (16a)

To a cold (0° C.) suspension of sodium hydride (0.163 g, 7.083 mmol) in THF (8.0 mL) was added 2-(diisopropoxy-phosphorylmethyl(isopropoxy)phosphoryl)-oxypropane (1.220 g, 3.542 mmol). After 15 minutes, a solution of (S)-2-((2-chloro-5-fluoropyrimidin-4-yl)amino)-3,3-dimethylbutanal, 15a, (0.580 g, 2.361 mmol) in THF (4 mL) was added dropwise. The reaction mixture was slowly warmed to room temperature over 1 hour. The mixture was diluted into aqueous saturated NH₄Cl solution and extracted with EtOAc. The organic phase was dried (MgSO₄), filtered and concentrated in vacuo. The resulting crude residue was purified via silica gel chromatography (10-50% EtOAc/CH₂Cl₂ gradient) to afford 810 mg of the desired product: LCMS Gradient 10-90%, 0.1% formic acid, 5 minutes, C18/ACN, RT=3.28 minutes (M+H) 408.36.

Formation of (R,E)-diisopropyl (3-((5-fluoro-2-(5-fluoro-1-tosyl-1H-pyrrolo[2,3-b]pyridin-3-yl)pyrimidin-4-yl)amino)-4,4-dimethylpent-1-en-1-yl)phosphonate (17a)

To a solution of (R,E)-diisopropyl (3-((2-chloro-5-fluoropyrimidin-4-yl)amino)-4,4-dimethylpent-1-en-1-yl)phosphonate, 16a, (0.81 g, 1.99 mmol) and 5-fluoro-1-(p-tolylsulfonyl)-3-(4,4,5,5-tetramethyl-1,3,2-dioxaborolan-2-yl)pyrrolo[2,3-b]pyridine, 7a, (1.24 g, 3.00 mmol) in 2-Me-THF (16 mL) was added K₃PO₄ (1.27 g, 3.00 mmol) and water (4 mL). The biphasic mixture was degassed under a stream of nitrogen for 15 minutes. Then, X-Phos (0.11 g, 0.24 mmol) and Pd₂(dba)₃ (0.06 g, 0.06 mmol) was added to the mixture. After degassing with nitrogen for an additional 5 minutes, the vessel was sealed and heated at 100° C. for 2 hours. The mixture was cooled to room temperature and diluted with EtOAc, filtered through celite. The filtrate was washed with brine, dried (MgSO₄), filtered and concentrated in vacuo. The crude residue was purified via silica gel chromatography (0-50% EtOAc/CH₂Cl₂ gradient) to afford 1.123 g of the desired product: ¹H NMR (400 MHz, d6-DMSO) δ 8.55-8.42 (m, 3H), 8.31 (d, J=3.7 Hz, 1H), 8.06 (d, J=8.3 Hz, 2H), 7.73 (d, J=8.9 Hz, 1H), 7.44 (d, J=8.4 Hz, 2H), 6.80 (ddd, J=22.2, 17.1, 6.9 Hz, 1H), 5.99 (dd, J=20.3, 17.1 Hz, 1H), 4.95 (t, J=7.6 Hz, 1H), 4.51-4.32 (m, 2H), 2.35 (s, 3H), 1.19-1.14 (m, 6H), 1.11 (dd, J=6.0, 4.4 Hz, 6H), 1.02 (s, 9H).); LCMS Gradient 10-90%, 0.1% formic acid, 5 minutes, C18/ACN, RT=4.06 minutes (M+H) 662.35.

Formation of (R,E)-diisopropyl (3-((5-fluoro-2-(5-fluoro-1H-pyrrolo[2,3-b]pyridin-3-yl)pyrimidin-4-yl)amino)-4,4-dimethylpent-1-en-1-yl)phosphonate (18a)

To a solution of (R,E)-diisopropyl (3-((5-fluoro-2-(5-fluoro-1-tosyl-1H-pyrrolo[2,3-b]pyridin-3-yl)pyrimidin-4-yl)amino)-4,4-dimethylpent-1-en-1-yl)phosphonate, 17a, (1.0 g, 1.51 mmol) in methanol (30 mL) was added sodium methoxide (8.2 mL of 25% wt solution in MeOH). After 3 minutes, the mixture was diluted into aqueous saturated NH₄Cl solution and extracted twice with EtOAc. The combined organic phases were dried (MgSO₄), filtered and concentrated in vacuo. The crude residue was purified via silica gel chromatography (0-15% MeOH/CH₂Cl₂ gradient) to

Formation of (R)-diisopropyl-(3-((5-fluoro-2-(5-fluoro-1H-pyrrolo[2,3-b]pyridin-3-yl)pyrimidin-4-yl)amino)-4,4-dimethylpentyl)phosphonate (19a)

To a solution of (R,E)-diisopropyl (3-((5-fluoro-2-(5-fluoro-1H-pyrrolo[2,3-b]pyridin-3-yl)pyrimidin-4-yl)amino)-4,4-dimethylpent-1-en-1-yl)phosphonate, 18a, (0.36 g, 0.71 mmol) in MeOH (7 mL) was added Pd on Carbon (10%, wet, Degussa, 0.07 g, 0.07 mmol). The reaction mixture was stirred in a Parr hydrogenation flask under 50 psi of hydrogen overnight. The mixture was diluted with EtOAc and filtered through celite. The filtrate was concentrated in vacuo to give the desired product as dark gray solid: $^1$H NMR (400 MHz, d6-DMSO) δ 12.28 (s, 1H), 8.46 (dd, J=9.9, 2.7 Hz, 1H), 8.30-8.21 (m, 2H), 8.15 (d, J=3.9 Hz, 1H), 7.29 (d, J=9.5 Hz, 1H), 4.51 (dt, J=12.3, 6.2 Hz, 2H), 4.37 (t, J=9.8 Hz, 1H), 1.95-1.60 (m, 3H), 1.59-1.35 (m, 1H), 1.24-1.09 (m, 12H), 0.99 (s, 9H); LCMS Gradient 10-90%, 0.1% formic acid, 5 minutes, C18/ACN, RT=2.46 minutes (M+H) 510.56.

Formation of (R)-(3-((5-fluoro-2-(5-fluoro-1H-pyrrolo[2,3-b]pyridin-3-yl)pyrimidin-4-yl)amino)-4,4-dimethylpentyl)phosphonic acid (69)

To a solution of (R)-diisopropyl-(3-((5-fluoro-2-(5-fluoro-1H-pyrrolo[2,3-b]pyridin-3-yl)pyrimidin-4-yl)amino)-4,4-dimethylpentyl)phosphonate, 19a, (0.16 g, 0.32 mmol) in dichloromethane (8 mL) was added iodotrimethylsilane (0.45 mL, 3.18 mmol). The reaction mixture was stirred at room temperature. After 1 hour, LCMS showed the reaction to be incomplete. An additional 0.90 mL of iodotrimethylsilane (0.64 mmol) was added to the reaction mixture. After 5 hours, the mixture was concentrated in vacuo and the resulting residue was purified via preparatory HPLC (CH$_3$CN/1% aqueous TFA) to afford 8 mg of phosphonic acid, 69, and 34 mg of phosphonate, 21a.

Spectral data for phosphonic acid, 69: $^1$H NMR (300 MHz, MeOD) δ 8.59-8.39 (m, 2H), 8.32 (t, J=5.3 Hz, 2H), 4.59 (d, J=9.5 Hz, 2H), 2.21 (s, 1H), 1.79 (dddd, J=28.6, 23.0, 13.2, 6.9 Hz, 3H), 1.11 (d, J=9.5 Hz, 9H); LCMS Gradient 10-90%, 0.1% formic acid, 5 minutes, C18/ACN, RT=1.81 minutes (M+H) 426.09.

Spectral data for phosphonate 21a: $^1$H NMR (300 MHz, MeOD) δ 8.57-8.41 (m, 2H), 8.32 (d, J=5.6 Hz, 2H), 4.73-4.41 (m, 2H), 2.25 (d, J=25.7 Hz, 1H), 2.06-1.43 (m, 3H), 1.32-1.20 (m, 6H), 1.11 (d, J=11.2 Hz, 9H); LCMS Gradient 10-90%, 0.1% formic acid, 5 minutes, C18/ACN, RT=2.06 minutes (M+H) 468.13.

Preparation of Compounds 16 and 17

Synthetic Scheme 4

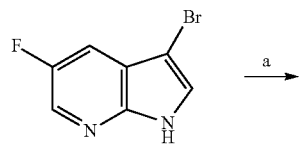

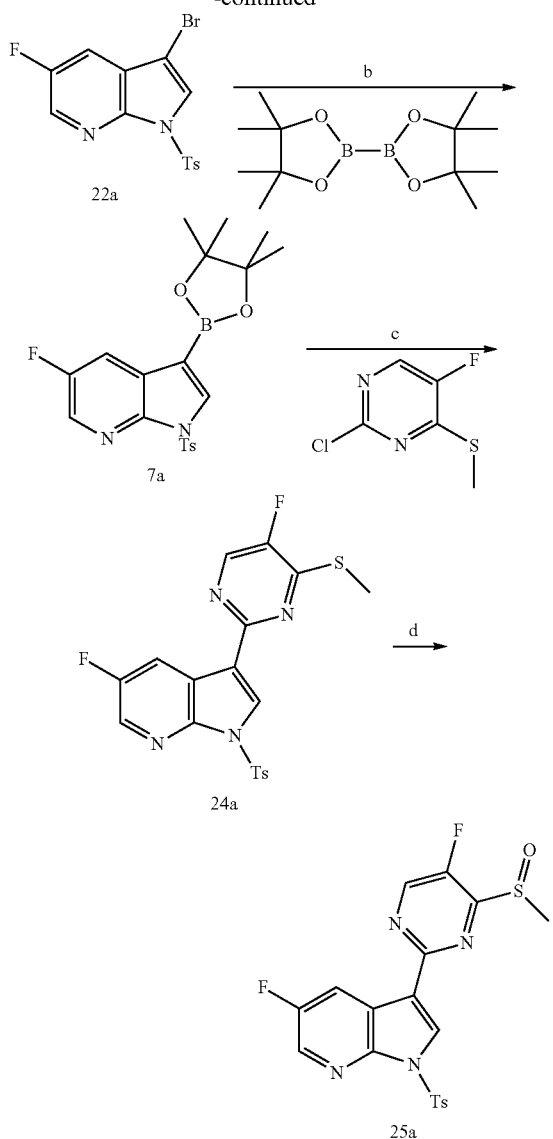

(a) NaH, TsCl, DMF; (b) KOAc, PdCl$_2$(dppf), dioxane, water, reflux; (c) Pd(PPh$_3$)$_4$, Na$_2$CO$_3$, DME, water; (d) morpholine-4-carbonyl chloride, $^i$Pr$_2$NEt, CH$_2$Cl$_2$;

Formation of 3-bromo-5-fluoro-1-(p-tolylsulfonyl)pyrrolo[2,3-b]pyridine (22a)

3-bromo-5-fluoro-1H-pyrrolo[2,3-b]pyridine (5.0 g, 23.3 mmol) was dissolved in DMF (37.5 mL) and cooled to 0° C. Sodium hydride (1.5 g, 37.2 mmol) was added and the reaction mixture was stirred for 10 minutes and then treated with tosyl chloride (6.6 g, 34.9 mmol). The mixture was stirred for 30 minutes at 0° C. and then at room temperature for another 90 minutes. The reaction mixture was poured into water (100 mL) and the resulting solid was collected, washed with water and hexanes three times and dried in vacuo to afford 8.26 g of 3-bromo-5-fluoro-1-(p-tolylsulfonyl)pyrrolo[2,3-b]pyridine, 22a: $^1$H NMR (300 MHz, DMSO-d$_6$) δ 8.48 (s, 1H), 8.31 (s, 1H), 8.01 (d, J=8.3 Hz, 2H), 7.92 (dd, J=8.4, 2.7 Hz, 1H), 7.44 (d, J=8.5 Hz, 2H), 2.35 (s, 3H).

Formation of 5-fluoro-1-(p-tolylsulfonyl)-3-(4,4,5,5-tetramethyl-1,3,2-dioxaborolan-2-yl)pyrrolo[2,3-b]pyridine (7a)

3-bromo-5-fluoro-1-(p-tolylsulfonyl)pyrrolo[2,3-b]pyridine, 22a, (4.0 g, 10.8 mmol), 4,4,5,5-tetramethyl-2-(4,4,5,5-tetramethyl-1,3,2-dioxaborolan-2-yl)-1,3,2-dioxaborolane (8.3 g, 32.5 mmol) and potassium acetate (3.2 g, 32.5 mmol) were taken in dioxane (40 mL) containing a few drops of water. After purging with nitrogen for 30 minutes, $PdCl_2$ (dppf) (0.8 g, 1.1 mmol) was added. Nitrogen purging was continued for an additional 40 minutes, then the reaction mixture was heated to reflux overnight. After cooling down, the mixture was filtered through Florisil (60 g), washed with dichloromethane (220 mL) and concentrated in vacuo to provide a brown oil. The crude product was taken into hexane (40 mL) and TBME (14 mL) and heated to reflux. After cooling to room temperature, the resulting suspension was filtered to provide 2.6 g of the desired product as a white solid: $^1$H NMR (300 MHz, DMSO-$d_6$) δ 8.42 (dd, J=2.7, 1.4 Hz, 1H), 8.14 (s, 1H), 8.06 (d, J=8.4 Hz, 2H), 7.85 (dd, J=8.6, 2.8 Hz, 1H), 7.44 (d, J=8.3 Hz, 2H), 2.36 (s, 3H), 1.32 (s, 12H).

Formation of 5-fluoro-3-(5-fluoro-4-methylsulfanyl-pyrimidin-2-yl)-1-(p-tolylsulfonyl)pyrrolo[2,3-b]pyridine (24a)

2-chloro-5-fluoro-4-methylsulfanyl-pyrimidine (1.6 g, 9.0 mmol), 5-fluoro-1-(p-tolylsulfonyl)-3-(4,4,5,5-tetramethyl-1,3,2-dioxaborolan-2-yl)pyrrolo[2,3-b]pyridine, 7a, (2.5 g, 6.0 mmol) and $Na_2CO_3$ (1.9 g, 18.0 mmol) were dissolved in DME (37.5 mL) and water (7.5 mL). The mixture was purged with nitrogen for 20 minutes, treated with $Pd(PPh_3)_4$, purged with nitrogen for another 20 minutes and heated to reflux overnight. After cooling to room temperature, water (35 mL) was added and the resulting suspension was stirred for 30 minutes. The precipitate was collected by filtration, washed with water and acetonitrile and dried overnight at 50° C., affording 2.3 g (88.5%) of the desired product as a white solid: $^1$H NMR (300 MHz, DMSO-$d_6$) δ 8.70-8.57 (m, 2H), 8.55-8.42 (m, 2H), 8.09 (d, J=8.4 Hz, 2H), 7.45 (d, J=8.4 Hz, 2H), 2.76 (s, 3H), 2.36 (s, 3H).

Formation of 5-fluoro-3-(5-fluoro-4-methylsulfinyl-pyrimidin-2-yl)-1-(p-tolylsulfonyl)pyrrolo[2,3-b]pyridine (25a)

5-fluoro-3-(5-fluoro-4-methylsulfanyl-pyrimidin-2-yl)-1-(p-tolylsulfonyl)pyrrolo[2,3-b]pyridine, 24a, (2.30 g, 5.32 mmol) was dissolved in dichloromethane (107 mL) and treated portionwise with 3-chloroperbenzoic acid (1.19 g, 5.30 mmol), keeping the temperature below 20° C. After stirring for 2 hours, another portion of 3-chloroperbenzoic acid (0.18 g, 0.80 mmol) was added, and stirring was continued for another hour. A third portion of 3-chloroperbenzoic acid (0.07 g, 0.05 mmol) was added and stirring was continued for 30 minutes. The reaction mixture was treated with an aqueous 15% $K_2CO_3$ solution (30 mL) and the layers were separated. The organic layer was washed with 15% $K_2CO_3$ and brine, dried ($Na_2SO_4$), filtered and concentrated in vacuo to afford 2.3 g (96%) of the desired product as a yellow solid, which was used without further purification: $^1$H NMR (300 MHz, DMSO-$d_6$) δ 9.12 (d, J=1.5 Hz, 1H), 8.70 (s, 1H), 8.67 (dd, J=9.1, 2.8 Hz, 1H), 8.53 (d, J=1.5 Hz, 1H), 8.11 (d, J=8.4 Hz, 2H), 7.46 (d, J=8.2 Hz, 2H), 3.05 (s, 3H), 2.36 (s, 3H).

The following analog was prepared in a similar fashion as the procedure described above for sulfoxide, 25a:

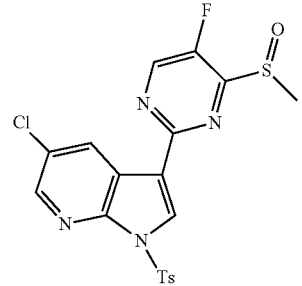

5-chloro-3-(5-fluoro-4-(methylsulfinyl)pyrimidin-2-yl)-1-tosyl-1H-pyrrolo[2,3-b]pyridine (1a)

$^1$H NMR (300 MHz, d6-DMSO) δ 9.12 (d, J=1.3 Hz, 1H), 8.90 (d, J=2.4 Hz, 1H), 8.68 (s, 1H), 8.53 (d, J=2.4 Hz, 1H), 8.12 (d, J=8.4 Hz, 2H), 7.46 (d, J=8.4 Hz, 2H), 2.54-2.48 (m, 3H), 2.36 (s, 3H).

Synthetic Scheme 5

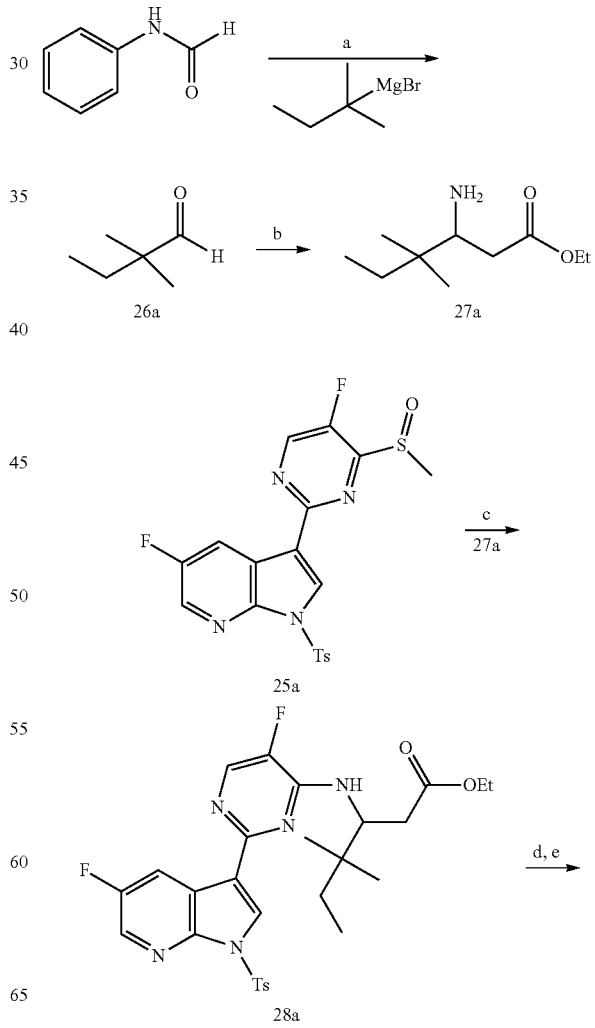

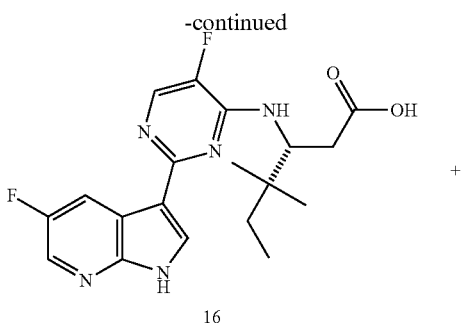

16

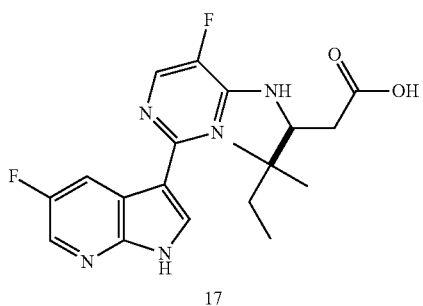

17 a) Et₂O; b) malonic acid, ammonium acetate, ethanol, 80° C.; c) 5-fluoro-3-(5-fluoro-4-(methylsulfinyl)pyrimidin-2-yl)-1-tosyl-1H-pyrrolo[2,3-b]pyridine, 25a, ⁱPr₂NEt, THF, 80° C.; (d) LiOH,THF—H₂O (3:1), 130° C. microwave; e) SFC chiral separation Formation of 2,2-dimethylbutanal (26a)

To a solution of 1,1-dimethylpropyl magnesium chloride (20.0 mL of 1 M, 20.0 mmol) in ether (25 mL) was added N-methyl-N-phenyl formamide (5.26 mL, 20.0 mmol) in one portion (exothermic). The yellow solution was gently refluxed for two hours and stirred at room temperature for three hours. At the end of this period the Grignard complex was quenched by pouring onto 500 g of crushed ice and 20 ml. of concentrated sulfuric acid. The ether layer was separated and the aqueous phase extracted three times with 50 mL portions of ether. The combined ether extracts were dried (MgSO₄) and concentrated in vacuo. The crude residue was purified by short-path distillation to afford 1.0 g of pure 2,2-dimethylbutanal as a colorless oil: $^1$H NMR (400 MHz, CDCl₃) δ 4.17 (q, J=7.1 Hz, 2H), 3.03 (dd, J=10.9, 2.3 Hz, 1H), 2.53 (dd, J=15.3, 2.3 Hz, 1H), 2.15 (dd, J=15.3, 10.9 Hz, 1H), 1.50-1.33 (m, 3H), 1.28 (dd, J=9.0, 5.3 Hz, 3H), 1.26-1.17 (m, 1H), 0.85 (d, J=5.8 Hz, 6H).

Formation of ethyl 3-amino-4,4-dimethylhexanoate (27a)

A mixture of 2,2-dimethylbutanal, 26a, (3.00 g, 26.75 mmol), malonic acid (2.08 g, 1.29 mL, 20.00 mmol), ammonium acetate (3.08 g, 40.00 mmol) in ethanol (5 mL) was refluxed for three hours. The precipitate was removed by filtration and washed with ethanol. The solution was used without further purification.

Sulfuric acid (1.962 g, 1.066 mL, 20.00 mmol) was added to above ethanol solution and the resulting mixture was heated to reflux for two hours. The solvent was removed under reduced pressure. Water (20 mL) and ether (10 mL) were added to the crude residue. The aqueous layer was separated and washed with ether (10 mL). The organic layers were discarded. The aqueous solution was neutralized with sodium hydroxide solution (6N) and saturated sodium bicarbonate solution to basic, and extracted with ethyl acetate (3×10 mL). The combined organic layers were washed with water (10 mL), brine (10 mL), filtered, dried (MgSO₄), filtered and concentrated in vacuo to give 0.5 g of the desired product as a light yellow sticky oil, which turned into solid upon standing. The crude product was used without further purification: $^1$H NMR (400 MHz, CDCl₃) δ 4.17 (q, J=7.1 Hz, 2H), 3.03 (dd, J=10.9, 2.3 Hz, 1H), 2.53 (dd, J=15.3, 2.3 Hz, 1H), 2.15 (dd, J=15.3, 10.9 Hz, 1H), 1.50-1.33 (m, 3H), 1.28 (dd, J=9.0, 5.3 Hz, 3H), 1.26-1.17 (m, 1H), 0.85 (d, J=5.8 Hz, 6H).

Formation of ethyl 3-((5-fluoro-2-(5-fluoro-1-tosyl-1H-pyrrolo[2,3-b]pyridin-3-yl)pyrimidin-4-yl)amino)-4,4-dimethylhexanoate (28a)

To a suspension of ethyl 3-amino-4,4-dimethylhexanoate, 27a, (0.19 g. 1.00 mmol) and 5-fluoro-3-(5-fluoro-4-methylsulfinyl-pyrimidin-2-yl)-1-(p-tolylsulfonyl)pyrrolo[2,3-b]pyridine, 25a, (0.54 g, 1.20 mmol) in THF (14.4 mL) was added N,N-diisopropylethylamine (0.26 mL, 1.50 mmol). The mixture was refluxed at 80° C. overnight. After removing the solvents under reduced pressure, the crude product was purified by silica gel chromatography (0-50% EtOAc/Hexane gradient) to afford 155 mg of the desired product as a light yellow solid: $^1$H NMR (300 MHz, CDCl₃) δ 8.61 (dd, J=9.0, 2.9 Hz, 1H), 8.56 (s, 1H), 8.33 (dd, J=2.7, 1.0 Hz, 1H), 8.11 (d, J=8.4 Hz, 2H), 7.30 (d, J=8.2 Hz, 2H), 5.19 (dd, J=10.1, 2.2 Hz, 1H), 4.94 (td, J=10.0, 3.7 Hz, 1H), 3.99 (dt, J=13.7, 6.8 Hz, 2H), 2.40 (s, 3H), 1.42 (dt, J=14.1, 6.9 Hz, 2H), 1.05 (t, J=7.1 Hz, 3H), 1.01-0.94 (m, 8H); $^{19}$F NMR (282 MHz, CDCl₃) δ −130.39-133.75 (dd, J=9.0, 1.1 Hz, 1F), −158.56 (s, 1F); LCMS Gradient 10-90%, 0.1% formic acid, 5 minutes, C18/ACN, RT=4.18 minutes (M+H) 572.07.

Formation of 3-((5-fluoro-2-(5-fluoro-1H-pyrrolo[2,3-b]pyridin-3-yl)pyrimidin-4-yl)amino)-4,4-dimethylhexanoic acid (16, 17)

To a solution of ethyl 3-((5-fluoro-2-(5-fluoro-1-tosyl-1H-pyrrolo[2,3-b]pyridin-3-yl)pyrimidin-4-yl)amino)-4,4-dimethylhexanoate, 28a, (0.16 g, 0.27 mmol) in THF (6 mL) was added LiOH (1.50 mL of 1 M solution, 1.50 mmol). The reaction mixture was heated in a microwave reactor at 130° C. for thirty minutes. The reaction was quenched by the addition of aqueous saturated NH₄Cl solution. The resulting white precipitate was collected and washed with water, acetonitrile and ether. The combined organic phases were then concentrated in vacuo to give pure desired carboxylic acid as a solid. The solid was diluted with hydrochloric acid (2 mL of 1N solution) and lyophilized to give 110 mg of the desired product as a hydrochloride salt (light yellow powder): $^1$H NMR (300 MHz, MeOD) δ 8.73 (d, J=9.5 Hz, 1H), 8.16 (s, 1H), 8.15-8.10 (m, 1H), 7.93 (d, J=4.0 Hz, 1H), 5.02 (d, J=6.4 Hz, 1H), 3.75 (ddd, J=6.7, 4.2, 2.5 Hz, 3H), 2.66 (d, J=11.2 Hz, 1H), 2.45 (dd, J=14.0, 9.9 Hz, 1H), 1.93-1.83 (m, 3H), 1.46 (d, J=7.5 Hz, 2H), 1.05-0.93 (m, 9H); $^{19}$F NMR (282 MHz, MeOD) 6-139.17 (s, 1F), −160.86 (s, 1F); LCMS Gradient 10-90%, 0.1% formic acid, 5 minutes, C18/ACN, RT=2.04 minutes (M+H) 390.23.

The racemic mixture was submitted to SFC chiral separation to give the individual enantiomers, 16, and 17.

Preparation of Compounds 14 and 15

Synthetic Scheme 6

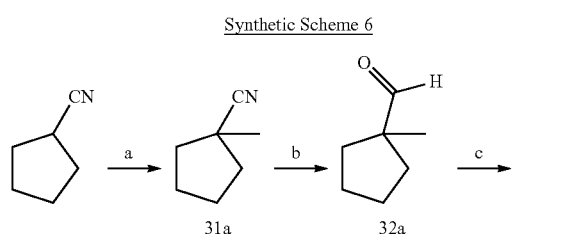

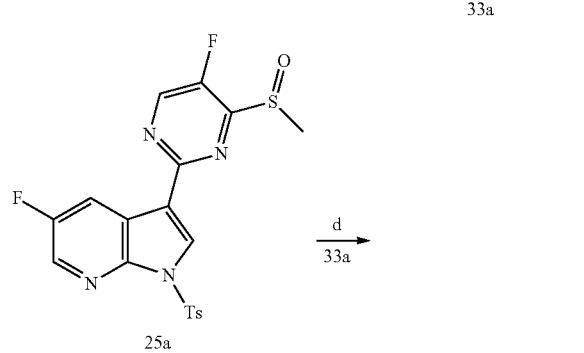

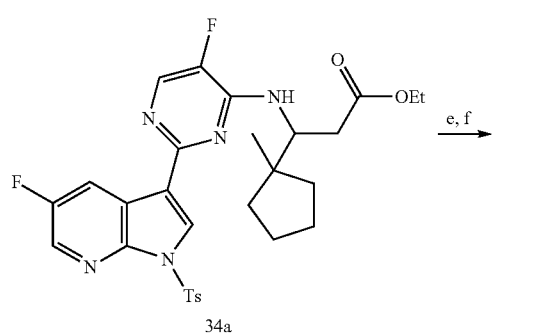

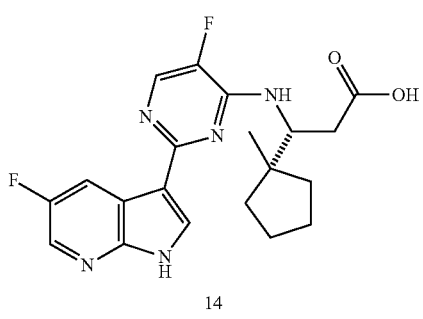
14

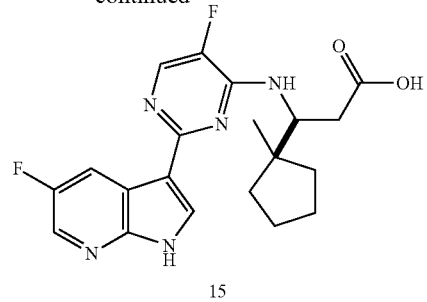
15 a) LiHMDS, MeI, THF -78° C.; b) DIBAL, CH₂Cl₂, -78° C.; c) malonic acid, ammonium acetate, ethanol, 80° C.; d) ⁱPr₂NEt, THF, 80° C.; e) LiOH, THF—H₂O (3:1), 130° C., microwave; f) SFC chiral separation Formation of 1-methylcyclopentanecarbonitrile (31a)

To a cold (−78° C.) solution of LiHMDS (48.0 mL of 1 M solution in tetrahydrofuran, 48.0 mmol) in tetrahydrofuran was added dropwise a solution of cyclopentanecarbonitrile (3.81 g, 40.0 mmol) in tetrahydrofuran (10 mL) over a 5 minute period. After stirring at −78° C. for thirty minutes, methyl iodide (3.74 mL, 60.00 mmol) was added in one portion. The reaction was allowed to warm to room temperature overnight. The solution was cooled to 0° C., ethyl acetate (50 mL) and aqueous saturated ammonium chloride solution (20 mL) was added. Additional water (10 mL) was added to dissolve the solid. The organic layer was separated and washed with aqueous saturated ammonium chloride (20 mL). The aqueous layer was extracted with ethyl acetate (2×20 mL). The combined organic phases were washed with brine, dried (MgSO₄), filtered and concentrated in vacuo to give a 4.7 g of a yellow oil that was used without further purification: ¹H NMR (400 MHz, CDCl₃) δ 2.04-1.93 (m, 2H), 1.77-1.65 (m, 2H), 1.66-1.55 (m, 2H), 1.54 (m, 2H), 1.25 (s, 3H).

Formation of 1-methylcyclopentanecarbaldehyde (32a)

To a cold (−78° C.) solution of diisobutylaluminum hydride (100.0 mL of 1 M solution, 100.0 mmol) in dichloromethane was added dropwise a solution of 1-methylcyclopentanecarbonitrile, 31a, (4.3 g, 40.0 mmol) in dichloromethane (5 mL). The reaction was kept at −78° C. for thirty minutes. The dry-ice bath was removed and methanol (1 mL) was added to quench the reaction. Potassium sodium tartrate solution (30 mL, 10% solution) was added and the mixture stirred vigorously. The organic layer was separated and the aqueous layer was extracted with dichloromethane (3×20 mL). The combined organic phases were washed with brine, dried over sodium sulfate, filtered and concentrated in vacuo to give 3 g of a light yellow oil that was used without further purification: ¹H NMR (400 MHz, CDCl₃) δ 2.04-1.93 (m, 2H), 1.77-1.65 (m, 2H), 1.66-1.55 (m, 2H), 1.54 (m, 2H), 1.25 (s, 3H).

Formation of ethyl 3-amino-3-(1-methylcyclopentyl)propanoate (33a)

A mixture of 1-methylcyclopentanecarbaldehyde, 32a, (3.00 g, 26.75 mmol), malonic acid (1.29 mL, 20.00 mmol) and ammonium acetate (3.08 g, 40.00 mmol) in ethanol (5 mL) was refluxed for 12 hours. The precipitate was removed by filtration and washed with ethanol. The filtrate was used without further purification.

Sulfuric acid (1.07 mL, 20.00 mmol) was added to the above ethanol solution and heated to reflux for 2 h. The solvent was removed under reduced pressure. The residue was diluted with water (20 mL) and ether (10 mL). The aqueous layer was separated and washed with ether (10 mL). The organic layers were discarded. The aqueous solution was neutralized with sodium hydroxide solution (6N) to basic, and extracted with ethyl acetate (3×10 mL). The combined organic layers were washed with water (10 mL), brine (10 mL), filtered, dried (MgSO$_4$), filtered and concentrated in vacuo to give 1.5 g of a light yellow sticky oil that turned into solid upon standing. The crude product was used without further purification: $^1$H NMR (400 MHz, CDCl$_3$) δ 4.25-4.14 (q, 2H), 3.40 (bs, 2H), 3.20-3.09 (m, 1H), 2.48 (ddd, J=26.2, 16.0, 6.6 Hz, 2H), 1.77-1.58 (m, 4H), 1.52 (m, 2H), 1.47-1.32 (m, 2H), 1.25 (m, 3H), 0.94 (s, 3H).

Formation of ethyl 3-((5-fluoro-2-(5-fluoro-1-tosyl-1H-pyrrolo[2,3-b]pyridin-3-yl)pyrimidin-4-yl) amino)-3-(1-methylcyclopentyl)propanoate (34a)

A suspension of ethyl 3-amino-3-(1-methylcyclopentyl) propanoate, 33a, (0.20 g, 1.00 mmol), 5-fluoro-3-(5-fluoro-4-methylsulfinyl-pyrimidin-2-yl)-1-(p-tolylsulfonyl)-pyrrolo[2,3-b]pyridine, 25a (0.54 g, 1.20 mmol), and N,N-diisopropylethylamine (0.26 mL, 1.50 mmol) in THF (14.4 mL) was refluxed at 80° C. overnight. After removing the solvent in vacuo, the crude product was purified by silica gel chromatography (0-50% EtOAc/Hexanes gradient) to afford 300 mg of the desired product as a light yellow solid: $^1$H NMR (400 MHz, CDCl$_3$) δ 8.49 (dd, J=9.0, 2.8 Hz, 1H), 8.46 (s, 1H), 8.23 (d, J=1.5 Hz, 1H), 8.02 (d, J=8.3 Hz, 2H), 7.99 (d, J=3.1 Hz, 1H), 7.20 (d, J=7.8 Hz, 2H), 5.23 (d, J=8.9 Hz, 1H), 4.80 (td, J=9.7, 3.6 Hz, 1H), 4.04 (q, J=7.1 Hz, 1H), 3.91 (q, J=7.1 Hz, 2H), 2.73-2.58 (m, 1H), 2.44 (dd, J=14.7, 9.6 Hz, 1H), 2.33-2.21 (m, 3H), 1.72-1.46 (m, 7H), 1.42-1.31 (m, 1H), 1.28 (t, J=6.1 Hz, 1H), 1.17 (dd, J=13.4, 6.2 Hz, 2H), 0.98 (t, J=7.1 Hz, 6H); LCMS Gradient 10-90%, 0.1% formic acid, 5 minutes, C18/ACN, RT=4.25 minutes (M+H) 584.29.

Formation of ethyl 3-((5-fluoro-2-(5-fluoro-1-tosyl-1H-pyrrolo[2,3-b]pyridin-3-yl)pyrimidin-4-yl) amino)-3-(1-methylcyclopentyl)propanoate (14, 15)

To a solution of ethyl 3-((5-fluoro-2-(5-fluoro-1-tosyl-1H-pyrrolo[2,3-b]pyridin-3-yl)pyrimidin-4-yl)amino)-3-(1-methylcyclopentyl)propanoate, 34a, (0.16 g, 0.27 mmol) in THF (6 mL) was added LiOH (1.50 mL of 1 M solution, 1.50 mmol). The reaction mixture was irradiated in a microwave reactor for 30 minutes at 130° C. Aqueous saturated NH$_4$Cl solution was added to acidify the mixture. The resulting white precipitate was collected and washed with water, acetonitrile and ether. The solid was then dried in vacuo to give pure desired acid. To the solid was added hydrochloric acid (2 mL of 1N solution) and the mixture was lyophilized to give 120 mg of the desired product as a hydrochloride salt (light yellow powder): $^1$H NMR (400 MHz, MeOD) δ 8.64 (d, J=9.3 Hz, 1H), 8.14 (d, J=8.3 Hz, 2H), 7.97 (d, J=3.6 Hz, 1H), 4.99 (d, J=6.3 Hz, 1H), 3.37 (s, 1H), 2.75 (dd, J=14.9, 3.6 Hz, 1H), 2.55 (dd, J=14.8, 9.7 Hz, 1H), 1.83-1.57 (m, 6H), 1.54-1.42 (m, 1H), 1.37 (dd, J=11.9, 5.6 Hz, 1H), 1.11 (d, J=19.2 Hz, 3H); LCMS Gradient 10-90%, 0.1% formic acid, 5 minutes, C18/ACN, RT=2.10 minutes (M+H) 401.94.

The racemic mixture of carboxylic acids was submitted to SFC chiral separation to give the individual enantiomers, 14 and 15.

Preparation of Compounds 20 and 23

Synthetic Scheme 7

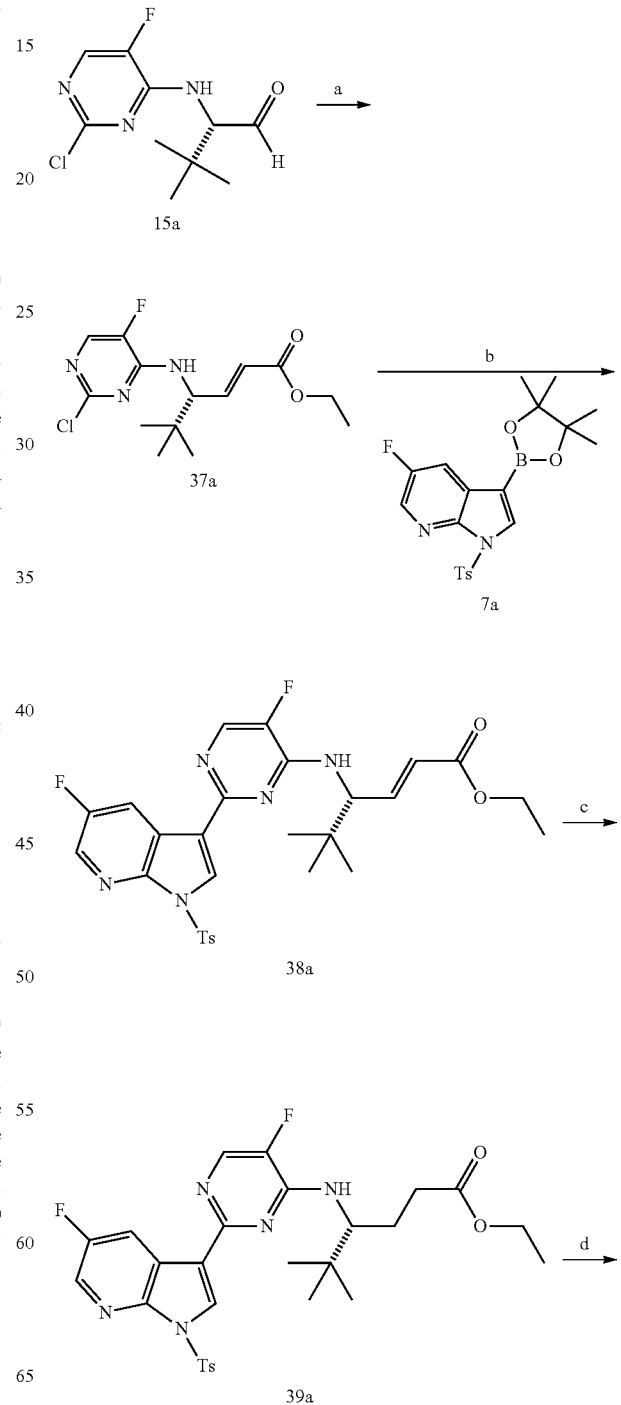

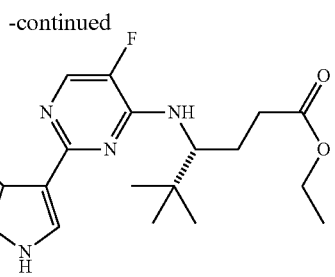

23

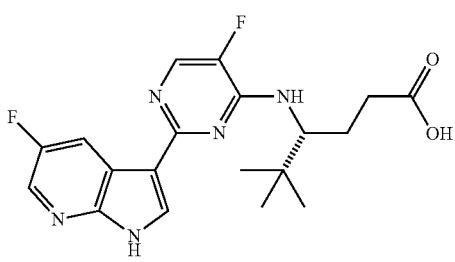

20

(a) ethyl-2-triphenylphosphoranylideneacetate, CH₂Cl₂; (b) 5-fluoro-3-(4,4,5,5-tetramethyl-1,3,2-dioxaborolan-2-yl)-1-tosyl-1H-pyrrolo[2,3-b]pyridine, 7a, aq. K₃PO₄, 2-Me—THF, H₂O, X-Phos, Pd₂(dba)₃; (c) H₂, 10% Pd/C, MeOH; (d) CH₃CN, 4N HCl/Dioxane Formation of (R,E)-ethyl 4-((2-chloro-5-fluoropyrimidin-4-yl)amino)-5,5-dimethylhex-2-enoate (37a)

To a solution of (S)-2-((2-chloro-5-fluoropyrimidin-4-yl)amino)-3,3-dimethylbutanal, 15a, (0.45 g, 1.84 mmol) in dichloromethane (9.0 mL) was added ethyl 2-triphenylphosphoranylideneacetate (0.96 g, 2.75 mmol). After allowing the reaction mixture to stir at room temperature overnight, approximately half of the solvent was removed under reduced pressure. The remaining crude mixture was purified by directly loading onto a silica gel column (0-100% EtOAc/hexanes) to afford 535 mg of the desired product: LCMS Gradient 10-90%, 0.1% formic acid, 5 minutes, C18/ACN, RT=3.41 minutes (M+H) 316.32.

Formation of (R,E)-ethyl 4-((5-fluoro-2-(5-fluoro-1-tosyl-1H-pyrrolo[2,3-b]pyridin-3-yl)pyrimidin-4-yl)amino)-5,5-dimethylhex-2-enoate (38a)

K₃PO₄ (1.078 g, 5.079 mmol) was dissolved in water (3.2 mL) and added to a solution of (R,E)-ethyl 4-((2-chloro-5-fluoropyrimidin-4-yl)amino)-5,5-dimethylhex-2-enoate, 37a, (0.534 g, 1.693 mmol) in 2-methyl-THF (10.7 mL) and the mixture was purged with nitrogen for 30 minutes. 5-fluoro-1-(p-tolylsulfonyl)-3-(4,4,5,5-tetramethyl-1,3,2-dioxaborolan-2-yl)pyrrolo[2,3-b]pyridine, 7a, (0.775 g, 1.862 mmol) was added and the nitrogen purging was continued for an additional 15 min. X-Phos (0.048 g, 0.102 mmol) and Pd₂(dba)₃ (0.031 g, 0.034 mmol) were added and the mixture was heated at 80° C. overnight. After cooling to room temperature, the reaction mixture was diluted with water and extracted with EtOAc. The layers were separated and the organic phase was washed with brine, dried over MgSO₄, filtered and evaporated to dryness. The crude residue was dissolved in a minimum volume of dichloromethane and purified by silica gel chromatography (0-100% EtOAc/hexanes gradient) to afford 650 mg of desired product: ¹H NMR (400 MHz, CDCl₃) δ 8.57-8.38 (m, 2H), 8.30 (s, 1H), 8.11 (dd, J=10.5, 5.5 Hz, 3H), 7.08 (dt, J=36.7, 18.3 Hz, 1H), 6.01 (d, J=15.7 Hz, 1H), 5.11 (d, J=8.7 Hz, 1H), 4.97-4.77 (m, 1H), 4.19 (q, J=7.1 Hz, 2H), 2.39 (d, J=10.7 Hz, 3H), 1.27 (q, J=7.4 Hz, 4H), 1.10 (s, 9H); LCMS Gradient 10-90%, 0.1% formic acid, 5 minutes, C18/ACN, RT=3.99 minutes (M+H) 570.01.

Formation of (R)-ethyl 4-((5-fluoro-2-(5-fluoro-1-tosyl-1H-pyrrolo[2,3-b]pyridin-3-yl)pyrimidin-4-yl)amino)-5,5-dimethylhexanoate (39a)

To a nitrogen purged flask charged with 10% Pd/C (0.033 g, 0.310 mmol) was added enough methanol to cover the catalyst. To this mixture was added a solution of (R,E)-ethyl 4-((5-fluoro-2-(5-fluoro-1-tosyl-1H-pyrrolo[2,3-b]pyridin-3-yl)pyrimidin-4-yl)amino)-5,5-dimethylhex-2-enoate, 38a, (0.330 g, 0.579 mmol) in MeOH. Note, a small amount of EtOAc was added to fully solubilize the starting material. The reaction mixture was then stirred under 1 atmosphere of hydrogen for 3 hours. LCMS shows presence of significant amounts of starting material. The contents of the reaction mixture were transferred to a pressure vessel containing a fresh source of palladium (0.033 g, 0.310 mmol). The reaction mixture was stirred in a Parr hydrogenation flask under 46 psi of hydrogen overnight. The mixture was diluted with methanol and filtered through celite. The filtrate was concentrated in vacuo to afford 331 mg of the desired product that was used without further purification: LCMS Gradient 10-90%, 0.1% formic acid, 5 minutes, C18/ACN, RT=3.75 minutes (M+H) 572.35.

Formation of (R)-4-((5-fluoro-2-(5-fluoro-1H-pyrrolo[2,3-b]pyridin-3-yl)pyrimidin-4-yl)amino)-5,5-dimethylhexanoic acid (20)

To a solution of (R)-ethyl 4-((5-fluoro-2-(5-fluoro-1-tosyl-1H-pyrrolo[2,3-b]pyridin-3-yl)pyrimidin-4-yl)amino)-5,5-dimethylhexanoate, 39a, (0.30 g, 0.53 mmol) was in acetonitrile (5 mL) was added HCl (0.70 mL of 4 M solution in dioxane, 2.80 mmol). The reaction mixture was heated at 60° C. for 3 hours and then heated to 80° C. for 6 hours to drive the reaction to completion. After cooling to room temperature, the mixture was then stirred overnight. LCMS showed remaining starting material. Fresh HCl (0.7 mL of 4 M solution in dioxane, 2.80 mmol) was added and the mixture was heated to 80° C. overnight. All volatiles were removed under reduced pressure and the residue was diluted with EtOAc and aqueous saturated NaHCO₃ solution. The layers were separated and the organic phase was washed with brine, dried over MgSO₄, filtered and evaporated to dryness. The crude residue was purified by silica gel chromatography (0-100% EtOAc/hexanes gradient) to afford 144 mg of (R)-ethyl 4-((5-fluoro-2-(5-fluoro-1H-pyrrolo[2,3-b]pyridin-3-yl)pyrimidin-4-yl)amino)-5,5-dimethylhexanoate, 23, and 29 mg of (R)-4-((5-fluoro-2-(5-fluoro-1H-pyrrolo[2,3-b]pyridin-3-yl)pyrimidin-4-yl)amino)-5,5-dimethylhexanoic acid, 20. Spectral data for 20: ¹H NMR (400 MHz, DMSO) δ 12.23 (s, 1H), 11.93 (s, 1H), 8.48 (d, J=9.9 Hz, 1H), 8.33-8.07 (m, 3H), 7.18 (d, J=9.3 Hz, 1H), 4.39 (t, J=10.2 Hz, 1H), 2.38-2.07 (m, 2H), 1.99-1.92 (m, 1H), 1.80-1.64 (m, 1H), 1.00 (d, J=20.2 Hz, 9H); LCMS Gradient 10-90%, 0.1% formic acid, 5 minutes, C18/ACN, RT=2.14 minutes (M+H) 390.06.

Preparation of Compound 59

Synthetic Scheme 8

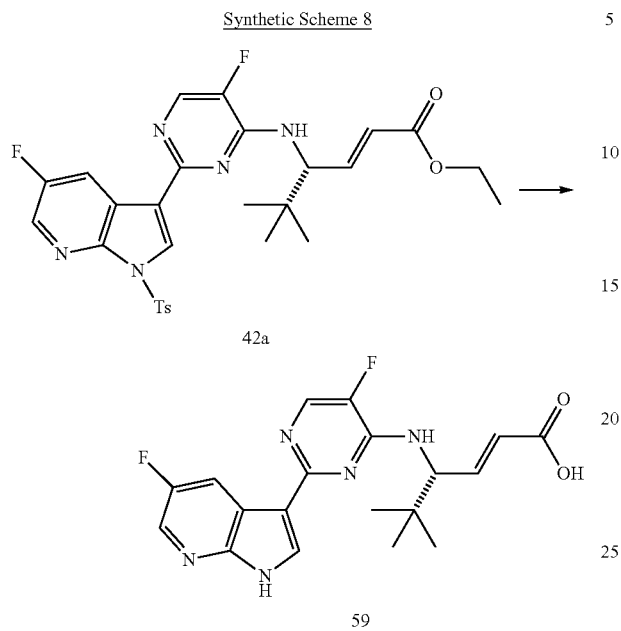

Formation of (R,E)-4-((5-fluoro-2-(5-fluoro-1H-pyrrolo[2,3-b]pyridin-3-yl)pyrimidin-4-yl)amino)-5,5-dimethylhex-2-enoic acid (59)

Starting ethyl ester, 42a, was prepared in the same fashion as the enantiomeric ethyl ester, 38a, shown in Synthetic Scheme 7.

To a solution of (S,E)-ethyl 4-((5-fluoro-2-(5-fluoro-1-tosyl-1H-pyrrolo[2,3-b]pyridin-3-yl)pyrimidin-4-yl)amino)-5,5-dimethylhex-2-enoate, 42a, (0.064 g, 0.112 mmol) in dioxane (2 mL) was added LiOH (2 mL of 2N solution). After heating at 100° C. for 2 hours, the mixture was acidified to pH 6 with 2N HCl. The aqueous phase was extracted with ethyl acetate (3×), dried (MgSO4), filtered and concentrated in vacuo. The resulting residue was purified via preparatory HPLC (CH$_3$CN/H$_2$O—TFA modifier) to afford 35 mg of the desired product as a TFA-salt: $^1$H NMR (300 MHz, MeOD) δ 8.54 (s, 1H), 8.50-8.18 (m, 3H), 7.18 (dd, J=15.7, 7.1 Hz, 1H), 6.08 (dd, J=15.7, 1.3 Hz, 1H), 5.21 (t, J=22.5 Hz, 1H), 1.12 (s, 9H); LCMS Gradient 10-90%, 0.1% formic acid, 5 minutes, C18/ACN, (M+H) 388.23.

Preparation of Compound 44

Synthetic scheme 9

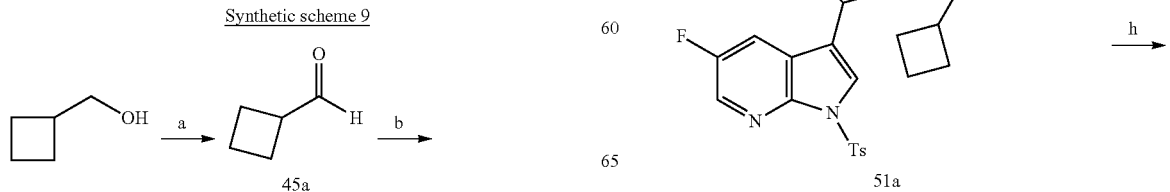

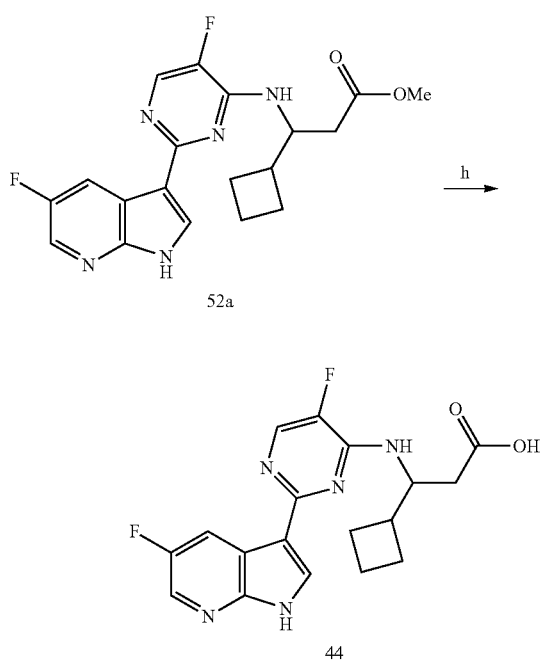

(a) Pyridinium chlorochromate, CH₂Cl₂; (b) ethyl-2-triphenyl-phosphoranylideneacetate, CH₂Cl₂; (c) N-benzylhydroxylamine, Et₃N, CH₂Cl₂ (d) H₂, palladium hydroxide, EtOH (e) diazomethyl-trimethylsilane, MeOH, benzene (f) 2,4-dichloro-5-fluoro-pyrimidine, Et₃N, THF, EtOH (g) 5-fluoro-3-(4,4,5,5-tetramethyl-1,3,2-dioxaborolan-2-yl)-1-tosyl-1H-pyrrolo[2,3-b]pyridine, 7a, Aq. K₃PO₄, 2-Me—THF, H₂O, X-Phos, Pd₂(dba)₃, 80° C.; (h) MeOH, NaOMe (i) aq. NaOH, THF, MeOH Formation of cyclobutanecarbaldehyde (45a)

To a stirred suspension of pyridinium chlorochromate (14.9 g, 69.1 mmol) in dichloromethane (150 mL) was added a solution of cyclobutylmethanol (4.0 g, 46.4 mmol) in dichloromethane (60 mL). The reaction mixture turned black within a few minutes and was allowed to stir at room temperature for 1 hour. The mixture was diluted with diethyl ether (500 mL) and filtered through a bed of florisil (100-200 mesh). The crude material was used without further purification. Note: the product is volatile, the solvent was carried with the product onto the next step.

Formation of (E)-ethyl 3-cyclobutylacrylate (46a)

Ethyl 2-triphenylphosphoranylideneacetate (9.32 g, 26.74 mmol) was added to a solution of cyclobutanecarbaldehyde, 45a, (1.50 g, 17.83 mmol) in dichloromethane (30 mL). The reaction mixture was briefly purged with nitrogen and capped allowed to stir at room temperature overnight. All volatiles were removed at reduced pressure and the residue was dissolved in Et₂O (100 mL) and hexanes (25 mL). The resulting pink precipitate was filtered off and discarded. The solvent was removed from the filtrate at reduced pressure. The crude product was purified via silica gel chromatography (0-20% EtOAc/Hexanes gradient) to afford 646 mg (23%) of the desired product: ¹H NMR (400 MHz, CDCl₃) δ 7.05 (dd, J=15.6, 6.8 Hz, 1H), 5.73 (dd, J=15.6, 1.4 Hz, 1H), 4.29-4.09 (m, 2H), 3.20-2.98 (m, 1H), 2.28-2.09 (m, 2H), 2.04-1.78 (m, 4H), 1.36-1.18 (m, 3H).

Formation of 2-benzyl-3-cyclobutylisoxazolidin-5-one (47a)

N-benzylhydroxylamine hydrochloride (0.77 g, 4.82 mmol) and triethylamine (0.76 mL, 5.45 mmol) were successively added to a solution of (E)-ethyl 3-cyclobutylacrylate, 46a, (0.65 g, 4.19 mmol) in dry dichloromethane (23.5 mL). The reaction mixture was allowed to stir at room temperature under an atmosphere of nitrogen for 3 days. The mixture was diluted with 75 mL of water and the layers were separated. The aqueous phase was reextracted twice more with dichloromethane (50 mL). The combined organic phases were dried over MgSO₄, filtered and evaporated to dryness. The residue was purified via silica gel chromatography (0-100% EtOAc/Hexanes gradient) to afford 834 mg (86%) of the desired product: ¹H NMR (400 MHz, CDCl₃) δ 7.38-7.26 (m, 5H), 4.64 (s, 1H), 3.82 (q, J=13.5 Hz, 2H), 3.37-3.18 (m, 1H), 2.80-2.52 (m, 2H), 2.33 (dd, J=14.5, 5.1 Hz, 1H), 2.22-2.09 (m, 1H), 2.01-1.68 (m, 5H).

Formation of (+/−)-3-amino-3-cyclobutylpropanoic acid (48a)

Dihydroxypalladium (0.252 g, 1.794 mmol) was charged into a flask and flushed with nitrogen. Ethanol (30 mL) was added followed by a solution of 2-benzyl-3-cyclobutylisoxazolidin-5-one, 47a, (0.834 g, 3.605 mmol) in approximately 90 mL of ethanol. The reaction mixture was subjected to 50 psi of hydrogen for 4 hours. The pressure was vented and the catalyst was filtered off. All volatiles were removed at reduced pressure. ¹H NMR shows the presence of starting material, 47a. The mixture was dissolved in approximately 100 mL of MeOH and added to 83 mg of 10% Pd/C that had been wet with 20 mL of MeOH. The mixture was subjected to 50 psi of H₂ overnight. The pressure was vented and the catalyst was filtered off. All volatiles were removed at reduced pressure to afford 340 mg of product. The resulting crude residue was used without further purification: ¹H NMR (400 MHz, d6-DMSO) δ 3.06-2.83 (m, 1H), 2.28 (ddd, J=23.7, 11.8, 7.7 Hz, 1H), 2.19-1.99 (m, 2H), 1.99-1.56 (m, 6H).

Formation of (+/−)-methyl 3-amino-3-cyclobutylpropanoate (49a)

To a solution of racemic 3-amino-3-cyclobutyl-propanoic acid, 48a, (0.34 g, 2.38 mmol) in MeOH (10.2 mL) and benzene (10.2 mL) was added diazomethyltrimethyl-silane (3.56 mL of 2 M solution, 7.13 mmol) and the reaction mixture was allowed to stir at room temperature under a nitrogen atmosphere overnight. The mixture was diluted with EtOAc and brine. The layers were separated and the organic phase was dried (MgSO₄), filtered and concentrated in vacuo to afford 354 mg (95%) of crude product that was used without further purification: ¹H NMR (400 MHz, CDCl₃) δ 3.71-3.66 (m, 3H), 3.18-2.98 (m, 1H), 2.46-2.32 (m, 2H), 2.27-1.63 (m, 10H).

Formation of methyl (+/−)-3-((2-chloro-5-fluoropyrimidin-4-yl)amino)-3-cyclobutylpropanoate (50a)

To a racemic solution of methyl 3-amino-3-cyclobutylpropanoate, 49a, (0.354 g, 2.252 mmol) and 2,4-dichloro-5-fluoro-pyrimidine (0.414 g, 2.477 mmol) in THF (10 mL) and ethanol (1 mL) was added triethylamine (0.628 mL, 4.504 mmol). The reaction mixture was heated and stirred at 70° C. for 5 hours. The mixture was filtered and the filtrate was concentrated in vacuo to approximately 5 mL final volume. The crude residue was purified via silica gel chromatography (0-100% EtOAC/hexanes gradient) to afford 289 mg (45%) of the desired product: $^1$H NMR (300 MHz, CDCl$^3$) δ 7.87 (s, 1H), 5.80 (s, 1H), 4.71-4.38 (m, 1H), 3.68 (s, 3H), 2.84-2.37 (m, 3H), 2.23-1.67 (m, 6H); LCMS Gradient 10-90%, 0.1% formic acid, 5 minutes, C18/ACN, RT=3.08 minutes (M+H) 287.98.

Formation of (+/−)-3-cyclobutyl-3-((5-fluoro-2-(5-fluoro-1-tosyl-1H-pyrrolo[2,3-b]pyridin-3-yl)pyrimidin-4-yl)amino)propanoate (51a)

A solution of tripotassium phosphate (0.640 g, 3.021 mmol) in water (1.735 mL) was added to a solution of racemic methyl 3-[(2-chloro-5-fluoro-pyrimidin-4-yl)amino]-3-cyclobutylpropanoate, 50a, (0.289 g, 1.005 mmol) in 2-methyltetrahydrofuran (5.782 mL). The mixture was then purged with nitrogen for 20 minutes. 5-fluoro-1-(p-tolylsulfonyl)-3-(4,4,5,5-tetramethyl-1,3,2-dioxaborolan-2-yl)pyrrolo[2,3-b]pyridine, 7a, (0.460 g, 1.106 mmol) was added and the mixture was purged with nitrogen for an additional 10 minutes. Dicyclohexyl-[2-(2,4,6-triisopropylphenyl)phenyl]phosphane (X-Phos: 0.029 g, 0.060 mmol) and Pd$_2${dba}$_3$ (0.018 g, 0.020 mmol) were added and the reaction mixture was warmed to 80° C. and stirred at this temperature for 5 hours. The mixture was allowed to cool to room temperature. The reaction mixture was diluted with water and extracted with EtOAc. The layers were separated and the organic phase was washed with brine, dried over MgSO$_4$, filtered and evaporated to dryness. The crude was dissolved in a minimum volume of dichloromethane and purified via silica gel chromatography (0-100% EtOAc/Hexanes). to afford 385 mg (71%) of the desired product: LCMS Gradient 10-90%, 0.1% formic acid, 5 minutes, C18/ACN, RT=3.68 minutes (M+H) 542.27.

Formation of (+/−)-methyl 3-cyclobutyl-3-((5-fluoro-2-(5-fluoro-1H-pyrrolo[2,3-b]pyridin-3-yl)pyrimidin-4-yl)amino)propanoate (52a)

To a racemic solution of methyl 3-cyclobutyl-3-((5-fluoro-2-(5-fluoro-1-tosyl-1H-pyrrolo[2,3-b]pyridin-3-yl)pyrimidin-4-yl)amino)propanoate, 51a, (0.151 g, 0.280 mmol) in methanol (1.5 mL) was added NaOMe (1.5 mL of 25% w/v solution, 6.941 mmol). After stirring the reaction mixture at room temperature for 5 minutes, the mixture was quenched with aqueous saturated NH$_4$Cl solution and diluted with EtOAc and water. The layers were separated and the organic phase was washed with brine, dried (MgSO$_4$), filtered and evaporated to dryness. The resulting crude residue was dissolved in a minimum volume of dichloromethane and purified via silica gel chromatography (0-100% EtOAc/Hexanes gradient) to afford 108 mg of the desired product: LCMS Gradient 10-90%, 0.1% formic acid, 5 minutes, C18/ACN, RT=2.29 minutes (M+H) 388.07.

Formation of (+/−)-3-cyclobutyl-3-((5-fluoro-2-(5-fluoro-1H-pyrrolo[2,3-b]pyridin-3-yl)pyrimidin-4-yl)amino)propanoic acid (44)

To a racemic solution of methyl 3-cyclobutyl-3-((5-fluoro-2-(5-fluoro-1H-pyrrolo[2,3-b]pyridin-3-yl)pyrimidin-4-yl)amino)propanoate (0.042 g, 0.109 mmol) in THF (1.5 mL) and MeOH (0.5 mL) was added NaOH (0.300 mL of 2 M solution, 0.600 mmol) and the reaction mixture was warmed to 50° C. After stirring the reaction mixture for 1 hour, the mixture was diluted with aqueous saturated NH$_4$Cl solution and EtOAc. The organic layer was dried (MgSO$_4$), filtered and evaporated to dryness to afford 36 mg of the desired product that was used without further purification: $^1$H NMR (400 MHz, d6-DMSO) δ 12.26 (s, 2H), 8.55 (d, J=9.7 Hz, 1H), 8.19 (dd, J=45.1, 15.8 Hz, 3H), 7.48 (d, J=8.1 Hz, 1H), 4.79 (s, 1H), 2.58 (dd, J=20.6, 12.2 Hz, 2H), 1.85 (ddd, J=29.4, 26.5, 21.1 Hz, 7H); LCMS Gradient 10-90%, 0.1% formic acid, 5 minutes, C18/ACN, RT=2.10 minutes (M+H) 374.02.

Preparation of Compounds 10, 11, 19, 21, 22, 32, 33, 34, 35, 38, 39, 40, 49, 57, and 58

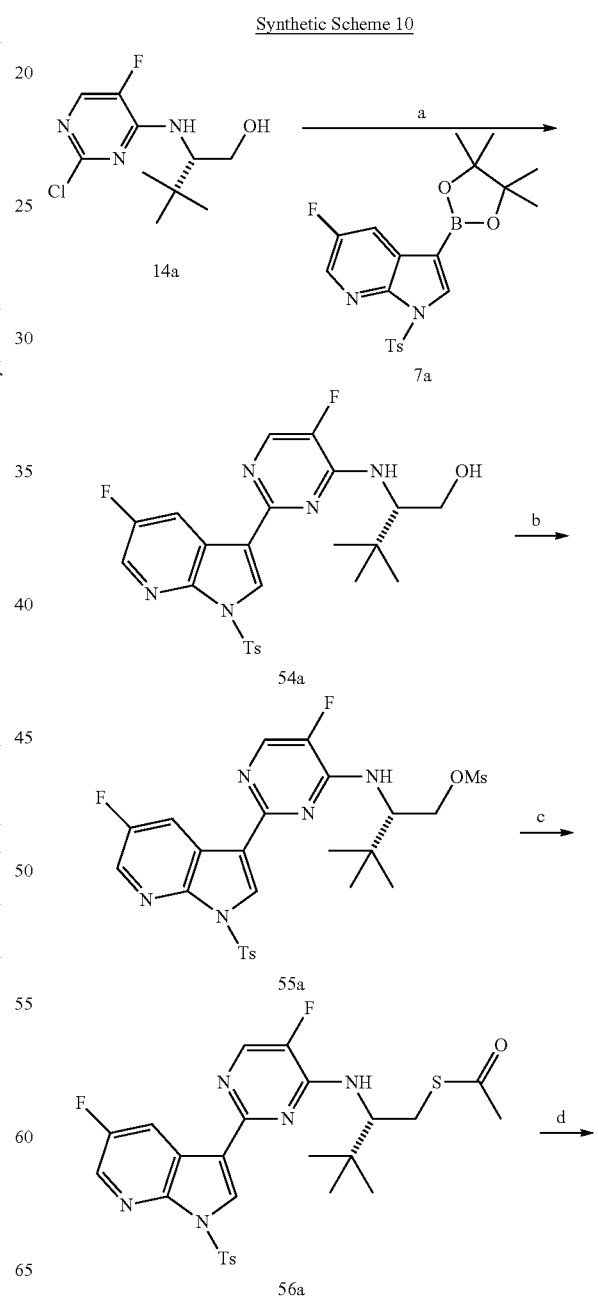

Synthetic Scheme 10

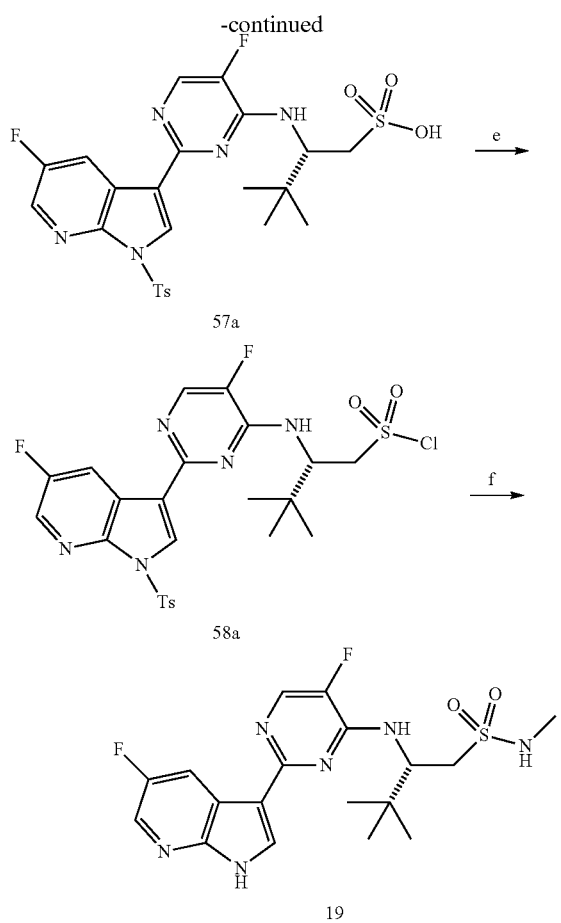

(a) 5-fluoro-1-(p-tolylsulfonyl)-3-(4,4,5,5-tetramethyl-1,3,2-dioxaborolan-2-yl)pyrrolo-[2,3-b]pyridine, 7a, K₃PO₄, X-Phos, Pd₂(dba)₃, 2-MeTHF, water, 120° C.; (b) MsCl. CH₂Cl₂; (c) KOAc, DMF, 80° C.; (d) 30% H₂O₂, HCOOH, RT, 2 hr; (e) oxalyl chloride, DMF, CH₂Cl₂; (f) (i) methylamine, THF (ii) 4M HCl, CH₃CN, 65° C.

(S)-2-(5-fluoro-2-(5-fluoro-1-tosyl-1H-pyrrolo[2,3-b]pyridin-3-yl)pyridin-4-ylamino)-3,3-dimethylbutan-1-ol (54a)

A mixture of 5-fluoro-1-(p-tolylsulfonyl)-3-(4,4,5,5-tetramethyl-1,3,2-dioxaborolan-2-yl)pyrrolo[2,3-b]pyridine, 7a, (11.09 g, 26.64 mmol), (S)-2-((2-chloro-5-fluoropyrimidin-4-yl)amino)-3,3-dimethylbutan-1-ol, 14a, (6.00 g, 24.22 mmol) and K₃PO₄ (15.42 g, 72.66 mmol) in 2-methyl THF (90 mL) and water (12.00 mL) was purged with nitrogen for 30 minutes. X-Phos (0.92 g, 1.94 mmol) and Pd₂(dba)₃ (0.44 g, 0.48 mmol) were added and the reaction mixture was heated at 120° C. in a pressure vial for 2 hr. The reaction mixture was cooled to room temperature, filtered and concentrated in vacuo. The residue was dissolved in EtOAc (100 mL) and washed with water. The organic layer was dried (MgSO₄), filtered and concentrated in vacuo. The crude product was purified by silica gel chromatography (0-40% EtOAc/Hexanes gradient) to afford 10 g of the desired product as a foamy solid: $^1$H NMR (400 MHz, CDCl₃) δ 8.54-8.40 (m, 2H), 8.22 (s, 1H), 8.09-8.00 (m, 3H), 7.29-7.16 (m, 2H), 5.15 (m, 1H), 4.32-4.14 (m, 1H), 3.98 (m, 1H), 3.70 (m, 1H), 2.30 (s, 3H), 1.01 (m, 9H); LC/MS (60-90% ACN/water 5 min with 0.9% FA, C4) m/z 502.43 (M+H) RT=1.52 min.

(S)-2-(5-fluoro-2-(5-fluoro-1-tosyl-1H-pyrrolo[2,3-b]pyridin-3-yl)pyridin-4-ylamino)-3,3-dimethylbutyl methanesulfonate (55a)

Methanesulfonyl chloride (1.83 mL, 23.67 mmol) was added to a cold (0° C.) solution of (S)-2-(5-fluoro-2-(5-fluoro-1-tosyl-1H-pyrrolo[2,3-b]pyridin-3-yl)pyridin-4-ylamino)-3,3-dimethylbutan-1-ol, 54a, (9.50 g, 18.94 mmol) and triethylamine (3.30 mL, 23.67 mmol) in dichloromethane (118 mL). The reaction mixture was stirred at room temperature for 1 hour. The solvent was removed under reduced pressure and the residue was diluted with water (100 mL) and EtOAc (200 mL). The organic layer was separated, dried (MgSO₄), filtered and concentrated under reduced pressure to afford 10.5 g of the desired product as a pale yellow foam: LC/MS (60-90% ACN/water 5 min with 0.9% FA, C4) m/z 580.41 (M+H) RT=2.00 minutes.

(S)-2-(5-fluoro-2-(5-fluoro-1-tosyl-1H-pyrrolo[2,3-b]pyridin-3-yl)pyridin-4-ylamino)-3,3-dimethylbutyl ethanethioate (56a)

To a solution of (S)-2-(5-fluoro-2-(5-fluoro-1-tosyl-1H-pyrrolo[2,3-b]pyridin-3-yl)pyridin-4-ylamino)-3,3-dimethylbutyl methanesulfonate, 55a, (10.5 g, 18.11 mmol) in dry DMF (200 mL) was added potassium thioacetate (3.1 g, 27.1 mmol). The brown solution was heated with stirring at 80° C. for 1 hour. The thick brown suspension was poured into water and extracted with EtOAc (3×100 mL). The combined organic phases were dried (MgSO₄), filtered and concentrated under reduced pressure. The crude residue was purified by silica gel chromatography (0-30% EtOAc/Hexanes gradient) to afford 6.8 g of the desired product, 56a, as a pale brown solid: $^1$H NMR (400 MHz, CDCl₃) δ 8.41 (m, 2H), 8.23 (s, 1H), 8.01 (m, 3H), 7.23-7.16 (m, 2H), 4.99 (d, J=10.1 Hz, 1H), 4.37 (m, 1H), 3.21 (dd, J=13.8, 2.3 Hz, 1H), 3.09-2.95 (m, 1H), 2.31 (s, 3H), 2.16 (s, 3H), 1.02 (s, 9H); LC/MS (10-90% ACN/water 5 min with 0.9% FA) m/z 560.99 (M+H) RT=4.14 minutes.

(S)-2-(5-fluoro-2-(5-fluoro-1-tosyl-1H-pyrrolo[2,3-b]pyridin-3-yl)pyridin-4-ylamino)-3,3-dimethylbutane-1-sulfonic acid (57a)

To a cold (0° C.) solution of formic acid (103.4 mL, 2.7 mol) was added H₂O₂ (34.2 mL of 30% solution, 0.3 mol). The solution was stirred at 0° C. for 1 hour. A solution of (S)-2-(5-fluoro-2-(5-fluoro-1-tosyl-1H-pyrrolo[2,3-b]pyridin-3-yl)pyridin-4-ylamino)-3,3-dimethylbutyl ethanethioate, 56a, (6.7 g, 12.0 mmol) in formic acid (20.0 mL) was added dropwise. The resulting mixture was stirred at room temperature for 2 hours to give a yellow solution. The solvent was removed under reduced pressure to afford the desired product as a foamy pale yellow solid that was used without further purification: $^1$H NMR (400 MHz, MeOD) δ 8.72 (m, 2H), 8.31 (s, 1H), 8.21 (d, J=4.8 Hz, 1H), 8.06 (d, J=8.1 Hz, 2H), 7.39 (d, J=8.0 Hz, 2H), 5.08 (d, J=10.0 Hz, 1H), 3.19 (m, 2H), 2.36 (s, 3H), 1.04 (m, 9H); LC/MS (10-90% ACN/water 5 min with 0.9% TFA, C18) m/z 566.0 (M+H) RT=2.66 minutes.

(S)-2-(5-fluoro-2-(5-fluoro-1-tosyl-1H-pyrrolo[2,3-b]pyridin-3-yl)pyridin-4-ylamino)-3,3-dimethylbutane-1-sulfonyl chloride (58a)

Oxalyl chloride (3.5 mL, 38.7 mmol) was added to a solution of (S)-2-(5-fluoro-2-(5-fluoro-1-tosyl-1H-pyrrolo[2,3- b]pyridin-3yl)pyridin-4-ylamino)-3,3-dimethylbutane-1-sulfonic acid, 57a, (7.3 g, 12.9 mmol) in dichloromethane (130 mL), followed by the slow, dropwise addition of DMF (2 mL). The yellow colored solution was stirred at room temperature for 1 hour. The solvent was removed under reduced pressure to afford 8.4 g of the desired product as a foamy yellow solid: LC/MS (60-90% ACN/water 5 min with 0.9% FA) m/z 585.72 (M+H) RT=2.30 minutes.

(S)-2-(5-fluoro-2-(5-fluoro-1H-pyrrolo[2,3-b]pyridin-3-yl)pyrimidin-4-ylamino)-N,3,3-trimethylbutane-1-sulfonamide (19)

Methylamine (0.75 mL of 2M solution, 1.53 mmol) was added to a solution of (S)-2-(5-fluoro-2-(5-fluoro-1-tosyl-1H-pyrrolo[2,3-b]pyridin-3-yl)pyridin-4-ylamino)-3,3-dimethylbutane-1-sulfonyl chloride, 58a, (0.15 g, 0.26 mmol) in THF (1 mL). The solution was stirred for 1 hour at room temperature and the solvent was then removed under reduced pressure. The crude sulfonamide was dissolved in acetonitrile (3 mL) and HCl (2 mL of a 4M solution in dioxane) was added. The mixture was heated at 65° C. for 3 hours and then cooled to room temperature. The solvent was removed under reduced pressure and the resulting crude residue was purified by preparative HPLC chromatography (10-80% CH$_3$CN/water, 0.5% TFA, 15 min) to give 26 mg of the desired product as a white solid: $^1$H NMR (400 MHz, CDCl$_3$) δ 9.75 (s, 1H), 8.12 (d, J=9.3 Hz, 1H), 7.94 (s, 1H), 7.73 (s, 2H), 7.67 (brs, 1H), 4.93-4.78 (m, 2H), 3.08 (m, 1H), 2.76 (s, 3H), 0.99 (m, 9H); LC/MS (10-90% ACN/water 5 min with 0.9% FA) m/z 425.3 (M+H), RT=2.0 minutes.

The following compounds can be prepared in a similar fashion as the procedure described above for Compound 19:

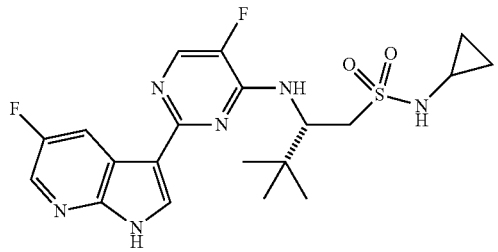 [SMILES: CC(C)(C)[C@@H](CS(=O)(=O)NC1CC1)Nc1nc(-c2c[nH]c3ncc(F)cc23)ncc1F]

(S)—N-Cyclopropyl-2-(5-fluoro-2-(5-fluoro-1H-pyrrolo[2,3-b]pyridin-3-yl)pyrimidin-4-ylamino)-3,3-dimethylbutane-1-sulfonamide (21)

$^1$H NMR (400 MHz, CDCl$_3$) δ 8.68 (dd, J=9.6, 2.5 Hz, 1H), 8.24-8.11 (m, 2H), 8.03 (d, J=3.8 Hz, 1H), 5.12 (d, J=8.5 Hz, 1H), 3.48 (d, J=9.2 Hz, 2H), 2.60-2.47 (m, 1H), 1.13 (s, 9H), 0.68-0.48 (m, 4H): LC/MS (10-90% ACN/water 5 min with 0.9% FA) m/z 451.14 (M+H) RT=2.2 minutes.

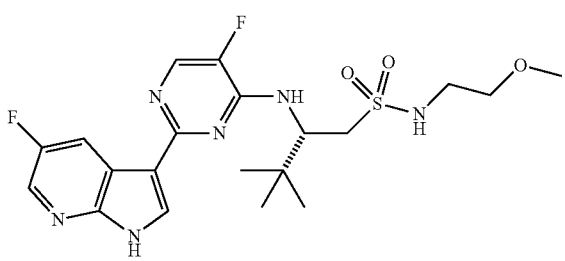 [SMILES: COCCNS(=O)(=O)C[C@@H](Nc1nc(-c2c[nH]c3ncc(F)cc23)ncc1F)C(C)(C)C]

(S)-2-(5-Fluoro-2-(5-fluoro-1H-pyrrolo[2,3-b]pyridin-3-yl)pyrimidin-4-ylamino)-N-(2-methoxyethyl)-3,3-dimethylbutane-1-sulfonamide (35)

LC/MS (10-90% ACN/water 5 min with 0.9% FA) m/z 469.28 (M+H) RT=2.11 minutes.

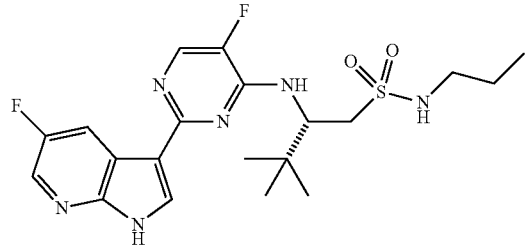 [SMILES: CCCNS(=O)(=O)C[C@@H](Nc1nc(-c2c[nH]c3ncc(F)cc23)ncc1F)C(C)(C)C]

(S)-2-(5-Fluoro-2-(5-fluoro-1H-pyrrolo[2,3-b]pyridin-3-yl)pyrimidin-4-ylamino)-3,3-dimethyl-N-propylbutane-1-sulfonamide (34)

$^1$H NMR (400 MHz, CDCl$_3$) δ 9.84 (s, 1H), 8.10 (d, J=9.5 Hz, 1H), 7.92 (d, J=1.2 Hz, 1H), 7.72 (d, J=14.2 Hz, 2H), 4.92 (m, 1H), 4.81 (m, 1H), 3.41 (d, J=15.0 Hz, 1H), 3.19-2.84 (m, 3H), 1.59-1.38 (m, 3H), 0.98 (s, 9H), 0.84 (t, J=7.4 Hz, 3H): LC/MS (10-90% ACN/water 5 min with 0.9% FA) m/z 453.44 (M+H) RT=2.42 minutes.

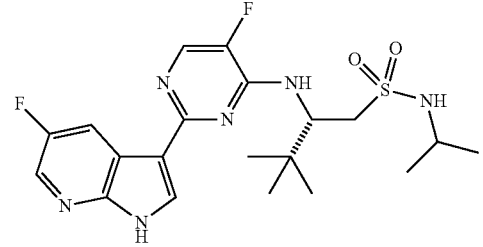 [SMILES: CC(C)NS(=O)(=O)C[C@@H](Nc1nc(-c2c[nH]c3ncc(F)cc23)ncc1F)C(C)(C)C]

(S)-2-(5-Fluoro-2-(5-fluoro-1H-pyrrolo[2,3-b]pyridin-3-yl)pyrimidin-4-ylamino)-N-isopropyl-3,3-dimethyl-N-propylbutane-1-sulfonamide (39)

$^1$H NMR (400 MHz, CDCl$_3$) δ 9.89 (s, 1H), 8.07 (d, J=8.9 Hz, 1H), 7.90 (s, 1H), 7.68 (s, 2H), 4.96 (t, J=9.8 Hz, 1H), 4.76 (d, J=9.8 Hz, 1H), 3.60 (dd, J=13.0, 6.6 Hz, 1H), 3.42 (m, 1H), 3.09-2.86 (m, 1H), 1.20 (d, J=4.9 Hz, 6H), 0.97 (s, 9H); LC/MS (10-90% ACN/water 5 min with 0.9% FA) m/z 453.19 (M+H) RT=2.22 minutes.

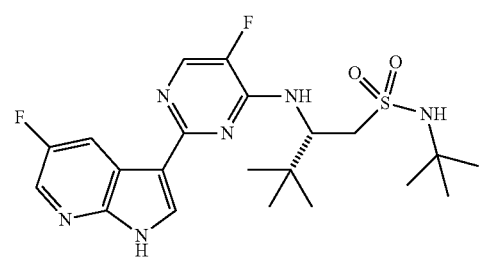 [SMILES: CC(C)(C)NS(=O)(=O)C[C@@H](Nc1nc(-c2c[nH]c3ncc(F)cc23)ncc1F)C(C)(C)C]

(S)-2-(5-Fluoro-2-(5-fluoro-1H-pyrrolo[2,3-b]pyridin-3-yl)pyrimidin-4-ylamino)-N-tert-butyl-3,3-dimethyl-N-propylbutane-1-sulfonamide (40)

LC/MS (10-90% ACN/water 5 min with 0.9% FA) m/z 467.20 (M+H) RT=2.36 minutes.

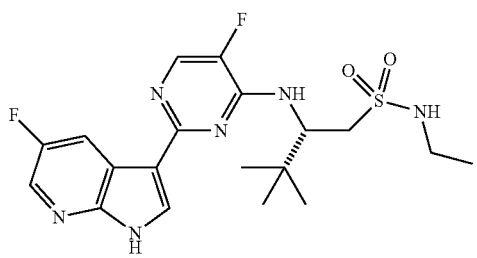 [SMILES: CCNS(=O)(=O)C[C@@H](Nc1nc(-c2c[nH]c3ncc(F)cc23)ncc1F)C(C)(C)C]

(S)—N-Ethyl-2-(5-fluoro-2-(5-fluoro-1H-pyrrolo[2,3-b]pyridin-3-yl)pyrimidin-4-ylamino)-3,3-dimethylbutane-1-sulfonamide (33)

$^1$H NMR (400 MHz, CDCl$_3$) δ 9.89 (brs, 1H), 8.07 (d, J=9.3 Hz, 1H), 7.89 (s, 1H), 7.66 (m, 2H), 4.95 (t, J=10.2 Hz, 1H), 4.80 (d, J=9.6 Hz, 1H), 3.38 (m, 1H), 3.18-2.96 (m, 3H), 1.35-1.12 (m, 3H), 0.90 (m, 9H); LC/MS (10-90% ACN/water 5 min with 0.9% FA) m/z 439.30 (M+H) RT=2.25 minutes.

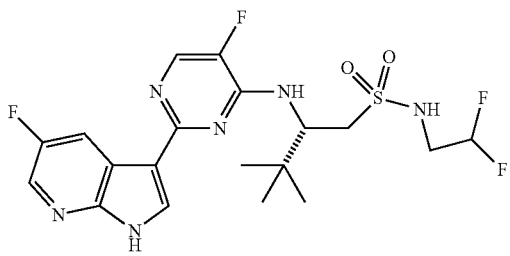 [SMILES: CC(C)(C)[C@@H](CS(=O)(=O)NCC(F)F)Nc1nc(-c2c[nH]c3ncc(F)cc23)ncc1F]

(S)—N-(2,2-difluoroethyl)-2-(5-fluoro-2-(5-fluoro-1H-pyrrolo[2,3-b]pyridin-3-yl)pyrimidin-4-ylamino)-3,3-dimethylbutane-1-sulfonamide (57)

$^1$H NMR (400 MHz, CDCl$_3$) δ 8.05 (d, J=7.9 Hz, 1H), 7.81 (d, J=2.1 Hz, 1H), 7.63 (s, 1H), 7.55 (s, 1H), 5.87 (t, J=54.9 Hz, 1H), 5.03 (t, J=10.4 Hz, 1H), 4.86 (m, 1H), 3.68 (brs, 1H), 3.43 (m, 2H), 3.19 (m, 1H), 0.94 (s, 9H); LC/MS (10-90% ACN/water 5 min with 0.9% FA) m/z 475.23 (M+H) RT=2.26 minutes.

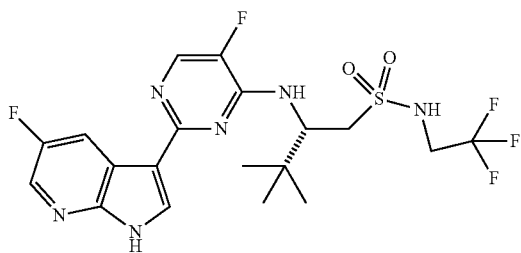 [SMILES: CC(C)(C)[C@@H](CS(=O)(=O)NCC(F)(F)F)Nc1nc(-c2c[nH]c3ncc(F)cc23)ncc1F]

(S)-2-(5-fluoro-2-(5-fluoro-1H-pyrrolo[2,3-b]pyridin-3-yl)pyrimidin-4-ylamino)-3,3-dimethyl-N-(2,2,2-trifluoroethyl)butane-1-sulfonamide (58)

$^1$H NMR (400 MHz, CDCl$_3$) δ 8.03 (dd, J=9.3, 2.4 Hz, 1H), 7.82 (t, J=11.2 Hz, 1H), 7.59 (s, 1H), 7.46 (s, 1H), 5.07 (t, J=10.6 Hz, 1H), 4.77 (m, 1H), 3.45 (m, 1H), 3.16-2.99 (m, 1H), 0.97-0.86 (m, 9H); LC/MS (10-90% ACN/water 5 min with 0.9% FA) m/z 493.31 (M+H) RT=2.37 minutes.

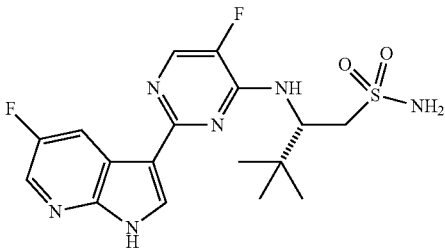 [SMILES: CC(C)(C)[C@@H](CS(N)(=O)=O)Nc1nc(-c2c[nH]c3ncc(F)cc23)ncc1F]

(S)-2-(5-fluoro-2-(5-fluoro-1H-pyrrolo[2,3-b]pyridin-3-yl)pyrimidin-4-ylamino)-3,3-dimethylbutane-1-sulfonamide (22)

Concentrated NH$_4$OH (1.0 mL, 25.7 mmol) was added dropwise to a solution of (S)-2-(5-fluoro-2-(5-fluoro-1-tosyl-1H-pyrrolo[2,3-b]pyridin-3-yl)pyridin-4-ylamino)-3,3-dimethylbutane-1-sulfonyl chloride, 58a, (0.3 g, 0.5 mmol) in THF (3 mL). The reaction mixture was stirred for 15 minutes at room temperature, resulting in a 1-to-1 mixture of the desired sulfonamide and sulfonic acid. The solvent was removed under reduced pressure. The crude product was purified by silica gel chromatography (0-70% EtOAc/Hexanes gradient) to afford 93 mg of the tosylated sulfonamide intermediate as a foamy solid.

The tosylated sulfonamide (93 mg) was dissolved in THF (10 mL) and a solution of NaOMe (0.15 mL of 25% solution in MeOH, 0.66 mmol) was added. The resulting yellow solution was stirred at room temperature for 15 minutes and then diluted into aqueous saturated NH$_4$Cl solution (5 mL). The solvent was removed under reduced pressure and the residue was dissolved in water (10 mL). The aqueous layer was extracted with EtOAc (3×10 mL) and dried (MgSO$_4$), filtered, and concentrated in vacuo. The crude residue was purified by HPLC preparative chromatography (10-80% CH$_3$CN/water, 0.5% TFA, 15 min) to afford 40 mg of the desired product, 22, as a white solid: $^1$H NMR (400 MHz, MeOD) δ 8.65 (d, J=9.3, 1H), 8.47 (s, 1H), 8.34 (m, 2H), 5.28 (d, J=10.4 Hz, 1H), 3.55 (m, 2H), 1.10 (m, 9H); LC/MS (10-90% ACN/water 5 min with 0.9% FA) m/z 411.0, 1.96 (M+H) RT=1.96 minutes.

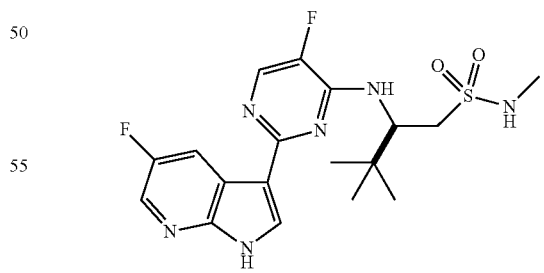

(R)-2-((5-fluoro-2-(5-fluoro-1H-pyrrolo[2,3-b]pyridin-3-yl)pyrimidin-4-yl)amino)-N,3,3-trimethylbutane-1-sulfonamide (38)

$^1$H NMR (300 MHz, d6-DMSO) δ 12.21 (s, 1H), 8.55 (dd, J=10.0, 2.8 Hz, 1H), 8.29-8.23 (m, 1H), 8.19 (d, J=2.7 Hz,

1H), 8.15 (d, J=4.0 Hz, 1H), 7.47 (d, J=8.4 Hz, 1H), 6.77-6.69 (m, 1H), 4.88 (t, J=9.1 Hz, 1H), 3.49-3.36 (m, 1H), 3.36-3.28 (m, J=10.5 Hz, 1H), 2.55 (t, J=5.6 Hz, 3H), 0.98 (s, 9H); LCMS Gradient 10-90%, 0.1% formic acid, 5 minutes, C18/ACN, RT=2.11 minutes (M+H) 425.03.

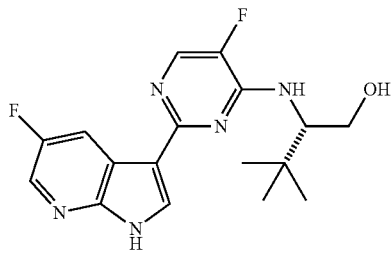 [SMILES: CC(C)(C)[C@@H](CO)Nc1nc(-c2c[nH]c3ncc(F)cc23)ncc1F]

(S)-2-(5-fluoro-2-(5-fluoro-1H-pyrrolo[2,3-b]pyridin-3-yl)pyrimidin-4-ylamino)-3,3-dimethylbutane-1-ol (32)

Alcohol, 32, was synthesized in a manner similar to compound 70a utilizing the same deprotection procedure, starting with compound 54a: $^1$H NMR (400 MHz, CDCl$_3$) δ 10.77 (brs, 1H), 8.25 (d, J=8.4 Hz, 1H), 8.07 (s, 1H), 8.03 (s, 1H), 7.88 (s, 1H), 5.59 (brs, 1H), 4.36 (t, J=8.3 Hz, 2H), 4.11 (m, 1H), 3.72 (m, 2H), 1.06 (s, 9H); LC/MS (10-90% ACN/water 5 min with 0.9% FA) m/z 348.13 (M+H) RT=1.83 minutes.

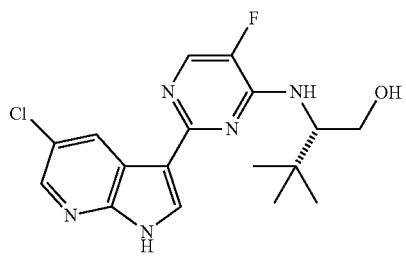 [SMILES: CC(C)(C)[C@@H](CO)Nc1nc(-c2c[nH]c3ncc(Cl)cc23)ncc1F]

(S)-2-((2-(5-chloro-1H-pyrrolo[2,3-b]pyridin-3-yl)-5-fluoropyrimidin-4-yl)amino)-3,3-dimethylbutan-1-ol (49)

Alcohol, 49, was synthesized in a manner similar to compound 32: $^1$H NMR (400 MHz, CDCl$_3$) δ 10.77 (brs, 1H), 8.25 (d, J=8.4 Hz, 1H), 8.07 (s, 1H), 8.03 (s, 1H), 7.88 (s, 1H), 5.59 (brs, 1H), 4.36 (t, J=8.3 Hz, 2H), 4.11 (m, 1H), 3.72 (m, 2H), 1.06 (s, 9H); LC/MS (10-90% ACN/water 5 min with 0.9% FA) m/z 348.13 (M+H) RT=1.83 minutes.

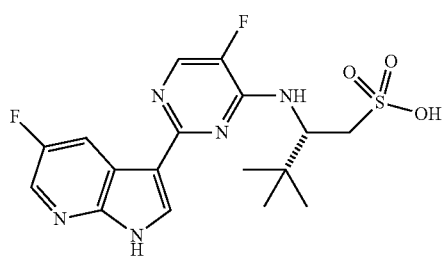 [SMILES: CC(C)(C)[C@@H](CS(=O)(=O)O)Nc1nc(-c2c[nH]c3ncc(F)cc23)ncc1F]

(S)-2-(5-fluoro-2-(5-fluoro-1H-pyrrolo[2,3-b]pyridin-3-yl)pyrimidin-4-ylamino)-3,3-dimethylbutane-1-sulfonic acid (11)

Sulfonic acid, 11, was synthesized in a manner similar to Compound 25 described below, using compound, 57a, as the starting material: $^1$H NMR (400 MHz, MeOD) δ 8.44 (s, 1H), 8.34 (dd, J=9.2, 2.6 Hz, 1H), 8.22 (d, J=5.7 Hz, 1H), 8.13 (s, 1H), 5.16 (d, J=4.1 Hz, 1H), 3.46-3.33 (m, 2H), 1.10 (d, 9H); LC/MS (10-90% ACN/water 5 min with 0.9% TFA, C18) m/z 412.19 (M+H) retention time=1.91 minutes.

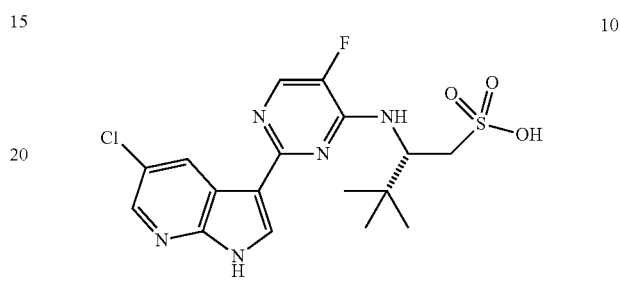

(S)-2-((2-(5-chloro-1-pyrrolo[2,3-b]pyridin-3-yl)-5-fluoropyrimidin-4-yl)amino)-3,3-dimethylbutane-1-sulfonic acid (10)

Sulfonic acid, 10, was synthesized in a manner similar to Compound 11, using 5-chloro-3-(4,4,5,5-tetramethyl-1,3,2-dioxaborolan-2-yl)-1-tosyl-1H-pyrrolo[2,3-b]pyridine instead of boronate ester, 7a, as the starting material: $^1$H NMR (400 MHz, MeOD) δ 8.44 (s, 1H), 8.34 (dd, J=9.2, 2.6 Hz, 1H), 8.22 (d, J=5.7 Hz, 1H), 8.13 (s, 1H), 5.16 (d, J=4.1 Hz, 1H), 3.46-3.33 (m, 2H), 1.10 (d, 9H); LC/MS (10-90% ACN/water 5 min with 0.9% TFA, C18) m/z 412.19 (M+H) retention time=1.91 minutes.

Preparation of Compounds 46

Synthetic Scheme 11

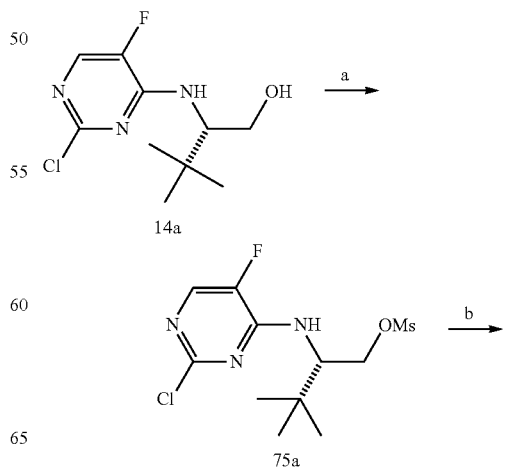

-continued

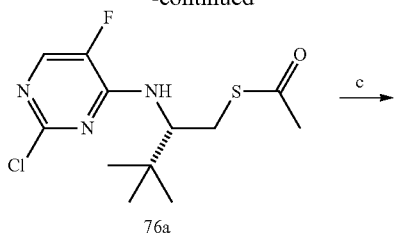

76a

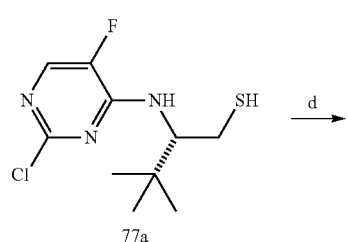

77a

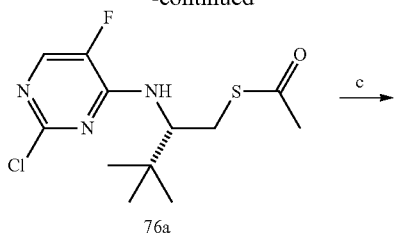

78a

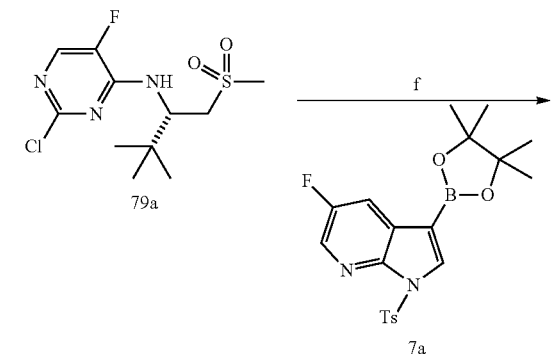

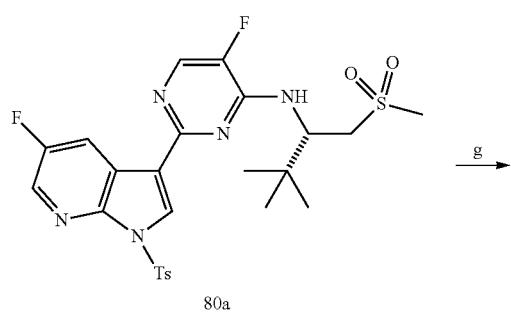

80a

-continued

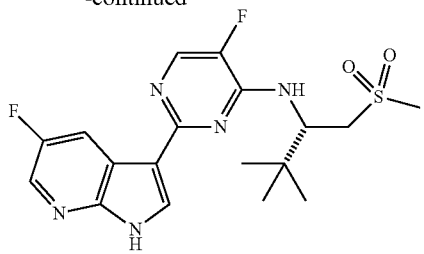

46

(a) MsCl, CH₂Cl₂; (b) KOAc, DMF; (c) NaOMe, MeOH; (d) MeI, K₂CO₃, acetone, 70° C.; (e) Oxone, water, MeOH, 3 hr, RT; (f) 5-fluoro-1-(p-tolylsulfonyl)-3-(4,4,5,5-tetramethyl-1,3,2-dioxaborolan-2-yl)pyrrolo[2,3-b]pyridine, 7a, K₃PO₄ X-Phos, Pd₂(dba)₃, 2-MeTHF, water, 120° C., 3 hr then 80° C., 1 hr; (g) NaOMe, MeOH.

(S)-2-(2-chloro-5-fluoropyrimidin-4-ylamino)-3,3-dimethylbutyl methanesulfonate (75a)

To a cold (0° C.) solution of (S)-2-((2-chloro-5-fluoropyrimidin-4-yl)amino)-3,3-dimethylbutan-1-ol, 14a, (1.95 g, 7.87 mmol) and triethylamine (1.37 mL, 9.84 mmol) in dichloromethane (25 mL) was added methanesulfonyl chloride (0.76 mL, 9.84 mmol). The solution was stirred at room temperature for 1 hour. The solvent was removed under reduced pressure and water (100 mL) and EtOAc (50 mL) were added. The organic phase was separated, dried (MgSO₄) and concentrated under reduced pressure to afford 2.55 g of the desired product as a pale yellow foamy solid: LC/MS (10-90% ACN/water 5 min with 0.9% FA, C4) m/z 326.99 (M+H) RT=2.96 minutes.

(S)—S-2-(2-chloro-5-fluoropyrimidin-4-ylamino)-3,3-dimethylbutyl ethanethioate (76a)

Potassium thioacetate (1.30 g, 11.51 mmol) was added to a stirring solution of (S)-2-(2-chloro-5-fluoropyrimidin-4-ylamino)-3,3-dimethylbutyl methanesulfonate, 75a, (2.50 g, 7.67 mmol) in dry DMF (50 mL). The resulting brown solution was heated with stirring at 78° C. for 1 hour. The brown suspension was poured into water and extracted with EtOAc (3×100 mL). The combined organic phases were dried (MgSO₄), filtered and concentrated under reduced pressure. The crude residue was purified by silica gel chromatography (0-30% EtOAc/Hexanes gradient) to afford 2.1 g of compound 76a as a pale brown solid: ¹H NMR (400 MHz, CDCl₃) δ 7.81 (s, 1H), 5.12 (m, 1H), 4.21 (t, J=9.1 Hz, 1H), 3.15-2.90 (m, 2H), 2.23 (s, 3H), 0.95 (m, 9H); LC/MS (10-90% ACN/water 5 min with 0.9% FA) m/z 306.02 (M+H) RT=3.32 min.

(S)-2-(2-chloro-5-fluoropyrimidin-4-ylamino)-3,3-dimethylbutane-1-thiol (77a)

To a nitrogen-purged solution of (S)—S-2-(2-chloro-5-fluoropyrimidin-4-ylamino)-3,3-dimethylbutyl ethanethioate, 76a, (1.00 g, 3.27 mmol) in methanol (20 mL) was added NaOMe (1.457 mL of 25% solution in MeOH, 6.540 mmol) and the solution was stirred at room temperature for 1 hour. The reaction mixture was concentrated in vacuo and the residue was dissolved in water (25 mL) and slowly acidified with 2N HCl to give a white precipitate that was extracted twice with EtOAc. The combined organic phases were dried (MgSO₄), filtered and concentrated under reduced pressure to afford 0.85 g of the desired product as a pale beige color solid: LC/MS (10-90% ACN/water 5 min with 0.9% FA) m/z 264.92 (M+H) RT=3.32 min.

(S)-2-chloro-N-(3,3-dimethyl-1-(methylthio)butan-2-yl)-5-fluoropyrimidin-4-amine (78a)

To a suspension of (S)-2-(2-chloro-5-fluoropyrimidin-4-ylamino)-3,3-dimethylbutane-1-thiol, 77a, (0.85 g, 3.60 mmol) and $K_2CO_3$ (2.26 g, 16.35 mmol) in acetone was added iodomethane (0.82 mL, 13.08 mmol). The suspension was heated at 70° C. for 1.30 hours and then cooled to room temperature. The solid was filtered and the solution was concentrated under reduced pressure. The crude residue was purified by silica gel chromatography (0-10% EtOAc/Hexanes gradient) to afford 310 mg of the desired product as a white solid: $^1$H NMR (400 MHz, $CDCl_3$) δ 7.81 (s, 1H), 5.12 (m, 1H), 4.21 (t, J=9.1 Hz, 1H), 3.15-2.90 (m, 2H), 2.23 (s, 3H), 0.95 (m, 9H); LC/MS (60-90% ACN/water 5 min with 0.9% FA) m/z 278.29 (M+H) RT=1.35 minutes.

(S)-2-chloro-N-(3,3-dimethyl-1-(methylsulfonyl)butan-2-yl)-5-fluoropyrimidin-4-amine (79a)

To a cold (0° C.) solution of (S)-2-chloro-N-(3,3-dimethyl-1-(methylthio)butan-2-yl)-5-fluoropyrimidin-4-amine, 78a, (0.15 g, 0.54 mmol) in methanol (10 mL) was added Oxone (0.50 g, 0.81 mmol). The solution was stirred at room temperature for 3 hours. The solution was concentrated in vacuo to give a white residue which was dissolved in water (10 mL). The aqueous layer was extracted with EtOAc (3×10 mL). The combined organic phases were dried ($MgSO_4$), filtered and concentrated in vacuo to afford 150 mg of the desired product as a white solid: LC/MS (60-90% ACN/water 5 min with 0.9% FA) m/z 310.31 (M+H) RT=2.60 minutes.

(S)—N-(3,3-dimethyl-1-(methylsulfonyl)butan-2-yl)-5-fluoro-2-(5-fluoro-1-tosyl-1H-pyrrolo[2,3-b]pyridin-3-yl)pyrimidin-4-amine. (80a)

A solution of (S)-2-chloro-N-(3,3-dimethyl-1-(methylsulfonyl)butan-2-yl)-5-fluoropyrimidin-4-amine, 79a, (0.15 g, 0.48 mmol), 5-fluoro-1-(p-tolylsulfonyl)-3-(4,4,5,5-tetramethyl-1,3,2-dioxaborolan-2-yl)pyrrolo[2,3-b]pyridine (0.24 g, 0.58 mmol), and $K_3PO_4$ (0.25 g, 1.16 mmol) in 2-methyl THF (5 mL) and water (1 mL) was purged with nitrogen for 30 minutes. X-Phos (0.015 g, 0.031 mmol) and $Pd_2(dba)_3$ (0.007 g, 0.008 mmol) were added and the reaction mixture was heated at 120° C. in a pressure vial for 2 hours. The reaction mixture was cooled to room temperature, filtered and concentrated in vacuo. The residue was dissolved in EtOAc (50 mL) and washed with water. The organic layer was dried ($MgSO_4$), filtered and concentrated in vacuo. The crude residue was purified by silica gel chromatography (0-40% EtOAc/Hexanes gradient) to afford 210 mg of the desired product as a white foamy solid: $^1$H NMR (400 MHz, $CDCl_3$) δ 8.54-8.43 (m, 2H), 8.24 (d, J=1.3 Hz, 1H), 8.09 (s, 1H), 8.03 (d, J=8.2 Hz, 2H), 7.23 (s, 1H), 4.99 (dt, J=20.3, 10.1 Hz, 2H), 3.37 (d, J=14.4 Hz, 1H), 3.07 (dt, J=31.3, 15.7 Hz, 1H), 2.83 (s, 3H), 2.33 (d, J=19.0 Hz, 3H), 0.98 (d, J=20.7 Hz, 9H); LC/MS (10-90% ACN/water 5 min with 0.9% FA, C4) m/z 564.20 (M+H) RT=3.70 minutes.

(S)—N-(3,3-dimethyl-1-(methylsulfonyl)butan-2-yl)-5-fluoro-2-(5-fluoro-1H-pyrrolo[2,3-b]pyridin-3-yl)pyrimidin-4-amine (46)

To a solution of (S)—N-(3,3-dimethyl-1-(methylsulfonyl)butan-2-yl)-5-fluoro-2-(5-fluoro-1-tosyl-1H-pyrrolo[2,3-b]pyridin-3-yl)pyrimidin-4-amine, 80a, (0.21 g, 0.37 mmol) in THF (10 mL) was added NaOMe (0.33 mL of 25% solution in MeOH, 1.45 mmol). The solution was stirred at room temperature for 10 minutes, then diluted into aqueous saturated $NH_4Cl$ solution. The solvent was removed under reduced pressure and the residue was dissolved in water (10 mL). The aqueous layer was extracted with EtOAc (3×10 mL), dried ($MgSO_4$), filtered and concentrated in vacuo. The product was purified by silica gel chromatography (0-10% MeOH/$CH_2Cl_2$ gradient) to afford 109 mg of the desired product as a white solid: $^1$H NMR (400 MHz, $CDCl_3$) δ 9.38 (s, 1H), 8.53 (d, J=6.9 Hz, 1H), 8.16 (m, 2H), 8.06 (s, 1H), 5.09-4.89 (m, 1H), 3.42-3.31 (m, 1H), 3.11 (m, 1H), 2.84 (s, 3H), 1.00 (s, 9H); LC/MS (10-90% ACN/water 5 min with 0.9% FA) m/z 410.19 (M+H) RT=2.03 minutes.

Preparation of Compound 62

Synthetic Scheme 12

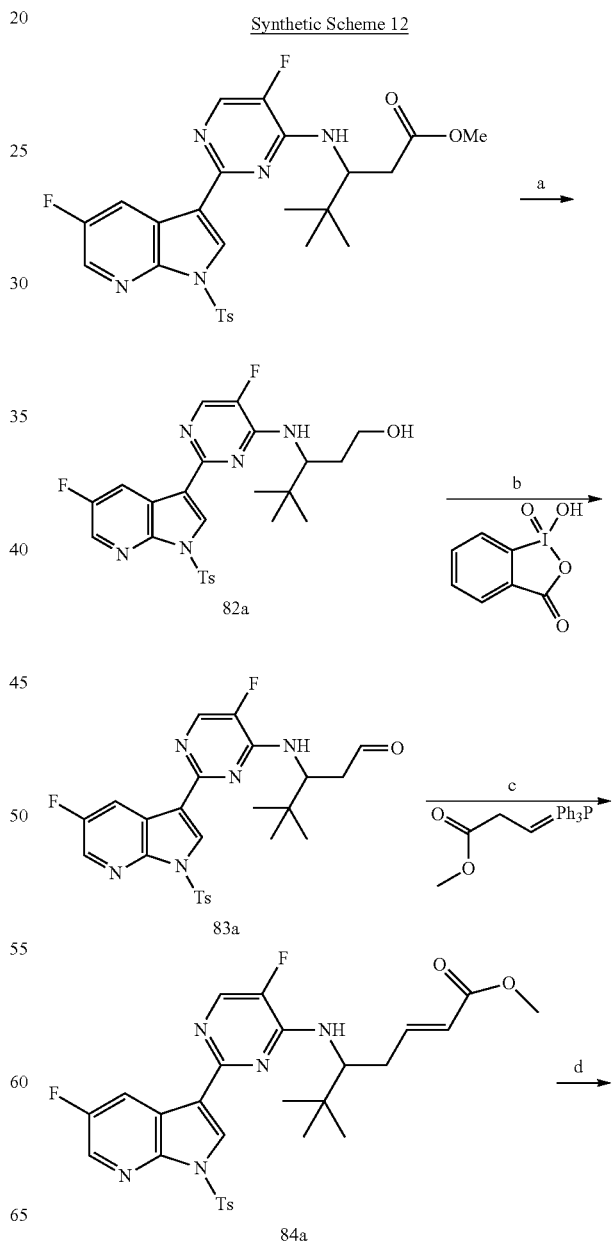

-continued

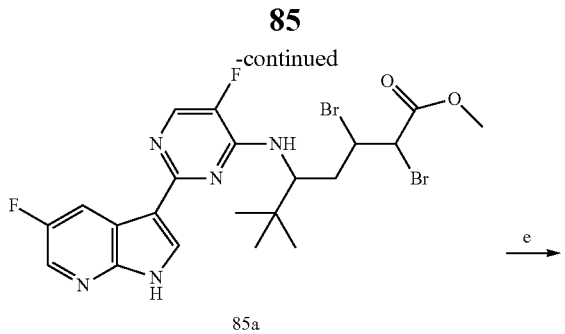

85a

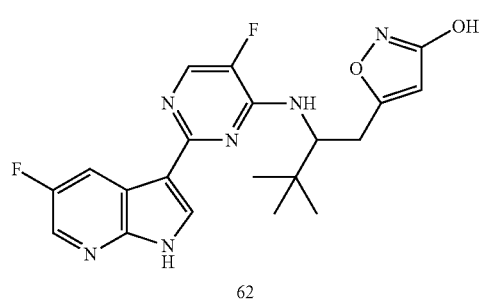

62

(a) LiBH4, THF, 1N HCl; (b) 2-iodoxybenzoic acid, THF, reflux; (c) Toluene; (d) Br₂, HBr, AcOH, 65° C.; (e) NaOH, hydroxyurea, MeOH.

Formation of (+/−)-3-((5-fluoro-2-(5-fluoro-1-tosyl-1H-pyrrolo[2,3-b]pyridin-3-yl)pyrimidin-4-yl)amino)-4,4-dimethylpentan-1-ol (82a)

To a cold (0° C.) solution of racemic methyl 3-((5-fluoro-2-(5-fluoro-1-tosyl-1H-pyrrolo[2,3-b]pyridin-3-yl)pyrimidin-4-yl)amino)-4,4-dimethylpentanoate (4.00 g, 7.36 mmol) in THF (160 mL) and MeOH (10 mL) was added lithium borohydride (29.44 mL of 2 M solution, 58.87 mmol) dropwise over 30 minutes. The reaction mixture was slowly warmed to room temperature and then re-cooled to 0° C. A 1N HCl solution (294 mL, 294 mmol) was added dropwise. The mixture was stirred for 15 minutes and then diluted with dichloromethane. The phases were separated and the aqueous phase was extracted again with dichloromethane. The combined organic phases were washed with aqueous saturated NaHCO₃ solution and brine, dried (Na₂SO₄), filtered and concentrated in vacuo. The resulting residue was purified via silica gel chromatography (EtOAc/Hexanes) to afford 3.79 g of the desired product.

Formation of (+/−)-3-((5-fluoro-2-(5-fluoro-1-tosyl-1H-pyrrolo[2,3-b]pyridin-3-yl)pyrimidin-4-yl)amino)-4,4-dimethylpentanal (83a)

To a solution of racemic 3-((5-fluoro-2-(5-fluoro-1-tosyl-1H-pyrrolo[2,3-b]pyridin-3-yl)pyrimidin-4-yl)amino)-4,4-dimethylpentan-1-ol, 82a, (1.60 g, 3.10 mmol) in THF (64 mL) was added 2-iodoxybenzoic acid (Ibx) (3.86 g, 6.21 mmol). The reaction mixture was heated to reflux under at atmosphere of nitrogen for 30 minutes. After cooling the mixture to room temperature, the solids were filtered. An aqueous saturated NaHCO₃ solution was added to the filtrate and the biphasic mixture was stirred for 30 minutes. The mixture was further diluted with dichloromethane and the phases separated. The aqueous layer was extracted again with dichloromethane. The combined organic phases were dried (Na₂SO₄), filtered and concentrated in vacuo. The resulting residue was purified via silica gel chromatography (EtOAc/Hexanes) to afford 1.59 g of the desired product Formation of (+/−)-methyl 5-((5-fluoro-2-(5-fluoro-1-tosyl-1H-pyrrolo[2,3-b]pyridin-3-yl)pyrimidin-4-yl)amino)-6,6-dimethylhept-2-enoate (84a)

To a solution of 3-((5-fluoro-2-(5-fluoro-1-tosyl-1H-pyrrolo[2,3-b]pyridin-3-yl)pyrimidin-4-yl)amino)-4,4-dimethylpentanal, 83a, (0.295 g, 0.574 mmol) in toluene (5.9 mL) was added methyl 2-(triphenylphosphoranylidene)acetate (0.300 g, 0.862 mmol). The mixture was stirred overnight at room temperature and then purified directly on silica gel (EtOAc/Hexanes) to afford 278 mg of the desired product: LCMS Gradient 10-90%, 0.1% formic acid, 5 minutes, C18/ACN, RT=2.54 minutes (M+H) 584.12.

Formation (+/−)-methyl 2,3-dibromo-5-((5-fluoro-2-(5-fluoro-1H-pyrrolo[2,3-b]pyridin-3-yl)pyrimidin-4-yl)amino)-6,6-dimethylheptanoate (85a)

To a solution of racemic methyl 5-((5-fluoro-2-(5-fluoro-1-tosyl-1H-pyrrolo[2,3-b]pyridin-3-yl)pyrimidin-4-yl)amino)-6,6-dimethylhept-2-enoate, 84a, (0.278 g, 0.476 mmol) acetic acid (2.5 mL) was added bromine (0.099 g, 0.620 mmol) followed by HBr (0.085 mL of 5.6 M solution in AcOH). The reaction mixture was heated at 65° C. overnight. The mixture was diluted into dichloromethane and aqueous saturated sodium bicarbonate solution. The phases were separated and the aqueous layer was washed with dichloromethane. The organic layers were combined and the solvents were removed under reduced pressure. The residue was purified via silica gel chromatography (EtOAc/Hexanes) to give the desired product: LCMS Gradient 10-90%, 0.1% formic acid, 5 minutes, C18/ACN, RT=3.00 minutes (M+H) 590.94.

Formation of (+/−)-5-(2-((5-fluoro-2-(5-fluoro-1H-pyrrolo[2,3-b]pyridin-3-yl)pyrimidin-4-yl)amino)-3,3-dimethylbutyl)isoxazol-3-ol (62)

To a solution of NaOH (0.015 g) dissolved in water (0.410 mL) was added hydroxyurea (0.008 g, 0.100 mmol). The resulting mixture was stirred for 30 minutes before the dropwise addition of methyl 2,3-dibromo-5-((5-fluoro-2-(5-fluoro-1H-pyrrolo[2,3-b]pyridin-3-yl)pyrimidin-4-yl)amino)-6,6-dimethylheptanoate, 85a, (0.064 g, 0.110 mmol) in MeOH (0.150 mL). The solution was stirred for 6 hours before the addition of AcOH (0.031 mL). The residue was purified by reverse phase preparative HPLC to afford the desired product: ¹H NMR (300 MHz, MeOD) δ 8.57 (dd, J=9.7, 2.8 Hz, 1H), 8.16 (d, J=5.5 Hz, 2H), 8.00 (d, J=4.1 Hz, 1H), 5.68 (s, 1H), 3.03 (ddd, J=27.4, 15.4, 12.3 Hz, 2H), 1.10

(d, J=3.3 Hz, 11H); LCMS Gradient 10-90%, 0.1% formic acid, 5 minutes, C18/ACN, RT=2.15 minutes (M+H) 416.04.

Preparation of Compound 45

Synthetic Scheme 13

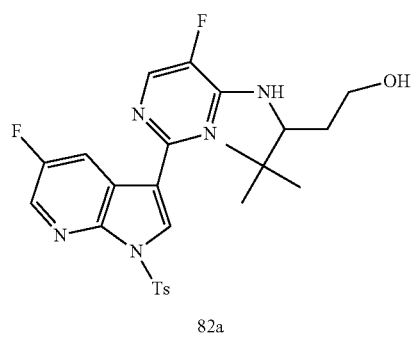

82a

↓ a

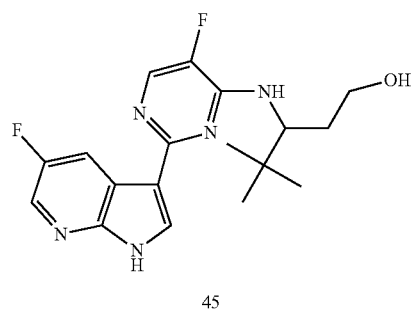

45

(a) LiOH, dioxane, H₂O, 100° C.

Formation of (+/−)-3-((5-fluoro-2-(5-fluoro-1H-pyrrolo[2,3-b]pyridin-3-yl)pyrimidin-4-yl)amino)-4,4-dimethylpentan-1-ol (45)

To a solution of racemic 3-((5-fluoro-2-(5-fluoro-1-tosyl-1H-pyrrolo[2,3-b]pyridin-3-yl)pyrimidin-4-yl)amino)-4,4-dimethylpentan-1-ol, 82a, (0.187 g, 0.363 mmol) in dioxane (4 mL) was added LiOH (0.91 mL of 2 M solution, 1.81 mmol). The reaction mixture was heated at 100° C. for 2 hours. The mixture was diluted with water (30 mL) and extracted twice with EtOAc. The combined organic phases were washed with brine, dried (MgSO4), filtered and concentrated in vacuo. The crude residue was washed with Hexanes to afford 76 mg of the desired product: ¹H NMR (300 MHz, CDCl₃) δ 10.42 (s, 1H), 8.47 (dd, J=9.3, 2.7 Hz, 1H), 8.13 (d, J=11.2 Hz, 1H), 8.10 (s, 1H), 8.04 (d, J=3.2 Hz, 1H), 4.89 (d, J=9.0 Hz, 1H), 4.26 (t, J=9.9 Hz, 1H), 3.65 (d, J=9.2 Hz, 1H), 3.54 (td, J=11.4, 2.9 Hz, 1H), 2.17-1.99 (m, 1H), 1.40 (dd, J=14.0, 11.9 Hz, 1H), 0.96 (d, J=18.4 Hz, 9H), 0.90-0.73 (m, 1H); LCMS Gradient 10-90%, 0.1% formic acid, 5 minutes, C18/ACN, (M+H) 362.

Preparation of Compounds 50, 51, and 52

Synthetic Scheme 14

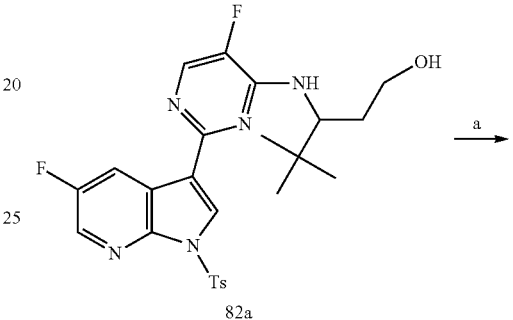

82a

↓ a

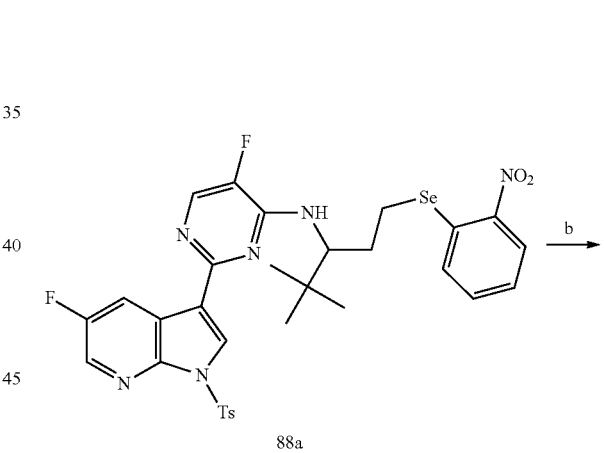

88a

↓ b

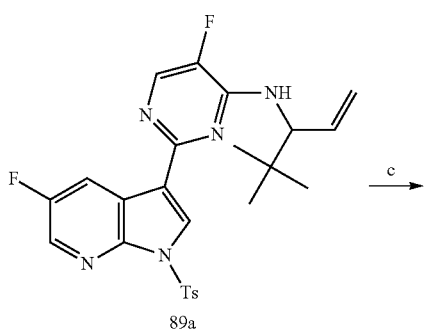

89a

↓ c

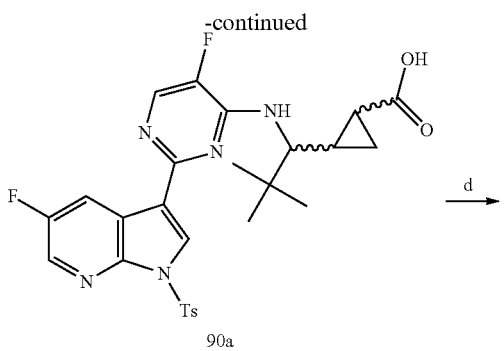

90a

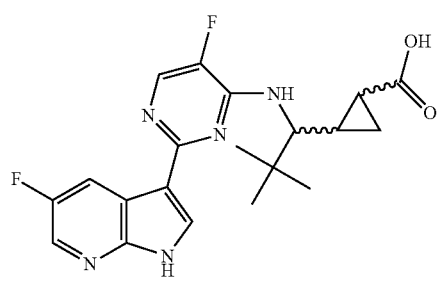

50, 51, and 52

(a) 2-nitrophenylselenocyanate, Bu₃P, THF; (b) mCPBA, CHCl₃; (c) Rh₂(OAc)₄, N₂CH₂CO₂Et, CH₂Cl₂; (d) LiOH, dioxane, H₂O.

Formation of (+/−)-N-(4,4-dimethyl-1-((2-nitrophenyl)selanyl)pentan-3-yl)-5-fluoro-2-(5-fluoro-1-tosyl-1H-pyrrolo[2,3-b]pyridin-3-yl)pyrimidin-4-amine (88a)

To a solution of racemic 3-[[5-fluoro-2-[5-fluoro-1-(p-tolylsulfonyl)pyrrolo[2,3-b]pyridin-3-yl]pyrimidin-4-yl]amino]-4,4-dimethyl-pentan-1-ol, 82a, (1.093 g, 2.120 mmol) and (2-nitrophenyl) selenocyanate (0.722 g, 3.180 mmol) in THF (8 mL) was added tributylphosphane (0.792 mL, 3.180 mmol). The reaction mixture was stirred overnight and then concentrated under reduced pressure. The crude residue was purified by silica gel (0 to 100% EtOAc/Hexanes gradient) to afford 1.20 g of the desired product.

Formation of (+/−)-N-(4,4-dimethylpent-1-en-3-yl)-5-fluoro-2-(5-fluoro-1-tosyl-1H-pyrrolo[2,3-b]pyridin-3-yl)pyrimidin-4-amine (89a)

To a cold (0° C.) solution of racemic N-(4,4-dimethyl-1-((2-nitrophenyl)selanyl)pentan-3-yl)-5-fluoro-2-(5-fluoro-1-tosyl-1H-pyrrolo[2,3-b]pyridin-3-yl)pyrimidin-4-amine, 88a, (1.01 g, 1.45 mmol) in chloroform (15 mL) was added mCPBA (0.40 g of 77%, 1.79 mmol). After stirring for 1 hour at room temperature, the mixture was diluted with dichloromethane (100 mL) and the resulting solution was washed with aqueous sodium bicarbonate solution. The organic phase was dried (MgSO₄), filtered and concentrated in vacuo. The crude residue was purified by silica gel chromatography (0 to 100% EtOAc/Hexanes) to afford 623 mg of the desired product: LCMS Gradient 10-90%, 0.1% formic acid, 5 minutes, C18/ACN, (M+H) 496.76.

Formation of 2-(1-((5-fluoro-2-(5-fluoro-1H-pyrrolo[2,3-b]pyridin-3-yl)pyrimidin-4-yl)amino)-2,2-dimethylpropyl)cyclopropanecarboxylic acid (50, 51, and 52)

To racemic N-(4,4-dimethylpent-1-en-3-yl)-5-fluoro-2-(5-fluoro-1-tosyl-1H-pyrrolo[2,3-b]pyridin-3-yl)pyrimidin-4-amine, 89a, (0.105 g, 0.211 mmol) and rhodium(II) acetate (0.019 g, 0.042 mmol) in dichloromethane (6.2 mL) was added dropwise a solution of ethyl 2-diazoacetate (0.181 g, 0.166 mL, 1.582 mmol) in 2 mL dichloromethane over 30 minutes. Pd(OAc)₂ (0.019 g, 0.042 mmol) in dichloromethane (2 mL) was added followed by ethyl 2-diazoacetate (0.181 g, 0.166 mL, 1.582 mmol) in dichloromethane (2 mL) dropwise. The reaction was stirred overnight and the solvent was concentrated in vacuo. The resulting crude residue was purified by silica gel chromatography (0 to 100% EtOAc/Hexanes gradient) to afford a racemic mixture of diasteromeric esters, 90a. The mixture of esters was dissolved in dioxane (2 mL) and 2N LiOH (1 mL). After heating at 100° C. for 2 h and cooling to room temperature, the mixture was acidified pH 6.5 with 2N HCl. The aqueous phase was extracted twice with EtOAc and once with dichloromethane. The combined organic phases were dried (MgSO₄), filtered and concentrated under reduced pressure. The crude residue was subjected to silica gel chromatography (0-20% MeOH/EtOAc gradient) to isolate the mixture of diastereomeric acids, which were further purified by preparatory HPLC (CH₃CN/H₂O—TFA modifier) to afford 3 diastereomers. Two of the diastereomers, 51 and 52, were isolated as a single diastereomer each. The third diastereomer, 50, was isolated as a mixture of diastereomers. All three diastereomers showed same LCMS: LCMS Gradient 10-90%, 0.1% formic acid, 5 minutes, C18/ACN, (M+H) 402.45.

1$^{st}$ fraction—a mixture of diastereomers with 4 peaks at 1.8, 1.9, 2.06 and 2.16 minutes—contains 50;

2$^{nd}$ fraction—single peak at 2.06 minutes—(51)

3$^{rd}$ fraction—single peak at 2.16 minutes—(52)

Preparation of Compound 41

Synthetic Scheme 15

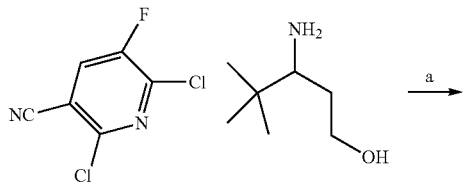

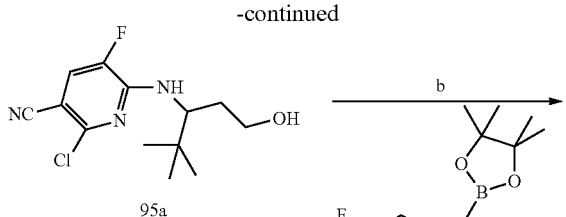

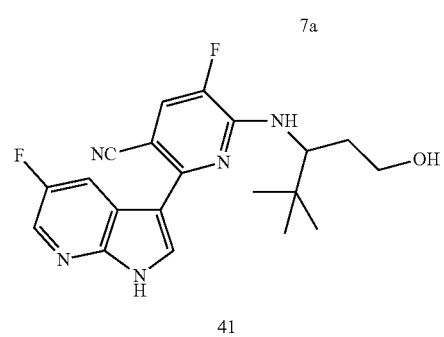

(a) <sup>i</sup>Pr₂NEt, EtOH, 75° C.; (b) Pd₂(dba)₃, XPhos, K₃PO₄, THF, H₂O, 135° C., microwave.

Formation of (+/−)-2-chloro-5-fluoro-6-(1-hydroxy-4,4-dimethylpentan-3-ylamino)pyridine-3-carbonitrile (95a)

To a solution of 3-amino-4,4-dimethylpentan-1-ol (2.00 g, 8.64 mmol) in ethanol (20 mL) was added racemic 2,6-dichloro-5-fluoro-pyridine-3-carbonitrile (1.65 g, 8.64 mmol) and 5 mL of N,N,-diisopropylethylamine. The solution was stirred at 75° C. for 12 hours and concentrated in vacuo. The residue was purified by silica gel chromatography (methylene chloride), yielding 2.2 g of 2-chloro-5-fluoro-6-(1-hydroxy-4,4-dimethylpentan-3-ylamino)pyridine-3-carbonitrile, 95a: LCMS Gradient 10-90%, 0.1% formic acid, 5 minutes, C18/ACN, RT=3.02 minutes (M+H) 286.16

Formation of (+/−)-5-fluoro-2-(5-fluoro-1H-pyrrolo[2,3-b]pyridin-3-yl)-6-(1-hydroxy-4,4-dimethylpentan-3-ylamino)pyridine-3-carbonitrile (41)

To a racemic solution of 2-chloro-5-fluoro-6-(1-hydroxy-4,4-dimethylpentan-3-ylamino)pyridine-3-carbonitrile, 95a, (0.20 g, 0.70 mmol) and 5-fluoro-3-(4,4,5,5-tetramethyl-1,3,2-dioxaborolan-2-yl)-1-tosyl-1H-pyrrolo[2,3-b]pyridine, 7a, (0.44 g, 1.05 mmol) in THF (15 mL) was added a solution of potassium phosphate (0.45 g) in 3 mL of water. The resulting mixture was degassed under a stream of nitrogen for 15 minutes. To the mixture was then added X-Phos (0.03 g, 0.07 mmol) and Pd₂(dba)₃ (0.02 g, 0.04 mmol). The reaction was warmed to 135° C. via microwave irradiation for 15 minutes and then extracted into EtOAc (3×15 mL) vs. water. The organic layers were combined and concentrated in vacuo to a dark oil which was redissolved in 20 mL of THF. To the solution was added 5 mL of 2 N LiOH and the reaction was warmed to 65° C. for 12 hrs and then concentrated in vacuo. The resulting residue was purified via silica gel chromatography (EtOAc) to afford 108 mg of the desired product, 41, as a yellow solid: ¹H NMR (300 MHz, d6-DMSO) δ 12.40 (s, H), 8.63 (dd, J=2.8, 10.1 Hz, H), 8.37-8.32 (m, H), 7.83 (d, J=11.4 Hz, H), 7.31 (d, J=9.7 Hz, H), 4.56-4.50 (m, H), 4.41 (dd, J=4.1, 5.2 Hz, H), 3.69 (s, H), 3.57 (s, H), 3.49 (t, J=6.6 Hz, H), 3.48 (s, H), 3.36-3.28 (m, H), 2.50 (qn, J=1.8 Hz, H), 1.86-1.67 (m, 2H), 1.21 (dd, J=7.0, 16.1 Hz, H) and 0.94 (s, 9H) ppm; LCMS Gradient 10-90%, 0.1% formic acid, 5 minutes, C18/ACN, RT=3.09 minutes (M+H) 386.39.

Preparation of Compounds 11, 24, 25 26, 27, 28, 29, 30, and 31

Synthetic Scheme 16

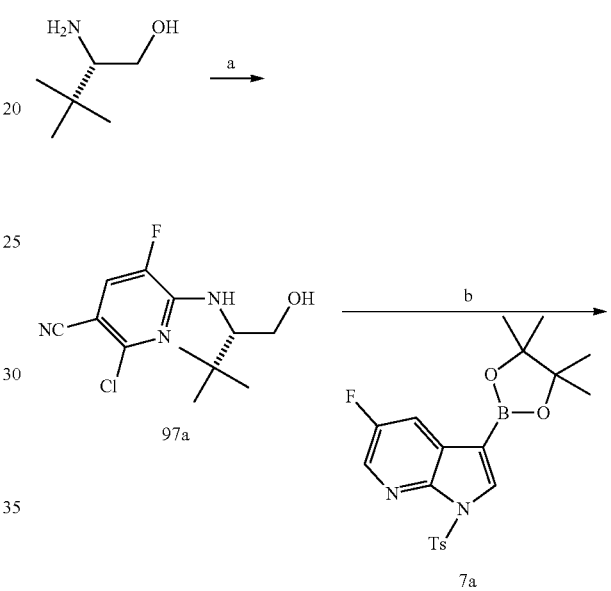

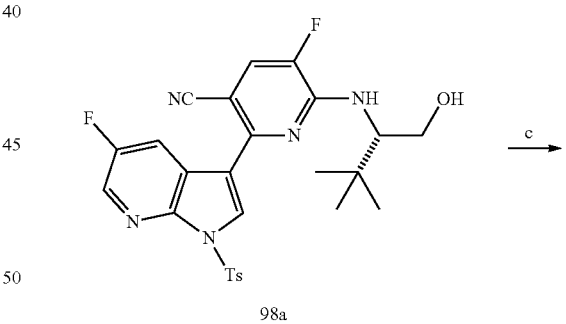

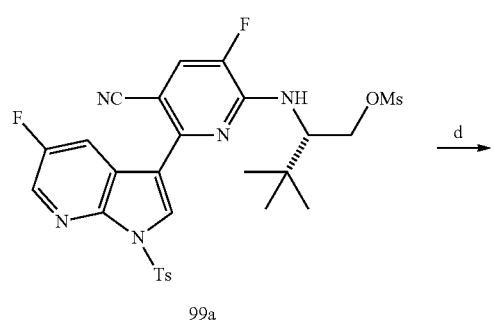

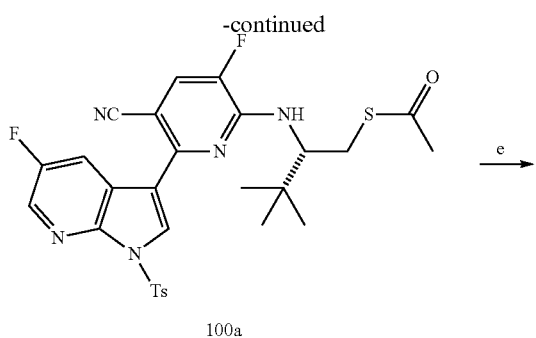

100a

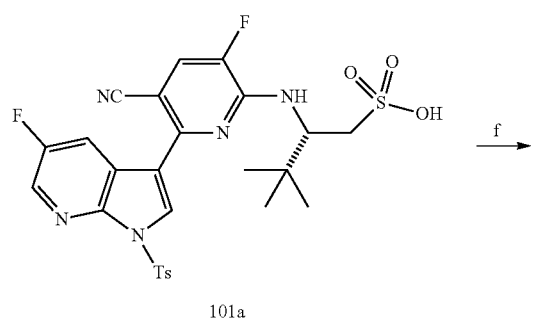

101a

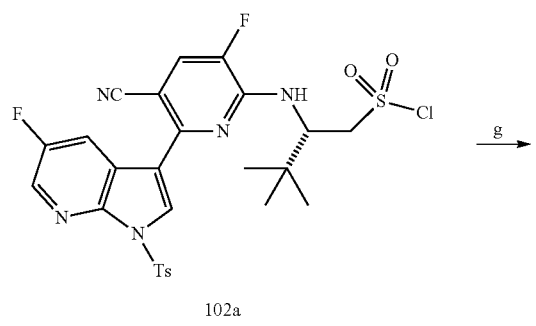

102a

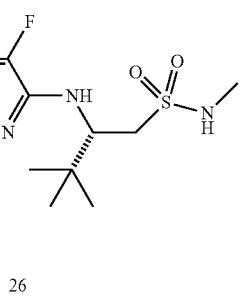

26

(a) 2-chloro-5,6-difluoropyridine-3-carbonitrile, $^{i}Pr_2NEt$, THF, MeOH, 95° C.; (b) 5-fluoro-1-(p-tolylsulfonyl)-3-(4,4,5,5-tetramethyl-1,3,2-dioxaborolan-2-yl)pyrrolo[2,3-b]pyridine, 7a, $K_3PO_4$, X-Phos, $Pd_2(dba)_3$, 2-Me THF, water, 120° C.; (c) MsCl. $CH_2Cl_2$; (d) KOAc, DMF, 80° C.; (e) 30% $H_2O_2$, HCOOH; (f) $(COCl)_2$, DMF, $CH_2Cl_2$. (g) i. Amine,THF; ii. 4M HCl, $CH_3CN$, 65° C.

(S)-2-chloro-5-fluoro-6-((1-hydroxy-3,3-dimethylbutan-2-yl)amino)nicotinonitrile (97a)

A mixture of 2-chloro-5,6-difluoropyridine-3-carbonitrile (6.52 g, 34.13 mmol), (2S)-2-amino-3,3-dimethyl-butan-1-ol (4.00 g, 34.13 mmol) and triethylamine (9.51 mL, 68.26 mmol) in $CH_3CN$ (50 mL) and THF (50 mL) was heated at 80° C. for 4 hours. The mixture was cooled to room temperature and the solvent was evaporated under reduced pressure. The crude product was purified via silica gel chromatography (0-60% EtOAc/Hexanes gradient) to afford 6.7 g of the desired product as an off white solid: $^1H$ NMR (400 MHz, $CDCl_3$) δ 7.25 (d, J=9.7 Hz, 1H), 5.32 (m, 1H), 4.19-4.08 (m, 1H), 3.95-3.83 (m, 1H), 3.74-3.51 (m, 1H), 0.92 (s, 9H); LC/MS (60-90% ACN/water 5 min with 0.9% FA) m/z 272.02 (M+H), retention time 1.02 minutes.

(S)-5-fluoro-2-(5-fluoro-1-tosyl-1H-pyrrolo[2,3-b]pyridin-3-yl)-6-((1-hydroxy-3,3-dimethylbutan-2-yl)amino)nicotinonitrile (98a)

A solution of 5-fluoro-1-(p-tolylsulfonyl)-3-(4,4,5,5-tetramethyl-1,3,2-dioxaborolan-2-yl)pyrrolo[2,3-b]pyridine, 7a, (1.84 g, 4.42 mmol), (S)-2-chloro-5-fluoro-6-((1-hydroxy-3,3-dimethylbutan-2-yl)amino)nicotinonitrile, 97a, (1.00 g, 3.68 mmol) and $K_3PO_4$ (2.40 g, 11.22 mmol) in 2-methyl-THF (12 mL) and water (2 mL) was purged with nitrogen for 30 minutes. X-Phos (0.14 g, 0.294 mmol) and $Pd_2(dba)_3$ (0.07 g, 0.07 mmol) were added and the reaction mixture was heated at 120° C. in a pressure vial for 2 hours. The reaction mixture was cooled to room temperature, filtered and concentrated in vacuo. The residue was dissolved in EtOAc (50 mL) and washed with water. The organic layer was dried ($MgSO_4$), filtered and concentrated in vacuo. The crude product was purified by silica gel chromatography (0-40% EtOAc/Hexanes gradient) to afford 1.88 g as a foamy solid: $^1H$ NMR (300 MHz, $CDCl_3$) δ 8.64 (s, 1H), 8.36 (d, J=2.0 Hz, 1H), 8.26 (m, 1H), 8.14 (d, J=8.4 Hz, 2H), 7.46 (d, J=12 Hz, 2H), 7.33 (d, J=7.5 Hz, 1H), 5.34 (m, 1H), 4.42-4.31 (m, 1H), 4.02 (m, 1H), 3.75 (m, 1H), 2.40 (s, 3H), 1.26 (s, 9H); LC/MS (60-90% ACN/water 5 min with 0.9% FA, C4) m/z 526.49 (M+H), retention time=1.83 minutes.

(S)-2-((5-cyano-3-fluoro-6-(5-fluoro-1-tosyl-1H-pyrrolo[2,3-b]pyridin-3-yl)pyridin-2-yl)amino)-3,3-dimethylbutyl methanesulfonate (99a)

To a cold (0° C.) solution of (S)-5-fluoro-2-(5-fluoro-1-tosyl-1H-pyrrolo[2,3-b]pyridin-3-yl)-6-((1-hydroxy-3,3-dimethylbutan-2-yl)amino)nicotinonitrile, 98a, (3.77 g, 7.17 mmol) and triethylamine (1.25 mL, 8.96 mmol) in dichloromethane (75 mL) was added methanesulfonyl chloride (0.69 mL, 8.96 mmol). The solution was stirred at room temperature for 1 hour. The solvent was removed under reduced pressure and water (100 mL) and EtOAc (200 mL) were added. The organic phase was separated, dried ($MgSO_4$), filtered and concentrated under reduced pressure to afford 4.22 g of the desired product as a yellow foamy solid that was used without further purification: LC/MS (60-90% ACN/water 5 min with 0.9% FA, C4) m/z 604.45 (M+H) retention time=2.03 minutes.

(S)-2-(5-Cyano-3-fluoro-6-(5-fluoro-1-tosyl-1H-pyrrolo[2,3-b]pyridin-2-ylamino)-3,3-dimethylbutyl ethanethiolate (100a)

Potassium thioacetate (1.2 g, 10.5 mmol) was added to a solution of (S)-2-((5-cyano-3-fluoro-6-(5-fluoro-1-tosyl-1H-pyrrolo[2,3-b]pyridin-3-yl)pyridin-2-yl)amino)-3,3-dimethylbutyl methanesulfonate, 99a, (4.22 g, 6.99 mmol) in dry DMF (90 mL). The brown solution was heated with stirring at 80° C. for 1 hour. The thick brown suspension was poured into water and extracted with EtOAc (3×100 mL). The organic layers were dried (MgSO$_4$), filtered and concentrated under reduced pressure. The crude product was purified by silica gel chromatography (0-30% EtOAc/Hexanes gradient) to afford 6.8 g of the desired product as a pale brown solid: $^1$H NMR (400 MHz, CDCl$_3$) δ 8.57 (s, 1H), 8.28 (d, J=1.3 Hz, 1H), 8.11 (dd, J=8.5, 2.3 Hz, 1H), 8.05 (d, J=8.3 Hz, 2H), 7.33 (d, J=10.2 Hz, 1H), 7.24 (d, J=8.3 Hz, 2H), 5.11 (m, 1H), 4.31 (m, 1H), 3.19 (dd, J=14.0, 3.0 Hz, 1H), 3.03 (dt, J=13.6, 6.9 Hz, 1H), 2.31 (s, 3H), 2.10 (m, 3H), 10.97 (s, 9H); LC/MS (60-90% ACN/water 5 min with 0.9% FA) m/z 584.0 (M+H) retention time=2.66 minutes.

(S)-2-(5-Cyano-3-fluoro-6-(5-fluoro-1-tosyl-1H-pyrrolo[2,3-b]pyridin-2-ylamino)-3,3-dimethylbutane-1-sulfonic acid (101a)

To a cold (0° C.) solution of formic acid (22.2 mL, 588.5 mmol) was added H$_2$O$_2$(7.35 mL of 30% solution, 71.96 mmol). The mixture was stirred at 0° C. for 1 hour. A solution of (S)—S-2-(5-cyano-3-fluoro-6-(5-fluoro-1-tosyl-1H-pyrrolo[2,3-b]pyridin-2ylamino)-3,3-dimethylbutyl ethanethiolate, 99a, (1.5 g, 2.57 mmol) in formic acid (5 mL) was added dropwise to the reaction mixture. The resulting solution was stirred for 2 hours at room temperature. The solvent was removed under reduced pressure 1.72 g of the desired sulfonic acid as a pale yellow foamy solid: LC/MS (10-90% ACN/water 5 min with 0.9% FA) m/z 586 (M+H) retention time=3.95 minutes.

(S)-2-(5-Cyano-3-fluoro-6-(5-fluoro-1-tosyl-1H-pyrrolo[2,3-b]pyridin-2ylamino)-3,3-dimethylbutane-1-sulfonyl chloride (102a)

To a solution of (S)-2-(5-cyano-3-fluoro-6-(5-fluoro-1-tosyl-1H-pyrrolo[2,3-b]pyridin-2ylamino)-3,3-dimethylbutane-1-sulfonic acid, 101a, (1.5 g, 2.54 mmol) and DMF (0.5 mL) in dichloromethane (30 mL) was added oxalyl dichloride (0.68 mL, 7.63 mmol) dropwise. The solution was stirred at room temperature for 1 hour. The solvent was removed under reduced pressure to afford 1.6 g of the desired product as a yellow solid: LC/MS (60-90% ACN/water 5 min with 0.9% FA) m/z 608 (M+H) retention time=2.40 minutes.

(S)-2-(5-Cyano-3-fluoro-6-(5-fluoro-1H-pyrrolo[2,3-b]pyridin-3-yl)pyridin-2ylamino)-N,3,3-trimethylbutane-1-sulfonamide (26)

Methyl amine (0.41 mL of 2M solution, 0.82 mmol) was added to a solution of (S)-2-(5-cyano-3-fluoro-6-(5-fluoro-1-tosyl-1H-pyrrolo[2,3-b]pyridin-2ylamino)-3,3-dimethylbutane-1-sulfonyl chloride, 102a, (0.10 g, 0.16 mmol) in THF (1 mL). The solution was stirred for 1 hour at room temperature and the solvent was removed under reduced pressure. The crude sulfonamide was dissolved in CH$_3$CN (3 mL) and HCl (2 mL of 4M solution in dioxane) was added. The reaction mixture was heated at 65° C. for 3 hours and then cooled to room temperature. The solvent was removed under reduced pressure and the resulting residue was purified by preparative HPLC chromatography (10-80% CH$_3$CN/water, 0.5% TFA, 15 min) to afford 26 mg of the desired product as a white solid: $^1$H NMR (400 MHz, CDCl$_3$) δ 9.68 (s, 1H), 8.45-8.33 (m, 1H), 8.17 (d, J=2.8 Hz, 1H), 7.88 (s, 1H), 7.36 (d, J=10.3 Hz, 1H), 6.47 (d, J=4.9 Hz, 1H), 5.11 (d, J=7.8 Hz, 1H), 4.90 (d, J=10.4 Hz, 1H), 3.52 (s, 1H), 3.04 (dd, J=15.0, 10.5 Hz, 1H), 2.67 (d, J=5.0 Hz, 3H), 1.02 (s, 9H); LC/MS (10-90% ACN/water 5 min with 0.9% FA) m/z 449.22 (M+H) retention time=2.97 minutes.

The following compounds can be prepared in a similar fashion as the procedure described above for Compound 26:

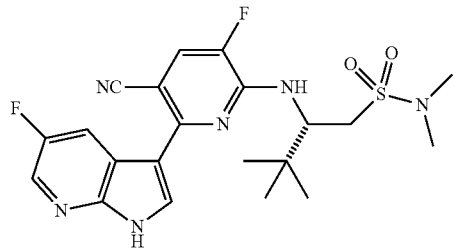 [SMILES: CN(C)S(=O)(=O)C[C@@H](Nc1nc(-c2c[nH]c3ncc(F)cc23)c(C#N)cc1F)C(C)(C)C]

(S)-2-(5-Cyano-3-fluoro-6-(5-fluoro-1H-pyrrolo[2,3-b]pyridin-3-yl)pyridin-2ylamino)-N,N,3,3-tetramethylbutane-1-sulfonamide (27)

$^1$H NMR (400 MHz, CDCl$_3$) δ 8.59 (dd, J=9.7, 2.6 Hz, 1H), 8.38 (s, 1H), 8.21 (s, 1H), 7.31 (m, 1H), 5.12 (brs, 1H), 4.97 (brs, 1H), 3.33 (m, 1H), 2.70 (s, 6H), 0.95 (m, 9H); LC/MS (10-90% ACN/water 5 min with 0.9% FA) m/z 463.49 (M+H) retention time=3.12 minutes.

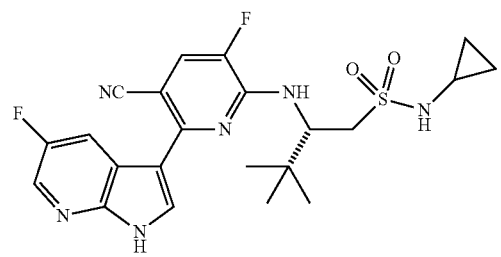 [SMILES: CC(C)(C)[C@@H](CS(=O)(=O)NC1CC1)Nc1nc(-c2c[nH]c3ncc(F)cc23)c(C#N)cc1F]

(S)-2-(5-Cyano-3-fluoro-6-(5-fluoro-1H-pyrrolo[2,3-b]pyridin-3-yl)pyridin-2ylamino)-N-cyclopropyl-3,3-dimethylbutane-1-sulfonamide (28)

LC/MS (10-90% ACN/water 5 min with 0.9% FA) m/z 475.0 (M+H) retention time=3.12 minutes.

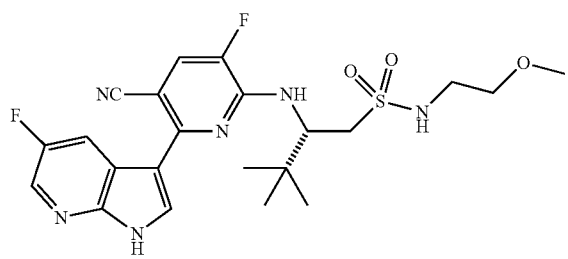 [SMILES: COCCNS(=O)(=O)C[C@@H](Nc1nc(-c2c[nH]c3ncc(F)cc23)c(C#N)cc1F)C(C)(C)C]

(S)-2-((5-cyano-3-fluoro-6-(5-fluoro-1H-pyrrolo[2,3-b]pyridin-3-yl)pyridin-2-yl)amino)-N-(2-methoxyethyl)-3,3-dimethylbutane-1-sulfonamide (29)

$^1$H NMR (400 MHz, MeOD) δ 8.71 (dd, J=9.7, 2.6 Hz, 1H), 8.37 (s, 1H), 8.20 (s, 1H), 7.57 (d, J=10.9 Hz, 1H), 5.08 (d, J=8.8 Hz, 1H), 3.54-3.40 (m, 2H), 3.32 (m, 5H), 3.15 (t, J=5.4 Hz, 2H), 1.03 (s, 9H); LC/MS (10-90% ACN/water 5 min with 0.9% FA) m/z 493.50 (M+H) retention time=3.05 minutes.

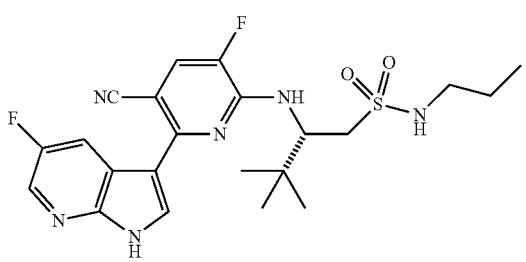 [SMILES: CCCNS(=O)(=O)C[C@@H](Nc1nc(-c2c[nH]c3ncc(F)cc23)c(C#N)cc1F)C(C)(C)C]

(S)-2-((5-cyano-3-fluoro-6-(5-fluoro-1H-pyrrolo[2,3-b]pyridin-3-yl)pyridin-2-yl)amino)-3,3-dimethyl-N-propylbutane-1-sulfonamide (31)

LC/MS (10-90% ACN/water 5 min with 0.9% FA) m/z 477.65 (M+H) retention time=3.27 minutes.

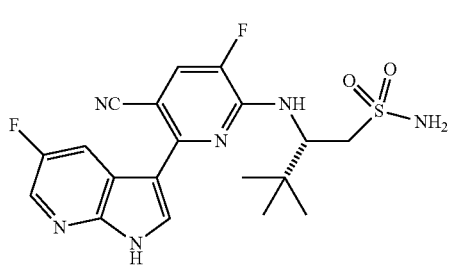 [SMILES: CC(C)(C)[C@@H](CS(N)(=O)=O)Nc1nc(-c2c[nH]c3ncc(F)cc23)c(C#N)cc1F]

(S)-2-((5-cyano-3-fluoro-6-(5-fluoro-1H-pyrrolo[2,3-b]pyridin-3-yl)pyridin-2-yl)amino)-3,3-dimethylbutane-1-sulfonamide (30)

LC/MS (10-90% ACN/water 5 min with 0.9% FA) m/z 435.46 (M+H) retention time=2.80 minutes.

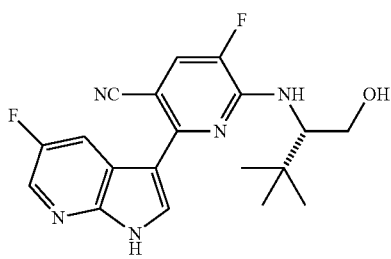 [SMILES: CC(C)(C)[C@@H](CO)Nc1nc(-c2c[nH]c3ncc(F)cc23)c(C#N)cc1F]

(S)-5-fluoro-2-(5-fluoro-1H-pyrrolo[2,3-b]pyridin-3-yl)-6-((1-hydroxy-3,3-dimethylbutan-2-yl)amino)nicotinonitrile (24)

Alcohol, 24, was synthesized in a manner similar to compound 32 utilizing the same deprotection procedure, starting with compound 98a: $^1$H NMR (400 MHz, CDCl$_3$) δ 10.27 (brs, 1H), 8.25 (d, J=9.4 Hz, 1H), 8.17 (s, 1H), 8.11 (s, 1H), 7.23 (d, J=10.3 Hz, 1H), 5.20 (d, J=9.6 Hz, 1H), 4.41 (t, J=7.4 Hz, 1H), 4.09 (d, J=11.3 Hz, 1H), 3.82-3.58 (m, 1H), 0.99 (d, J=19.5 Hz, 9H).

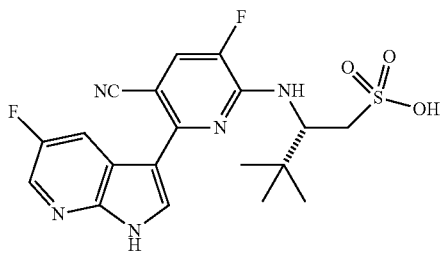 [SMILES: CC(C)(C)[C@@H](CS(=O)(=O)O)Nc1nc(-c2c[nH]c3ncc(F)cc23)c(C#N)cc1F]

(S)-2-(5-cyano-3-fluoro-6-(5-fluoro-1H-pyrrolo[2,3-b]pyridin-3-yl)pyridin-2-ylamino)-3,3-dimethylbutane-1-sulfonic acid (25)

To a solution of (S)-2-((5-cyano-3-fluoro-6-(5-fluoro-1-tosyl-1H-pyrrolo[2,3-b]pyridin-3-yl)pyridin-2-yl)amino)-3,3-dimethylbutane-1-sulfonic acid, 101a, (0.12 g, 0.21 mmol) in CH$_3$CN (5 mL) was added HCl (2 mL of 4M solution in dioxane). The reaction mixture was heated at 100° C. for 18 hours in a pressure vial and then cooled to room temperature. The solvent was removed under reduced pressure and the product was purified by preparative HPLC chromatography (10-80% CH$_3$CN/water, 0.5% TFA, 15 min) to give 42 mg of the desired product as an off-white solid: $^1$H NMR (400 MHz, MeOD) δ 8.44 (s, 1H), 8.34 (dd, J=9.2, 2.6 Hz, 1H), 8.22 (d, J=5.7 Hz, 1H), 8.13 (s, 1H), 5.16 (m, 1H), 3.46-3.33 (m, 3H), 1.10 (s, 9H); LC/MS (10-90% ACN/water 5 min with 0.9% TFA, C18) m/z 449.22 (M+H).

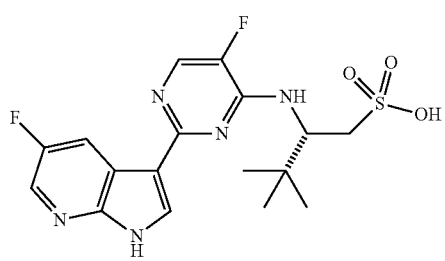 [SMILES: CC(C)(C)[C@@H](CS(=O)(=O)O)Nc1nc(-c2c[nH]c3ncc(F)cc23)ncc1F]
(S)-2-((5-fluoro-2-(5-fluoro-1H-pyrrolo[2,3-b]pyridin-3-yl)pyrimidin-4-yl)amino)-3,3-dimethylbutane-1-sulfonic acid (11)
Sulfonic acid, 11, was synthesized in a manner similar to compound 30, using compound 57a: ¹H NMR (400 MHz, MeOD) δ 8.44 (s, 1H), 8.34 (dd, J=9.2, 2.6 Hz, 1H), 8.22 (d, J=5.7 Hz, 1H), 8.13 (s, 1H), 5.16 (d, J=4.1 Hz, 1H), 3.46-3.33 (m, 2H), 1.10 (d, 9H); LC/MS (10-90% ACN/water 5 min with 0.9% TFA, C18) m/z 412.19 (M+H) retention time=1.91 minutes.
Preparation of Compounds 62, 87, and 88
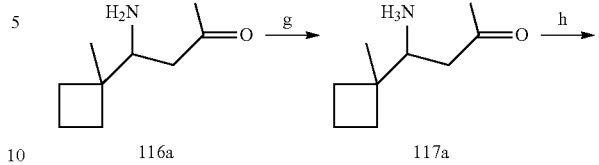
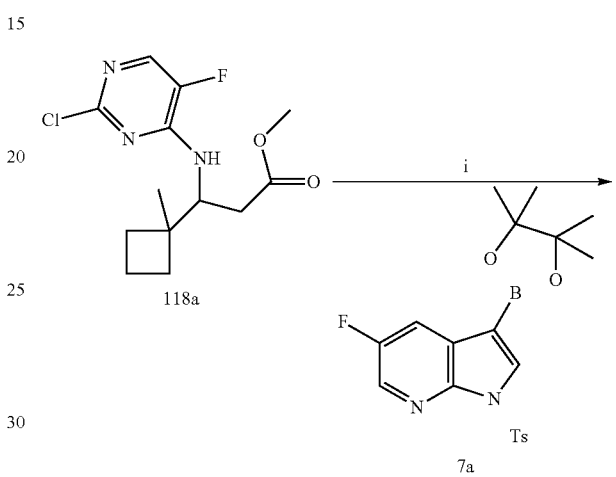
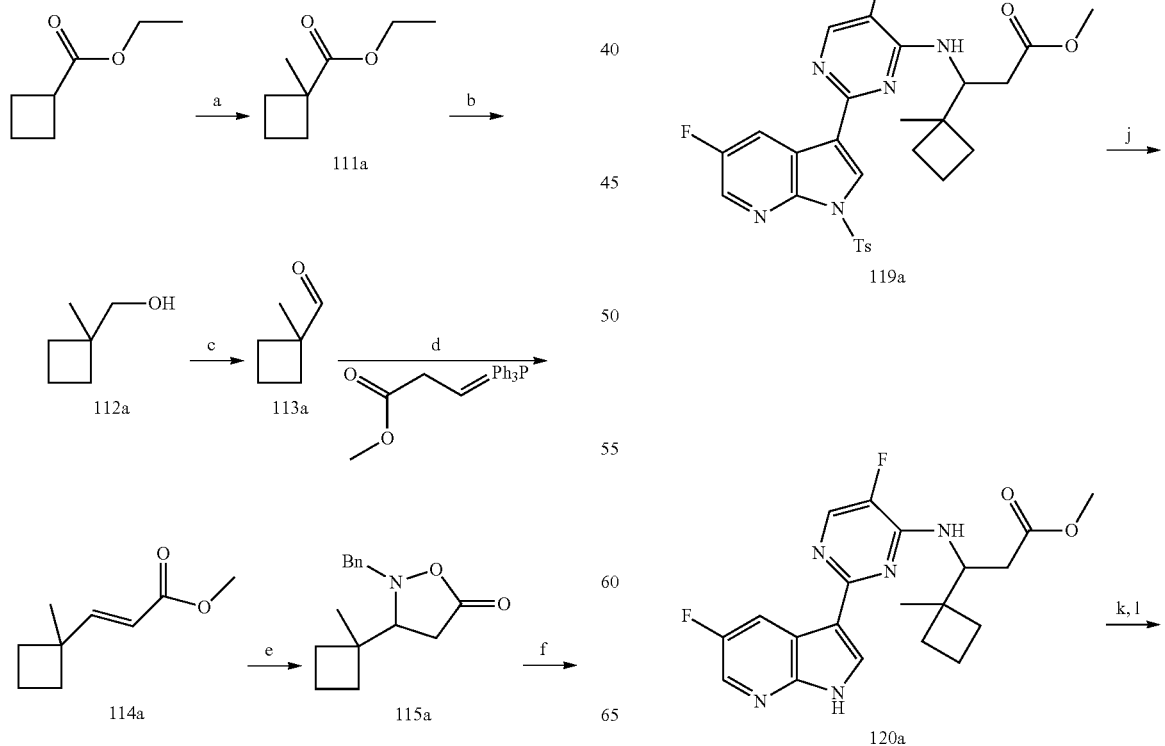

-continued

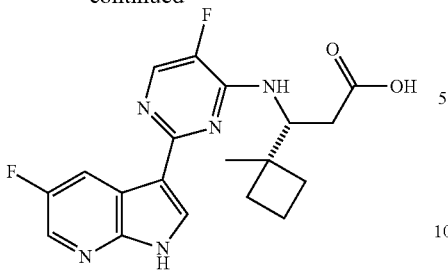

87

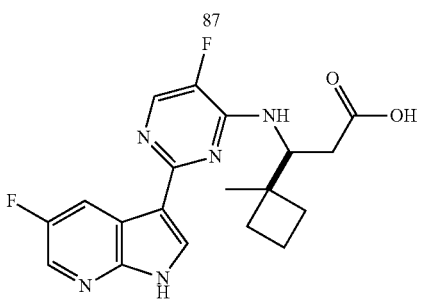

88

(a) LDA, MeI, THF; (b) LiAlH₄, ether; (c) PCC, CH₂Cl₂; (d) 2-(triphenylphosphoranylidene)acetate, CH₂Cl₂; (e) N-benzylhydroxylamine·HCl, CH₂Cl₂; (f) H₂, Pd/C, MeOH; (g) AcCl, MeOH, reflux; (h) 2,4-dichloro-5-fluoropyrimidine, Et₃N, EtOH, THF, 55° C.; (i) 5-fluoro-1-(p-tolylsulfonyl)-3-(4,4,5,5-tetramethyl-1,3,2-dioxaborolan-2-yl)pyrrolo-[2,3-b]pyridine, 7a, Pd₂(dba)₃, XPhos, K₃PO₄, 2-MeTHF, H₂O, 115° C.; (j) HCl, dioxane, acetonitrile, 65° C.; (k) LiOH, THF, H₂O, 50° C.

Formation of ethyl 1-methylcyclobutanecarboxylate (111a)

A solution of ethyl cyclobutanecarboxylate (20.0 g, 156.0 mmol) in THF (160 mL) was added dropwise to a cold (−78° C.) solution of LDA (164 mmol of 2M solution) in THF (40 mL). The solution was warmed to 0° C. and then cooled again to −40° C. before the addition of iodomethane (10.2 mL, 163.8 mmol). The solution was slowly warmed to room temperature and stirred overnight. The reaction was quenched with an aqueous saturated solution of ammonium chloride and ether was added. The layers were separated and the aqueous layer was washed with ether. The combined organic layers were washed with 1N HCl then dried over MgSO₄. The product was purified by distillation: ¹H NMR (400 MHz, MeOD) δ 4.20-4.05 (m, 2H), 2.57-2.33 (m, 2H), 2.08-1.94 (m, 1H), 1.94-1.77 (m, 3H), 1.40 (s, 3H), 1.27 (tt, J=7.1, 1.5 Hz, 3H).

Formation of (1-methylcyclobutyl)methanol (112a)

Lithium aluminum hydride (2.1 g, 59.4 mmol) was suspended in ether (150 mL) and cooled to 0° C. A solution of ethyl 1-methylcyclobutanecarboxylate, 111a, (13.0 g, 91.4 mmol) in ether (60 mL) was added dropwise to the LiAlH₄ suspension. The mixture was stirred 2 hours in an ice bath then quenched slowly with 1N HCl. The layers were separated and the aqueous layer was washed with ether. The combined organic layers were washed with brine and the volatiles were removed with a gentle stream of nitrogen to afford the desired product that was used without further purification: ¹H NMR (400 MHz, CDCl₃) δ 3.54-3.39 (m, 4H), 1.99-1.74 (m, 8H), 1.74-1.62 (m, 4H), 1.46-1.18 (m, 3H), 1.13 (d, J=1.7 Hz, 6H).

Formation of 1-methylcyclobutanecarbaldehyde (113a) and methyl 3-(1-methylcyclobutyl)acrylate (114a)

A solution of (1-methylcyclobutyl)methanol, 112a, (1.00 g, 9.98 mmol) in dichloromethane (25 mL) was added to a suspension of PCC (2.69 g, 12.50 mmol) and Celite (2.70 g) in dichloromethane (25 mL). The reaction mixture was stirred 2 hours and filtered through a pad of silica gel (eluting with dichloromethane). The solvents were removed with a stream of nitrogen until volume was approximately 20 mL. 2-(triphenyl-phosphoranylidene)acetate (0.98 g, 10.00 mmol) was added in one portion and the mixture was stirred for 7 hours. The volatiles were removed under reduced pressure and a solution of 10% Hexanes/ether was added. The resulting solid was filtered off and discarded. The resulting solution was poured directly on silica gel and eluted with EtOAc/Hexanes to afford the desired product: ¹H NMR (400 MHz, CDCl₃) δ 7.05 (d, J=15.8 Hz, 1H), 5.66 (dd, J=15.8, 1.3 Hz, 1H), 4.21-4.00 (m, 2H), 2.12-1.73 (m, 7H), 1.29-1.17 (m, 6H).

Formation (+/−)-2-benzyl-3-(1-methylcyclobutyl)isoxazolidin-5-one (115a)

N-benzylhydroxylamine (hydrochloric acid) (0.28 g, 1.80 mmol) and triethylamine (0.28 mL, 2.00 mmol) were added to a solution of methyl 3-(1-methylcyclobutyl)acrylate, 114a, (0.26 g, 1.50 mmol) in dichloromethane (9.5 mL). The reaction mixture was stirred at 50° C. overnight. The reaction mixture was cooled to room temperature and the mixture was diluted with dichloromethane and water. The layers were separated with a phase separator and the aqueous layer was washed with dichloromethane. The organic layers were combined and the volatiles removed under reduced pressure. The residue was purified on silica gel (EtOAc/Hexanes) to afford the desired product as a racemic mixture: LCMS Gradient 10-90%, 0.1% formic acid, 5 minutes, C18/ACN, RT=1.47 minutes (M+H) 246.10.

Formation of (+/−)-3-amino-3-(1-methylcyclobutyl)propanoic acid (116a)

A solution of racemic 2-benzyl-3-(1-methylcyclobutyl)isoxazolidin-5-one, 115a, (0.18 g, 1.28 mmol) in MeOH (2.9 mL) was shaken overnight under 50 psi hydrogen in the presence of 50 mg palladium hydroxide catalyst. The mixture was filtered through Celite and the volatiles were removed under reduced pressure to afford the desired product that was used without further purification: ¹H NMR (400 MHz, MeOD) δ 3.42 (dd, J=11.0, 1.9 Hz, 1H), 2.26 (ddd, J=27.8, 16.7, 6.5 Hz, 2H), 1.86 (dddd, J=36.9, 26.3, 11.2, 7.6 Hz, 6H), 1.18 (s, 3H).

Formation of (+/−)-methyl 3-((2-chloro-5-fluoropyrimidin-4-yl)amino)-3-(1-methylcyclobutyl)propanoate (118a)

Racemic 3-amino-3-(1-methylcyclobutyl)propanoic acid, 116a, (2.3 g, 14.4 mmol) was dissolved in methanol (104 mL). The solution was cooled in an ice bath and acetyl chloride (5.6 g, 71.9 mmol) was added dropwise (Temp kept <10° C.). The reaction mixture was heated to 65° C. and stirred at that temperature for 3 hours. The reaction mixture was cooled to room temperature and then flushed with toluene to remove volatiles. Crude racemic 3-methoxy-1-(1-methylcyclobutyl)-3-oxopropan-1-aminium chloride, 117a, was used without further purification.

Racemic 3-methoxy-1-(1-methylcyclobutyl)-3-oxopropan-1-aminium chloride, 117a, (3.3 g, 15.9 mmol) was dissolved in a mixture of 59 mL THF and 6.6 mL EtOH and the solution was cooled in an ice bath. 2,4-Dichloro-5-fluoropyrimidine (2.9 g, 18.0 mmol) was added followed by dropwise addition of triethylamine (5.1 g, 51.0 mmol). The reaction mixture was stirred at 55° C. for 17 hours. The reaction mixture was cooled to room temperature after which water and dichloromethane were added. The phases were separated and the aqueous layer was washed with dichloromethane. The organic layers were combined and washed with brine. The solvents were removed and the residue was purified via silica gel chromatography (EtOAc/Hexanes) to afford the desired product: LCMS Gradient 10-90%, 0.1% formic acid, 5 minutes, C18/ACN, RT=3.23 minutes (M+H) 302.35.

Formation of (+/−)-methyl 3-((5-fluoro-2-(5-fluoro-1-tosyl-1H-pyrrolo[2,3-b]pyridin-3-yl)pyrimidin-4-yl)amino)-3-(1-methylcyclobutyl)propanoate (119a)

A solution of 5-fluoro-1-(p-tolylsulfonyl)-3-(4,4,5,5-tetramethyl-1,3,2-dioxaborolan-2-yl)pyrrolo[2,3-b]pyridine, 7a, (3.31 g, 7.95 mmol), racemic methyl 3-((2-chloro-5-fluoropyrimidin-4-yl)amino)-3-(1-methylcyclobutyl)propanoate, 118a, (2.00 g, 6.63 mmol) and $K_3PO_4$ (4.22 g, 20.00 mmol) in 2-MeTHF (253 mL) and water (56 mL) was purged with nitrogen for 0.75 h. XPhos (0.38 g, 0.80 mmol) and $Pd_2(dba)_3$ (0.15 g, 0.17 mmol) were added and the reaction mixture was stirred at 115° C. in a sealed tube for 2 hours. The reaction mixture was cooled and the aqueous phase was removed. The organic phase was filtered through a pad of Celite and the mixture was concentrated to dryness. The residue was purified via silica gel chromatography (EtOAc/Hexanes) to afford the desired product: LCMS Gradient 10-90%, 0.1% formic acid, 5 minutes, C18/ACN, RT=2.32 minutes (M+H) 556.44.

Formation of (+/−)-methyl 3-((5-fluoro-2-(5-fluoro-1H-pyrrolo[2,3-b]pyridin-3-yl)pyrimidin-4-yl)amino)-3-(1-methylcyclobutyl)propanoate (120a)

To a racemic solution of methyl 3-((5-fluoro-2-(5-fluoro-1-tosyl-1H-pyrrolo[2,3-b]pyridin-3-yl)pyrimidin-4-yl)amino)-3-(1-methylcyclobutyl)propanoate, 119a, (3.3 g, 5.9 mmol) in acetonitrile (25 mL) was added HCl (26 mL of 4N solution in dioxane). The reaction mixture was heated to 65° C. for 4 hours. The solution was cooled to room temperature and the solvents were removed under reduced pressure. The mixture was flushed with acetonitrile after which aqueous sodium bicarbonate and ethyl acetate were added. The phases were separated and the aqueous layer washed with ethyl acetate. The combined organic phases were dried with $Na_2SO_4$, filtered and concentrated in vacuo. The resulting residue was purified via silica gel chromatography (EtOAc/Hexanes) to afford the desired product: LCMS Gradient 10-90%, 0.1% formic acid, 5 minutes, C18/ACN, RT=2.34 minutes (M+H) 403.11.

Formation of 3-((5-fluoro-2-(5-fluoro-1H-pyrrolo[2,3-b]pyridin-3-yl)pyrimidin-4-yl)amino)-3-(1-methylcyclobutyl)propanoic acid (87 and 88)

To a solution of methyl 3-((5-fluoro-2-(5-fluoro-1H-pyrrolo[2,3-b]pyridin-3-yl)pyrimidin-4-yl)amino)-3-(1-methylcyclobutyl)propanoate (11) (1.75 g, 4.36 mmol) in THF (25 mL) was added aqueous 1N LiOH (13.1 mL). The mixture was heated to 50° C. for 3.5 hours. The reaction mixture was cooled to room temperature and diluted with water. The THF was removed under reduced pressure and the residue was then flushed twice with hexanes. Ether was added and the layers separated (the ether layer was discarded). The pH was adjusted to 5.5 with 1N HCl and the resulting solid was filtered and washed with water. The solid was flushed with heptanes and dried over $P_2O_5$ to give the desired product: $^1$H NMR (400 MHz, DMSO) δ 12.17 (d, J=60.2 Hz, 2H), 8.59 (d, J=8.4 Hz, 1H), 8.39-8.05 (m, 3H), 7.52 (s, 1H), 5.00 (s, 1H), 2.23 (d, J=7.7 Hz, 1H), 2.00 (s, 1H), 1.81 (d, J=48.3 Hz, 2H), 1.62 (s, 1H), 1.46 (s, 1H), 1.21 (s, 3H); LCMS Gradient 10-90%, 0.1% formic acid, 5 minutes, C18/ACN, RT=2.08 minutes (M+H) 388.46. The racemic mixture was submitted to SFC chiral separation to obtain the individual enantiomers, 87 and 88.

Preparation of Compound 65

Synthetic Scheme 18

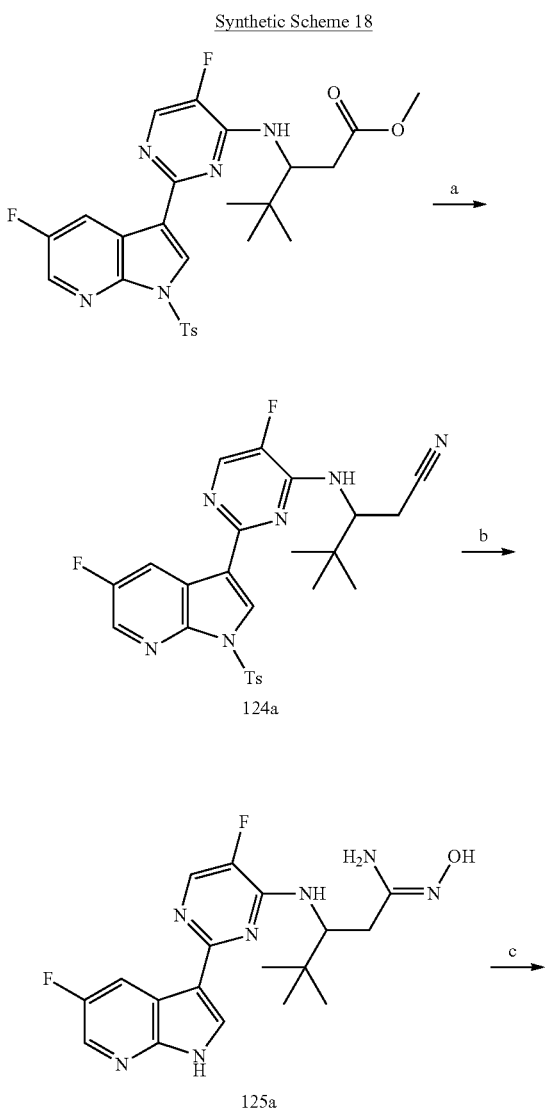

-continued

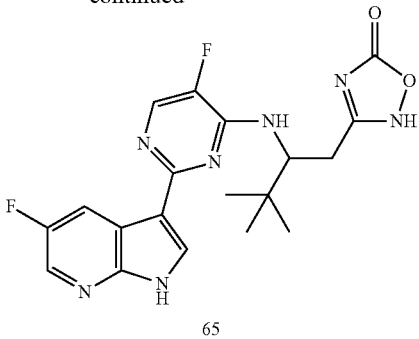

65

(a) AlMe₃, NH₄Cl, toluene; (b) hydroxylamine, DMSO, 140° C.; (c) CDI, ᶦPr₂NEt, THF.

Formation of (+/−)-3-((5-fluoro-2-(5-fluoro-1-tosyl-1H-pyrrolo[2,3-b]pyridin-3-yl)pyrimidin-4-yl)amino)-4,4-dimethylpentanenitrile (124a)

Ammonium chloride (0.12 g, 2.30 mmol) was suspended in toluene (4.5 mL). The mixture was cooled in an ice bath and AlMe₃ (1.15 mL of a 2 M solution in toluene, 2.30 mmol) was added dropwise. The mixture was stirred 30 minutes and another 30 min at room temperature. A solution of racemic methyl 3-[[5-fluoro-2-[5-fluoro-1-(p-tolylsulfonyl)pyrrolo[2,3-b]pyridin-3-yl]pyrimidin-4-yl]amino]-4,4-dimethylpentanoate (0.25 g, 0.46 mmol) in 4.5 mL toluene was added and the resulting mixture was stirred 60° C. overnight. The reaction mixture was cooled in an ice bath and quenched with 1N HCl. The mixture was extracted with dichloromethane and filtered through a phase separator. The residue was purified on silica gel (EA/Hex): LCMS Gradient 10-90%, 0.1% formic acid, 5 minutes, C18/ACN, RT=2.04 minutes (M+H) 511.42.

Formation of (+/−)-3-((5-fluoro-2-(5-fluoro-1H-pyrrolo[2,3-b]pyridin-3-yl)pyrimidin-4-yl)amino)-N'-hydroxy-4,4-dimethylpentanimidamide (125a)

To a solution of racemic 3-[[5-fluoro-2-[5-fluoro-1-(p-tolylsulfonyl)pyrrolo[2,3-b]pyridin-3-yl]pyrimidin-4-yl]amino]-4,4-dimethyl-pentanenitrile, 124a, (0.059 g, 0.116 mmol) in DMSO (0.500 mL) was added hydroxylamine (0.031 g, 0.470 mmol). The mixture was heated in a microwave at 140° C. for 30 minutes. The residue was purified on a C18 column (acetonitrile/0.1% formic acid) to afford the desired product: LCMS Gradient 10-90%, 0.1% formic acid, 5 minutes, C18/ACN, RT=1.58 minutes (M+H) 390.06.

Formation of (+/−)-3-(2-((5-fluoro-2-(5-fluoro-1H-pyrrolo[2,3-b]pyridin-3-yl)pyrimidin-4-yl)amino)-3,3-dimethylbutyl)-1,2,4-oxadiazol-5(2H)-one (65)

To a solution of racemic 3-[[5-fluoro-2-(5-fluoro-1H-pyrrolo[2,3-b]pyridin-3-yl)pyrimidin-4-yl]amino]-N'-hydroxy-4,4-dimethyl-pentanamidine, 125a, (0.034 g, 0.087 mmol) and carbonyl diimidazole (0.014 g, 0.087 mmol) in THF (1 mL) was added N,N-diisopropylethylamine (0.045 mL, 0.260 mmol). The reaction mixture was stirred at room temperature for 48 hours. Aqueous ammonium chloride and dichloromethane were added and the layers were separated with a phase separator. The residue was purified on a C18 column (acetonitrile/0.1% formic acid) to afford the final product: ¹H NMR (400 MHz, Acetone) δ 11.23 (s, 1H), 8.54 (dd, J=9.8, 2.8 Hz, 1H), 8.36 (s, 1H), 8.20 (s, 1H), 8.13 (d, J=3.7 Hz, 1H), 6.81 (s, 1H), 5.00 (d, J=11.2 Hz, 1H), 3.15 (d, J=14.8 Hz, 3H), 2.94 (dd, J=14.4, 11.9 Hz, 2H), 1.16 (s, 8H); LCMS Gradient 10-90%, 0.1% formic acid, 5 minutes, C18/ACN, RT=1.58 minutes (M+H) 390.06.

Preparation of Compound 47

Synthetic Scheme 19

(a) Na₂CO₃, CH₃CN—THF, 125-150° C.; (b) 4M HCl, 1,4-dioxane-CH₃CN, 60° C.

(R)-3-((2-(5-fluoro-1-tosyl-1H-pyrrolo[2,3-b]pyridin-3-yl)pyrimidin-4-yl)amino)-4,4-dimethylpentanoic acid (128a)

Sulfoxide, 127a, was prepared in same fashion as sulfoxide, 25a, (see Synthetic Scheme 4) using 2,4-dichloropyrimidine instead of 2-chloro-5-fluoro-4-methylsulfanyl-pyrimidine.

A mixture of 5-fluoro-3-(4-(methylsulfinyl)pyrimidin-2-yl)-1-tosyl-1H-pyrrolo[2,3-b]pyridine, 127a, (0.052 g, 0.121 mmol) and (3R)-3-amino-4,4-dimethyl-pentanoic acid, 2a, (0.035 g, 0.242 mmol) along with Na₂CO₃ (0.051 g, 0.483 mmol) in a mixture of THF (0.780 mL) and acetonitrile (0.260 mL) was heated to 125° C. for 30 minutes under microwave irradiation. Then, the temperature was raised to 150° C. for a further 2.5 hours. The mixture was neutralized with aqueous 2N HCl and extracted with several portions of EtOAc. The organic solvents were evaporated in vacuo. Purification by flash chromatography (SiO₂, 0-100% hexanes-EtOAc (with 10% MeOH)) provided 19 mg of the desired material (31% yield), which was used in the next step without further purification: LCMS Gradient 10-90%, 0.1% trifluoroacetic acid, 5 minutes, C18/ACN, RT=2.70 minutes (M+H) 512.00.

(R)-3-((2-(5-fluoro-1H-pyrrolo[2,3-b]pyridin-3-yl)pyrimidin-4-yl)amino)-4,4-dimethylpentanoic acid (47)

To a solution of (R)-3-((2-(5-fluoro-1-tosyl-1H-pyrrolo[2,3-b]pyridin-3-yl)pyrimidin-4-yl)amino)-4,4-dimethylpentanoic acid, 128a (0.019 g, 0.037 mmol) in acetonitrile (0.6 mL) was added HCl (0.15 mL of 4 M in dioxane, 0.60 mmol). The solution was heated to 60° C. for 18 hours. Then, additional HCl (0.36 mL of 4 M in dioxane) was added and heating was continued for 4 hours. The mixture was cooled and concentrated in vacuo. Trituration with Et$_2$O followed by purification by preparatory HPLC provided 17.5 mg of the desired product as a TFA salt. The NMR indicated a 4 to 1 ratio of atropisomers: $^1$H NMR (400 MHz, MeOD, major atropsomer) δ 8.70 (dd, J=8.9, 2.3 Hz, 1H), 8.50 (s, 1H), 8.35 (s, 1H), 7.99 (d, J=7.3 Hz, 1H), 6.60 (d, J=7.2 Hz, 1H), 5.05 (d, J=10.7 Hz, 1H), 2.93 (dd, J=15.9, 1.8 Hz, 1H), 2.53 (dd, J=15.9, 11.2 Hz, 1H), 1.08 (d, J=0.8 Hz, 9H); LCMS Gradient 10-90%, 0.1% trifluoroacetic acid, 5 minutes, C18/ACN, RT=2.17 minutes (M+H) 358.02.

Preparation of Compound 48

Synthetic Scheme 20

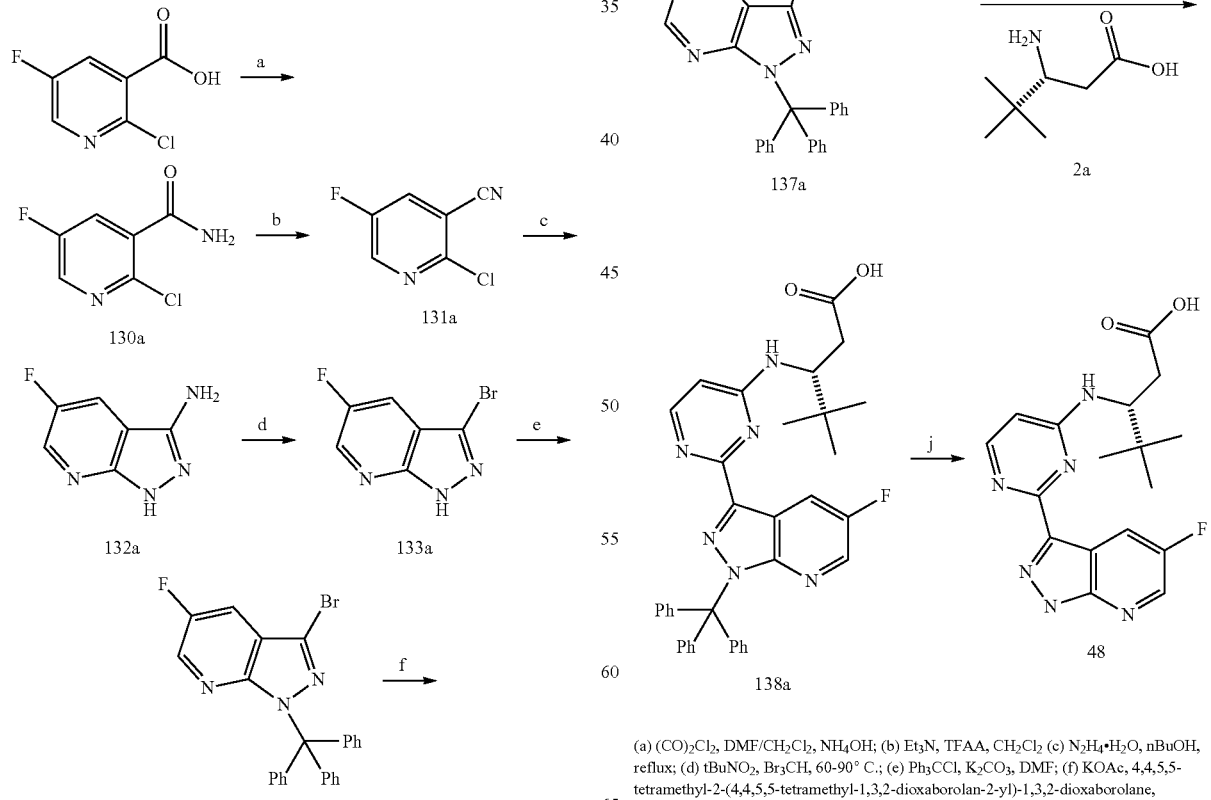

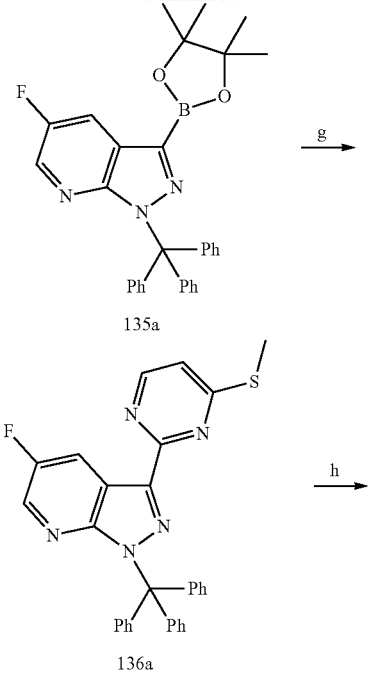

(a) (CO)$_2$Cl$_2$, DMF/CH$_2$Cl$_2$, NH$_4$OH; (b) Et$_3$N, TFAA, CH$_2$Cl$_2$ (c) N$_2$H$_4$•H$_2$O, nBuOH, reflux; (d) tBuNO$_2$, Br$_3$CH, 60-90° C.; (e) Ph$_3$CCl, K$_2$CO$_3$, DMF; (f) KOAc, 4,4,5,5-tetramethyl-2-(4,4,5,5-tetramethyl-1,3,2-dioxaborolan-2-yl)-1,3,2-dioxaborolane, Pd(dppf)$_2$Cl$_2$, DMF, 100° C.; (g) 2-chloro-4-methylsulfanyl-pyrimidine, Pd$_2$(dba)$_3$, XPhos, K$_3$PO$_4$, 2-MeTHF, H$_2$O, 115° C.; (h) mCPBA, CH$_2$Cl$_2$, 0° C.; (i) Na$_2$CO$_3$, CH$_3$CN—THF, 125-150° C.; (c) Et$_3$SiH, TFA, CH$_2$Cl$_2$.

Formation of 2-chloro-5-fluoropyridine-3-carboxamide (130a)

To the suspension of 2-chloro-5-fluoropyridine-3-carboxylic acid (37.0 g, 210.8 mmol) in dichloromethane (555 mL) was added oxalyl chloride (56.2 g, 442.7 mmol) under nitrogen. DMF (1.54 g, 21.08 mmol) was added slowly to the reaction mixture. The mixture was stirred at room temperature for 2 h and dichloromethane was removed under reduced pressure. The residue was dissolved in THF (300 mL) and cooled down to 0° C. by ice bath. Ammonium hydroxide (28-30%, 113.0 mL, 1.8 mmol) was added in one portion. The mixture was stirred for another 15 min. The mixture was diluted into ethyl acetate (300 mL) and water (300 mL) and the phases were separated. The organic layer was washed with brine and dried over $Na_2SO_4$, filtered, and concentrated in vacuo to afford 29.8 g desired product as white solid: $^1$H NMR (300 MHz, DMSO-d6) δ 8.53 (d, J=3.0 Hz, 1H), 8.11 (s, 1H), 8.00 (dd, J=8.0, 3.0 Hz, 1H), 7.89 (s, 1H); LCMS Gradient 10-90%, 0.1% formic acid, 5 minutes, C18/ACN, RT=1.11 minutes, (M+H) 175.02.

Formation of 2-chloro-5-fluoropyridine-3-carbonitrile (131a)

To a suspension of 2-chloro-5-fluoropyridine-3-carboxamide, 130a, (29.8 g, 170.4 mmol) in dichloromethane (327 mL) was added triethylamine (52.3 mL, 374.9 mmol). This mixture was cooled down to 0° C. Trifluoroacetic anhydride (26.1 mL, 187.4 mmol) was added slowly over period of 15 min. The mixture was stirred at 0° C. for 90 min. The mixture was diluted into dichloromethane (300 mL) and the resulting organic phase was washed with aqueous saturated $NaHCO_3$ solution (300 mL) and brine (300 mL). The organic layer was dried over $Na_2SO_4$, filtered, concentrated in vacuo. The product was purified by silica gel chromatography (40% to 60% ethyl acetate/hexanes gradient) giving 24.7 g of product as a white solid: $^1$H NMR (300 MHz, $CDCl_3$) δ 8.50 (d, J=3.0 Hz, 1H), 7.77 (dd, J=6.8, 3.0 Hz, 1H); LCMS Gradient 10-90%, 0.1% formic acid, 5 minutes, C18/ACN, Retention Time=2.50 minutes, (M+H) 157.06.

Formation of 5-fluoro-1H-pyrazolo[3,4-b]pyridin-3-amine (132a)

To the mixture of 2-chloro-5-fluoropyridine-3-carbonitrile, 131a, (29.6 g, 157.1 mmol) in n-butanol (492 mL) was added hydrazine hydrate (76.4 mL, 1.6 mol). This mixture was heated to reflux for 4.5 h and cooled down. n-Butanol was removed under reduced pressure and water (300 mL) was added resulting in a yellow precipitate. The suspension was filtered and washed with water twice, followed by a MTBE wash. The yellow solid was dried in a vacuum oven to give 18 g of the desired product: $^1$H NMR (300 MHz, DMSO-d6) δ 12.08 (s, 1H), 8.38 (dd, J=2.7, 1.9 Hz, 1H), 7.97 (dd, J=8.8, 2.7 Hz, 1H), 5.56 (s, 2H). LCMS Gradient 10-90%, 0.1% formic acid, 5 minutes, C18/ACN, Retention Time=1.25 minutes (M+H) 152.95.

Formation of 3-bromo-5-fluoro-1H-pyrazolo[3,4-b]pyridine (133a)

To a mixture of 5-fluoro-1H-pyrazolo[3,4-b]pyridin-3-amine, 132a, (0.88 g, 5.79 mmol) in bromoform (8.8 mL) was added tert-butyl nitrite (1.38 mL, 11.57 mmol). This mixture was heated to 61° C. for 1 h and then heated to 90° C. for an additional hour. The mixture was cooled to room temperature and bromoform was removed under reduced pressure. The resulting crude residue was purified by silica gel chromatography (5-50% ethyl acetate/hexanes) to afford 970 mg of the desired product as a white solid: $^1$H NMR (300 MHz, DMSO-d6) δ 14.22 (s, 1H), 8.67 (dd, J=2.7, 1.9 Hz, 1H), 8.07 (dd, J=8.2, 2.7 Hz, 1H); LCMS Gradient 10-90%, 0.1% formic acid, 5 minutes, C18/ACN, Retention Time=2.42 minutes (M+H) 216.11.

Formation of 3-bromo-5-fluoro-1-trityl-1H-pyrazolo [3,4-b]pyridine (134a)

A mixture of 3-bromo-5-fluoro-1H-pyrazolo[3,4-b]pyridine, 133a, (0.97 g, 4.49 mmol) and $K_2CO_3$ (1.86 g, 13.47 mmol) in DMF (9.7 mL) was cooled to 0° C. Chlorodiphenylmethylbenzene (1.38 g, 4.94 mmol) was added. The mixture was stirred at room temperature overnight. The mixture was diluted into ethyl acetate (40 mL) and water (30 mL) and the layers were separated. The organic layer was washed with brine, dried over $Na_2SO_4$, filtered and concentrated in vacuo. The product was purified by silica gel chromatography (40% ethyl acetate/hexanes) to afford 1.68 g of the desired product as a white solid: $^1$H NMR (300 MHz, DMSO-d6) δ 8.45-8.38 (m, 1H), 8.04 (dd, J=8.0, 2.7 Hz, 1H), 7.35-7.16 (m, 15H); LCMS Gradient 10-90%, 0.1% formic acid, 5 minutes, C18/ACN, Retention Time=3.03 minutes (M+H) 459.46.

Formation of 5-fluoro-3-(4,4,5,5-tetramethyl-1,3,2-dioxaborolan-2-yl)-1-trityl-1H-pyrazolo[3,4-b]pyridine (135a)

A solution of 3-bromo-5-fluoro-1-trityl-pyrazolo[3,4-b]pyridine, 134a (3.43 g, 7.48 mmol), KOAc (2.20 g, 22.45 mmol) and 4,4,5,5-tetramethyl-2-(4,4,5,5-tetramethyl-1,3,2-dioxaborolan-2-yl)-1,3,2-dioxaborolane (2.85 g, 11.23 mmol) in DMF (50 ml) was degassed under a stream of nitrogen for 40 min. To the mixture was added $Pd(dppf)_2Cl_2$ (0.610 g, 0.748 mmol) The reaction mixture was heated at 100° C. for 90 minutes. The reaction mixture was filtered through a pad of Celite. To the resulting filtrate was added ether and brine. The organic phase was dried over $MgSO_4$, filtered and concentrated in vacuo to afford 4.0 g crude product that was used in the next step without further purification (note, the product decomposes if purification is attempted via silica gel chromatography).

Formation of 5-fluoro-3-(4-(methylthio)pyrimidin-2-yl)-1-trityl-1H-pyrazolo[3,4-b]pyridine (136a)

A solution of 2-chloro-4-methylsulfanyl-pyrimidine (0.25 g, 1.56 mmol), $K_3PO_4$ (0.99 g, 4.67 mmol) and 5-fluoro-3-(4,4,5,5-tetramethyl-1,3,2-dioxaborolan-2-yl)-1-trityl-1H-pyrazolo[3,4-b]pyridine, 135a, (0.87 g, 1.71 mmol) in water (1 mL) and 2-methyltetrahydrofuran (9 mL) was degassed under a stream of nitrogen for 15 minutes. Then, $Pd_2(dba)_3$ (0.04 g, 0.05 mmol) was added and the mixture was degassed for an additional 2-3 minutes. The vessel was sealed and heated to 95° C. overnight. After separating the layers, the organic phase was washed with water. The resulting solid was filtered and washed with ether and MeTHF. Filtered through PSA cartridge with MeOH/dichloromethane mixture to give the desired product as a white solid: LCMS Gradient 60-98%, 0.1% formic acid, 7 min, C4/ACN, Retention Time=2.68 min (M+Na) 526.1.

Formation of 5-fluoro-3-(4-(methylsulfinyl)pyrimidin-2-yl)-1-trityl-1H-pyrazolo[3,4-b]pyridine (137a)

To a cold (0° C.) mixture of 5-fluoro-3-(4-(methylthio)pyrimidin-2-yl)-1-trityl-1H-pyrazolo[3,4-b]pyridine, 135a, (0.70 g, 1.38 mmol) in dichloromethane (10.4 mL) was added mCPBA (0.43 g, 1.93 mmol). After 30 minutes, the mixture was diluted with dichloromethane and washed with 2N NaOH and brine. The organic phase was brine dried over Na₂SO₄, filtered and stripped down twice with CH₃CN to afford 660 mg of desired product that was used without further purification: LCMS Gradient 60-98%, 0.1% formic acid, 7 min, C4/ACN, Retention Time=2.68 minutes (M+H) 520.

(R)-3-((2-(5-fluoro-1-trityl-1H-pyrazolo[3,4-b]pyridin-3-yl)pyrimidin-4-yl)amino)-4,4-dimethylpentanoic acid (138a)

A stirred suspension of 5-fluoro-3-(4-(methylsulfinyl)pyrimidin-2-yl)-1-trityl-1H-indazole, 137a, (0.09 g, 0.18 mmol), (3R)-3-amino-4,4-dimethyl-pentanoic acid (0.05 g, 0.36 mmol) and Na₂CO₃ (0.76 g, 0.72 mmol) in acetonitrile (0.62 mL) and 2-MeTHF (0.31 mL) was heated to 125° C. in microwave reactor for 1 hour. After cooling to room temperature, the mixture was diluted with EtOAc, neutralized with HCl (0.72 mL of 2 M solution, 1.42 mmol) and the product was extracted with several portions of EtOAc and CH₂Cl₂. Evaporation of the combined organic phases provided 109 mg of the desired crude product which was used in the next reaction without further purification: LCMS Gradient 10-90%, 0.1% trifluoroacetic acid, 5 minutes, C18/ACN, Retention Time=3.08 minutes (M+H) 601.05.

(R)-3-((2-(5-fluoro-1H-pyrazolo[3,4-b]pyridin-3-yl)pyrimidin-4-yl)amino)-4,4-dimethylpentanoic acid (48)

To a solution of crude (R)-3-((2-(5-fluoro-1-trityl-1H-pyrazolo[3,4-b]pyridin-3-yl)pyrimidin-4-yl)amino)-4,4-dimethylpentanoic acid, 138a, (0.11 g, 0.21 mmol) in CH₂Cl₂ was added triethylsilane (0.15 mL, 0.94 mmol) followed by trifluoroacetic acid (0.15 mL, 1.95 mmol). After stirring the resulting solution at room temperature for 1 hour, the reaction mixture was kept below 5° C. overnight (refrigerator). The mixture was then allowed to warm to room temperature and kept at that temperature for an additional 5 hours. The solution was diluted with toluene and concentrated in vacuo. Trituration with Et₂O followed by preparative HPLC purification provided 15 mg of the desired product as the TFA salt. ¹H NMR indicated a 3 to 1 mixture of atropisomers: ¹H NMR (400 MHz, MeOD, major isomer) δ 8.63-8.45 (m, 2H), 7.96 (d, J=7.3 Hz, 2H), 6.66 (d, J=7.3 Hz, 2H), 4.95 (d, J=10.6 Hz, 2H), 2.84 (dd, J=15.4, 2.4 Hz, 2H), 2.44 (dd, J=15.9, 10.7 Hz, 2H), 0.98 (s, 9H); LCMS Gradient 10-90%, 0.1% trifluoroacetic acid, 5 minutes, C18/ACN, Retention Time=2.12 minutes (M+H) 359.02.

Preparation of Compound 42

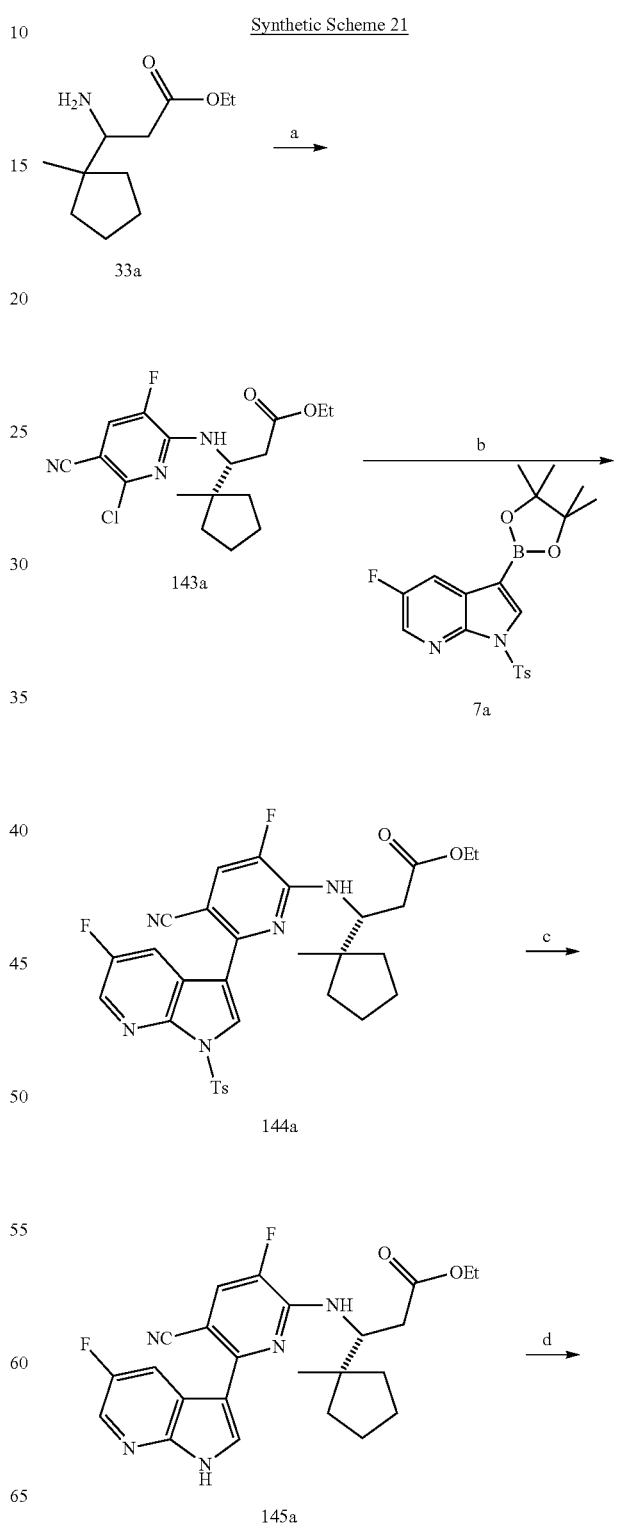

Synthetic Scheme 21

-continued

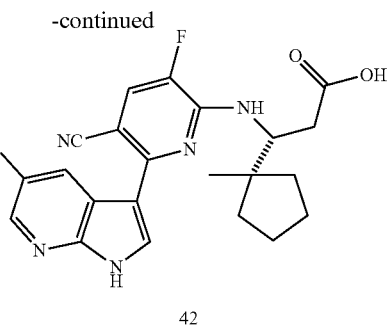

42

(a) 2-chloro-5,6-difluoropyridine-3-carbonitrile, Et₃N, THF, EtOH; (b) 5-fluoro-1-(p-tolylsulfonyl)-3-(4,4,5,5-tetramethyl-1,3,2-dioxaborolan-2-yl)pyrrolo[2,3-b]pyridine, 7a, X-phos, Pd₂(dba)₃, K₃PO₄, 2-methyl THF, H₂O, 130° C.; c) NaOMe, THF; d) LiOH, THF, H₂O.

Formation of (R)-ethyl 3-(6-chloro-5-cyano-3-fluoropyridin-2-ylamino)-3-(1-methylcyclopentyl)propanoate (143a)

To a solution of racemic ethyl 3-amino-3-(1-methylcyclopentyl)propanoate, 33a, (0.40 g, 2.01 mmol) and 2,6-dichloro-5-fluoro-pyridine-3-carbonitrile (0.46 g, 2.41 mmol) in THF (20 mL) was added triethylamine (0.67 mL, 4.82 mmol). The reaction mixture was stirred at 90° C. in a pressure tube for 18 hours. The reaction mixture was filtered and the resulting filtrate was concentrated in vacuo. The product was purified by silica gel chromatography (25% EtOAc/Hexanes) to afford 380 mg of the desired product as a racemic mixture: $^1$H NMR (400 MHz, CDCl₃) δ 7.31 (d, J=9.7 Hz, 1H), 5.56 (d, J=8.9 Hz, 1H), 4.68 (td, J=9.6, 3.6 Hz, 1H), 4.07 (q, J=7.1 Hz, 2H), 2.68 (dd, J=14.8, 3.7 Hz, 1H), 2.46 (dd, J=14.8, 9.3 Hz, 1H), 1.77-1.62 (m, 4H), 1.61-1.49 (m, 2H), 1.47-1.37 (m, 1H), 1.35-1.26 (m, 1H), 1.19 (t, J=7.1 Hz, 3H), 1.01 (s, 3H); LCMS Gradient 10-90%, 0.1% formic acid, 5 minutes, C18/ACN, Retention Time=3.81 minutes (M+H) 354.98. The racemic mixture was submitted to SFC chiral separation to give the individual enantiomers, 143a and 143b. The (R)-enantiomer, 143a, was taken forward into the next synthetic step.

Formation of (R)-ethyl 3-(5-cyano-3-fluoro-6-(5-fluoro-1-tosyl-1H-pyrrolo[2,3-b]pyridin-3-yl)pyridin-2-ylamino)-3-(1-methylcyclopentyl)propanoate (144a)

A solution of 5-fluoro-1-(p-tolylsulfonyl)-3-(4,4,5,5-tetramethyl-1,3,2-dioxaborolan-2-yl)pyrrolo[2,3-b]pyridine, 7a, (0.155 g, 0.373 mmol), racemic ethyl 3-[(6-chloro-5-cyano-3-fluoro-2-pyridyl)amino]-3-(1-methylcyclopentyl)propanoate, 143a, (0.120 g, 0.339 mmol) and K₃PO₄ (0.288 g, 1.357 mmol) in 2-methyl THF (10.0 mL) and H₂O (0.24 mL) was degassed under a stream of nitrogen for 30 minutes. To the mixture was added X-phos (0.020 g, 0.041 mmol) and Pd₂(dba)₃ (0.008 g, 0.008 mmol). The reaction mixture was stirred at 130° C. in a pressure tube for 45 minutes. The organic phase was filtered through a pad of celite and concentrated in vacuo. The resulting crude material was purified by silica gel chromatography (30% EtOAc/Hexanes) to afford 150 mg of the desired product: $^1$H NMR (400 MHz, CDCl₃) δ 8.67 (s, 1H), 8.44 (dt, J=15.3, 7.7 Hz, 1H), 8.37 (d, J=1.5 Hz, 1H), 8.13 (t, J=7.6 Hz, 2H), 7.41 (d, J=10.3 Hz, 1H), 7.32 (d, J=7.5 Hz, 2H), 5.38 (t, J=9.7 Hz, 1H), 4.89 (td, J=10.1, 3.3 Hz, 1H), 4.02-3.91 (m, 2H), 2.74 (dd, J=15.1, 3.5 Hz, 1H), 2.52 (dd, J=15.1, 10.2 Hz, 1H), 2.40 (s, 3H), 1.61 (ddt, J=32.0, 20.7, 7.7 Hz, 7H), 1.49-1.30 (m, 3H), 1.27 (t, J=7.1 Hz, 3H), 1.08-0.97 (m, 3H). LCMS Gradient 10-90%, 0.1% formic acid, 5 minutes, C18/ACN, Retention Time=4.22 min (M+H) 608.29.

Formation of (R)-methyl 3-(5-cyano-3-fluoro-6-(5-fluoro-1H-pyrrolo[2,3-b]pyridin-3-yl)pyridin-2-ylamino)-3-(1-methylcyclopentyl)propanoate (145a)

To a solution of racemic ethyl 3-(5-cyano-3-fluoro-6-(5-fluoro-1-tosyl-1H-pyrrolo[2,3-b]pyridin-3-yl)pyridin-2-ylamino)-3-(1-methylcyclopentyl)propanoate, 144a, (0.150 g, 0.247 mmol) in THF (20 mL) was added sodium methoxide (0.053 mL of 25% wt solution in MeOH, 0.247 mmol). The reaction mixture was stirred at room temperature for 5 minutes. The reaction mixture was diluted with aqueous saturated NaHCO₃ solution and EtOAc. The organic phase was dried over MgSO₄, filtered and concentrated in vacuo. The product was purified by silica gel chromatography (40% EtOAc/Hexanes) to afford 90 mg of the desired product as a mixture of ethyl and methyl esters. The mixture was taken onto the next step without further purification: $^1$H NMR (400 MHz, CDCl₃) δ 10.18 (s, 1H), 8.65 (dd, J=9.6, 2.5 Hz, 1H), 8.48 (d, J=2.8 Hz, 1H), 8.32 (s, 1H), 7.37 (t, J=14.1 Hz, 1H), 5.38 (d, J=7.9 Hz, 1H), 5.02 (td, J=9.8, 3.5 Hz, 1H), 3.54 (s, 3H), 2.80 (dt, J=15.8, 7.9 Hz, 1H), 2.57 (dd, J=14.9, 9.8 Hz, 1H), 1.80-1.57 (m, 7H), 1.43 (ddd, J=24.5, 14.1, 6.0 Hz, 3H), 1.08 (s, 3H); LCMS Gradient 10-90%, 0.1% formic acid, 5 minutes, C18/ACN, Retention Time=3.60 minutes (M+H) 440.26.

Formation of (R)-3-(5-cyano-3-fluoro-6-(5-fluoro-1H-pyrrolo[2,3-b]pyridin-3-yl)pyridin-2-ylamino)-3-(1-methylcyclopentyl)propanoic acid (42)

To a solution of racemic methyl 3-(5-cyano-3-fluoro-6-(5-fluoro-1H-pyrrolo[2,3-b]pyridin-3-yl)pyridin-2-ylamino)-3-(1-methylcyclopentyl)propanoate, 145a, (0.090 g, 0.204 mmol) in THF (30 mL) was added a solution of lithium hydroxide (0.035 g, 0.819 mmol) in H₂O (10 mL). The reaction mixture was stirred at 70° C. overnight. The organic phase was removed under reduced pressure and the resulting residue was purified by preparatory HPLC. The appropriate HPLC fractions were extracted with EtOAc, and the solvent was removed under reduced pressure: $^1$H NMR (400 MHz, MeOD) δ 8.64 (dd, J=8.4, 2.4 Hz, 1H), 8.57 (s, 1H), 8.24 (d, J=4.4 Hz, 1H), 5.19 (d, J=8.7 Hz, 1H), 2.78 (qd, J=15.9, 6.6 Hz, 2H), 1.85-1.57 (m, 6H), 1.48 (dd, J=11.8, 6.0 Hz, 1H), 1.36 (dt, J=12.0, 6.0 Hz, 1H), 1.11 (s, 3H); LCMS Gradient 10-90%, 0.1% formic acid, 5 minutes, C18/ACN, Retention Time=3.21 minutes (M+H) 426.25.

Preparation of Compounds 5, 6 and 12

Synthetic Scheme 22

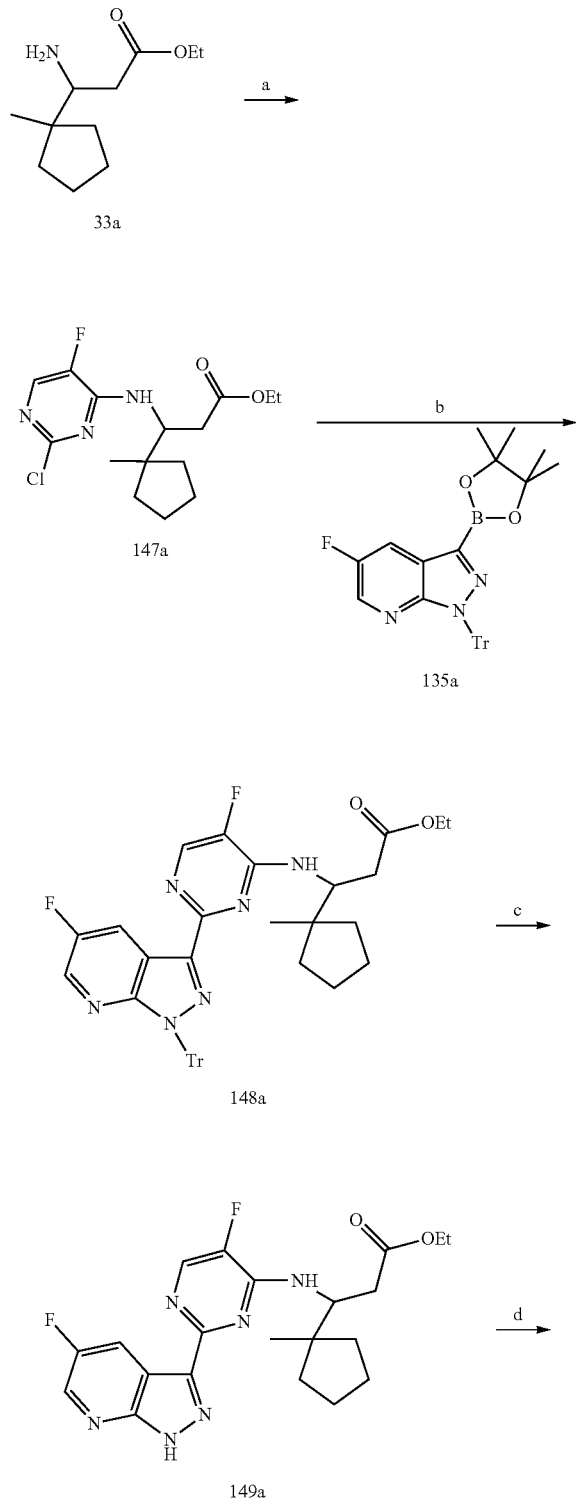

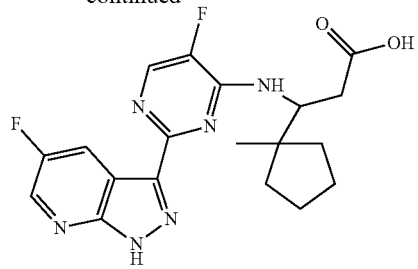

(a) Et₃N, THF, EtOH; (b) 5-fluoro-3-(4,4,5,5-tetramethyl-1,3,2-dioxaborolan-2-yl)-1-trityl-1H-pyrazolo[3,4-b]pyridine, 135a, X-phos, Pd₂(dba)₃, K₃PO₄, 2-methyl THF, H₂O, 135° C.; (c) Et₃SiH, TFA, CH₂Cl₂; (d) LiOH, THF, H₂O.

Formation of (+/−)-ethyl 3-(2-chloro-5-fluoropyrimidin-4-ylamino)-3-(1-methylcyclopentyl)propanoate (147a)

To a solution of 2,4-dichloro-5-fluoro-pyrimidine (0.184 g, 1.100 mmol) and racemic ethyl 3-amino-3-(1-methylcyclopentyl)propanoate, 33a, (0.199 g, 1.000 mmol) in THF (10 mL) and ethanol (1 mL) was added triethylamine (0.307 mL, 2.200 mmol). The reaction mixture was stirred at 70° C. for 5 hours. The mixture was filtered and the filtrate was concentrated in vacuo. The resulting residue was purified via silica gel chromatography (25% EtOAc/Hexanes) to afford 180 mg of the desired product: ¹H NMR (400 MHz, CDCl₃) δ 7.88 (d, J=2.7 Hz, 1H), 5.54 (d, J=9.2 Hz, 1H), 4.74-4.54 (m, 1H), 4.08 (q, J=7.2 Hz, 2H), 2.68 (dd, J=14.8, 3.7 Hz, 1H), 2.46 (dd, J=14.8, 9.3 Hz, 1H), 1.69 (dd, J=12.8, 8.8 Hz, 4H), 1.63-1.50 (m, 2H), 1.46-1.38 (m, 1H), 1.37-1.23 (m, 1H), 1.23-1.14 (m, 3H), 1.00 (s, 3H). LCMS Gradient 10-90%, 0.1% formic acid, 5 minutes, C18/ACN, Retention Time=3.54 minutes (M+H) 330.17.

Formation of (+/−)-ethyl 3-(5-fluoro-2-(5-fluoro-1-trityl-1H-pyrazolo[3,4-b]pyridin-3-yl)pyrimidin-4-ylamino)-3-(1-methylcyclopentyl)propanoate (148a)

A solution of K₃PO₄ (0.464 g, 2.183 mmol), racemic ethyl 3-[(2-chloro-5-fluoro-pyrimidin-4-yl)amino]-3-(1-methylcyclopentyl)propanoate, 147a, (0.180 g, 0.546 mmol) and 5-fluoro-3-(4,4,5,5-tetramethyl-1,3,2-dioxaborolan-2-yl)-1-trityl-pyrazolo[3,4-b]pyridine, 135a, (303.4 mg, 0.6004 mmol) in 2-Methyl THF (3.240 mL) and H₂O (0.360 mL) was degassed under a stream of nitrogen for 30 minutes. To this mixture was added X-phos (0.031 g, 0.066 mmol) and Pd₂(dba)₃ (0.013 g, 0.014 mmol). The reaction mixture was stirred at 135° C. in a pressure tube for 1 hour. The organic phase was filtered through a pad of celite and concentrated in vacuo. The resulting residue was purified by silica gel chromatography (30% EtOAc/Hexanes) to afford 240 mg of the desired product: ¹H NMR (400 MHz, CDCl₃) δ 8.55 (dd, J=8.5, 2.7 Hz, 1H), 8.15 (d, J=2.4 Hz, 2H), 7.27 (dd, J=11.0, 5.0 Hz, 15H), 5.38 (d, J=9.7 Hz, 1H), 4.89 (dd, J=9.7, 6.0 Hz, 1H), 3.99 (q, J=7.1 Hz, 2H), 2.73 (dd, J=14.7, 3.8 Hz, 1H), 2.52 (dd, J=14.8, 9.4 Hz, 1H), 1.68 (dd, J=12.0, 6.6 Hz, 2H), 1.64-1.52 (m, 4H), 1.47-1.36 (m, 1H), 1.30 (dt, J=14.3, 7.2 Hz, 2H), 1.11-0.99 (m, 4H). LCMS Gradient 60-98%, formic acid, 7 minutes, C18/can, Retention Time=3.24 minutes (M+H) 672.85.

Formation of (+/−)-ethyl 3-(5-fluoro-2-(5-fluoro-1H-pyrazolo[3,4-b]pyridin-3-yl)pyrimidin-4-ylamino)-3-(1-methylcyclopentyl)propanoate (149a)

To a solution of racemic ethyl 3-[[5-fluoro-2-(5-fluoro-1-trityl-pyrazolo[3,4-b]pyridin-3-yl)pyrimidin-4-yl]amino]-3-(1-methylcyclopentyl)propanoate, 148a, (0.240 g, 0.357 mmol) in dichloromethane (20 mL) was added triethylsilane (0.285 mL, 1.784 mmol) followed by trifluoroacetic acid (0.275 mL, 3.567 mmol). The reaction mixture was stirred at room temperature overnight. The reaction mixture was concentrated in vacuo and the resulting crude residue was purified by silica gel chromatography (5% MeOH/CH$_2$Cl$_2$) to afford the desired product: $^1$H NMR (400 MHz, CDCl$_3$) δ 11.80 (s, 2H), 8.59 (d, J=12.3 Hz, 2H), 8.48 (d, J=7.9 Hz, 1H), 6.60 (d, J=8.3 Hz, 1H), 5.07 (s, 1H), 4.09 (q, J=7.0 Hz, 2H), 2.97-2.59 (m, 2H), 1.70 (dd, J=27.7, 13.9 Hz, 6H), 1.57-1.33 (m, 2H), 1.16 (dd, J=18.1, 11.1 Hz, 6H); LCMS Gradient 10-90%, 0.1% formic acid, 5 minutes, C18/ACN, Retention Time=2.97 minutes (M+H) 431.24.

Formation of (+/−)-3-(5-fluoro-2-(5-fluoro-1H-pyrazolo[3,4-b]pyridin-3-yl)pyrimidin-4-ylamino)-3-(1-methylcyclopentyl)propanoic acid (12)

To a solution of racemic ethyl 3-[[5-fluoro-2-(5-fluoro-1H-pyrazolo[3,4-b]pyridin-3-yl)pyrimidin-4-yl]amino]-3-(1-methylcyclopentyl)propanoate, 149a, (0.110 g, 0.256 mmol) in THF (30 mL) was added a solution of lithium hydroxide hydrate (0.043 g, 1.022 mmol) in H$_2$O (20 mL). The reaction mixture was stirred at 70° C. overnight. The organic solvent was removed under reduced pressure and the remaining aqueous phase was used directly in the purification via preparatory HPLC. The resulting HPLC fractions were extracted with EtOAc. The organic phase was dried over MgSO$_4$, filtered and the solvent was removed under reduced pressure to afford the desired product: $^1$H NMR (400 MHz, MeOD) δ 8.64 (dd, J=8.4, 2.4 Hz, 1H), 8.57 (s, 1H), 8.24 (d, J=4.4 Hz, 1H), 5.19 (d, J=8.7 Hz, 1H), 2.78 (qd, J=15.9, 6.6 Hz, 2H), 1.85-1.57 (m, 6H), 1.48 (dd, J=11.8, 6.0 Hz, 1H), 1.36 (dt, J=12.0, 6.0 Hz, 1H), 1.11 (s, 3H). LCMS Gradient 10-90%, 0.1% formic acid, 5 minutes, C18/ACN, Retention Time=2.37 min, (M+H) 403.22.

The following compounds can be prepared in a similar fashion as the procedure described above for Compound 12:

(R)-3-((5-fluoro-2-(5-fluoro-1H-pyrazolo[3,4-b]pyridin-3-yl)pyrimidin-4-yl)amino)-4,4-dimethylpentanoic acid (5)

Compound 5 was synthesized in a manner similar to compound 12, starting with compound 6a: $^1$H NMR (400 MHz, d6-DMSO) δ 12.65 (s, 1H), 9.43 (s, 1H), 9.15 (s, 1H), 8.44 (d, J=4.7 Hz, 1H), 8.41-8.29 (m, 2H), 3.93 (s, 1H), 3.54 (s, 1H), 1.19 (d, J=20.0 Hz, 9H); LCMS Gradient 10-90%, 0.1% formic acid, 5 minutes, C18/ACN, Retention Time=2.70 min, (M+H) 393.32.

(R)-3-((3,5-difluoro-6-(5-fluoro-1H-pyrazolo[3,4-b]pyridin-3-yl)pyridin-2-yl)amino)-4,4-dimethylpentanoic acid (6)

Compound 6 was synthesized in a manner similar to compound 12, utilizing (R)-ethyl 3-((6-bromo-3,5-difluoropyridin-2-yl)amino)-4,4-dimethylpentanoate as the intermediate for the Suzuki coupling. (R)-ethyl 3-((6-bromo-3,5-difluoro-pyridin-2-yl)amino)-4,4-dimethyl-pentanoate was prepared in the same fashion as intermediate, 143a, utilizing 2-bromo-3,5,6-trifluoropyridine as the starting material instead of 2-chloro-5,6-difluoropyridine-3-carbonitrile: $^1$H NMR (400 MHz, CDCl$_3$) δ 8.31 (d, J=6.4 Hz, 1H), 8.06 (s, 1H), 7.06 (t, J=9.7 Hz, 1H), 4.58 (s, 2H), 2.80 (d, J=13.2 Hz, 1H), 2.29 (dd, J=13.3, 8.7 Hz, 1H), 0.98 (s, 9H).; LCMS Gradient 10-90%, 0.1% formic acid, 5 minutes, C18/ACN, Retention Time=2.92 min, (M+H)

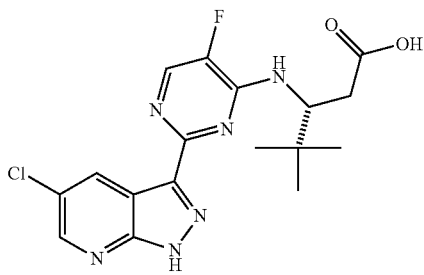

(R)-3-((2-(5-chloro-1H-pyrazolo[3,4-b]pyridin-3-yl)-5-fluoropyrimidin-4-yl)amino)-4,4-dimethylpentanoic acid (97) and methylester (96)

Compounds 96 and 97 were synthesized in a manner similar to compound 12, starting with compound 6a: $^1$H NMR (300 MHz, MeOD) for Compound 97: δ 8.95 (d, J=2.3 Hz, 1H), 8.66 (d, J=2.3 Hz, 1H), 8.35 (d, J=5.2 Hz, 1H), 5.12 (dd, J=10.7, 2.9 Hz, 1H), 2.93 (dd, J=16.5, 2.9 Hz, 1H), 2.73 (dd, J=16.4, 10.7 Hz, 1H), 1.10 (s, 9H); LCMS Gradient 10-90%, 0.1% formic acid, 5 minutes, C18/ACN, Retention Time=2.79 min, (M+H) 407.37.

Preparation of Compounds 54, 56 and 53

Synthetic Scheme 23

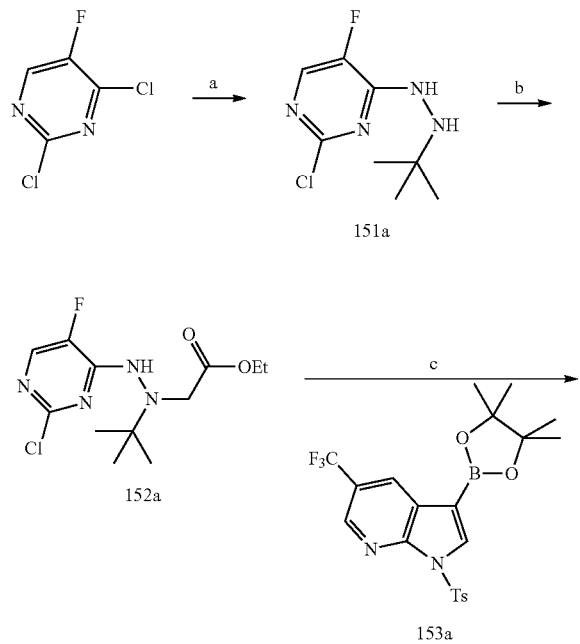

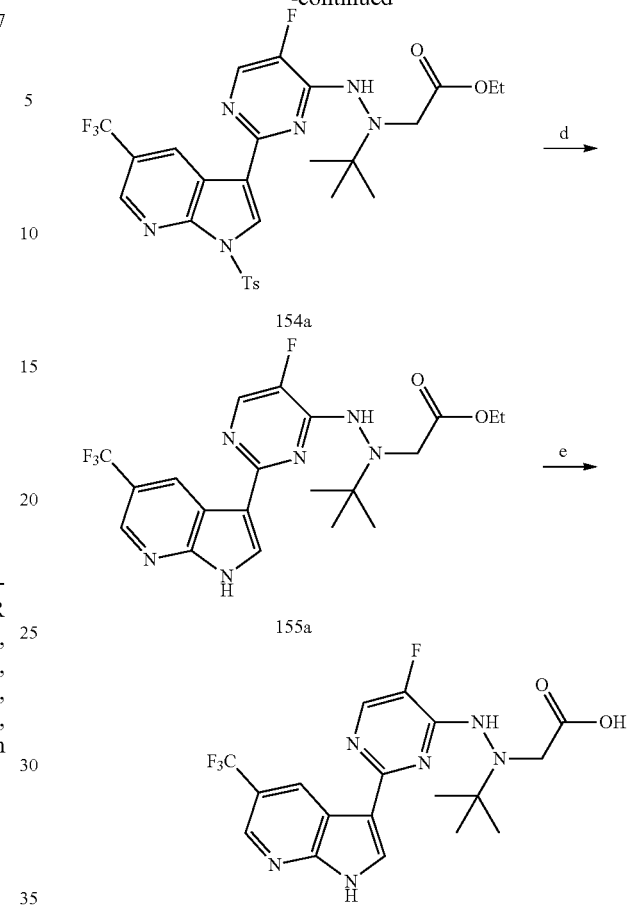

(a) tert-butylhydrazine-HCl, Et$_3$N, THF, EtOH; (b) 2-bromoethyl acetate, K$_2$CO$_3$, CH$_3$CN; (c) 3-(4,4,5,5-tetramethyl-1,3,2-dioxaborolan-2-yl)-1-tosyl-5-(trifluoromethyl)-1H-pyrrolo[2,3-b]pyridine, 153a, X-phos, Pd$_2$(dba)$_3$, K$_3$PO$_4$, THF, H$_2$O; (d) TBAF/THF; (e) LiOH, H$_2$O, THF.

Formation of 4-(2-tert-butylhydrazinyl)-2-chloro-5-fluoropyrimidine (151a)

To a solution of 2,4-dichloro-5-fluoro-pyrimidine (1.84 g, 11.00 mmol) and tert-butylhydrazine hydrochloride (1.25 g, 10.00 mmol) in THF (50 mL) and EtOH (5 mL) was added triethylamine (4.18 mL, 30.00 mmol). The reaction mixture was stirred at room temperature overnight. The reaction mixture was filtered to remove triethylamine HCl salt and the filtrate concentrated in vacuo. The resulting residue was purified by silica gel chromatography (EtOAc/Hexanes) to afford 1.7 g of the desired product: $^1$H NMR (400 MHz, CDCl$_3$) δ 7.82 (d, J=2.8 Hz, 1H), 6.47 (s, 1H), 4.60 (d, J=5.8 Hz, 1H), 1.09 (s, 9H). LCMS Gradient 10-90%, 0.1% formic acid, 5 minutes, C18/ACN, Retention Time=2.19 minutes (M+H) 218.81.

Formation of ethyl 2-(1-tert-butyl-2-(2-chloro-5-fluoropyrimidin-4-yl)hydrazinyl)ethanoate (152a)

To a suspension of 4-(2-tert-butylhydrazinyl)-2-chloro-5-fluoropyrimidine, 151a, (1.50 g, 6.86 mmol) in acetonitrile (68 mL) was added 2-bromoethyl acetate (0.84 mL, 7.55 mmol) and K$_2$CO$_3$ (2.28 g, 16.46 mmol). The reaction mixture was stirred at room temperature overnight. The mixture was diluted into EtOAc and brine. The organic phase was dried over MgSO₄, filtered and concentrated in vacuo. The residue was purified by silica gel chromatography (30% EtOAc/Hexanes) to afford 1 g of the desired product: ¹H NMR (400 MHz, CDCl₃) δ 7.96 (d, J=3.1 Hz, 1H), 4.16 (dt, J=7.1, 5.9 Hz, 2H), 3.74 (s, 2H), 1.30-1.23 (m, 3H), 1.20 (s, 9H). LCMS Gradient 10-90%, 0.1% formic acid, 5 minutes, C18/ACN, Retention Time=2.69 minutes (M+H) 305.09.

Formation of ethyl 2-(1-tert-butyl-2-(5-fluoro-2-(1-tosyl-5-(trifluoromethyl)-1H-pyrrolo[2,3-b]pyridin-3-yl)pyrimidin-4-yl)hydrazinyl)ethanoate (154a)

Boronate ester, 153a, was prepared in same fashion as boronate ester, 7a, (see Synthetic Scheme 4) using 3-bromo-5-(trifluoromethyl)-1H-pyrrolo[2,3-b]pyridine instead of 3-bromo-5-fluoro-1H-pyrrolo[2,3-b]pyridine.

A solution of 1-(p-tolylsulfonyl)-3-(4,4,5,5-tetramethyl-1,3,2-dioxaborolan-2-yl)-5-(trifluoromethyl)pyrrolo[2,3-b]pyridine, 153a, (0.551 g, 1.181 mmol), ethyl 2-(1-tert-butyl-2-(2-chloro-5-fluoropyrimidin-4-yl)hydrazinyl)ethanoate, 152a, (0.300 g, 0.984 mmol) and K₃PO₄ (0.627 g, 2.953 mmol) in 2-MethylTHF (26 mL) and H₂O (5 mL) was degassed under a stream of nitrogen for 45 minutes. To the reaction mixture was added X-phos (0.056 g, 0.118 mmol) and Pd₂(dba)₃ (0.022 g, 0.025 mmol). The reaction mixture was heated at 120° C. for 75 minutes. The aqueous phase was removed and the organic phase was filtered through a pad of celite, concentrated in vacuo and purified by silica gel chromatography (30% EtOAc/Hexanes) to afford 540 mg of the desired product: ¹H NMR (400 MHz, CDCl₃) δ 9.49 (s, 1H), 8.71 (t, J=7.0 Hz, 1H), 8.63 (d, J=11.1 Hz, 1H), 8.16-8.11 (m, 3H), 7.31 (d, J=8.2 Hz, 2H), 7.11 (d, J=21.4 Hz, 1H), 4.10 (dd, J=13.4, 6.3 Hz, 2H), 3.79 (s, 2H), 2.39 (s, 3H), 1.24 (s, 9H), 1.17 (t, J=7.1 Hz, 3H); LCMS Gradient 10-90%, 0.1% formic acid, 5 minutes, C18/ACN, Retention Time=4.18 minutes (M+H) 609.37.

Formation of ethyl 2-(1-(tert-butyl)-2-(5-fluoro-2-(5-(trifluoromethyl)-1H-pyrrolo[2,3-b]pyridin-3-yl)pyrimidin-4-yl)hydrazinyl)acetate (155a)

To a solution of ethyl 2-(1-tert-butyl-2-(5-fluoro-2-(1-tosyl-5-(trifluoromethyl)-1H-pyrrolo[2,3-b]pyridin-3-yl)pyrimidin-4-yl)hydrazinyl)ethanoate, 154a, (0.54 g, 0.89 mmol) in THF (20 mL) was added tetrabutylammonium fluoride (1.78 mL of 1 M, 1.78 mmol). The reaction mixture was stirred at room temperature for 30 minutes. The reaction mixture was diluted into EtOAc and brine. The organic phase was dried over MgSO₄, filtered and concentrated in vacuo. The resulting residue was purified via silica gel chromatography (70% EtOAc/Hexanes) to afford 300 mg of the desired product. ¹H NMR (400 MHz, CDCl₃) δ 10.59 (s, 1H), 9.55 (s, 1H), 8.66 (s, 1H), 8.29 (d, J=2.2 Hz, 1H), 8.13 (dd, J=3.8, 1.5 Hz, 1H), 7.14 (s, 1H), 4.20-4.04 (m, 2H), 3.85 (s, 2H), 1.28 (d, J=9.1 Hz, 9H), 1.19 (dt, J=7.1, 3.6 Hz, 3H). LCMS Gradient 10-90%, 0.1% formic acid, 5 minutes, C18/ACN, Retention Time=2.93 min, (M+H) 455.43.

Formation of 2-(1-(tert-butyl)-2-(5-fluoro-2-(5-(trifluoromethyl)-1H-pyrrolo[2,3-b]pyridin-3-yl)pyrimidin-4-yl)hydrazinyl)acetic acid (54)

To a solution of ethyl 2-[tert-butyl-[[5-fluoro-2-[5-(trifluoromethyl)-1H-pyrrolo[2,3-b]pyridin-3-yl]pyrimidin-4-yl]amino]amino]acetate, 155a, (0.200 g, 0.440 mmol) in THF (40 mL) was added a solution of lithium hydroxide hydrate (0.074 g, 1.760 mmol) in H₂O (4 mL). The reaction mixture was stirred at room temperature overnight. The reaction mixture concentrated in vacuo to remove the THF. The remaining aqueous phase was diluted to 8 mL and the solution was used directly in a preparatory HPLC. The product precipitated when the fraction was concentrated on rotavaporator. The solid was filtered and dried in desiccator with P₂O₅ to afford 120 mg of the desired product: ¹H NMR (400 MHz, d6-DMSO) δ 12.65 (s, 1H), 12.41 (s, 1H), 9.28 (s, 1H), 8.86 (s, 1H), 8.65 (s, 1H), 8.30 (d, J=3.5 Hz, 2H), 3.97-3.70 (m, 1H), 3.51 (s, 1H), 1.18 (s, 9H); LCMS Gradient 10-90%, 0.1% formic acid, 5 minutes, C18/ACN, Retention Time=2.92 min, (M+H) 427.40

The following compounds can be prepared in a similar fashion as the procedure described above for Compound 54:

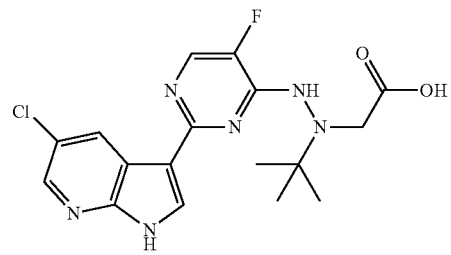

56

Formation of 2-(1-(tert-butyl)-2-(2-(5-chloro-1H-pyrrolo[2,3-b]pyridin-3-yl)-5-fluoropyrimidin-4-yl)hydrazinyl)acetic acid-TFA (trifluoro acetic acid) salt (56)

¹H NMR (400 MHz, d6-DMSO) δ 12.65 (s, 1H), 9.43 (s, 1H), 9.15 (s, 1H), 8.44 (d, J=4.7 Hz, 1H), 8.41-8.29 (m, 2H), 3.93 (s, 1H), 3.54 (s, 1H), 1.19 (d, J=20.0 Hz, 9H); LCMS Gradient 10-90%, 0.1% formic acid, 5 minutes, C18/ACN, Retention Time=2.70 min, (M+H) 393.32.

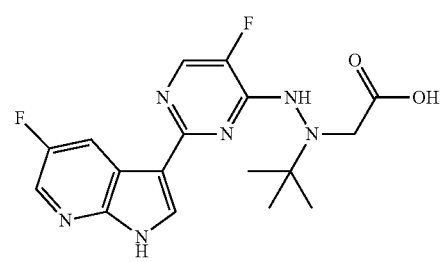

53

Formation of 2-(1-(tert-butyl)-2-(5-fluoro-2-(5-fluoro-1H-pyrrolo[2,3-b]pyridin-3-yl)pyrimidin-4-yl)hydrazinyl)acetic acid-TFA salt (53)

¹H NMR (400 MHz, d6-DMSO) δ 12.57 (s, 1H), 9.40 (s, 1H), 8.88 (s, 1H), 8.40 (d, J=18.7 Hz, 2H), 8.34 (s, 1H), 3.93 (s, 1H), 3.52 (s, 1H), 1.20 (s, 9H); LCMS Gradient 10-90%, 0.1% formic acid, 5 minutes, C18/ACN, Retention Time=2.50 min, (M+H) 377.42.

Preparation of Compounds 7, 8, and 18

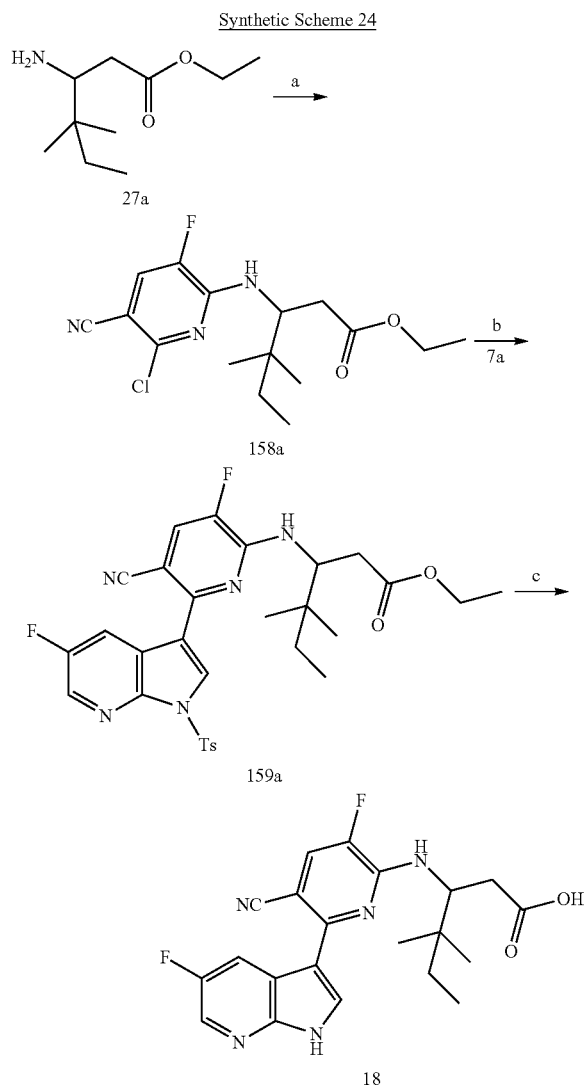

(a) 2,6-dichloro-5-fluoro-pyridine-3-carbonitrile, Et₃N, acetonitrile;
(b) 5-fluoro-1-(p-tolylsulfonyl)-3-(4,4,5,5-tetramethyl-1,3,2-dioxaborolan-2-yl) pyrrolo[2,3-b]pyridine, 7a, Pd₂(dba)₃, X-Phos, K₃PO₄, 2-MeTHF, H₂O, 125° C.;
(c) LiOH, THF, H₂O Formation of ethyl 3-[(6-chloro-5-cyano-3-fluoro-2-pyridyl)amino]-4,4-dimethyl-hexanoate (158a)

A solution of ethyl 3-amino-4,4-dimethyl-hexanoate, 27a, (0.24 g, 1.28 mmol), 2,6-dichloro-5-fluoro-pyridine-3-carbonitrile (0.29 g, 1.53 mmol) and Et₃N (0.43 mL, 3.07 mmol) in acetonitrile (4.8 mL) was stirred at 70° C. overnight. The reaction mixture was concentrated in vacuo and purified by silica gel chromatography (10-40% EtOAc/Hexanes gradient) to provide 205 mg of ethyl 3-[(6-chloro-5-cyano-3-fluoro-2-pyridyl)amino]-4,4-dimethyl-hexanoate; LCMS Gradient 10-90%, 0.1% formic acid, 5 minutes, C18/ACN, Retention Time=3.75 minutes (M+H) 342.04.

Formation of ethyl 3-[[5-cyano-3-fluoro-6-[5-fluoro-1-(p-tolylsulfonyl)pyrrolo[2,3-b]pyridin-3-yl]-2-pyridyl]amino]-4,4-dimethyl-hexanoate (159a)

A solution of ethyl 3-[(6-chloro-5-cyano-3-fluoro-2-pyridyl)amino]-4,4-dimethyl-hexanoate, 158a, (0.21 g, 0.600 mmol), 5-fluoro-1-(p-tolylsulfonyl)-3-(4,4,5,5-tetramethyl-1,3,2-dioxaborolan-2-yl)pyrrolo[2,3-b]pyridine, 7a, (0.30 g, 0.72 mmol) and K₃PO₄ (0.51 g, 2.40 mmol) in 2-methyl THF (20.5 mL) and H₂O (2.7 mL) was degassed for 45 minutes and treated with X-phos (0.03 g, 0.07 mmol) and Pd₂(dba)₃ (0.01 g, 0.02 mmol). The reaction vessel was sealed and heated to 125° C. for 90 minutes. After cooling to room temperature, the aqueous phase was removed and the organic phase was filtered and concentrated in vacuo. The crude residue was purified by silica gel chromatography (0-40% EtOAc/Hexanes gradient) to provide 270 mg of the desired product: ¹H NMR (400 MHz, CDCl₃) δ 8.69 (s, 1H), 8.51 (dd, J=9.1, 2.7 Hz, 1H), 8.37 (d, J=1.8 Hz, 1H), 8.15 (d, J=8.4 Hz, 2H), 7.41 (d, J=10.3 Hz, 1H), 7.33 (d, J=8.1 Hz, 2H), 5.28-5.22 (m, 1H), 4.92 (td, J=10.4, 3.2 Hz, 1H), 4.03-3.91 (m, 2H), 2.75 (dd, J=14.9, 3.5 Hz, 1H), 2.45 (dd, J=12.6, 8.2 Hz, 1H), 2.40 (s, J=4.7 Hz, 3H), 1.36 (q, J=7.4 Hz, 2H), 1.01 (t, J=7.1 Hz, 3H), 0.92 (d, J=8.8 Hz, 6H), 0.88 (t, J=7.5 Hz, 3H). LCMS Gradient 10-90%, 0.1% formic acid, 5 minutes, C18/ACN, Retention Time=2.86 minutes (M+H) 596.02.

Formation of 3-[[5-cyano-3-fluoro-6-(5-fluoro-1H-pyrrolo[2,3-b]pyridin-3-yl)-2-pyridyl]amino]-4,4-dimethyl-hexanoic acid (18)

Ethyl 3-[[5-cyano-3-fluoro-6-[5-fluoro-1-(p-tolylsulfonyl)pyrrolo[2,3-b]pyridin-3-yl]-2-pyridyl]amino]-4,4-dimethyl-hexanoate, 159a, (0.27 g, 0.45 mmol) was dissolved in THF (7 mL) and treated with LiOH (4.50 mL of 1 M, 4.50 mmol). The reaction mixture was heated to 70° C. for 10 hours. After cooling to room temperature, water (20 mL) and ethyl acetate (20 mL) were added and the layers were separated. The aqueous layer was brought to a neutral pH by addition of 1N HCl, and the resulting precipitate was collected by filtration, washed with water and concentrated in vacuo to provide 77 mg of the desired product: ¹H NMR (400 MHz, DMSO-d₆) δ 12.37 (s, 1H), 12.12 (s, 1H), 8.75 (d, J=9.9 Hz, 1H), 8.32 (s, 2H), 7.83 (d, J=11.4 Hz, 1H), 7.48 (d, J=9.5 Hz, 1H), 5.00 (t, J=9.1 Hz, 1H), 2.71-2.54 (m, 2H), 1.30 (d, J=7.4 Hz, 2H), 0.80 (t, J=18.7 Hz, 9H); LCMS Gradient 10-90%, 0.1% formic acid, 5 minutes, C18/ACN, Retention Time=3.14 minutes (M+H) 414.31.

The following compounds can be prepared in a similar fashion as the procedure described above for Compound 18:

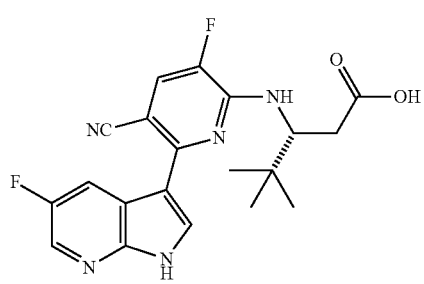

7

Formation of (R)-3-(5-cyano-3-fluoro-6-(5-fluoro-1H-pyrrolo[2,3-b]pyridin-3-yl)pyridin-2-ylamino)-4,4-dimethylpentanoic acid (7)

$^1$H NMR (400 MHz, MeOD) δ 8.81 (dd, J=9.8, 2.7 Hz, 1H), 8.36 (s, 1H), 8.20 (s, 1H), 7.53 (d, J=11.0 Hz, 1H), 5.04 (d, J=8.7 Hz, 1H), 2.80 (dd, J=15.2, 2.5 Hz, 1H), 2.59 (dd, J=15.0, 11.0 Hz, 1H), 0.99 (s, 9H); LCMS Gradient 10-90%, 0.1% formic acid, 5 minutes, C18/ACN, Retention Time=3.0 minutes (M+H) 400.39.

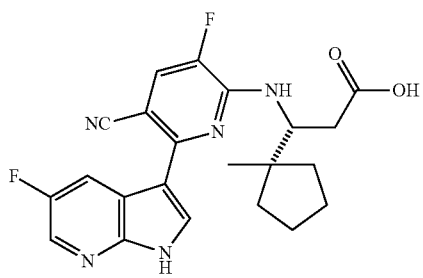

8

Formation of (R)-3-(5-cyano-3-fluoro-6-(5-fluoro-1H-pyrrolo[2,3-b]pyridin-3-yl)pyridin-2-ylamino)-3-(1-methylcyclopentyl)propanoic acid (8)

$^1$H NMR (300 MHz, CDCl$_3$) δ 10.70 (s, 1H), 8.42 (dd, J=9.6, 2.6 Hz, 1H), 8.05 (s, 1H), 7.73 (s, 1H), 7.40 (t, J=8.4 Hz, 1H), 5.32 (d, J=6.6 Hz, 1H), 4.83 (t, J=9.4 Hz, 1H), 2.89 (d, J=5.3 Hz, 1H), 2.34 (dd, J=12.8, 9.6 Hz, 1H), 1.92-1.37 (m, 8H), 1.32-1.24 (m, 1H), 1.20-1.06 (m, 3H); LCMS Gradient 10-90%, 0.1% formic acid, 5 minutes, C18/ACN, Retention Time=3.27 minutes (M+H) 426.31.

Preparation of Compound 55

Synthetic Scheme 25

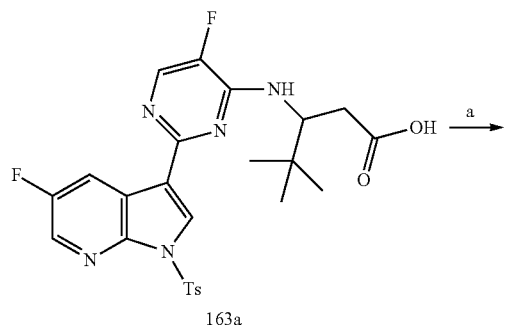

163a

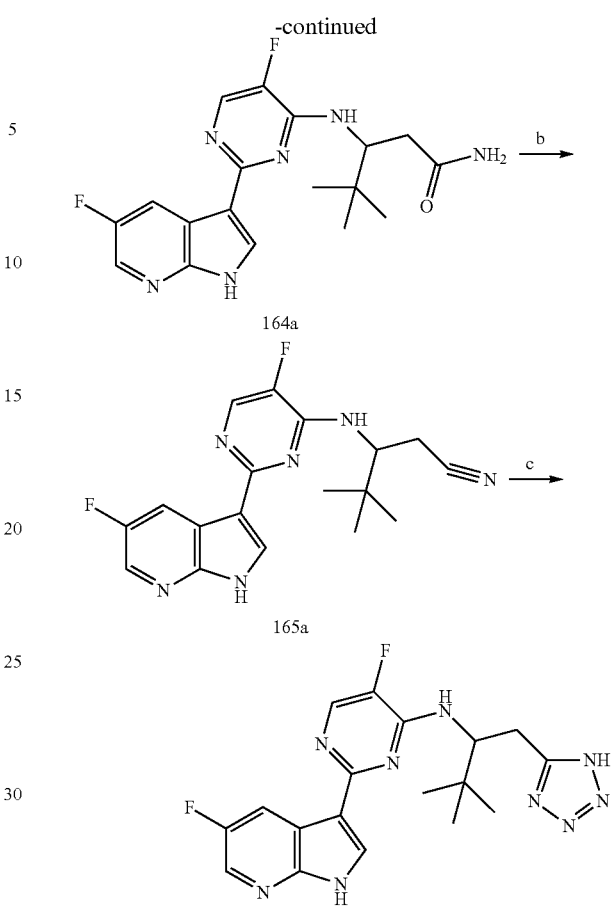

55

(a) (i) NH$_3$, HBTU, THF, (ii) 2N LiOH, MeOH; (b) TFAA, pyridine; (c) Bu$_3$SnN$_3$, dioxane, 130° C.;

Formation of (+/−)-3-(5-fluoro-2-(5-fluoro-1H-pyrrolo[2,3-b]pyridin-3-yl)pyrimidin-4-ylamino)-4,4-dimethylpentanamide (164a)

To a solution of racemic 3-(5-fluoro-2-(5-fluoro-1-tosyl-1H-pyrrolo[2,3-b]pyridin-3-yl)pyrimidin-4-ylamino)-4,4-dimethylpentanoic acid, 163a, (0.50 g, 0.94 mmol) in 15 mL of THF was added HBTU (0.36 g, 0.95 mmol). The reaction was stirred for 15 minutes and then ammonia gas was bubbled through for 5 minutes. The reaction was allowed to stir for 12 hours and then concentrated to dryness. The residue was redissolved in 20 mL of MeOH and treated with 3 mL of 2N LiOH. The reaction was warmed to 60° C. for 3 hours and then concentrated to dryness. The residue was purified by silica gel chromatography (EtOAc) to afford 250 mg of desired product: LCMS Gradient 10-90%, 0.1% formic acid, 5 minutes, C18/ACN, Retention Time=1.78 minutes (M+H) 375.45.

Formation of (+/−)-3-(5-fluoro-2-(5-fluoro-1H-pyrrolo[2,3-b]pyridin-3-yl)pyrimidin-4-ylamino)-4,4-dimethylpentanenitrile (165a)

A solution of racemic 3-(5-fluoro-2-(5-fluoro-1H-pyrrolo[2,3-b]pyridin-3-yl)pyrimidin-4-ylamino)-4,4-dimethylpentanamide, 164a, (0.250 g, 0.668 mmol) in pyridine was cooled to 0° C. and treated with trifluoroacetic acid anhydride (0.278 mL, 2.003 mmol). After 2 hours at 0° C., the reaction was concentrated to dryness and the residue was purified by silica gel chromatography (EtOAc) to afford 150 mg of desired product: LCMS Gradient 10-90%, 0.1% formic acid, 5 minutes, C18/ACN, Retention Time=2.41 minutes (M+H) 357.47.

Formation of (+/−)-N-(3,3-dimethyl-1-(2H-tetrazol-5-yl)butan-2-yl)-5-fluoro-2-yl)-5-2-(5-fluoro-1H-pyrrolo[2,3-b]pyridin-3-yl)pyrimidin-4-amine (55)

To a solution of racemic 3-(5-fluoro-2-(5-fluoro-1H-pyrrolo[2,3-b]pyridin-3-yl)pyrimidin-4-ylamino)-4,4-dimethylpentanenitrile, 165a, (0.150 g, 0.420 mmol) in 10 mL of dioxane was added azido-tributylstannane (0.221 g, 0.668 mmol). The reaction vessel was sealed and warmed to 130° C. for 12 hours. Upon cooling, the reaction was concentrated to dryness and the resulting residue was purified by silica gel chromatography to afford 48 mg of desired product: $^1$H NMR (300.0 MHz, d6-DMSO) δ 12.23 (s, H), 8.49 (d, J=9.6 Hz, H), 8.26-8.05 (m, H), 4.03 (d, J=7.1 Hz, H), 3.48-3.35 (m, H), 3.17 (s, H), 2.50 (s, H), 1.99 (s, H), 1.13 (dt, J=25.1, 8.0 Hz, H), 1.01 (s, H), 0.96 (s, H) and 0.87 (d, J=6.6 Hz, H) ppm; LCMS Gradient 10-90%, 0.1% formic acid, 5 minutes, C18/ACN, Retention Time=1.94 minutes (M+H) 400.46.

Preparation of Compounds 60 and 61

Synthetic Scheme 26

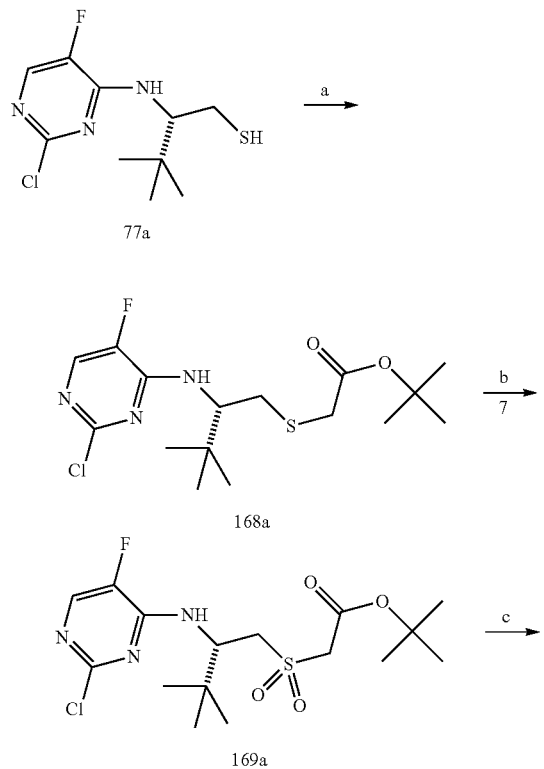

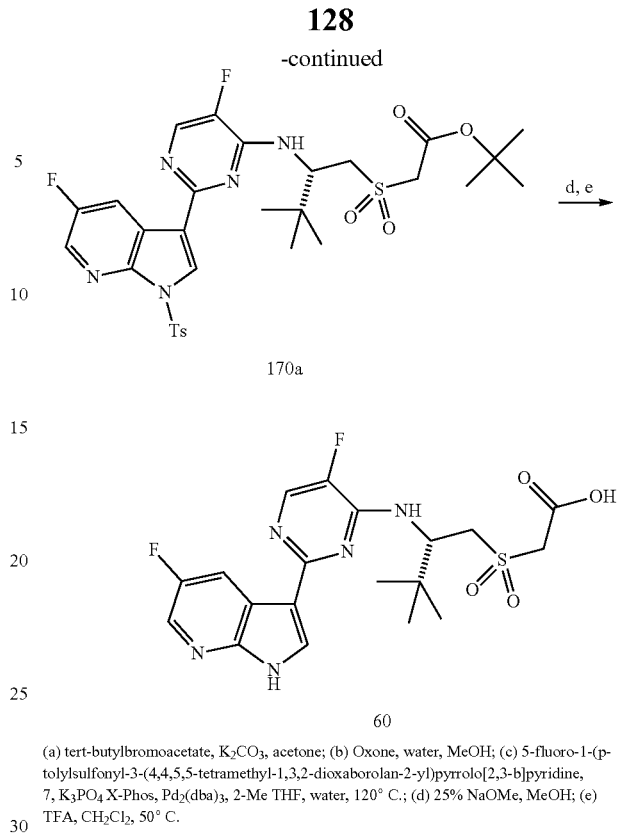

170a

60

(a) tert-butylbromoacetate, K$_2$CO$_3$, acetone; (b) Oxone, water, MeOH; (c) 5-fluoro-1-(p-tolylsulfonyl-3-(4,4,5,5-tetramethyl-1,3,2-dioxaborolan-2-yl)pyrrolo[2,3-b]pyridine, 7, K$_3$PO$_4$ X-Phos, Pd$_2$(dba)$_3$, 2-Me THF, water, 120° C.; (d) 25% NaOMe, MeOH; (e) TFA, CH$_2$Cl$_2$, 50° C.

Formation of (S)-tert-Butyl 2-(2-(2-chloro-5-fluoro-pyrimidin-4-ylamino)-3,3-dimethyl-butylthio)ethanoate (168a)

To a stirring suspension of (S)-2-((2-chloro-5-fluoropyrimidin-4-yl)amino)-3,3-dimethylbutane-1-thiol, 77a, (1.50 g, 5.69 mmol) and K$_2$CO$_3$ (2.36 g, 17.06 mmol) in acetone (15 mL) was added tert-butyl bromoacetate (1.26 mL, 8.53 mmol). The suspension was stirred at room temperature for 18 hours. The resulting solid was filtered, washed with acetone and the filtrate was concentrated under reduced pressure. The crude residue was purified by silica gel chromatography (0-30% EtOAc/Hexanes gradient) to afford 1.6 g of the desired product as an off-white solid: LCMS Gradient 10-90%, 0.1% formic acid, 5 minutes, C18/ACN, Retention Time=3.81 minutes (M+H) 378.06.

Formation of (S)-tert-Butyl 2-(2-(2-chloro-5-fluoro-pyrimidin-4-ylamino)-3,3-dimethylbutyl-sulfonyl)ethanoate (169a)

Oxone (5.37 g, 8.73 mmol) was added to a solution of (S)-tert-Butyl 2-(2-(2-chloro-5-fluoropyrimidin-4-ylamino)-3,3-dimethyl-butylthio)ethanoate, 168a, (1.10 g, 2.91 mmol) in methanol (50 mL) and water (20 mL) and the solution was stirred 3 hours at room temperature. The solution was concentrated in vacuo to give a white residue that was dissolved in water (100 mL). The aqueous layer was extracted with EtOAc (3×50 mL) and the combined organic phases was dried (MgSO$_4$), filtered and concentrated in vacuo to afford 750 mg of the desired product as a white solid: LCMS Gradient 10-90%, 0.1% formic acid, 5 minutes, C18/ACN, Retention Time=1.29 minutes (M+H) 410.19.

Formation of (S)-tert-Butyl 2-(2-(5-fluoro-2-(5-fluoro-1-tosyl-1H-pyrrolo[2,3-b]pyridin-3-yl)pyrimidin-4-ylamino)-3,3-dimethylbutylsulfonyl)ethanoate (170a)

A solution of 5-fluoro-1-(p-tolylsulfonyl)-3-(4,4,5,5-tetramethyl-1,3,2-dioxaborolan-2-yl)pyrrolo[2,3-b]pyridine, 7a, (0.76 g, 1.83 mmol), (S)-tert-Butyl 2-(2-(2-chloro-5-fluoropyrimidin-4-ylamino)-3,3-dimethylbutyl-sulfonyl)ethanoate, 169a, (0.75 g, 1.83 mmol) and K$_3$PO$_4$ (0.93 g, 4.39 mmol) in 2-methyl THF (10 mL) and water (2 mL) was degassed under a stream of nitrogen for 30 minutes. X-Phos (0.06 g, 0.12 mmol) and Pd$_2$(dba)$_3$ (0.03 g, 0.03 mmol) were added and the reaction mixture was heated at 115° C. in a pressure vial for 2.5 hours. The reaction mixture was cooled to room temperature, filtered and concentrated in vacuo. The residue was dissolved in EtOAc (50 mL) and washed with water. The organic layer was dried (MgSO$_4$), filtered and concentrated in vacuo. The crude product was purified via silica gel chromatography (0-60% EtOAc/Hexanes gradient) to afford 1.0 g of the desired product as a foamy solid: LCMS Gradient 60-98% ACN/water, 0.9% formic acid, 7 minutes, C4, Retention Time=2.39 minutes (M+H) 564.34.

Formation of (S)-2-(2-(5-fluoro-2-(5-fluoro-1H-pyrrolo[2,3-b]pyridin-3-yl)pyrimidin-4-ylamino)-3,3-dimethylbutylsulfonyl)ethanoic acid (60)

To a solution of (S)-tert-butyl 2-(2-(5-fluoro-2-(5-fluoro-1-tosyl-1H-pyrrolo[2,3-b]pyridin-3-yl)pyrimidin-4-ylamino)-3,3-dimethylbutylsulfonyl)ethanoate, 170a, (1.00 g, 1.50 mmol) in THF (50 mL) was added NaOMe (1.30 mL of 25% solution in MeOH, 1.45 mmol). The yellow colored solution was stirred at room temperature for 30 minutes and then the mixture was diluted with aqueous saturated NH$_4$Cl solution. The solvent was removed under reduced pressure and the residue was dissolved in water (50 mL). The aqueous layer was extracted with EtOAc (3×50 mL) and dried (MgSO$_4$), filtered and concentrated in vacuo. The product was purified by silica gel chromatography (0-10% MeOH/CH$_2$Cl$_2$ gradient) to afford 0.50 g of the detosylated ester intermediate as a white solid.

The ester (0.50 g) was dissolved in CH$_2$Cl$_2$ (4 mL) and trifluoroacetic acid (2 mL) was added. The solution was heated at 50° C. for 2 hours. The solvent was evaporated under reduced pressure. The residue was diluted with water (10 mL) and the solution was neutralized with aqueous saturated NaHCO$_3$ solution. The aqueous phase was extracted with EtOAc (3×10 mL), dried (MgSO$_4$), filtered and concentrated in vacuo. The crude product was purified by silica gel chromatography (0-15% MeOH/CH$_2$Cl$_2$ gradient) to afford 204 mg of the desired product, 60, as a white solid: LCMS Gradient 10-90%, 0.1% formic acid, 5 minutes, C18/ACN, Retention Time=2.01 minutes (M+H) 454.21.

The following compounds can be prepared in the same fashion using the procedure described above:

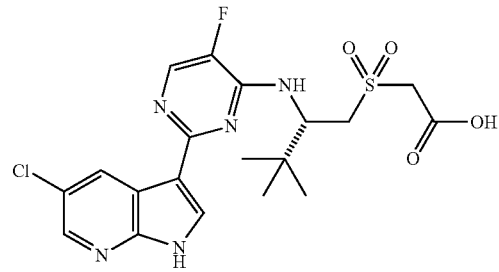

61

(S)-2-(2-(2-(5-chloro-1H-pyrrolo[2,3-b]pyridin-3-yl)-5-fluoropyrimidin-4-ylamino)-3,3-dimethylbutylsulfonyl)ethanoic acid (61)

$^1$H NMR (300 MHz, MeOD) δ 8.95 (s, 1H), 8.29-8.14 (m, 2H), 8.08 (d, J=4.0 Hz, 1H), 5.26 (m, 1H), 4.21 (d, J=15.3 Hz, 1H), 3.92 (dd, J=30.0, 14.5 Hz, 2H), 3.77-3.57 (m, 1H), 1.10 (s, 9H); LCMS Gradient 60-98% ACN/water, 0.9% formic acid, 7 minutes, C4, Retention Time=2.23 minutes (M+H) 470.14.

Preparation of Compound 64

Synthetic Scheme 28

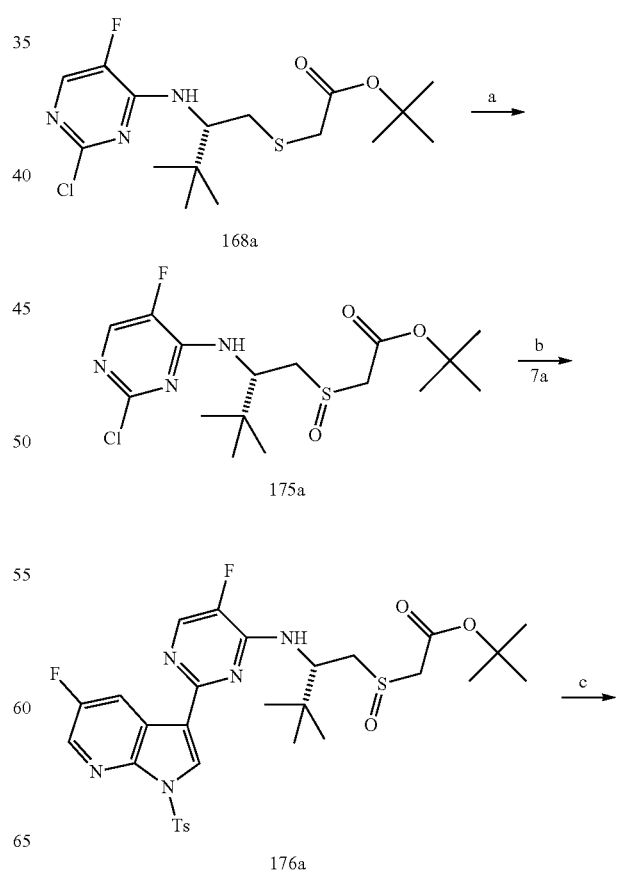

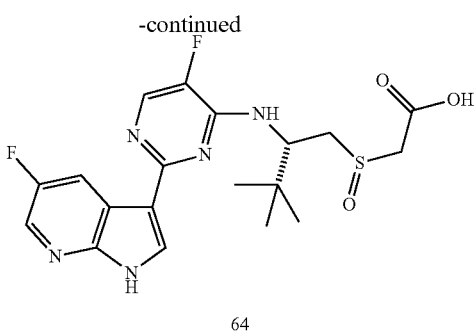

(a) Oxone, MeOH; (b) 5-fluoro-1-(p-tolylsulfonyl)-3-(4,4,5,5-tetramethyl-1,3,2-dioxaborolan-2-yl)pyrrolo[2,3-b]pyridine, 7a, K₃PO₄ X-Phos, Pd₂(dba)₃, 2-Me THF, water, 120° C.; (c) NaOMe, MeOH, THF.

Formation of tert-butyl-((S)-2(2-chloro-5-fluoropyrimidin-4-ylamino)-3,3-dimethylbutylsulfinyl)ethanoate (175a)

Oxone (1.04 g, 1.69 mmol) was added to a stirring solution of (S)-tert-Butyl 2-(2-(2-chloro-5-fluoropyrimidin-4-ylamino)-3,3-dimethyl-butylthio)ethanoate, 168a, (0.53 g, 1.41 mmol) in methanol (20 mL). The solution was stirred for 15 minutes at room temperature. The solution was concentrated to give white residue which was dissolved in water (50 mL). The aqueous layer was extracted with EtOAc (3×25 mL) and the organic layer was dried (MgSO₄), filtered and concentrated in vacuo to give 540 mg of the desired product as a white solid: LCMS Gradient 10-90%, 0.1% formic acid, 5 minutes, C18/ACN, Retention Time=3.05 minutes (M+H) 394.28.

tert-Butyl 2-((S)-2-(5-fluoro-2-(5-fluoro-1-tosyl-1H-pyrrolo[2,3-b]pyridin-3-yl)pyrimidin-4-ylamino)-3,3-dimethylbutylsulfinyl)ethanoate (176a)

A solution of 5-fluoro-1-(p-tolylsulfonyl)-3-(4,4,5,5-tetramethyl-1,3,2-dioxaborolan-2-yl)pyrrolo[2,3-b]pyridine, 7a, (0.66 g, 1.58 mmol), tert-butyl((S)-2(2-chloro-5-fluoropyrimidin-4-ylamino)-3,3-dimethylbutylsulfinyl)ethanoate, 175a, (0.50 g, 1.27 mmol) and K₃PO₄ (0.65 g, 3.05 mmol) in 2-methyl THF (10 mL) and water (2 mL) was degassed under a stream of nitrogen for 30 minutes. X-Phos (0.04 g, 0.08 mmol) and Pd₂(dba)₃ (0.02 g, 0.02 mmol) were added and the reaction mixture was heated at 115° C. in a pressure vial for 4 hours. The reaction mixture was cooled to room temperature, filtered and concentrated in vacuo. The residue was dissolved in EtOAc (50 mL) and washed with water. The organic layer was dried (MgSO₄), filtered and concentrated in vacuo. The crude residue was purified by silica gel chromatography (0-60% EtOAc/Hexanes gradient) to afford 450 mg of the desired product as a white foamy solid: LCMS Gradient 10-90%, 0.1% formic acid, 5 minutes, C18/ACN, Retention Time=3.91 minutes (M+H) 648.40.

2-((S)-2-(5-fluoro-2-(5-fluoro-1H-pyrrolo[2,3-b]pyridin-3-yl)pyrimidin-4-ylamino)-3,3-dimethylbutylsulfinyl)ethanoic acid (64)

To a solution of tert-butyl 2-((S)-2-(5-fluoro-2-(5-fluoro-1-tosyl-1H-pyrrolo[2,3-b]pyridin-3-yl)pyrimidin-4-ylamino)-3,3-dimethylbutylsulfinyl)ethanoate, 176a, (0.42 g, 0.64 mmol) in THF (10 mL) was added NaOMe (0.21 mL of 25% solution in MeOH, 0.96 mmol). The solution was stirred at room temperature for 30 minutes. Aqueous saturated NH₄Cl solution was added and the solvent was removed under reduced pressure. The residue was dissolved in water (20 mL) and the aqueous layer was extracted with EtOAc (3×20 mL). The combined organic phases were dried (MgSO₄), filtered and concentrated in vacuo. The residue was purified by silica gel chromatography (0-15% MeOH/CH₂Cl₂ gradient) to afford 36 mg of the desired product as a white solid: ¹H NMR (400 MHz, MeOD) δ 8.60-8.52 (m, 1H), 8.46 (s, 1H), 8.32 (d, J=5.3 Hz, 2H), 5.16 (m, 2H), 4.00 (d, J=14.7 Hz, 1H), 3.80 (d, J=14.7 Hz, 1H), 3.59 (d, J=13.9, 1H), 1.12 (s, 9H); LCMS Gradient 10-90%, 0.1% formic acid, 5 minutes, C18/ACN, Retention Time=1.93 minutes (M+H) 438.25.

Preparation of Compounds 66, 67, 72, and 73

Synthetic Scheme 29

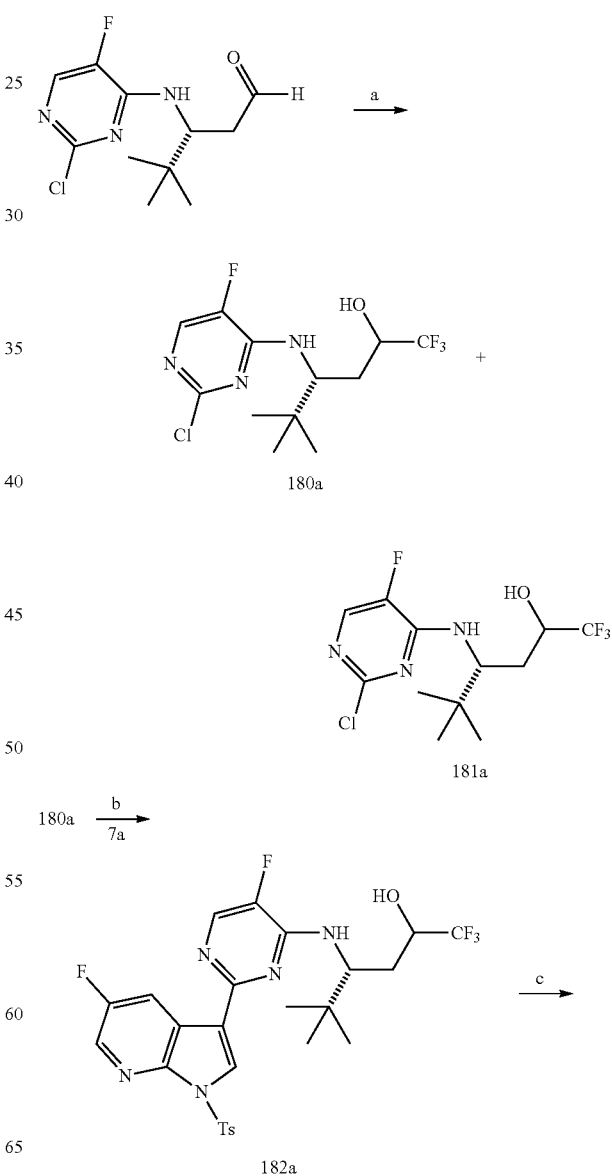

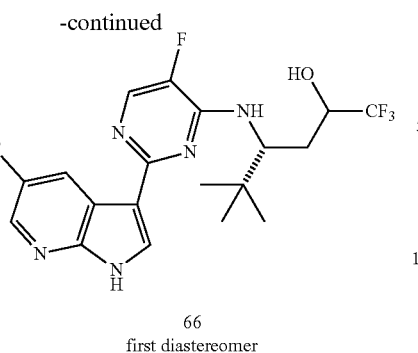

66
first diastereomer

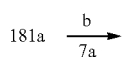

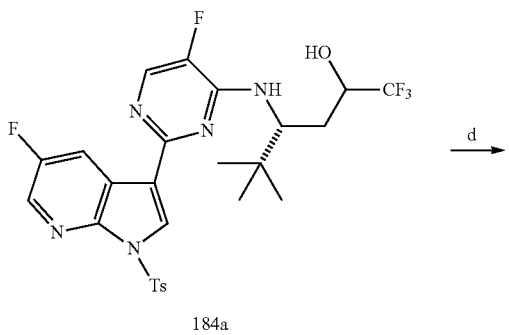

184a

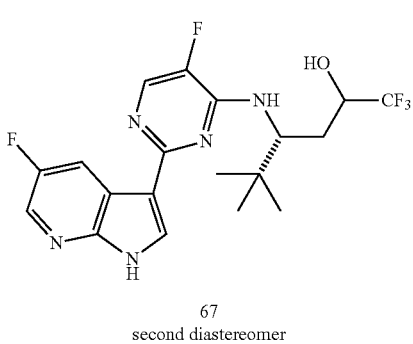

67
second diastereomer (a) i. TMS—CF₃, CsF, THF, ii. TFA, CH₂Cl₂; (b) 5-fluoro-1-(p-tolylsulfonyl)-3-(4,4,5,5-tetramethyl-1,3,2-dioxaborolan-2-yl)pyrrolo[2,3-b]pyridine, 7a, X-phos, Pd₂(dba)₃, K₃PO₄, 120° C.; (c) NaOMe, THF; (d) TBAF, THF.

Formation of (4R)-4-((2-chloro-5-fluoropyrimidin-4-yl)amino)-1,1,1-trifluoro-5,5-dimethylhexan-2-ol (180a) and (181a)

To a solution of (3R)-3-[(2-chloro-5-fluoro-pyrimidin-4-yl)amino]-4,4-dimethyl-pentanal (0.212 g, 0.817 mmol) and (trifluoromethyl)trimethylsilane (1.96 mL, 0.980 mmol) in THF (20 mL) was added cesium fluoride (0.001 g, 0.008 mmol). The reaction mixture was stirred at room temperature for 1 hour. The reaction mixture was diluted into brine and EtOAc. The organic phase was dried over MgSO₄, filtered and concentrated in vacuo. The crude residue was purified via silica gel chromatography (EtOAc/Hexanes) to afford 190 mg of the silylated alcohol. This intermediate was diluted with dichloromethane (10 mL) and trifluoroacetic acid (1 mL) was added to the mixture. The reaction mixture was stirred at room temperature for 30 minutes. The reaction mixture was concentrated in vacuo and the resulting residue was purified via silica gel chromatography (60% EtOAc/Hexanes) to afford 60 mg of diastereomer 180a and 100 mg of diastereomer 181a. Each diastereomer was taken on separately through the remaining synthetic sequence.

Diastereomer, 180a: ¹H NMR (400 MHz, CDCl₃) δ 7.93 (dd, J=43.4, 2.6 Hz, 1H), 5.10 (d, J=8.9 Hz, 1H), 4.13 (dd, J=15.8, 5.8 Hz, 1H), 3.94-3.71 (m, 1H), 2.05 (ddd, J=13.7, 9.2, 2.1 Hz, 1H), 1.64 (t, J=12.9 Hz, 1H), 1.05 (s, 9H); LCMS Gradient 10-90%, 0.1% formic acid, 5 minutes, C18/ACN, Retention Time=3.18 minutes (M+H) 330.42.

Diastereomer, 181a: ¹H NMR (400 MHz, CDCl₃) δ 7.79 (d, J=2.7 Hz, 1H), 5.30 (d, J=11.6 Hz, 1H), 4.22-4.07 (m, 2H), 2.19 (ddd, J=28.7, 15.3, 13.4 Hz, 1H), 1.74-1.59 (m, 1H), 1.04 (s, 9H). LCMS Gradient 10-90%, 0.1% formic acid, 5 minutes, C18/ACN, Retention Time=3.26 minutes (M+H) 330.42.

Formation of (4R)-1,1,1-trifluoro-4-((5-fluoro-2-(5-fluoro-1-tosyl-1H-pyrrolo[2,3-b]pyridin-3-yl)pyrimidin-4-yl)amino)-5,5-dimethylhexan-2-ol (182a)

A solution of 5-fluoro-1-(p-tolylsulfonyl)-3-(4,4,5,5-tetramethyl-1,3,2-dioxaborolan-2-yl)pyrrolo[2,3-b]pyridine (0.091 g, 0.218 mmol), 7a, (4R)-4-[(2-chloro-5-fluoro-pyrimidin-4-yl)amino]-1,1,1-trifluoro-5,5-dimethyl-hexan-2-ol, 180a, (0.060 g, 0.182 mmol) and K₃PO₄ (0.116 g, 0.546 mmol) in 2-methyl THF (5 mL) and H₂O (1.5 mL) was degassed under a stream of nitrogen for 45 minutes. To the reaction mixture was added X-phos (0.010 g, 0.022 mmol) and Pd₂(dba)₃ (0.004 g, 0.005 mmol). The reaction mixture was stirred at 120° C. in a pressure tube for 2 hours. The aqueous phase was removed. The organic phase was filtered through a pad of celite and concentrated in vacuo. The resulting residue was purified via silica gel chromatography (40% EtOAc/Hexanes) to afford 60 mg of the desired product: ¹H NMR (400 MHz, CDCl₃) δ 8.41 (s, 1H), 8.37 (dd, J=8.9, 2.8 Hz, 1H), 8.24 (t, J=8.7 Hz, 1H), 8.16 (d, J=2.9 Hz, 1H), 8.00 (d, J=8.4 Hz, 2H), 7.24 (d, J=8.1 Hz, 2H), 4.92 (t, J=7.8 Hz, 2H), 4.44 (t, J=10.3 Hz, 1H), 4.06 (s, 1H), 2.34 (s, 3H), 2.13 (dt, J=13.6, 4.9 Hz, 1H), 1.66 (dd, J=23.0, 9.3 Hz, 1H), 1.07 (d, J=8.4 Hz, 9H). LCMS Gradient 10-90%, 0.1% formic acid, 5 minutes, C18/ACN, Retention Time=4.02 min (M+H) 584.41.

The second diastereomeric alcohol, 181a, was also reacted in the same fashion to produce the diastereomeric Suzuki product. 184a: ¹H NMR (400 MHz, CDCl₃) δ 8.53 (s, 1H), 8.47 (dt, J=11.5, 5.7 Hz, 1H), 8.30 (d, J=1.9 Hz, 1H), 8.11-8.06 (m, 1H), 7.29-7.24 (m, 1H), 5.30-5.21 (m, 1H), 4.61 (d, J=4.1 Hz, 1H), 4.29-4.16 (m, 2H), 2.43-2.33 (m, 4H), 1.75-1.66 (m, 1H), 1.09 (d, J=10.8 Hz, 9H). LCMS Gradient 10-90%, 0.1% formic acid, 5 minutes, C18/ACN, Retention Time=4.02 minutes (M+H) 584.44.

Formation of (4R)-1,1,1-trifluoro-4-((5-fluoro-2-(5-fluoro-1H-pyrrolo[2,3-b]pyridin-3-yl)pyrimidin-4-yl)amino)-5,5-dimethylhexan-2-ol (66 and 67)

To a solution of (4R)-1,1,1-trifluoro-4-((5-fluoro-2-(5-fluoro-1-tosyl-1H-pyrrolo[2,3-b]pyridin-3-yl)pyrimidin-4-yl)amino)-5,5-dimethylhexan-2-ol, 182a, (0.053 g, 0.091 mmol) was added NaOMe (0.019 g of 25% solution in MeOH, 0.091 mmol). The reaction mixture was stirred at room temperature for 5 minutes. The reaction mixture was diluted into EtOAc and aqueous saturated $NaHCO_3$ solution. The organic phase was dried over $MgSO_4$, filtered and concentrated in vacuo. The crude residue was purified by silica gel chromatography (EtOAc/Hexanes) to afford 26 mg of the desired product, 66: $^1$H NMR (400 MHz, $CDCl_3$) δ 9.40 (s, 1H), 8.47 (dd, J=9.3, 2.7 Hz, 1H), 8.15 (s, 1H), 8.10 (d, J=2.7 Hz, 1H), 7.99 (d, J=2.8 Hz, 1H), 5.54 (s, 1H), 4.84 (d, J=7.5 Hz, 1H), 4.23 (t, J=9.9 Hz, 1H), 3.91 (s, 1H), 2.07-1.97 (m, 1H), 1.62 (t, J=13.0 Hz, 1H), 1.01 (s, 9H); LCMS Gradient 10-90%, 0.1% formic acid, 5 minutes, C18/ACN, Retention Time=2.42 minutes (M+H) 430.44.

The second diastereomeric product, 67, was made by removal of the tosyl-protecting group on intermediate, 184a, using the following procedure:

To a solution of (4R)-1,1,1-trifluoro-4-[[5-fluoro-2-[5-fluoro-1-(p-tolylsulfonyl)pyrrolo[2,3-b]pyridin-3-yl]pyrimidin-4-yl]amino]-5,5-dimethyl-hexan-2-ol, 184a, (0.060 g, 0.103 mmol) in THF (5 mL) was added tetrabutylammonium fluoride (0.411 mL of 1 M solution, 0.412 mmol) at room temperature. The reaction mixture was stirred at room temperature for 30 minutes. The reaction mixture was diluted into EtOAc and aqueous saturated $NaHCO_3$ solution. The organic phase was dried over $MgSO_4$, filtered and concentrated in vacuo. The residue was purified by silica gel chromatography (50% EtOAc/Hexanes) to afford 30 mg of desired product. $^1$H NMR (400 MHz, $CDCl_3$) δ 10.15 (s, 1H), 8.49 (dd, J=9.3, 2.6 Hz, 1H), 8.16 (s, 1H), 8.10 (d, J=2.6 Hz, 1H), 8.06 (d, J=3.0 Hz, 1H), 5.30 (d, J=15.0 Hz, 1H), 5.19-5.10 (m, 1H), 4.32-4.24 (m, 1H), 4.23-4.17 (m, 1H), 2.37 (dt, J=14.9, 3.4 Hz, 1H), 1.85-1.71 (m, 2H), 1.09 (s, 9H); LCMS Gradient 10-90%, 0.1% formic acid, 5 minutes, C18/ACN, Retention Time=2.37 minutes (M+H) 430.47.

The following two diastereomers can be prepared in a similar fashion as the procedure described above:

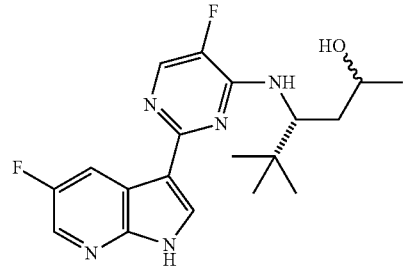

(4R)-4-((5-Fluoro-2-(5-fluoro-1H-pyrrolo[2,3-b]pyridin-3-yl)pyrimidin-4-yl)amino)-5,5-dimethyl-hexan-2-ol (72 and 73)

Diastereomer 72:

$^1$H NMR (400 MHz, $CDCl_3$) δ 9.99 (s, 1H), 8.60 (dd, J=9.4, 2.7 Hz, 1H), 8.26 (s, 1H), 8.20 (d, J=2.6 Hz, 1H), 8.10 (d, J=3.2 Hz, 1H), 5.06 (t, J=12.3 Hz, 1H), 4.28 (dd, J=9.6, 7.2 Hz, 1H), 3.96 (d, J=5.7 Hz, 1H), 2.71 (s, 1H), 1.97 (ddd, J=14.2, 5.8, 2.9 Hz, 1H), 1.66-1.58 (m, 1H), 1.28 (dd, J=6.5, 5.5 Hz, 4H), 1.04 (d, J=10.1 Hz, 9H); LCMS Gradient 10-90%, 0.1% formic acid, 5 minutes, C18/ACN, Retention Time=1.93 minutes (M+H) 376.46.

Diastereomer 73:

$^1$H NMR (400 MHz, $CDCl_3$) δ 10.81 (s, 1H), 8.47 (dd, J=9.3, 2.7 Hz, 1H), 8.14 (s, 1H), 8.05 (dd, J=8.4, 2.9 Hz, 2H), 4.95 (s, 1H), 4.81 (d, J=8.3 Hz, 1H), 4.31-4.14 (m, 1H), 3.72 (dd, J=8.9, 6.0 Hz, 1H), 1.83-1.70 (m, 1H), 1.48-1.32 (m, 1H), 1.24-1.11 (m, 4H), 0.98 (s, 9H); LCMS Gradient 10-90%, 0.1% formic acid, 5 minutes, C18/ACN, Retention Time=2.01 minutes (M+H) 376.46.

Preparation of Compounds 70 and 71

Synthetic Scheme 30

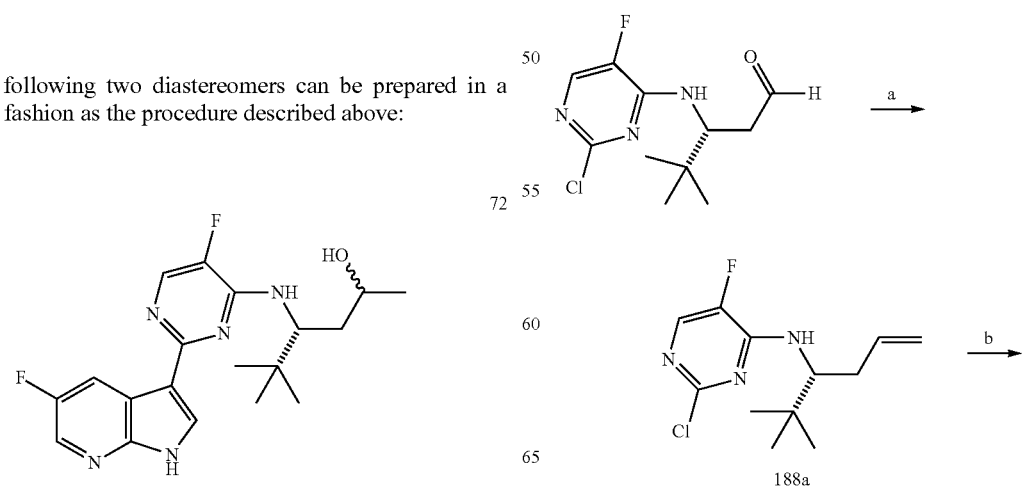

188a

137
-continued

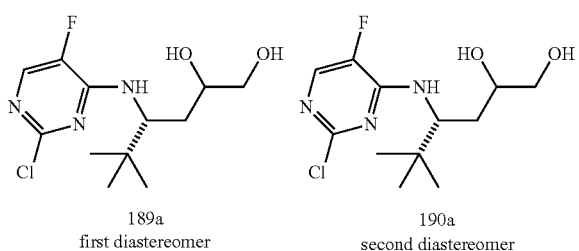

189a
first diastereomer 190a
second diastereomer

189a $\xrightarrow[7a]{c}$

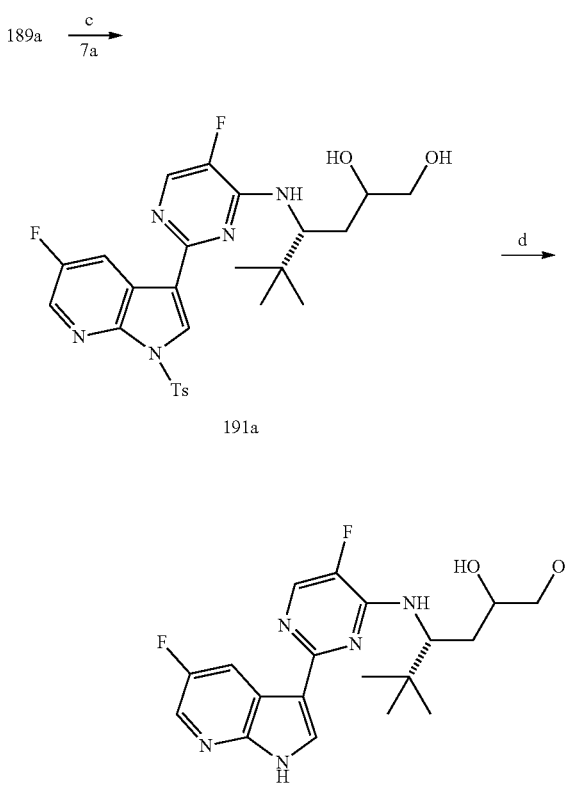

191a 70, 71

(a) Ph₃P—Br, LiHMDS, THF; (b) OsO₄, 4-methylmorpholine 4-oxide, THF, H₂O;
(c) X-phos, Pd₂(dba)₃, K₃PO₄, 2-methyl THF, H₂O; (d) MeONa, THF; (e) 5-fluoro-1-
(p-tolylsulfonyl)-3-(4,4,5,5-tetramethyl-1,3,2-dioxaborolan-2-yl)pyrrolo[2,3-b]
pyridine, 7a, X-phos, Pd₂(dba)₃, K₃PO₄, 2-methyl THF, H₂O, 120° C.; (f) MeONa, THF Formation of (R)-2-chloro-N-(2,2-dimethylhex-5-en-3-yl)-5-fluoropyrimidin-4-amine (188a)

To a solution of methyl(triphenyl)phosphonium bromide (0.983 g, 2.753 mmol) in THF (40 mL) was added LiHMDS (2.753 mL of 1 M solution, 2.753 mmol). The reaction mixture was stirred at room temperature for 1 hour. A solution of (3R)-3-[(2-chloro-5-fluoro-pyrimidin-4-yl)amino]-4,4-dimethyl-pentanal (0.550 g, 2.118 mmol) in THF (20 mL) was added to the reaction mixture resulting in significant precipitate formation. The reaction mixture was stirred at room temperature for 45 minutes. The reaction mixture was diluted into EtOAc and aqueous saturated NH₄Cl solution. The organic phase was separated, dried over MgSO₄, filtered and concentrated in vacuo. The resulting residue was purified by silica gel chromatography (EtOAc/Hexanes) to afford 180 mg of desired product: ¹H NMR (400 MHz, CDCl₃) δ 7.80 (d, J=2.8 Hz, 1H), 5.76-5.60 (m, 1H), 5.05-4.91 (m, 2H), 4.82 (t, J=22.1 Hz, 1H), 4.26-4.11 (m, 1H), 2.58-2.48 (m, 1H), 2.07-1.92 (m, 1H), 0.94 (s, 9H); LCMS Gradient 10-90%, 0.1% formic acid, 5 minutes, C18/ACN, Retention Time=3.60 minutes (M+H) 258.38.

Formation of (4R)-4-((2-chloro-5-fluoropyrimidin-4-yl)amino)-5,5-dimethylhexane-1,2-diol (189a) and (190a)

To a solution of (R)-2-chloro-N-(2,2-dimethylhex-5-en-3-yl)-5-fluoropyrimidin-4-amine, 188a, (0.140 g, 0.543 mmol) in THF (10 mL) and H₂O (10 mL) was added osmium tetraoxide (0.138 g, 0.014 mmol) and 4-methylmorpholine-4-oxide (0.085 mL, 0.815 mmol). The reaction mixture was stirred at room temperature for 2.5 hours. The mixture was diluted with aqueous saturated Na₂S₂O₃. The resulting mixture was stirred for 20 minutes and extracted with EtOAc. The organic phase was dried over MgSO₄, filtered and concentrated in vacuo. The resulting residue was purified by silica gel chromatography (MeOH/CH₂Cl₂) to afford 90 mg of the first diastereomer, 189a, and 65 mg of the second diastereomer, 190a.

Diastereomer 189a:
¹H NMR (400 MHz, CDCl₃) δ 7.86 (d, J=2.6 Hz, 1H), 5.00 (d, J=9.2 Hz, 1H), 4.17 (s, 1H), 4.08-3.96 (m, 1H), 3.49 (dd, J=19.2, 8.4 Hz, 3H), 2.15 (s, 1H), 1.74 (ddd, J=13.2, 10.8, 2.2 Hz, 1H), 1.27 (dd, J=19.3, 7.0 Hz, 1H), 0.92 (d, J=10.5 Hz, 9H); LCMS Gradient 10-90%, 0.1% formic acid, 5 minutes, C18/ACN, Retention Time=2.24 minutes (M+H) 292.36.

Diastereomer 190a:
¹H NMR (400 MHz, CDCl₃) δ 7.88 (d, J=2.7 Hz, 1H), 5.29 (d, J=8.9 Hz, 1H), 4.12-4.02 (m, 1H), 3.74 (d, J=9.0 Hz, 2H), 3.50 (s, 1H), 3.22 (s, 1H), 2.12 (s, 1H), 1.95 (dt, J=14.7, 4.2 Hz, 1H), 1.56 (ddd, J=14.8, 9.2, 7.4 Hz, 1H), 0.99 (s, 9H); LCMS Gradient 10-90%, 0.1% formic acid, 5 minutes, C18/ACN, Retention Time=2.24 minutes (M+H) 292.39.

Formation of (4R)-4-((5-fluoro-2-(5-fluoro-1-tosyl-1H-pyrrolo[2,3-b]pyridin-3-yl)pyrimidin-4-yl)amino)-5,5-dimethylhexane-1,2-diol (191a)

To a solution of (4R)-4-[(2-chloro-5-fluoro-pyrimidin-4-yl)amino]-5,5-dimethyl-hexane-1,2-diol, 189a, (0.090 g, 0.309 mmol), 5-fluoro-1-(p-tolylsulfonyl)-3-(4,4,5,5-tetramethyl-1,3,2-dioxaborolan-2-yl)pyrrolo[2,3-b]pyridine (0.167 g, 0.401 mmol) and K₃PO₄ (0.196 g, 0.926 mmol) in 2-Methyl THF (15 mL) and H₂O (2 mL) was degassed under a stream of nitrogen for 45 minutes. To the reaction mixture was added X-phos (0.018 g, 0.037 mmol) and Pd₂(dba)₃ (0.007 g, 0.008 mmol). The reaction mixture was stirred at 120° C. in a pressure tube for 2 hours. The aqueous phase was removed and the organic phase was filtered through a pad of celite and concentrated in vacuo. The resulting crude material was purified by silica gel chromatography (60% EtOAc/Hexanes) to afford 140 mg of the desired product, 191a: ¹H NMR (400 MHz, CDCl₃) δ 8.51 (dt, J=7.6, 3.8 Hz, 1H), 8.48 (s, 1H), 8.32 (d, J=1.7 Hz, 1H), 8.12 (dd, J=7.2, 5.7 Hz, 3H), 7.30

(d, J=8.1 Hz, 2H), 4.99 (d, J=10.1 Hz, 1H), 4.42-4.28 (m, 2H), 3.72-3.47 (m, 3H), 2.40 (s, 3H), 2.19-2.09 (m, 1H), 1.97-1.83 (m, 1H), 1.49-1.34 (m, 1H), 1.06 (s, 9H); LCMS Gradient 10-90%, 0.1% formic acid, 5 minutes, C18/ACN, Retention Time=3.53 minutes (M+H) 546.49.

The second diastereomeric 1,2-diol, 190a, was also reacted in the same fashion to produce the diastereomeric Suzuki product. 193a: $^1$H NMR (400 MHz, CDCl$_3$) δ 8.56-8.49 (m, 2H), 8.32 (dd, J=2.8, 1.1 Hz, 1H), 8.15-8.02 (m, 3H), 7.30 (d, J=9.2 Hz, 2H), 5.21-5.12 (m, 1H), 4.27 (td, J=9.7, 3.0 Hz, 1H), 3.93-3.74 (m, 2H), 3.55 (d, J=7.7 Hz, 1H), 3.11 (s, 1H), 2.39 (s, 3H), 2.01 (m, 1H), 1.65-1.50 (m, 1H), 1.05 (s, 9H). LCMS Gradient 10-90%, 0.1% formic acid, 5 minutes, C18/ACN, Retention Time=3.54 minutes (M+H) 546.49.

Formation of (4R)-4-((5-fluoro-2-(5-fluoro-1H-pyrrolo[2,3-b]pyridin-3-yl)pyrimidin-4-yl)amino)-5,5-dimethylhexane-1,2-diol (70, 71)

To a solution of (4R)-4-[[5-fluoro-2-[5-fluoro-1-(p-tolylsulfonyl)pyrrolo[2,3-b]pyridin-3-yl]pyrimidin-4-yl]amino]-5,5-dimethyl-hexane-1,2-diol, 191a, (0.140 g, 0.257 mmol) in THF (10 mL) was added sodium methoxide (0.055 g of 25% w/w solution, 0.257 mmol). The reaction mixture was stirred at room temperature for 5 minutes. The reaction mixture was diluted into EtOAc and aqueous saturated NaHCO$_3$ solution. The organic phase was dried over MgSO$_4$, filtered and concentrated in vacuo. The crude residue was purified via silica gel chromatography (MeOH/CH$_2$Cl$_2$) followed by preparative HPLC to afford 10 mg pure desired product: $^1$H NMR (400 MHz, d6-DMSO) δ 8.61 (dd, J=9.9, 2.6 Hz, 1H), 8.26 (s, 1H), 8.18 (s, 1H), 8.11 (d, J=4.1 Hz, 1H), 4.66 (d, J=10.4 Hz, 1H), 4.43 (s, 1H), 4.29 (d, J=4.1 Hz, 1H), 4.04 (s, 1H), 3.35 (s, 1H), 3.26 (d, J=6.1 Hz, 2H), 1.69 (t, J=12.3 Hz, 1H), 1.59-1.45 (m, 1H), 0.96 (s, 9H). LCMS Gradient 10-90%, 0.1% formic acid, 5 minutes, C18/ACN, Retention Time=1.76 minutes (M+H) 392.46.

The second diastereomeric 1,2-diol, 193a, was also reacted in the same fashion to produce the diastereomeric final product: $^1$H NMR (400 MHz, CDCl$_3$) δ 8.61 (dd, J=9.6, 2.7 Hz, 1H), 8.17 (s, 2H), 8.01 (d, J=4.1 Hz, 1H), 4.53 (d, J=10.0 Hz, 1H), 3.75-3.56 (m, 2H), 3.48 (dd, J=11.0, 6.3 Hz, 1H), 2.08-1.97 (m, 1H), 1.75 (dt, J=28.7, 9.4 Hz, 1H), 1.04 (s, 9H). LCMS Gradient 10-90%, 0.1% formic acid, 5 minutes, C18/ACN, Retention Time=1.79 minutes (M+H) 392.46.

Preparation of Compounds 75, 76, 79, 85, 93, and 95

Synthetic Scheme 31

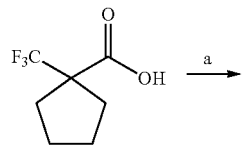

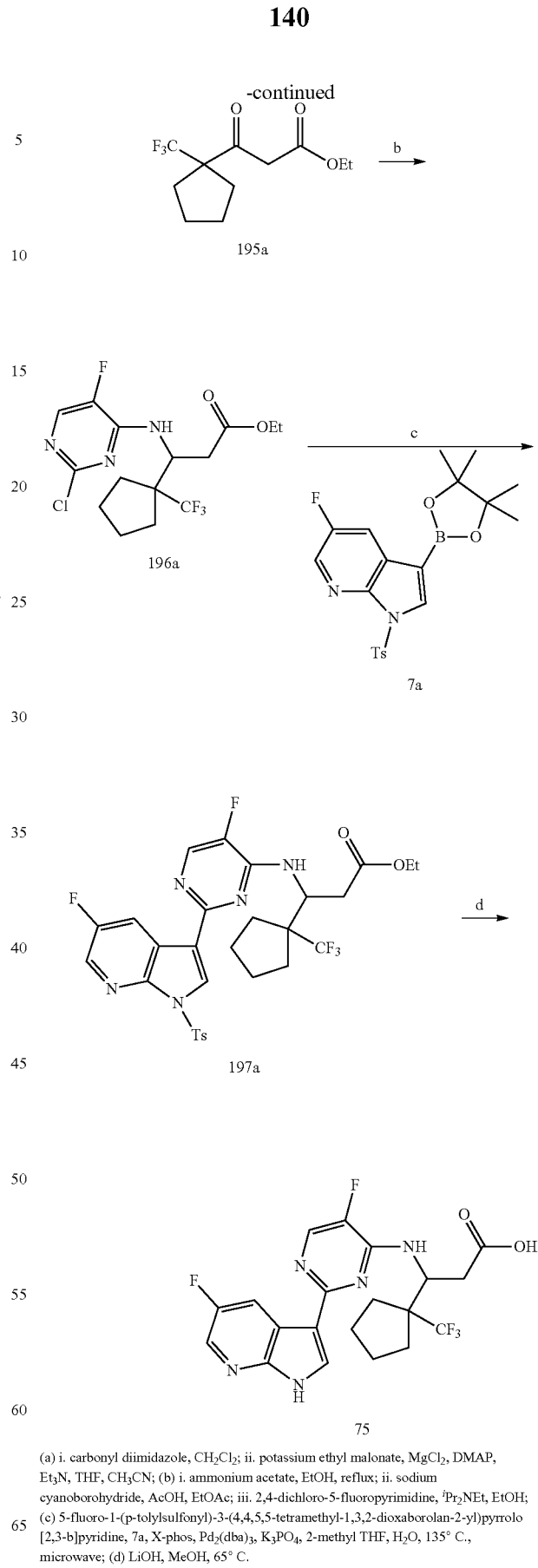

(a) i. carbonyl diimidazole, CH$_2$Cl$_2$; ii. potassium ethyl malonate, MgCl$_2$, DMAP, Et$_3$N, THF, CH$_3$CN; (b) i. ammonium acetate, EtOH, reflux; ii. sodium cyanoborohydride, AcOH, EtOAc; iii. 2,4-dichloro-5-fluoropyrimidine, $^i$Pr$_2$NEt, EtOH; (c) 5-fluoro-1-(p-tolylsulfonyl)-3-(4,4,5,5-tetramethyl-1,3,2-dioxaborolan-2-yl)pyrrolo[2,3-b]pyridine, 7a, X-phos, Pd$_2$(dba)$_3$, K$_3$PO$_4$, 2-methyl THF, H$_2$O, 135° C., microwave; (d) LiOH, MeOH, 65° C.

Formation of ethyl
3-oxo-3-(1-(trifluoromethyl)cyclopentyl)propanoate
(195a)

To a solution of 1-(trifluoromethyl)cyclopentanecarboxylic acid (1.30 g, 7.14 mmol) in dichloromethane (14 mL) was added carbonyl diimidazole (5.46 g, 33.68 mmol). After stirring 5 hours at room temperature, the reaction was concentrated in vacuo to a residue.

In another flask, 3-ethoxy-3-oxo-propanoate (Potassium Ion) (2.03 g, 11.90 mmol) was mixed with dichloromagnesium (1.13 g, 11.90 mmol) and DMAP (72.65 mg, 0.59 mmol) in THF (23.13 mL) and acetonitrile (11.57 mL). After 3 hours, the above crude solution in THF (10 mL) was added, followed by triethylamine (1.66 mL, 11.90 mmol). The reaction was allowed to stir at 25° C. for 8 hours. The crude product was isolated by extracting into ethyl acetate (2×100 mL) vs 1N HCl (100 mL), dried over sodium sulfate and concentrated in vacuo to afford 1.0 g of the desired product as a yellow oil: $^1$H NMR (300 MHz, CDCl$_3$) δ 12.58 (s, H), 5.32 (s, H), 4.27-4.18 (m, 2H), 2.33-2.14 (m, 2H), 2.05-1.85 (m, 4H), 1.77-1.69 (m, 2H) and 1.30 (td, J=7.1, 3.2 Hz, 3H) ppm.

Formation of (+/−)-ethyl 3-(2-chloro-5-fluoropyrimidin-4-ylamino)-3-(1-(trifluoromethyl)-cyclopentyl)propanoate (196a)

A solution of ethyl 3-oxo-3-(1-(trifluoromethyl)cyclopentyl)propanoate, 195a, (0.500 g, 1.982 mmol) and ammonium acetate (0.458 g, 5.946 mmol) in EtOH (20 mL) was warmed to reflux for 3 hours. The crude reaction was concentrated in vacuo to a residue and redissolved in EtOAc (20 mL). The new mixture was cooled to 0° C., and acetic acid (0.338 mL, 5.946 mmol) and sodium cyanoborohydride (0.498 g, 7.928 mmol, 4 equiv) were added to the mixture. The reaction was allowed to warm to room temperature and stirred overnight. The reaction was quenched with aqueous saturated sodium bicarbonate solution (10 mL) and extracted with ethyl acetate (2×20 mL). The organic phase was concentrated in vacuo and redissolved in EtOH (20 mL). To the solution was added 2,4-dichloro-5-fluoro-pyrimidine (0.496 g, 2.973 mmol) and N,N-diisopropylethylamine base (2.0 mL). The reaction was refluxed for 12 hours and then concentrated in vacuo. The residue was purified by silica gel chromatography (EtOAc) yielding 84 mg of the desired product as a yellow oil: LCMS Gradient 10-90%, 0.1% formic acid, 5 minutes, C18/ACN, Retention Time=3.54 minutes (M+H) 384.40.

Formation of (+/−)-ethyl 3-(5-fluoro-2-(5-fluoro-1-tosyl-1H-pyrrolo[2,3-b]pyridin-3-yl)pyrimidin-4-ylamino)-3-(1-(trifluoromethyl)cyclopentyl)propanoate (197a)

To a solution of racemic ethyl 3-(2-chloro-5-fluoropyrimidin-4-ylamino)-3-(1-(trifluoromethyl)cyclopentyl)propanoate, 196a, (0.084 g, 0.219 mmol) in THF (10 mL) and water (1 mL) was added 5-fluoro-1-(p-tolylsulfonyl)-3-(4,4,5,5-tetramethyl-1,3,2-dioxaborolan-2-yl)pyrrolo[2,3-b]pyridine, 7a, (0.137 g, 0.328 mmol) and potassium phosphate (0.140 g, 0.657 mmol). The resulting mixture was degassed under a stream of nitrogen for 10 minutes. To the reaction was then added X-Phos (0.010 g, 0.021 mmol) and Pd$_2$(dba)$_3$ (0.010 g, 0.011 mmol). The reaction was irradiated for 15 minutes at 135° C. in a microwave. The resulting mixture was concentrated in vacuo to a brown oil which was purified by silica gel chromatography (EtOAc/CH$_2$Cl$_2$) to afford 80 mg of the desired product as a pale yellow solid: LCMS Gradient 10-90%, 0.1% formic acid, 5 minutes, C18/ACN, Retention Time=4.22 minutes (M+H) 638.42.

Formation of (+/−)-3-(5-fluoro-2-(5-fluoro-1H-pyrrolo[2,3-b]pyridin-3-yl)pyrimidin-4-ylamino)-3-(1-(trifluoromethyl)cyclopentyl)propanoic acid (75)

To a solution of racemic ethyl 3-(5-fluoro-2-(5-fluoro-1-tosyl-1H-pyrrolo[2,3-b]pyridin-3-yl)pyrimidin-4-ylamino)-3-(1-(trifluoromethyl)cyclopentyl)propanoate, 197a, (0.080 g, 0.120 mmol) in THF (10 mL) was added lithium hydroxide (2 mL of 2N solution). The reaction was refluxed for 3 hours and cooled to room temperature. The non aqueous solvent was removed under reduced pressure and the aqueous layer was adjusted to pH 4. The aqueous layer was extracted with ethyl acetate (2×20 mL). The combined organic phases concentrated in vacuo to afford 16 mg of the desired product as a pale yellow solid: $^1$H NMR (300 MHz, d6-DMSO) δ 8.51 (s, H), 8.25-7.97 (m, 2H), 7.58-7.42 (m, 2H), 7.12 (d, J=7.5 Hz, H), 4.35 (m, H), 2.85 (m, 2H) and 1.27-0.70 (m, 8H) ppm; LCMS Gradient 10-90%, 0.1% formic acid, 5 minutes, C18/ACN, Retention Time=2.55 minutes (M+H) 456.45.

The following analogs can be prepared in a similar fashion as the procedure described above Compound 75:

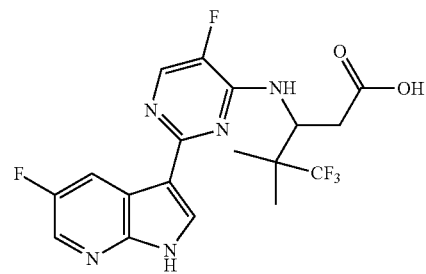

(+/−)-5,5,5-Trifluoro-3-(5-fluoro-2-(5-fluoro-1H-pyrrolo[2,3-b]pyridin-3-yl)pyrimidin-4-ylamino)-4,4-dimethylpentanoic acid (79)

$^1$H NMR (300 MHz, MeOD) δ 8.66 (d, J=8.9 Hz, H), 8.29 (s, H), 8.22-8.18 (m, 2H), 4.16-4.06 (m, H), 2.97 (s, H), 2.92 (s, H), and 1.27-1.21 (m, 6H) ppm; LCMS Gradient 10-90%, 0.1% formic acid, 5 minutes, C18/ACN, Retention Time=2.22 minutes (M+H) 430.41.

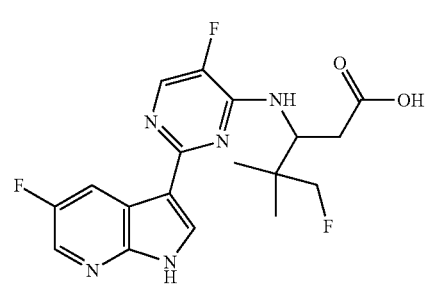

(+/−)-5-Fluoro-3-((5-fluoro-2-(5-fluoro-1H-pyrrolo[2,3-b]pyridin-3-yl)pyrimidin-4-yl)amino)-4,4-dimethylpentanoic acid (76)

$^1$H NMR (300 MHz, MeOD) δ 8.70 (dd, J=9.7, 2.8 Hz, 1H), 8.15 (dd, J=6.1, 4.0 Hz, 2H), 8.02 (d, J=4.1 Hz, 1H), 5.23

(dd, J=10.7, 3.1 Hz, 1H), 4.30 (d, J=47.9 Hz, 2H), 3.63 (d, J=18.2 Hz, 1H), 3.31 (dt, J=3.3, 1.6 Hz, 3H), 2.83 (dd, J=15.3, 3.3 Hz, 1H), 2.63 (dd, J=15.3, 10.8 Hz, 1H), 1.07 (s, 6H); LCMS Gradient 10-90%, 0.1% formic acid, 5 minutes, C18/ACN, (M+H) 394.

1H), 5.42 (dd, J=10.0, 3.4 Hz, 1H), 2.84 (m, 2H), 2.18 (s, 1H), 1.65 (m, 4H), 1.39 (m, 6H); LCMS Gradient 10-90%, 0.1% formic acid, 5 minutes, C18/ACN, Retention Time=2.12 minutes (M+H) 414.28.

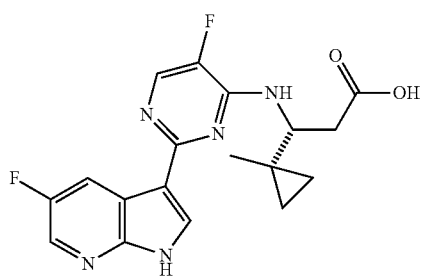

(R)-3-((5-fluoro-2-(5-fluoro-1H-pyrrolo[2,3-b]pyridin-3-yl)pyrimidin-4-yl)amino)-3-(1-methylcyclopropyl)propanoic acid (91)

LCMS Gradient 10-90%, 0.1% formic acid, 5 minutes, C18/ACN, (M+H) 374.

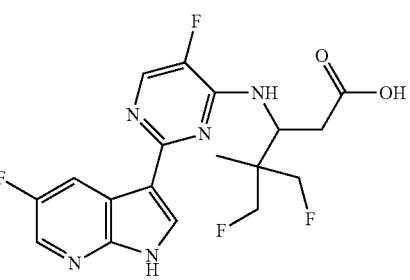

(+/−)-5-Fluoro-3-((5-fluoro-2-(5-fluoro-1H-pyrrolo[2,3-b]pyridin-3-yl)pyrimidin-4-yl)amino)-4-(fluoromethyl)-4-methylpentanoic acid (84)

$^1$H NMR (300 MHz, MeOD) δ 8.67 (dd, J=9.6, 2.8 Hz, 1H), 8.16 (m, 2H), 8.04 (d, J=4.0 Hz, 1H), 5.38 (dd, J=10.8, 3.2 Hz, 1H), 4.72-4.23 (m, 4H), 2.86 (dd, J=15.5, 3.3 Hz, 1H), 2.70 (dd, J=15.5, 10.9 Hz, 1H), 1.15 (s, 3H); LCMS Gradient 10-90%, 0.1% formic acid, 5 minutes, C18/ACN, (M+H) 412.

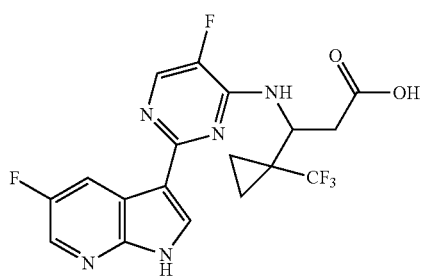

(+/−)-3-((5-fluoro-2-(5-fluoro-1H-pyrrolo[2,3-b]pyridin-3-yl)pyrimidin-4-yl)amino)-3-(1-(trifluoromethyl)cyclopropyl)propanoic acid (93)

LCMS Gradient 10-90%, 0.1% formic acid, 5 minutes, C18/ACN, Retention Time=2.37 minutes (M+H) 428.49.

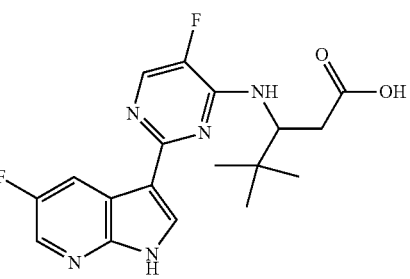

(+/−)-3-((5-chloro-2-(5-fluoro-1H-pyrrolo[2,3-b]pyridin-3-yl)pyrimidin-4-yl)amino)-4,4-dimethylpentanoic acid (85)

Carboxylic acid, 203, was prepared in same fashion as carboxylic acid, 4, (see Synthetic Scheme 1) using 5-chloro-3-(5-chloro-4-(methylsulfinyl)pyrimidin-2-yl)-1-tosyl-1H-pyrrolo[2,3-b]pyridine instead of sulfoxide, 1: $^1$H NMR (400 MHz, MeOD) δ 8.68 (dd, J=9.3, 2.7 Hz, 1H), 8.47 (s, 1H), 8.38 (s, 1H), 8.32 (s, 1H), 5.17 (dd, J=9.8, 3.5 Hz, 1H), 2.87

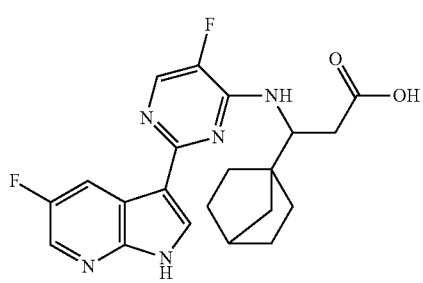

(+/−)-3-(Bicyclo[2.2.1]heptan-1-yl)-3-(5-fluoro-2-(5-fluoro-1H-pyrrolo[2,3-b]pyridin-3-yl)pyrimidin-4-ylamino)propanoic acid (95)

$^1$H NMR (400 MHz, CD$_3$OD) δ 8.62 (dd, J=9.3, 2.6 Hz, 1H), 8.48 (t, J=5.4 Hz, 1H), 8.32 (s, 1H), 8.29 (d, J=5.5 Hz, (m, 2H), 1.06 (s, 9H); LCMS Gradient 10-90%, 0.1% formic acid, 5 minutes, C18/ACN, Retention Time=2.1 minutes (M+H) 383.38.

Preparation of Compounds 77, 78, 83, 86, and 94

Synthetic Scheme 32

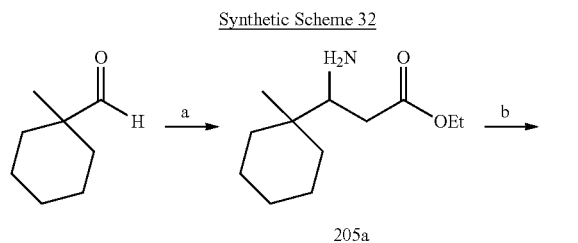

205a

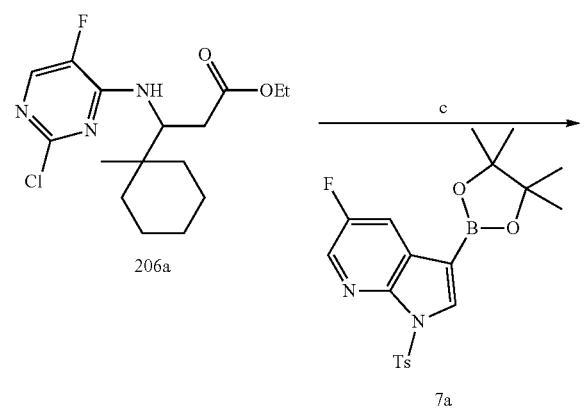

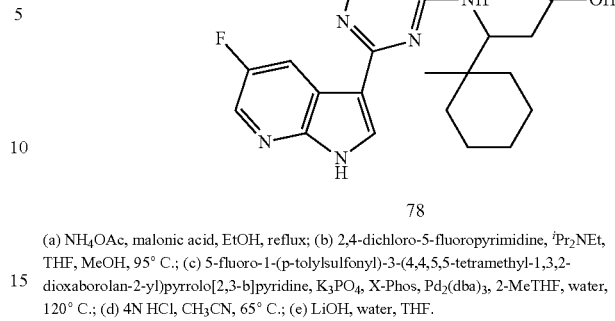

78

(a) NH₄OAc, malonic acid, EtOH, reflux; (b) 2,4-dichloro-5-fluoropyrimidine, ⁱPr₂NEt, THF, MeOH, 95° C.; (c) 5-fluoro-1-(p-tolylsulfonyl)-3-(4,4,5,5-tetramethyl-1,3,2-dioxaborolan-2-yl)pyrrolo[2,3-b]pyridine, K₃PO₄, X-Phos, Pd₂(dba)₃, 2-MeTHF, water, 120° C.; (d) 4N HCl, CH₃CN, 65° C.; (e) LiOH, water, THF.

Formation of (+/−)-ethyl-3-amino-3-(1-methylcyclohexyl)propanoate (205a)

A solution of 1-methylcyclohexanecarbaldehyde (2.75 g, 21.79 mmol), malonic acid (2.27 g, 21.79 mmol) and ammonium acetate (3.36 g, 43.58 mmol) in absolute ethanol (5 mL) was heated at reflux for 4 hours. The solid was filtered and washed with ethanol (10 mL). The filtrate was concentrated in vacuo to give a thick oil that was diluted with CH₂Cl₂ (50 mL). The precipitated solid was filtered and the filtrate was concentrated in vacuo to afford 4.3 grams of a yellow oil. Concentrated sulfuric acid (1.16 mL, 21.79 mmol) was added to a solution of the crude material in absolute ethanol (25 mL) and the mixture was refluxed for 12 hours. The solution was cooled to room temperature and concentrated in vacuo to give a thick oil. Water (10 mL) was added and the solution was neutralized with 2N NaOH. The aqueous layer was extracted with EtOAc (3×25 mL), dried (MgSO₄), filtered and concentrated in vacuo to afford 2.4 grams of desired product: LCMS Gradient 10-90%, 0.1% formic acid, 5 minutes, C18/ACN, Retention Time=1.54 minutes (M+H) 214.14.

Formation of (+/−)-ethyl 3-(2-chloro-5-fluoropyrimidin-4-ylamino)-3-(1-methylcyclohexyl)propanoate (206a)

A mixture of 2,4-dichloro-5-fluoro-pyrimidine (1.83 g, 85.33 mmol), racemic ethyl-3-amino-3-(1-methylcyclohexyl)propanoate, 205a, (2.34 g, 11.0 mmol) and N,N-diisopropylethylamine (4.79 g, 27.50 mmol) in THF (40 mL) and methanol (10 mL) was heated at 95° C. for 3 hours. The solution was cooled to room temperature and the solvent was evaporated under reduced pressure. The crude residue was purified by silica gel chromatography (0-60% EtOAc/Hexanes gradient) to afford 620 mg of the desired product as a white foamy solid: ¹H NMR (400 MHz, CDCl₃) δ 7.80 (d, J=2.6 Hz, 1H), 5.37 (m, 1H), 4.59 (m, 1H), 4.00 (q, 7.2 Hz, 2H), 2.62 (dd, J=14.7, 3.8 Hz, 1H), 1.67 (m, 1H), 1.17 (m, 10H), 1.10 (t, J=7.1 Hz, 3H), 0.85 (s, 3H); LCMS Gradient 10-90%, 0.1% formic acid, 5 minutes, C18/ACN, Retention Time=3.69 minutes (M+H) 344.39.

Formation of (+/−)-ethyl 3-(5-fluoro-2-(5-fluoro-1-tosyl-1H-pyrrolo[2,3-b]pyridin-3-yl)pyrimidin-4ylamino)-3-(1-methylcyclohexyl)propanoate (207a)

A solution of 5-fluoro-1-(p-tolylsulfonyl)-3-(4,4,5,5-tetramethyl-1,3,2-dioxaborolan-2-yl)pyrrolo[2,3-b]pyridine, 7a, (0.51 g, 1.22 mmol), racemic ethyl 3-(2-chloro-5-fluoropyrimidin-4-ylamino)-3-(1-methylcyclohexyl)propanoate, 206a, (0.35 g, 1.02 mmol) and K₃PO₄ (0.52 g, 2.44 mmol) in 2-methyl THF (8 mL) and water (2 mL) was degassed under a stream of nitrogen for 30 minutes. X-Phos (0.03 g, 0.07 mmol) and Pd₂(dba)₃ (0.02 g, 0.02 mmol) were added and the resulting mixture was heated at 115° C. in a pressure vial for 4 hours. The reaction mixture was cooled to room temperature, filtered and concentrated in vacuo. The residue was dissolved in EtOAc (50 mL) and washed with water. The organic layer was dried (MgSO₄), filtered and concentrated in vacuo. The crude residue was purified via silica gel chromatography (0-35% EtOAc/Hexanes gradient) to afford 486 mg of the desired product as a white solid: $^1$H NMR (400 MHz, CDCl₃) δ 8.50 (m, 1H), 8.48 (s, 1H), 8.24 (d, J=1.7 Hz, 1H), 8.01 (m, 3H), 7.20 (m, 2H), 5.12 (m, 1H), 4.88 (m, 1H), 3.89 (q, J=7.4 Hz, 2H), 2.71 (dd, J=14.5, 3.8 Hz, 1H), 2.39 ? 2.32 (m, 1H), 2.31 (s, 3H), 1.60-1.32 (m 10H), 0.95 (t, J=7.4 3H). 0.87 (s, 3H); LCMS Gradient 60-98%, 0.1% formic acid, 7 minutes, C18/ACN, Retention Time=2.81 minutes (M+H) 599.19.

Formation of (+/−)-ethyl 3-(5-fluoro-2-(5-fluoro-1H-pyrrolo[2,3-b]pyridin-3-yl)pyrimidin-4-ylamino)-3-(1-methylcyclohexyl)propanoate (77)

To a solution of ethyl 3-(5-fluoro-2-(5-fluoro-1-tosyl-1H-pyrrolo[2,3-b]pyridin-3-yl)pyrimidin-4ylamino)-3-(1-methylcyclohexyl)propanoate, 207a, (0.49 mg, 0.81 mmol) in CH₃CN (3 mL) was added HCl (2.0 mL of 4M solution in dioxane, 8.1 mmol). The solution was heated at 70° C. for 3 hours and then cooled to room temperature. The solvent was removed under reduced pressure and the product was neutralized with aqueous saturated NaHCO₃ solution. The precipitate was extracted with EtOAc (3×10 mL). The solvent was dried (MgSO₄), filtered and concentrated in vacuo. The crude residue was purified by silica gel chromatography (0-70% EtOAc/Hexanes gradient) to afford 230 mg of the desired product as an off-white solid: $^1$H NMR (400 MHz, CDCl₃) δ 9.55 (s, 1H), 8.58 (dd, J=9.3, 2.5 Hz, 1H), 8.18 (s, 2H), 8.00 (d, J=2.7 Hz, 1H), 5.13 (brs, 1H), 4.95 (t, J=8.2 Hz, 1H), 3.84 (m, 2H), 2.72 (m, 1H), 2.38 (m, 1H), 1.67-1.15 (m, 10H), 0.94 (m, 3H); LCMS Gradient 10-90%, 0.1% formic acid, 5 minutes, C18/ACN, Retention Time=2.77 minutes (M+H) 444.36.

3-(5-fluoro-2-(5-fluoro-1H-pyrrolo[2,3-b]pyridin-3-yl)pyrimidin-4-ylamino)-3-(1-methylcyclohexyl)propanoic acid (78)

LiOH (0.118 mg, 4.927 mmol) was added to a solution of ethyl 3-(5-fluoro-2-(5-fluoro-1H-pyrrolo[2,3-b]pyridin-3-yl)pyrimidin-4-ylamino)-3-(1-methylcyclohexyl)-propanoate, 77, (0.23 g, 0.49 mmol) in water (5 mL) and THF (5 mL). The solution was stirred at 95° C. for 18 hours and then cooled to room temperature. The solvent was removed under reduced pressure. The residue was diluted with water (10 mL) and neutralized with 2N HCl. The resulting precipitate was extracted with EtOAc (3×10 mL). The organic phase was dried (MgSO₄), filtered and concentrated in vacuo to afford 210 mg of the desired product as an off-white solid: $^1$H NMR (400 MHz, CD₃OD) δ 8.78 (dd, J=9.7, 2.7 Hz, 1H), 8.16 (s, 2H), 7.99 (d, J=4.1 Hz, 1H), 5.20 (d, J=9.9 Hz, 1H), 2.86-2.69 (m, 1H), 2.53 (dd, J=14.7, 11.0 Hz, 1H), 1.76-1.56 (m, 4H), 1.29 (m, 4H), 1.02 (s, 3H); LCMS Gradient 10-90%, 0.1% formic acid, 5 minutes, C18/ACN, Retention Time=2.20 minutes (M+H) 416.27.

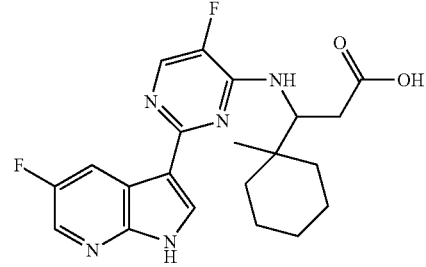

(+/−)-3-(2-(5-Chloro-1H-pyrrolo[2,3-b]pyridin-3-yl)-5-fluoropyrimidin-4-ylamino)-3-(1-methylcyclohexyl)propanoic acid (83)

Compound 83 was synthesized in a manner similar to 3-(5-fluoro-2-(5-fluoro-1H-pyrrolo[2,3-b]pyridin-3-yl)pyrimidin-4-ylamino)-3-(1-methylcyclohexyl)propanoic acid, 78, using 5-chloro-1-(p-tolylsulfonyl)-3-(4,4,5,5-tetramethyl-1,3,2-dioxaborolan-2-yl)pyrrolo[2,3-b]pyridine instead of boronate ester, 7a: $^1$H NMR (400 MHz, MeOD) δ 9.05 (d, J=2.1 Hz, 1H), 8.39-8.24 (m, 2H), 8.16 (d, J=4.9 Hz, 1H), 5.23 (d, J=10.4 Hz, 1H), 2.86 (d, J=15.6 Hz, 1H), 2.65 (m, 1H), 1.58 (m, 7H), 1.37 (m, 3H), 1.05 (s, 3H); LCMS Gradient 10-90%, 0.1% formic acid, 5 minutes, C18/ACN, Retention Time=2.37 minutes (M+H) 442.36.

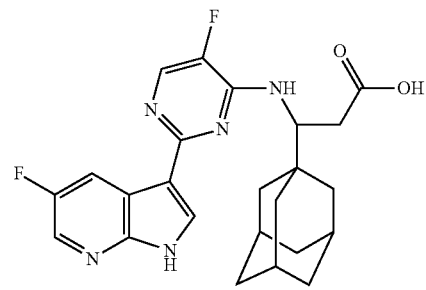

(+/−)-3-(1-Adamantyl)-3-[[5-fluoro-2-(5-fluoro-1H-pyrrolo[2,3-b]pyridin-3-yl)pyrimidin-4-yl]amino] propionic acid (86)

Compound 86 was synthesized in a manner similar to 3-(5-fluoro-2-(5-fluoro-1H-pyrrolo[2,3-b]pyridin-3-yl)pyrimidin-4-ylamino)-3-(1-methylcyclohexyl)propanoic acid, 78, using adamantine-1-carbaldehyde as the starting material: $^1$H NMR (400 MHz, CD₃OD) δ 8.75 (dd, J=9.7, 2.7 Hz, 1H), 8.18 (s, 2H), 8.00 (d, J=4.2 Hz, 1H), 2.81 (dd, J=15.2, 3.1 Hz, 1H), 2.55 (dd, J=15.2, 10.8 Hz, 1H), 2.00 (m, 3H), 1.82-1.49 (m, 12H); LCMS Gradient 10-90%, 0.1% formic acid, 5 minutes, C18/ACN, Retention Time=2.40 minutes (M+H) 454.34.

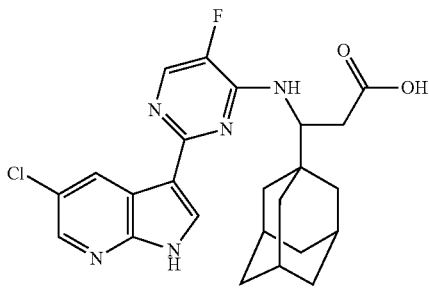

(+/−)-3-(1-Adamantyl)-3-[[2-(5-chloro-1H-pyrrolo[2,3-b]pyridin-3-yl)-5-fluoro-pyrimidin-4-yl]amino]propanoic acid (94)

Compound 94 was synthesized in a manner similar to 3-(1-Adamantyl)-3-[[5-fluoro-2-(5-fluoro-1H-pyrrolo[2,3-b]pyridin-3-yl)pyrimidin-4-yl]amino]propionic acid, 86, using 5-chloro-1-(p-tolylsulfonyl)-3-(4,4,5,5-tetramethyl-1,3,2-dioxaborolan-2-yl)pyrrolo[2,3-b]pyridine instead of boronate ester, 7a: $^1$H NMR (400 MHz, CD$_3$OD) δ 9.02 (d, J=2.3 Hz, 1H), 8.40-8.24 (m, 2H), 8.18 (d, J=5.0 Hz, 1H), 4.91 (d, J=11.6 Hz, 1H), 2.88 (dd, J=16.0, 2.8 Hz, 1H), 2.65 (dd, J=15.9, 11.0 Hz, 1H), 2.01 (s, 3H), 1.77 (dd, J=27.9, 11.9 Hz, 12H); LCMS Gradient 10-90%, 0.1% formic acid, 5 minutes, C18/ACN, Retention Time=2.60 minutes (M+H) 470.27.

Preparation of Compound 68

Synthetic Scheme 33

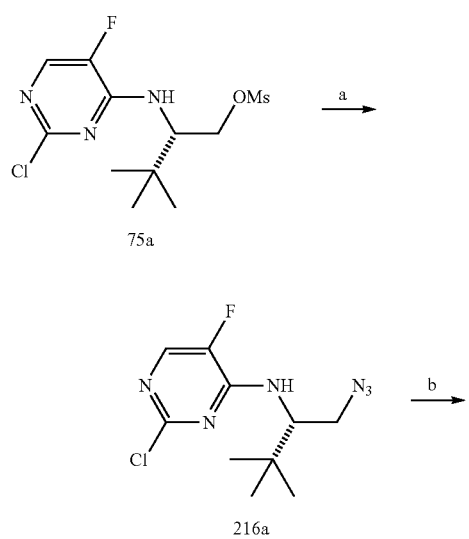

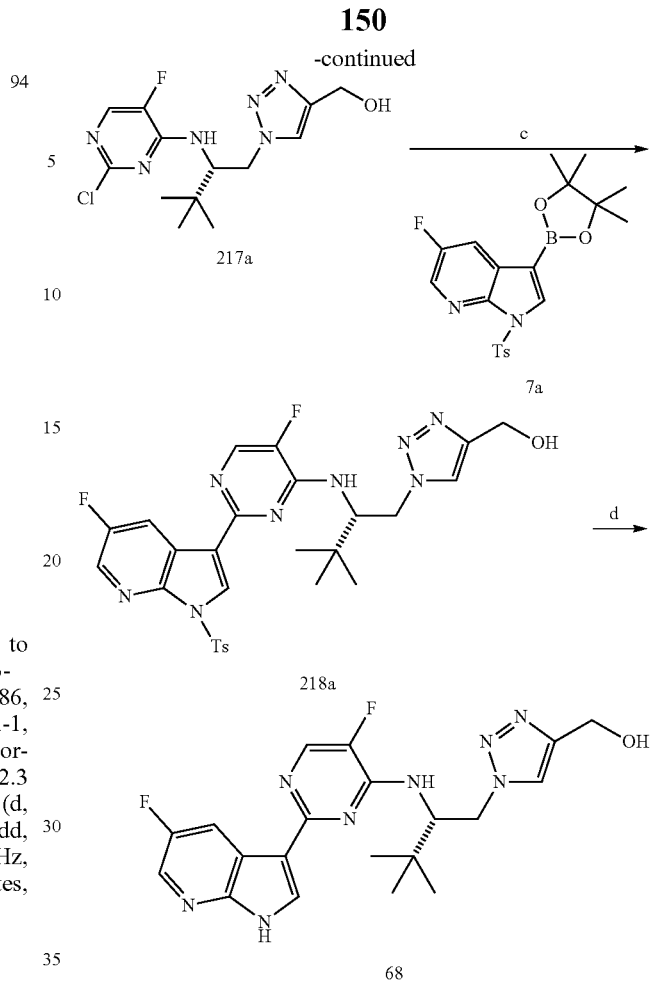

(a) NaN$_3$, DMF, 70° C.; (b) propargyl alcohol, THF, toluene, 120° C.; (c) 5-fluoro-1-(p-tolylsulfonyl)-3-(4,4,5,5-tetramethyl-1,3,2-dioxaborolan-2-yl)pyrrolo[2,3-b]pyridine, K$_3$PO$_4$, X-Phos, Pd$_2$(dba)$_3$, 2-MeTHF, water, 120° C.; (d) 4N HCl, CH$_3$CN, 65° C.

Formation of (S)—N-(1-azido-3,3-dimethylbutan-2-yl)-2-chloro-5-fluoropyrimidin-4-amine (216a)

A mixture of (S)-2-((2-chloro-5-fluoropyrimidin-4-yl)amino)-3,3-dimethylbutyl methanesulfonate, 75a, (2.37 g, 7.26 mmol) and sodium azide (1.89 g, 29.07 mmol) in DMF (50 mL) was heated at 70° C. for 6 hours. The reaction mixture was cooled to room temperature and poured into water. The aqueous phase was extracted with EtOAc (2×25 mL), dried (MgSO$_4$), filtered and concentrated in vacuo. The crude product was purified via silica gel chromatography (0-20% EtOAc/Hexanes gradient) to afford 1.2 g of the desired product as a white crystalline solid: $^1$H NMR (400 MHz, CDCl$_3$) δ 7.86 (dd, J=2.6, 1.1 Hz, 1H), 5.07 (m, 1H), 4.32-4.09 (m, 1H), 3.60 (dd, J=12.8, 3.9 Hz, 1H), 3.34 (dd, J=12.8, 7.6 Hz, 1H), 0.96 (m, 9H); LCMS Gradient 10-90%, 0.1% formic acid, 5 minutes, C18/ACN, Retention Time=3.28 minutes (M+H) 273.14.

Formation of (S)-(1-(2-((2-chloro-5-fluoropyrimidin-4-yl)amino)-3,3-dimethylbutyl)-1H-1,2,3-triazol-4-yl)methanol (217a)

A mixture of prop-2-yn-1-ol (0.22 g, 3.85 mmol) and (S)—N-(1-azido-3,3-dimethylbutan-2-yl)-2-chloro-5-fluoropyrimidin-4-amine, 216a, (0.21 g, 0.77 mmol) in THF (4 mL) and toluene (4 mL) was heated in a pressure vial at 120° C. for 8 hours. The reaction mixture was cooled to room temperature and concentrated under reduced pressure. The crude product which contained two regioisomers was purified by silica gel chromatography (0-5% MeOH/CH$_2$Cl$_2$ gradient) to afford 100 mg of desired regioisomer, 217a, as well as 70 mg of the minor regioisomer (5-hydroxymethyl triazole).

4-Hydroxymethyl triazole regioisomer 217a: $^1$H NMR (400 MHz, CDCl$_3$) δ 7.71 (d, J=2.6 Hz, 1H), 7.19 (s, 1H), 5.31-5.16 (m, 1H), 4.86 (m, 1H), 4.79-4.60 (m, 2H), 4.44 (m, 1H), 1.07 (s, 9H); LCMS Gradient 10-90%, 0.1% formic acid, 5 minutes, C18/ACN, Retention Time=2.26 minutes (M+H) 329.31.

Formation of (S)-(1-(2-((5-fluoro-2-(5-fluoro-1-to-syl-1H-pyrrolo[2,3-b]pyridin-3-yl)pyrimidin-4-yl) amino)-3,3-dimethylbutyl)-1H-1,2,3-triazol-4-yl) methanol (218a)

A solution of 5-fluoro-1-(p-tolylsulfonyl)-3-(4,4,5,5-tetramethyl-1,3,2-dioxaborolan-2-yl)pyrrolo[2,3-b]pyridine, 7a, (0.158 g, 0.380 mmol), (S)-(1-(2-((2-chloro-5-fluoropyrimidin-4-yl)amino)-3,3-dimethylbutyl)-1H-1,2,3-triazol-4-yl)methanol, 217a, (0.100 g, 0.304 mmol) and K$_3$PO$_4$ (0.520 g, 2.440 mmol) in 2-methyl THF (8 mL) and water (2 mL) was degassed under a stream of nitrogen for 30 minutes. X-Phos (0.008 g, 0.018 mmol) and Pd$_2$(dba)$_3$ (0.006 g, 0.006 mmol) were added and the reaction mixture was heated at 115° C. in a pressure vial for 4 hours. The reaction mixture was cooled to room temperature and filtered. The filtrate was concentrated in vacuo. The residue was dissolved in EtOAc (50 mL) and washed with water. The organic layer was dried (MgSO$_4$), filtered concentrated in vacuo. The crude residue was purified via silica gel chromatography (0-70% EtOAc/Hexanes gradient) to afford 120 mg of the desired product as a white foamy solid: $^1$H NMR (400 MHz, CDCl$_3$) δ 8.37 (s, 1H), 8.33 (s, 1H), 8.21 (s, 1H), 8.03 (d, J=8.4 Hz, 2H), 7.90 (d, J=3.0 Hz, 1H), 5.37 (m, 1H), 4.92 ? 4.83 (m, 1H), 4.78-4.69 (m, 2H), 4.44 (dd, J=13.9, 11.3 Hz, 1H), 2.32 (s, 3H), 1.11 (s, 9H); LCMS Gradient 60-98%, 0.1% formic acid, 7 minutes, C18/ACN, Retention Time=1.29 minutes (M+H) 583.33

Formation of (S)-(1-(2-((5-fluoro-2-(5-fluoro-1H-pyrrolo[2,3-b]pyridin-3-yl)pyrimidin-4-yl)amino)-3, 3-dimethylbutyl)-1H-1,2,3-triazol-4-yl)methanol (68)

To a solution of (S)-(1-(2-((5-fluoro-2-(5-fluoro-1-tosyl-1H-pyrrolo[2,3-b]pyridin-3-yl)pyrimidin-4-yl)amino)-3,3-dimethylbutyl)-1H-1,2,3-triazol-4-yl)methanol, 218a, (0.11 g, 0.19 mmol) in THF (5 mL) was added NaOMe (0.17 mL of 25% solution in MeOH, 0.75 mmol). After stirring the reaction mixture at room temperature for 30 minutes, the mixture was diluted into aqueous saturated NH$_4$Cl solution (5 mL) and EtOAc (10 mL). The organic layer was separated, dried (MgSO$_4$), filtered concentrated in vacuo. The crude product was purified by silica gel chromatography (0-10% MeOH/CH$_2$Cl$_2$) to afford 41 mg of the desired product as an off-white solid: $^1$H NMR (400 MHz, CD$_3$OD) δ 8.51 (d, J=8.0 Hz, 1H), 8.16 (s, 1H), 8.09 (s, 1H), 7.93 (d, J=3.5 Hz, 1H), 7.38 (s, 1H), 5.08 (m, 1H), 5.00-4.90 (m, 1H), 4.74 (s, 2H), 4.60 (m, 1H), 1.2 (s, 9H); LCMS Gradient 10-90%, 0.1% formic acid, 5 minutes, C18/ACN, Retention Time=1.90 minutes (M+H) 429.26.

Example 2

Influenza Antiviral Assay

Antiviral assays were performed using two cell-based methods:

A 384-well microtiter plate modification of the standard cytopathic effect (CPE) assay method was developed, similar to that of Noah, et al. (Antiviral Res. 73:50-60, 2006). Briefly, MDCK cells were incubated with test compounds and influenza A virus (A/PR/8/34), at a low multiplicity of infection (approximate MOI=0.005), for 72 hours at 37° C., and cell viability was measured using ATP detection (CellTiter Glo, Promega Inc.). Control wells containing cells and virus show cell death while wells containing cells, virus, and active antiviral compounds show cell survival (cell protection). Different concentrations of test compounds were evaluated, in quadruplicate, for example, over a range from approximately 20 µM to 1 nM. Dose-response curves were prepared using standard 4-parameter curve fitting methods, and the concentration of test compound resulting in 50% cell protection, or cell survival equivalent to 50% of the uninfected wells, was reported as the IC$_{50}$.

A second cell-based antiviral assay was developed that depends on the multiplication of virus-specific RNA molecules in the infected cells, with RNA levels being directly measured using the branched-chain DNA (bDNA), hybridization method (Wagaman et al, J. Virol Meth, 105:105-114, 2002). In this assay, cells are initially infected in wells of a 96-well microtiter plate, the virus is allowed to replicate in the infected cells and spread to additional rounds of cells, then the cells are lysed and viral RNA content is measured. This assay is stopped earlier that the CPE assay, usually after 18-36 hours, while all the target cells are still viable. Viral RNA is quantitated by hybridization of well lysates to specific oligonucleotide probes fixed to wells of an assay plate, then amplification of the signal by hybridization with additional probes linked to a reporter enzyme, according to the kit manufacturer's instructions (Quantigene 1.0, Panomics, Inc.). Minus-strand viral RNA is measured using probes designed for the consensus type A hemagglutination gene. Control wells containing cells and virus were used to define the 100% viral replication level, and dose-response curves for antiviral test compounds were analyzed using 4-parameter curve fitting methods. The concentration of test compound resulting in viral RNA levels equal to that of 50% of the control wells were reported as EC$_{50}$.

Virus and Cell culture methods: Madin-Darby Canine Kidney cells (CCL-34 American Type Culture Collection) were maintained in Dulbecco's Modified Eagle Medium (DMEM) supplemented with 2 mM L-glutamine, 1,000 U/ml penicillin, 1,000 ug/ml streptomycin, 10 mM HEPES, and 10% fetal bovine medium. For the CPE assay, the day before the assay, cells were suspended by trypsinization and 10,000 cells per well were distributed to wells of a 384 well plate in 50 µl. On the day of the assay, adherent cells were washed with three changes of DMEM containing 1 ug/ml TPCK-treated trypsin, without fetal bovine serum. Assays were initiated with the addition of 30 TCID$_{50}$ of virus and test compound, in medium containing 1 g/ml TPCK-treated trypsin, in a final volume of 50 µl. Plates were incubated for 72 hours at 37° C. in a humidified, 5% CO$_2$ atmosphere. Alternatively, cells were grown in DMEM+fetal bovine serum as above, but on the day of the assay they were trypsinized, washed 2 times and suspended in serum-free EX-Cell MDCK cell medium (SAFC Biosciences, Lenexa, Kans.) and plated into wells at 20,000 cells per well. These wells were then used for assay after 5 hours of incubation, without the need for washing.

Influenza virus, strain A/PR/8/34 (tissue culture adapted) was obtained from ATCC (VR-1469). Low-passage virus stocks were prepared in MDCK cells using standard methods (WHO Manual on Animal Influenza Diagnosis and Surveillance, 2002), and $TCID_{50}$ measurements were performed by testing serial dilutions on MDCK cells in the 384-well CPE assay format, above, and calculating results using the Karber method.

Mean $IC_{50}$ values (mean all) for certain specific compounds are summarized in Table 1:
A: $IC_{50}$ (mean all)<0.3 μM;
B 0.3 μM≤$IC_{50}$ (mean all)≤3.3 μM;
C $IC_{50}$ (mean all)>3.3 μM.

Mean $EC_{50}$ values (mean all) for certain compounds are also summarized in Table 1:
A: $EC_{50}$ (mean all)<0.3 μM;
B 0.3 μM≤$EC_{50}$ (mean all)≤3.3 μM;
C $EC_{50}$ (mean all)>3.3 μM.

Mean $EC_{99}$ values (mean all) for certain compounds are also summarized in Table 1:
A: $EC_{99}$ (mean all)<0.3 M;
B 0.3 M≤$EC_{99}$ (mean all)≤3.3 M;
C $EC_{99}$ (mean all)>3.3 μM.

Some exemplary data are as follows: Compound 1: $IC_{50}$=0.006 M, $EC_{50}$=0.009 M, $EC_{99}$=0.0094 M; Compound 2: $IC_{50}$=0.004 M, $EC_{50}$=0.009 M, $EC_{99}$=0.0063 M; Compound 6: $IC_{50}$=0.004 M, $EC_{50}$=0.015 M, $EC_{99}$=0.082 M; Compound 69: $IC_{50}$=2.31 M, $EC_{50}$=0.8 μM, $EC_{99}$=8.4 μM; Compound 76: $IC_{50}$=0.423 M, $EC_{50}$=0.25 M, $EC_{99}$=1.4 μM.

For comparison purposes, some compounds disclosed in WO2005/095400 were also tested against influenza virus using the bDNA and MDCK cell protection assays described above, and their mean $IC_{50}$, $EC_{50}$, and $EC_{99}$ values are summarized in Table 2.

TABLE 1

$IC_{50}$, $EC_{50}$, NMR and LCMS Data of Compounds of Invention.

| Compound nos. | MDCK IC50 (uM) | bDNA EC50 (uM) | bDNA EC99 (uM) | NMR | M + 1 | LCMS RT |
|---|---|---|---|---|---|---|
| 1 | A | A | A | 12.25 (s, 1H): 12.0 (bs, 1H): 8.8 (s, 1H): 8.3 (s, 1H): 8.25 (s, 1H); 8.1 (s, 1H): 7.45 (d, 1H); 4.75 (t, 1H); 2.5 (m, 2H), 1.0 (s, 9H). | 392.21 | 2.07 |
| 2 | A | A | A | 12.25 (s, 1H): 12.0 (bs, 1H): 8.6 (d, 1H): 8.3 (s, 1H): 8.2 (s, 1H); 8.15 (s, 1H): 7.45 (d, 1H); 4.8 (t, 1H); 2.5 (m, 2H), 1.0 (s, 9H). | 376.21 | 1.92 |
| 3 | B | B | C | | 392.21 | 2.06 |
| 4 | C | C | C | | 376.21 | 1.93 |
| 5 | A | A | A | 1H NMR (300 MHz, MeOD) d 8.60 (d, J = 7.7 Hz, 2H), 8.33 (s, 1H), 5.08 (t, J = 17.2 Hz, 1H), 2.93 (dd, J = 16.3, 2.8 Hz, 1H), 2.73 (dd, J = 16.3, 10.6 Hz, 1H), 1.08 (s, 9H). | 377.24 | 2.17 |
| 6 | A | A | A | 1H NMR (400 MHz, CDCl3) d 8.31 (d, J = 6.4 Hz, 1H), 8.06 (s, 1H), 7.06 (t, J = 9.7 Hz, 1H), 4.58 (s, 2H), 2.80 (d, J = 13.2 Hz, 1H), 2.29 (dd, J = 13.3, 8.7 Hz, 1H), 0.98 (s, 9H). | 394.19 | 2.92 |
| 7 | A | A | A | 1H NMR (300 MHz, MeOD) ? 8.86 (dd, J = 9.8, 2.8 Hz, 1H), 8.37 (s, 1H), 8.26-8.14 (m, 1H), 7.53 (d, J = 11.0 Hz, 1H), 5.04 (dd, J = 11.0, 2.9 Hz, 1H), 2.81 (dd, J = 15.4, 3.0 Hz, 1H), 2.60 (dd, J = 15.4, 11.0 Hz, 1H), 0.99 (s, 9H). | 400.27 | 2.99 |
| 8 (diastereomer of Compound 15) | A | A | A | | 401.94 | 2.1 |
| 9 | A | A | A | | 390.23 | 2.04 |
| 10 | A | A | A | 1H NMR (400 MHz, MeOD) ? 8.60 (s, 1H), 8.44 (s, 1H), 8.23 (d, J = 5.3 Hz, 1H), 8.16 (s, 1H), 5.15 (m, 1H), 3.39 (d, J = 8 Hz, 2H), 1.08 (s 9H). | 428 | 2.02 |
| 11 | A | A | A | 1H NMR (400 MHz, MeOD) ? 8.44 (s, 1H), 8.34 (dd, J = 9.2, 2.6 Hz, 1H), 8.22 (d, J = 5.7 Hz, 1H), 8.13 (s, 1H), 5.16 (d, J = 4.1 Hz, 1H), 3.46-3.33 (m, 3H), 1.10 (d, J = 19.9 Hz, 10H). | 412.13 | 1.91 |
| 12 | A | A | A | 1H NMR (400 MHz, MeOD) ? 8.64 (dd, J = 8.4, 2.4 Hz, 1H), 8.57 (s, 1H), 8.24 (d, J = 4.4 Hz, 1H), 5.19 (d, J = 8.7 Hz, 1H), 2.78 (qd, J = 15.9, 6.6 Hz, 2H), 1.85-1.57 (m, 6H), 1.48 (dd, J = 11.8, 6.0 Hz, 1H), 1.36 (dt, J = 12.0, 6.0 Hz, 1H), 1.11 (s, 3H). | 403.22 | 2.37 |
| 13 | A | A | A | 1H NMR (400 MHz, MeOD) ? 8.64 (dd, J = 8.4, 2.4 Hz, 1H), 8.57 (s, 1H), | 426.25 | 3.21 |

TABLE 1-continued

IC$_{50}$, EC$_{50}$, NMR and LCMS Data of Compounds of Invention.

| Compound nos. | MDCK IC50 (uM) | bDNA EC50 (uM) | bDNA EC99 (uM) | NMR | M + 1 | LCMS RT |
|---|---|---|---|---|---|---|
| | | | | 8.24 (d, J = 4.4 Hz, 1H), 5.19 (d, J = 8.7 Hz, 1H), 2.78 (qd, J = 15.9, 6.6 Hz, 2H), 1.85-1.57 (m, 6H), 1.48 (dd, J = 11.8, 6.0 Hz, 1H), 1.36 (dt, J = 12.0, 6.0 Hz, 1H), 1.11 (s, 3H). | | |
| 14 | A | A | A | | 402.32 | 2.13 |
| 15 (diastereomer of Compound 8) | B | B | C | | 402.38 | 2.12 |
| 16 | A | A | A | | 390.35 | 2.03 |
| 17 | B | B | C | | 389.97 | 2.03 |
| 18 | A | A | A | 1H NMR (400 MHz, DMSO) ? 12.37 (s, 1H), 12.12 (s, 1H), 8.75 (d, J = 9.9 Hz, 1H), 8.32 (s, 2H), 7.83 (d, J = 11.4 Hz, 1H), 7.48 (d, J = 9.5 Hz, 1H), 5.00 (t, J = 9.1 Hz, 1H), 2.71-2.54 (m, 2H), 1.30 (d, J = 7.4 Hz, 2H), 0.80 (t, J = 18.7 Hz, 9H). | 414.31 | 3.14 |
| 19 | A | A | A | 1H NMR (400 MHz, CDCl3) ? 9.75 (s, 1H), 8.12 (d, J = 9.3 Hz, 1H), 7.94 (s, 1H), 7.73 (s, 2H), 7.67 (brs, 1H), 4.93-4.78 (m, 2H), 3.08 (m, 1H), 2.76 (s, 3H), 0.99 (m, 9H). | 425.3 | 1.98 |
| 20 | A | A | A | 1H NMR (400 MHz, DMSO) ? 12.23 (s, 1H), 11.93 (s, 1H), 8.48 (d, J = 9.9 Hz, 1H), 8.33-8.07 (m, 3H), 7.18 (d, J = 9.3 Hz, 1H), 4.39 (t, J = 10.2 Hz, 1H), 2.38-2.07 (m, 2H), 1.99-1.92 (m, 1H), 1.80-1.64 (m, 1H), 1.00 (d, J = 20.2 Hz, 9H). | 390.06 | 2.14 |
| 21 | A | A | A | 1H NMR (400 MHz, MeOD) ? 8.68 (dd, J = 9.6, 2.5 Hz, 1H), 8.24-8.11 (m, 2H), 8.03 (d, J = 3.8 Hz, 1H), 5.12 (d, J = 8.5 Hz, 1H), 3.48 (d, J = 9.2 Hz, 2H), 2.60-2.47 (m, 1H), 0.68-0.48 (m, 4H). | 451.14 | 2.2 |
| 22 | A | A | B | 1H NMR (400 MHz, MeOD) ? 8.65 (d, J = 9.3, 1H), 8.47 (s, 1H), 8.34 (m,, 2H), 5.28 (d, J = 10.4 Hz, 1H), 3.55 (dt, J = 14.5, 13.0 Hz, 2H), 1.20-1.03 (m, 9H). | 411 | 1.96 |
| 23 | B | B | C | 1H NMR (400 MHz, DMSO) ? 12.23 (s, 1H), 8.44 (d, J = 7.6 Hz, 1H), 8.32-8.06 (m, 3H), 7.18 (d, J = 9.6 Hz, 1H), 4.36 (t, J = 10.4 Hz, 1H), 4.00-3.67 (m, 2H), 2.41-2.13 (m, 2H), 2.08-1.93 (m, 1H), 1.87-1.65 (m, 1H), 1.06-0.84 (m, 12H). | 419.08 | 2.41 |
| 24 | A | A | A | 1H NMR (400 MHz, CDCl3) ? 10.27 (brs, 1H), 8.25 (d, J = 9.4 Hz, 1H), 8.17 (s, 1H), 8.11 (s, 1H), 7.23 (d, J = 10.3 Hz, 1H), 5.20 (d, J = 9.6 Hz, 1H), 4.41 (t, J = 7.4 Hz, 1H), 4.09 (d, J = 11.3 Hz, 1H), 3.82-3.58 (m, 1H), 0.99 (d, J = 19.5 Hz, 9H). | 373.03 | 3.08 |
| 25 | A | A | A | 1H NMR (400 MHz, MeOD) ? 9.26 (dd, J = 9.0, 2.2 Hz, 1H), 8.43 (s, 1H), 8.22 (s, 1H), 7.66-7.35 (m, 1H), 5.00 (m, 1H), 3.45-3.17 (m, 2H), 1.03 (m, 9H). | 436 | 2.54 |
| 26 | | A | A | 1H NMR (400 MHz, CDCl3) ? 9.68 (s, 1H), 8.45-8.33 (m, 1H), 8.17 (d, J = 2.8 Hz, 1H), 7.88 (s, 1H), 7.36 (d, J = 10.3 Hz, 1H), 6.47 (d, J = 4.9 Hz, 1H), 5.11 (d, J = 7.8 Hz, 1H), 4.90 (d, J = 10.4 Hz, 1H), 3.52 (s, 1H), 3.04 (dd, J = 15.0, 10.5 Hz, 1H), 2.67 (d, J = 5.0 Hz, 3H), 1.02 (s, 9H). | 449.22 | 2.97 |
| 27 | | A | B | 1H NMR (400 MHz, CDCl3) ? 8.59 (dd, J = 9.7, 2.6 Hz, 1H), 8.38 (s, 1H), 8.21 (s, 1H), 7.31 (m, 1H), 5.12 (brs, 1H), 4.97 (brs, 1H), 3.33 (m, 1H), 2.70 (s, 6H), 0.95 (s, 9H). | 463.49 | 3.12 |

TABLE 1-continued

IC$_{50}$, EC$_{50}$, NMR and LCMS Data of Compounds of Invention.

| Compound nos. | MDCK IC50 (uM) | bDNA EC50 (uM) | bDNA EC99 (uM) | NMR | M + 1 | LCMS RT |
|---|---|---|---|---|---|---|
| 28 | | A | A | | 475 | 3.12 |
| 29 | | A | B | 1H NMR (400 MHz, MeOD) ? 8.71 (dd, J = 9.7, 2.6 Hz, 1H), 8.37 (s, 1H), 8.20 (s, 1H), 7.57 (d, J = 10.9 Hz, 1H), 5.08 (d, J = 8.8 Hz, 1H), 3.54-3.40 (m, 2H), 3.32 (m, 5H), 3.15 (t, J = 5.4 Hz, 2H). 1.03 (s, 9H) | 493.5 | 3.05 |
| 30 | | A | A | | 435.46 | 2.8 |
| 31 | | A | A | | 477.65 | 3.27 |
| 32 | A | A | A | 1H NMR (400 MHz, CDCl3) ? 10.77 (brs, 1H), 8.25 (d, J = 8.4 Hz, 1H), 8.07 (s, 1H), 8.03 (s, 1H), 7.88 (s, 1H), 5.59 (brs, 1H), 4.36 (t, J = 8.3 Hz, 2H), 4.11 (m, 1H), 3.72 (m, 2H), 1.06 (s, 9H). | 348.13 | 1.83 |
| 33 | A | A | A | 1H NMR (400 MHz, CDCl3) ? 9.89 (brs, 1H), 8.07 (d, J = 9.3 Hz, 1H), 7.89 (s, 1H), 7.66 (m, 2H), 4.95 (t, J = 10.2 Hz, 1H), 4.80 (d, J = 9.6 Hz, 1H), 3.38 (m,, 1H), 3.18-2.96 (m, 3H), 1 1.35-1.12 (m, 3H), 1.08-0.90 (m, 9H). | 439.3 | 2.25 |
| 34 | A | A | B | .1H NMR (400 MHz, CDCl3) ? 9.84 (s, 1H), 8.10 (d, J = 9.5 Hz, 1H), 7.92 (d, J = 1.2 Hz, 1H), 7.72 (d, J = 14.2 Hz, 2H), 4.92 (m, 1H), 4.81 (m, 1H), 3.41 (d, J = 15.0 Hz, 1H), 3.19-2.84 (m, 3H), 1.59-1.38 (m, 3H), 0.98 (s, 9H), 0.84 (t, J = 7.4 Hz, 3H). | 453.44 | 2.42 |
| 35 | A | A | B | | 469.18 | 2.11 |
| 36 | B | C | C | | 390.29 | 1.98 |
| 37 | C | C | C | 1H NMR (300 MHz, d6-DMSO) ? 12.21 (s, 1H), 8.52 (dd, J = 9.9, 2.9 Hz, 1H), 8.30-8.23 (m, J = 2.8, 1.5 Hz, 1H), 8.20 (d, J = 2.6 Hz, 1H), 8.12 (d, J = 4.1 Hz, 1H), 7.07 (d, J = 8.9 Hz, 1H), 4.53 (t, J = 5.4 Hz, 1H), 4.44-4.27 (m, J = 9.1, 5.8 Hz, 1H), 3.77 (ddd, J = 11.0, 5.1, 3.5 Hz, 1H), 3.59 (ddd, J = 11.1, 8.9, 5.8 Hz, 1H), 0.99 (s, 9H). | | |
| 38 | C | C | C | 1H NMR (300 MHz, d6-DMSO) ? 12.21 (s, 1H), 8.55 (dd, J = 10.0, 2.8 Hz, 1H), 8.29-8.23 (m, 1H), 8.19 (d, J = 2.7 Hz, 1H), 8.15 (d, J = 4.0 Hz, 1H), 7.47 (d, J = 8.4 Hz, 1H), 6.77-6.69 (m, 1H), 4.88 (t, J = 9.1 Hz, 1H), 3.49-3.36 (m, 1H), 3.36-3.28 (m, J = 10.5 Hz, 1H), 2.55 (t, J = 5.6 Hz, 3H), 0.98 (s, 9H). | 425.03 | 2.11 |
| 39 | A | A | B | 1H NMR (400 MHz, CDCl3) ? 9.89 (s, 1H), 8.07 (d, J = 8.9 Hz, 1H), 7.90 (s, 1H), 7.68 (s, 2H), 4.96 (t, J = 9.8 Hz, 1H), 4.76 (d, J = 9.8 Hz, 1H), 3.60 (dd, J = 13.0, 6.6 Hz, 1H), 3.42 (m, 1H), 3.09-2.86 (m, 1H), 1.20 (d, J = 4.9 Hz, 6H), 0.97 (s, 9H). | 453.19 | 2.22 |
| 40 | A | A | B | | 467.2 | 2.36 |
| 41 | A | A | B | | 386.39 | 3.09 |
| 42 | A | A | A | 1 H NMR (300 MHz, CDCl3) ? 10.70 (s, 1H), 8.42 (dd, J = 9.6, 2.6 Hz, 1H), 8.05 (s, 1H), 7.73 (s, 1H), 7.40 (t, J = 8.4 Hz, 1H), 5.32 (d, J = 6.6 Hz, 1H), 4.83 (t, J = 9.4 Hz, 1H), 2.89 (d, J = 5.3 Hz, 1H), 2.34 (dd, J = 12.8, 9.6 Hz, 1H), 1.92-1.37 (m, 8H), 1.32-1.24 (m, 1H), 1.20-1.06 (m, 3H). | 426.31 | 3.27 |
| 43 | A | A | A | 1H NMR (300 MHz, CDCl3) ? 11.16 (s, 1H), 8.70 (s, 1H), 8.04 (d, J = 3.2 Hz, 1H), 7.96 (s, 1H), 7.87 (s, 1H), 5.02 (d, J = 8.1 Hz, 1H), 4.80 (t, J = 9.6 Hz, 1H), 2.81 (d, J = 9.9 Hz, 1H), 2.34 (t, J = 11.3 Hz, 1H), 1.14 (s, 9H). | 426.47 | 2.49 |

TABLE 1-continued

IC$_{50}$, EC$_{50}$, NMR and LCMS Data of Compounds of Invention.

| Compound nos. | MDCK IC50 (uM) | bDNA EC50 (uM) | bDNA EC99 (uM) | NMR | M + 1 | LCMS RT |
|---|---|---|---|---|---|---|
| 44 | A | B | B | 1H NMR (400 MHz, DMSO) ? 12.26 (s, 2H), 8.55 (d, J = 9.7 Hz, 1H), 8.19 (dd, J = 45.1, 15.8 Hz, 3H), 7.48 (d, J = 8.1 Hz, 1H), 4.79 (s, 1H), 2.58 (dd, J = 20.6, 12.2 Hz, 2H), 1.85 (ddd, J = 29.4, 26.5, 21.1 Hz, 7H). | 374.02 | 2.1 |
| 45 | B | A | C | 1H NMR (300 MHz, CDCl3) ? 10.42 (s, 1H), 8.47 (dd, J = 9.3, 2.7 Hz, 1H), 8.13 (d, J = 11.2 Hz, 1H), 8.10 (s, 1H), 8.04 (d, J = 3.2 Hz, 1H), 4.89 (d, J = 9.0 Hz, 1H), 4.26 (t, J = 9.9 Hz, 1H), 3.65 (d, J = 9.2 Hz, 1H), 3.54 (td, J = 11.4, 2.9 Hz, 1H), 2.17-1.99 (m, 1H), 1.40 (dd, J = 14.0, 11.9 Hz, 1H), 0.96 (d, J = 18.4 Hz, 9H), 0.90-0.73 (m, 1H). | 362.39 | 1.89 |
| 46 | A | B | C | 1H NMR (400 MHz, CDCl3) ? 9.38 (s, 1H), 8.53 (d, J = 6.9 Hz, 1H), 8.16 (m, 2H), 8.06 (s, 1H), 5.09-4.89 (m, 1H), 3.42-3.31 (m, 1H), 3.11 (m, 1H), 2.84 (s, 3H), 1.00 (s, 9H). | 410.19 | 2.03 |
| 47 | A | A | B | 1H NMR (400 MHz, MeOD) ? 8.70 (dd, J = 8.9, 2.3 Hz, 1H), 8.50 (s, 1H), 8.35 (s, 1H), 7.99 (d, J = 7.3 Hz, 1H), 6.60 (d, J = 7.2 Hz, 1H), 5.05 (d, J = 10.7 Hz, 1H), 2.93 (dd, J = 15.9, 1.8 Hz, 1H), 2.53 (dd, J = 15.9, 11.2 Hz, 1H), 1.08 (d, J = 0.8 Hz, 9H) | 358.02 | 2.17 |
| 48 | A | B | B | 1H NMR (400 MHz, MeOD) ? 8.63-8.45 (m, 2H), 7.96 (d, J = 7.3 Hz, 2H), 6.66 (d, J = 7.3 Hz, 2H), 4.95 (d, J = 10.6 Hz, 2H), 2.84 (dd, J = 15.4, 2.4 Hz, 2H), 2.44 (dd, J = 15.9, 10.7 Hz, 2H), 0.98 (s, 9H). | 359.02 | 2.12 |
| 49 | A | A | B | 1H NMR (300 MHz, MeOD) ? 8.73 (t, J = 5.0 Hz, 1H), 8.44 (s, 1H), 8.37-8.22 (m, 2H), 4.69 (dd, J = 9.9, 2.9 Hz, 1H), 4.11 (dd, J = 11.5, 3.1 Hz, 1H), 3.83 (dd, J = 11.4, 10.0 Hz, 1H), 3.32 (dt, J = 3.3, 1.6 Hz, 1H), 1.12 (s, 9H). | 364.44 | 2.1 |
| 50 (diastereomer of Compounds 51 and 52) | A | A | B | | 402.45 | 1.98 |
| 51 (diastereomer of Compounds 50 and 52) | A | A | C | | 402.45 | 2.06 |
| 52 (diastereomer of Compounds 50 and 51) | A | A | B | | 402.25 | 2.16 |
| 53 | A | A | B | 1H NMR (400 MHz, DMSO) ? 12.57 (s, 1H), 9.40 (s, 1H), 8.88 (s, 1H), 8.40 (d, J = 18.7 Hz, 2H), 8.34 (s, 1H), 3.93 (s, 1H), 3.52 (s, 1H), 1.20 (s, 9H). | 377.42 | 2.5 |
| 54 | A | A | B | 1H NMR (400 MHz, DMSO) ? 12.65 (s, 1H), 12.41 (s, 1H), 9.28 (s, 1H), 8.86 (s, 1H), 8.65 (s, 1H), 8.30 (d, J = 3.5 Hz, 2H), 3.97-3.70 (m, 1H), 3.51 (s, 1H), 1.18 (s, 9H) | 427.4 | 2.92 |
| 55 | A | A | B | | 400.46 | 1.94 |
| 56 | A | A | A | 1 H NMR (400 MHz, DMSO) ? 12.65 (s, 1H), 9.43 (s, 1H), 9.15 (s, 1H), 8.44 (d, J = 4.7 Hz, 1H), 8.41-8.29 (m, 2H), 3.93 (s, 1H), 3.54 (s, 1H), 1.19 (d, J = 20.0 Hz, 9H). | 393.32 | 2.7 |
| 57 | A | A | A | 1H NMR (400 MHz, CDCl3) ? 8.05 (d, J = 7.9 Hz, 1H), 7.81 (d, J = 2.1 Hz, | 475.23 | 2.26 |

TABLE 1-continued

IC$_{50}$, EC$_{50}$, NMR and LCMS Data of Compounds of Invention.

| Compound nos. | MDCK IC50 (uM) | bDNA EC50 (uM) | bDNA EC99 (uM) | NMR | M + 1 | LCMS RT |
|---|---|---|---|---|---|---|
| | | | | 1H), 7.63 (s, 1H), 7.55 (s, 1H), 5.87 (t, J = 54.9 Hz, 1H), 5.03 (t, J = 10.4 Hz, 1H), 4.86 (m, 1H), 3.68 (brs, 1H), 3.43 (m, 2H), 3.19 (m, 1H), 0.94 (s, 9H). | | |
| 58 | A | A | A | NMR (400 MHz, CDCl3) ? 8.03 (dd, J = 9.3, 2.4 Hz, 1H), 7.82 (t, J = 11.2 Hz, 1H), 7.59 (s, 1H), 7.46 (s, 1H), 5.07 (t, J = 10.6 Hz, 1H), 4.77 (m, 1H), 3.45 (m, 1H), 3.16-2.99 (m, 1H), 0.97-0.86 (m, 9H). | 493.31 | 2.37 |
| 59 | A | A | B | 1H NMR (300 MHz, MeOD) ? 8.54 (s, 1H), 8.50-8.18 (m, 3H), 7.18 (dd, J = 15.7, 7.1 Hz, 1H), 6.08 (dd, J = 15.7, 1.3 Hz, 1H), 5.21 (t, J = 22.5 Hz, 1H), 1.12 (s, 9H). | 388.23 | 2.21 |
| 60 | A | B | C | | 454.21 | 2.01 |
| 61 | A | A | B | 1H NMR (300 MHz, MeOD) ? 8.95 (s, 1H), 8.29-8.14 (m, 2H), 8.08 (d, J = 4.0 Hz, 1H), 5.26 (m, 1H), 4.21 (d, J = 15.3 Hz, 1H), 3.92 (dd, J = 30.0, 14.5 Hz, 2H), 3.77-3.57 (m, 1H), 1.10 (s, 9H). | 470.14 | 2.23 |
| 62 | A | B | B | | 416.04 | 2.15 |
| 63 | A | A | A | | 389.06 | 2.08 |
| 64 | | A | C | 1H NMR (400 MHz, MeOD) ? 8.60-8.52 (m, 1H), 8.46 (s, 1H), 8.32 (d, J = 5.3 Hz, 2H), 5.16 (m, 2H), 4.00 (d, J = 14.7 Hz, 1H), 3.80 (d, J = 14.7 Hz, 1H), 3.59 (d, J = 13.9, 1H), 1.12 (s, 9H). | 438.25 | 1.93 |
| 65 | A | A | B | | 416.07 | 2.11 |
| 66 (diastereomer of Compound 67) | A | A | B | 1H NMR (400 MHz, CDCl3) ? 10.15 (s, 1H), 8.49 (dd, J = 9.3, 2.6 Hz, 1H), 8.16 (s, 1H), 8.10 (d, J = 2.6 Hz, 1H), 8.06 (d, J = 3.0 Hz, 1H), 5.30 (d, J = 15.0 Hz, 1H), 5.19-5.10 (m, 1H), 4.32-4.24 (m, 1H), 4.23-4.17 (m, 1H), 2.37 (dt, J = 14.9, 3.4 Hz, 1H), 1.85-1.71 (m, 2H), 1.09 (s, 9H). | 430.47 | 2.37 |
| 67 (diastereomer of Compound 66) | A | A | B | 1H NMR (400 MHz, CDCl3) ? 9.40 (s, 1H), 8.47 (dd, J = 9.3, 2.7 Hz, 1H), 8.15 (s, 1H), 8.10 (d, J = 2.7 Hz, 1H), 7.99 (d, J = 2.8 Hz, 1H), 5.54 (s, 1H), 4.84 (d, J = 7.5 Hz, 1H), 4.23 (t, J = 9.9 Hz, 1H), 3.91 (s, 1H), 2.07-1.97 (m, 1H), 1.62 (t, J = 13.0 Hz, 1H), 1.01 (s, 9H). | 430.44 | 2.42 |
| 68 | B | A | B | 1H NMR (400 MHz, MeOD) ? 8.51 (d, J = 8.0 Hz, 1H), 8.16 (s, 1H), 8.09 (s, 1H), 7.93 (d, J = 3.5 Hz, 1H), 7.38 (s, 1H), 5.08 (m, 1H), 5.00-4.90 (m, 1H), 4.74 (s, 2H), 4.60 (m, 1H), 1.2 (s, 9H). | 429.26 | 1.9 |
| 69 | B | B | C | 1H NMR (300 MHz, MeOD) ? 8.59-8.39 (m, 2H), 8.32 (t, J = 5.3 Hz, 2H), 4.59 (d, J = 9.5 Hz, 2H), 2.21 (s, 1H), 1.79 (dddd, J = 28.6, 23.0, 13.2, 6.9 Hz, 3H), 1.11 (d, J = 9.5 Hz, 9H). | 426.09 | 1.81 |
| 70 (diastereomer of Compound 71) | A | A | B | 1H NMR (400 MHz, DMSO) ? 8.61 (dd, J = 9.9, 2.6 Hz, 1H), 8.26 (s, 1H), 8.18 (s, 1H), 8.11 (d, J = 4.1 Hz, 1H), 4.66 (d, J = 10.4 Hz, 1H), 4.43 (s, 1H), 4.29 (d, J = 4.1 Hz, 1H), 4.04 (s, 1H), 3.35 (s, 1H), 3.26 (d, J = 6.1 Hz, 2H), 1.69 (t, J = 12.3 Hz, 1H), 1.59-1.45 (m, 1H), 0.96 (s, 9H). | 392.46 | 1.76 |
| 71 (diastereomer of Compound 70) | A | A | A | 1H NMR (400 MHz, MeOD) ? 8.61 (dd, J = 9.6, 2.7 Hz, 1H), 8.17 (s, 2H), 8.01 (d, J = 4.1 Hz, 1H), 4.53 (d, J = 10.0 Hz, 1H), 3.75-3.56 (m, 2H), 3.48 (dd, J = 11.0, 6.3 Hz, 1H), 2.08-1.97 (m, 1H), 1.75 (dt, J = 28.7, 9.4 Hz, 1H), 1.04 (s, 9H). | 392.46 | 1.79 |

TABLE 1-continued

IC50, EC50, NMR and LCMS Data of Compounds of Invention.

| Compound nos. | MDCK IC50 (uM) | bDNA EC50 (uM) | bDNA EC99 (uM) | NMR | M + 1 | LCMS RT |
|---|---|---|---|---|---|---|
| 72 (diastereomer of Compound 73) | | | C | 1H NMR (400 MHz, CDCl3) ? 9.99 (s, 1H), 8.60 (dd, J = 9.4, 2.7 Hz, 1H), 8.26 (s, 1H), 8.20 (d, J = 2.6 Hz, 1H), 8.10 (d, J = 3.2 Hz, 1H), 5.06 (t, J = 12.3 Hz, 1H), 4.28 (dd, J = 9.6, 7.2 Hz, 1H), 3.96 (d, J = 5.7 Hz, 1H), 2.71 (s, 1H), 1.97 (ddd, J = 14.2, 5.8, 2.9 Hz, 1H), 1.66 ? 1.58 (m, 1H), 1.28 (dd, J = 6.5, 5.5 Hz, 4H), 1.04 (d, J = 10.1 Hz, 9H). | 376.46 | 1.93 |
| 73 (diastereomer of Compound 72) | C | B | C | 1H NMR (400 MHz, CDCl3) ? 10.81 (s, 1H), 8.47 (dd, J = 9.3, 2.7 Hz, 1H), 8.14 (s, 1H), 8.05 (dd, J = 8.4, 2.9 Hz, 2H), 4.95 (s, 1H), 4.81 (d, J = 8.3 Hz, 1H), 4.31 ? 4.14 (m, 1H), 3.72 (dd, J = 8.9, 6.0 Hz, 1H), 1.83 ? 1.70 (m, 1H), 1.48 ? 1.32 (m, 1H), 1.24 ? 1.11 (m, 4H), 0.98 (s, 9H). | 376.46 | 2.01 |
| 74 | B | B | B | 1H NMR (300 MHz, MeOD) ? 8.59 (dd, J = 9.6, 2.9 Hz, 1H), 8.15 (d, J = 2.7 Hz, 2H), 8.01 (d, J = 4.1 Hz, 1H), 4.60 (dd, J = 8.3, 6.0 Hz, 1H), 2.90-2.68 (m, 2H), 1.17 (s, 3H), 0.85 (dt, J = 9.7, 6.7 Hz, 1H), 0.64 (dt, J = 9.4, 4.9 Hz, 1H), 0.47-0.33 (m, 1H), 0.27 (ddd, J = 21.3, 12.8, 10.1 Hz, 1H). | 374.42 | 1.94 |
| 75 | C | B | C | | 456.45 | 2.55 |
| 76 | B | A | B | 1H NMR (300 MHz, MeOD) ? 8.70 (dd, J = 9.7, 2.8 Hz, 1H), 8.15 (dd, J = 6.1, 4.0 Hz, 2H), 8.02 (d, J = 4.1 Hz, 1H), 5.23 (dd, J = 10.7, 3.1 Hz, 1H), 4.30 (d, J = 47.9 Hz, 2H), 3.63 (d, J = 18.2 Hz, 1H), 3.31 (dt, J = 3.3, 1.6 Hz, 3H), 2.83 (dd, J = 15.3, 3.3 Hz, 1H), 2.63 (dd, J = 15.3, 10.8 Hz, 1H), 1.07 (s, 6H). | 394.45 | 1.87 |
| 77 | C | B | C | 1H NMR (400 MHz, CDCl3) ? 9.55 (s, 1H), 8.58 (dd, J = 9.3, 2.5 Hz, 1H), 8.18 (s, 2H), 8.00 (d, J = 2.7 Hz, 1H), 5.13 (brs, 1H), 4.95 (t, J = 8.2 Hz, 1H), 3.84 (m, 2H), 2.72 (m, 1H), 2.38 (m, 1H), 1.67-1.15 (m, 10H), 0.94 (m, 3H). | 444.36 | 2.77 |
| 78 | A | A | B | 1H NMR (400 MHz, MeOD) ? 8.78 (dd, J = 9.7, 2.7 Hz, 1H), 8.16 (s, 2H), 7.99 (d, J = 4.1 Hz, 1H), 5.20 (d, J = 9.9 Hz, 1H), 2.86-2.69 (m, 1H), 2.53 (dd, J = 14.7, 11.0 Hz, 1H), 1.76-1.56 (m, 2H), 1.53 (m, 4H), 1.29 (m, 4H), 1.02 (s, 3H). | 416.27 | 2.2 |
| 79 | B | A | B | H NMR (300.0 MHz, MeOD) d 8.66 (d, J = 8.9 Hz, H), 8.29 (s, H), 8.22-8.18 (m, H), 5.49 (s, H), 4.16-4.06 (m, H), 2.97 (s, H), 2.92 (s, H), 2.86-2.78 (m, H), 2.45 (s, H), 2.06 (s, H), 1.93 (s, H), 1.80 (s, H) and 1.27-1.21 (m, 6 H) ppm | 430.41 | 2.22 |
| 80 | C | B | C | 1H NMR (400 MHz, CDCl3) ? 8.66 (dd, J = 9.2, 2.6 Hz, 1H), 8.53 (d, J = 9.6 Hz, 2H), 8.43 (s, 1H), 8.36 (s, 1H), 5.27-5.13 (m, 1H), 3.60 (s, 3H), 3.02-2.87 (m, 2H), 1.94 (s, 1H), 1.06 (s, 9H). | 406.09 | 2.41 |
| 81 | C | C | C | 1H NMR (300 MHz, CDCl3) ? 9.83 (s, 1H), 8.58 (dd, J = 9.3, 2.7 Hz, 1H), 8.37 (s, 1H), 8.25 (s, 1H), 8.13 (d, J = 3.3 Hz, 1H), 5.66 (s, 1H), 5.32-5.16 (m, 1H), 4.71-4.32 (m, 4H), 4.04 (q, J = 7.1 Hz, 2H), 2.94-2.77 (m, 2H), 2.70 (dd, J = 15.1, 9.1 Hz, 1H), 1.26 (s, 3H), 1.08-1.04 (t, J = 7.1 Hz, 3 H). | 440.45 | 2.35 |
| 82 | C | C | C | 1H NMR (400 MHz, CDCl3) ? 9.93 (s, 1H), 8.89 (d, J = 2.1 Hz, 1H), 8.24 (d, J = 2.4 Hz, 1H), 8.18 (s, 1H), 8.00 (d, | 460.29 | 3.08 |

TABLE 1-continued

IC$_{50}$, EC$_{50}$, NMR and LCMS Data of Compounds of Invention.

| Compound nos. | MDCK IC50 (uM) | bDNA EC50 (uM) | bDNA EC99 (uM) | NMR | M + 1 | LCMS RT |
|---|---|---|---|---|---|---|
| | | | | J = 3.4 Hz, 1H), 5.19 (m, 1H), 4.98 (m, 1H), 3.98-3.65 (m, 2H), 2.73 (dd, J = 14.3, 3.6 Hz, 1H), 2.38 (m, 1H), 1.69-1.23 (m, 10H), 0.93 (t, J = 6.8, 3H). | | |
| 83 | B | A | B | 1H NMR (400 MHz, MeOD) ? 9.05 (d, J = 2.1 Hz, 1H), 8.39-8.24 (m, 2H), 8.16 (d, J = 4.9 Hz, 1H), 5.23 (d, J = 10.4 Hz, 1H), 2.86 (d, J = 15.6 Hz, 1H), 2.65 (m, 1H), 1.58 (m,, 7H), 1.37 (m, 3H), 1.05 (s, 3H). | 432.36 | 2.37 |
| 84 | B | B | C | 1H NMR (300 MHz, MeOD) ? 8.67 (dd, J = 9.6, 2.8 Hz, 1H), 8.16 (m, 2H), 8.04 (d, J = 4.0 Hz, 1H), 5.38 (dd, J = 10.8, 3.2 Hz, 1H), 4.72-4.23 (m, 4H), 2.86 (dd, J = 15.5, 3.3 Hz, 1H), 2.70 (dd, J = 15.5, 10.9 Hz, 1H), 1.15 (s, 3H). | 412.43 | 1.9 |
| 85 | B | A | C | 1H NMR (400 MHz, MeOD) ? 8.68 (dd, J = 9.3, 2.7 Hz, 1H), 8.47 (s, 1H), 8.38 (s, 1H), 8.32 (s, 1H), 5.17 (dd, J = 9.8, 3.5 Hz, 1H), 2.87 (m, 2H), 1.06 (s, 9H). | 392.1 | 2.23 |
| 86 | A | A | B | 1H NMR (400 MHz, MeOD) ? 8.75 (dd, J = 9.7, 2.7 Hz, 1H), 8.18 (s, 2H), 8.00 (d, J = 4.2 Hz, 1H), 2.81 (dd, J = 15.2, 3.1 Hz, 1H), 2.55 (dd, J = 15.2, 10.8 Hz, 1H), 2.00 (m, 3H), 1.82-1.49 (m, 12H). | 454.34 | 2.4 |
| 87 | A | A | A | | 389.13 | 2.02 |
| 88 | A | A | B | | 388.36 | 2.01 |
| 89 | A | A | B | | 383.38 | 2.1 |
| 90 | A | A | B | 1H NMR (300 MHz, DMSO) ? 8.68 (s, 1H), 8.43 (d, J = 14.1 Hz, 2H), 8.23 (s, 1H), 4.96 (s, 2H), 2.88-2.55 (m, 4H), 2.45 (s, 3H), 1.00 (s, 9H). | 372.5 | 1.8 |
| 91 | A | A | B | | 374.42 | 1.96 |
| 92 | B | B | C | | 374.42 | 1.94 |
| 93 | B | B | C | | 428.49 | 2.37 |
| 94 | A | A | A | 1H NMR (400 MHz, MeOD) ? 9.02 (d, J = 2.3 Hz, 1H), 8.40-8.24 (m, 2H), 8.18 (d, J = 5.0 Hz, 1H), 4.91 (d, J = 11.6 Hz, 1H), 2.88 (dd, J = 16.0, 2.8 Hz, 1H), 2.65 (dd, J = 15.9, 11.0 Hz, 1H), 2.01 (s, 3H), 1.77 (dd, J = 27.9, 11.9 Hz, 12H). | 470.27 | 2.6 |
| 95 | A | A | B | 1H NMR (400 MHz, MeOD) ? 8.62 (dd, J = 9.3, 2.6 Hz, 1H), 8.48 (t, J = 5.4 Hz, 1H), 8.32 (s, 1H), 8.29 (d, J = 5.5 Hz, 1H), 5.42 (dd, J = 10.0, 3.4 Hz, 1H), 2.84 (m, 2H), 2.18 (s, 1H), 1.65 (m, 4H), 1.39 (m, 6H). | 414.28 | 2.12 |
| 96 | A | A | B | | 407.37 | 2.79 |
| 97 | A | A | A | $^1$H NMR (300 MHz, MeOD) δ 8.95 (d, J = 2.3 Hz, 1H), 8.66 (d, J = 2.3 Hz, 1H), 8.35 (d, J = 5.2 Hz, 1H), 5.12 (dd, J = 10.7, 2.9 Hz, 1H), 2.93 (dd, J = 16.5, 2.9 Hz, 1H), 2.73 (dd, J = 16.4, 10.7 Hz, 1H), 1.10 (s, 9H); LCMS Gradient 10-90%, 0.1% formic acid, 5 minutes, C18/ACN, Retention Time = 2.79 min, (M + H) 407.37 | 393.43 | 2.5 |

TABLE 2

IC$_{50}$, EC$_{50}$, NMR and LCMS Data of Compounds of WO2005/095400

| Compounds | Molecule | MDCK cell IC50 (uM) | bDNA EC50 (uM) | bDNA EC99 (uM) |
|---|---|---|---|---|
| C1 | 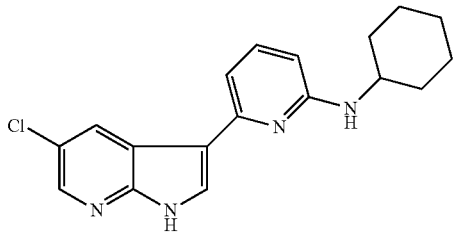 [SMILES: Clc1cnc2[nH]cc(-c3cccc(NC4CCCCC4)n3)c2c1] | >20 (C) | | |
| C2 | 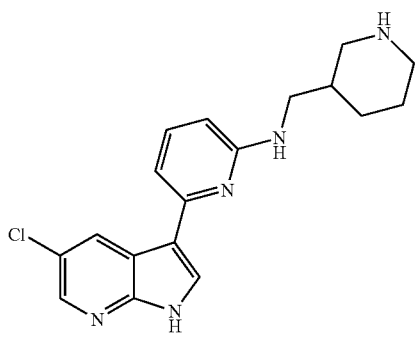 [SMILES: Clc1cnc2[nH]cc(-c3cccc(NCC4CCCNC4)n3)c2c1] | >20 (C) | | |
| C3 | 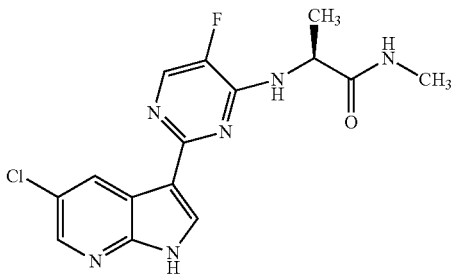 [SMILES: CNC(=O)[C@H](C)Nc1nc(-c2c[nH]c3ncc(Cl)cc23)ncc1F] | >20 (C) | 3.38 (C) | 9.37 (C) |
| C4 | 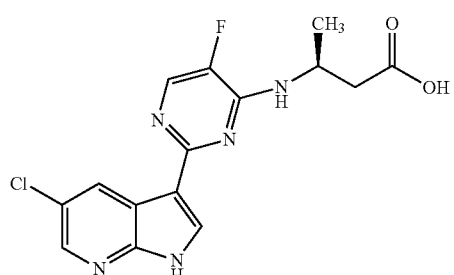 | 2.33 (B) | 6.4 (C) | >16.7 (C) |

Example 3

In Vivo Assay

For efficacy studies, Balb/c mice (4-5 weeks of age) were challenged with 5×10³ TCID$_{50}$ in a total volume of 50 μl by intranasal by intranasal instillation (25 μl/nostril) under general anesthesia (Ketamine/Xylazine). Uninfected controls were challenged with tissue culture media (DMEM, 50 μl total volume). 48 hours post infection mice began treatment with Compounds 1 and 2 at 30 mg/kg bid for 10 days. Body weights and survival is scored daily for 21 days. In addition, Whole Body Plethysmography is conducted approximately every third day following challenge and is reported as enhanced pause (Penh). Total Survival, Percent Body Weight Loss on post challenge day 8 and Penh on study day 6/7 are reported.

TABLE 3

Influneza Therapeutic Mouse Model (Dosing @ 48 hours post infection with 30 mg/kg BID X 10 days)

| Compounds | Percent Survival | Percent Weight Loss (Day 8)[1] | WBP (Penh; Day 6)[2] |
|---|---|---|---|
| 1 | 100 | 26.6 | 1.88 |
| 2 | 100 | 14 | 2.03 |

[1]Average weight loss for untreated controls on day 8 is 30-32%.

[2]Average Penh scores for untreated controls on study day 6 or 7 is 2.2-2.5, and for uninfected mice is ~0.35-0.45.

Example 4

Synergistic/Antagonism Analyses

For synergy/antagonism analysis, test compounds were evaluated in a three day MDCK cell CPE-based assay, infected with A/Puerto Rico/8/34 at an MOI of 0.01, in combination experiments with either the neuraminidase inhibitors oseltamivir carboxylate or zanamivir, or the polymerase inhibitor T-705 (see, e.g., Ruruta et al., Antiviral Reasearch, 82: 95-102 (2009), "T-705 (flavipiravir) and related compounds: Novel broad-spectrum inhibitors of RNA viral infections"), using the Bliss independence method (Macsynergy, Pritchard and Shipman, 1990). See, e.g., Prichard, M. N. and C. Shipman, Jr., *A three-dimensional model to analyze drug-drug interactions*. Antiviral Res, 1990. 14(4-5): p. 181-205. This standard method involves testing different concentration combinations of inhibitors in a checkerboard fashion and a synergy volume is calculated by comparing the observed response surface with the expected result calculated from simple additivity of the single agents alone. Synergy volumes greater than 100 are considered strong synergy and volumes between 50 and 100 are considered moderate synergy. Synergy volumes of zero represent additivity and negative synergy volumes represent antagonism between the agents.

TABLE 4

Synergy/Antagonism Data
Combination experiments using the Bliss
Independence (Macsynergy) Method

| Bliss Independence | Synergy Volume, 95% Confidence | Result |
|---|---|---|
| Compound 1 + oseltamivir | 360 | strong synergy |
| Compound 1 + favipiravir | 1221 | strong synergy |
| Compound 1 + zanamivir | 231 | strong synergy |
| Compound 2 + oseltamivir | 250 | strong synergy |
| Compound 2 + favipiravir | 100 | synergy |
| Compound 2 + zanamivir | 220 | strong synergy |
| Compound 14 + oseltamivir | 545 | strong synergy |
| Compound 14 + favipiravir | 349 | strong synergy |
| Compound 14 + zanamivir | 255 | strong synergy |
| Compound 57 + oseltamivir | 268 | strong synergy |
| Compound 57 + favipiravir | 430 | strong synergy |
| Compound 57 + zanamivir | 171 | strong synergy |

TABLE 4-continued

Synergy/Antagonism Data
Combination experiments using the Bliss
Independence (Macsynergy) Method

| Bliss Independence | Synergy Volume, 95% Confidence | Result |
|---|---|---|
| Compound 87 + oseltamivir | 348 | strong synergy |
| Compound 87 + favipiravir | 412 | strong synergy |
| Compound 87 + zanamivir | 2.7 | insignificant |

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of the formula

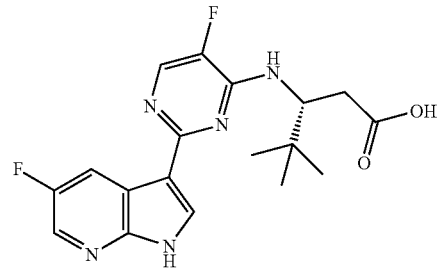 [SMILES: CC(C)(C)[C@@H](CC(=O)O)Nc1nc(-c2c[nH]c3ncc(F)cc23)ncc1F]

or a pharmaceutically acceptable salt thereof.

2. A pharmaceutical composition comprising the compound of claim 1 and a pharmaceutically acceptable carrier, adjuvant, or vehicle.

* * * * *